US012805958B2

(12) United States Patent
Lee et al.

(10) Patent No.: US 12,805,958 B2
(45) Date of Patent: Nov. 24, 2026

(54) MAGNETIC COUPLING THROUGH A STERILE FIELD BARRIER

(71) Applicant: Imperative Care, Inc., Campbell, CA (US)

(72) Inventors: Jason Jin Lee, Seattle, WA (US); John Frederick Kubel, San Carlos, CA (US)

(73) Assignee: Imperative Care, Inc., Campbell, CA (US)

( * ) Notice: Subject to any disclaimer, the term of this patent is extended or adjusted under 35 U.S.C. 154(b) by 0 days.

(21) Appl. No.: 19/406,652

(22) Filed: Dec. 2, 2025

(65) Prior Publication Data

US 2026/0151205 A1 Jun. 4, 2026

Related U.S. Application Data

(63) Continuation-in-part of application No. 18/678,766, filed on May 30, 2024, now Pat. No. 12,508,093.

(60) Provisional application No. 63/727,544, filed on Dec. 3, 2024, provisional application No. 63/470,115, filed on May 31, 2023.

(51) Int. Cl.

| | |
|---|---|
| ***A61B 34/30*** | (2016.01) |
| ***A61B 34/00*** | (2016.01) |
| ***A61B 46/10*** | (2016.01) |

(52) U.S. Cl.

CPC .............. *A61B 34/73* (2016.02); *A61B 46/10* (2016.02); *A61B 2034/301* (2016.02); *A61B 2034/303* (2016.02)

(58) Field of Classification Search

None

See application file for complete search history.

(56) References Cited

U.S. PATENT DOCUMENTS

| | | | |
|---|---|---|---|
| 1,286,033 | A | 11/1918 | Lambeth |
| 4,819,653 | A | 4/1989 | Marks |
| 4,925,444 | A | 5/1990 | Orkin |

(Continued)

FOREIGN PATENT DOCUMENTS

| | | |
|---|---|---|
| AU | 2006268156 | 4/2012 |
| CN | 102462533 | 5/2012 |

(Continued)

OTHER PUBLICATIONS

US 12,076,032 B1, 09/2024, Teigen et al. (withdrawn)

(Continued)

*Primary Examiner* — James Kish

(74) *Attorney, Agent, or Firm* — Knobbe, Martens, Olson & Bear, LLP

(57) ABSTRACT

A hub assembly for a robotically driven interventional device includes an interventional device hub having an interventional device, at least one magnet, wherein the hub assembly is configured to be positioned on a sterile side of a sterile field barrier, wherein the at least one magnet is configured to magnetically couple to a hub adapter on a non-sterile side of the sterile field barrier so that the hub assembly moves axially in response to axial movement of the hub adapter. The hub assembly also includes a plurality of detection components in the form of either a plurality of sensors configured to detect a plurality of detectable objects of the hub adapter or a plurality of detectable objects configured to be detected by a plurality of sensors of the hub adapter.

20 Claims, 93 Drawing Sheets

(56) References Cited

U.S. PATENT DOCUMENTS 5,037,404 A 8/1991 Gold et al.
5,120,317 A 6/1992 Luther
5,131,391 A 7/1992 Sakai et al.
5,380,268 A 1/1995 Wheeler
5,638,818 A 6/1997 Diab et al.
5,766,184 A 6/1998 Matsuno
5,817,031 A 10/1998 Masuo
5,882,333 A 3/1999 Schaer et al.
5,989,208 A 11/1999 Nita
6,096,004 A 8/2000 Meglan et al.
6,375,471 B1 4/2002 Wendlandt et al.
6,400,971 B1 6/2002 Firanov et al.
6,547,766 B1 4/2003 Fitz
6,726,675 B1 4/2004 Beyar
6,821,287 B1 11/2004 Jang
7,172,572 B2 2/2007 Diamond
7,192,433 B2 3/2007 Osypka et al.
7,214,230 B2 5/2007 Brock et al.
7,251,552 B2 7/2007 Schmeisser
7,331,967 B2 2/2008 Lee et al.
7,379,790 B2 5/2008 Toth et al.
D572,615 S 7/2008 Gerold
7,556,611 B2 7/2009 Kolenbrander et al.
7,567,233 B2 7/2009 Garibaldi et al.
7,608,083 B2 10/2009 Lee et al.
7,615,042 B2 11/2009 Beyar et al.
7,727,185 B2 6/2010 Weitzner
7,747,960 B2 6/2010 Garibaldi et al.
7,756,308 B2 7/2010 Viswanathan
7,761,133 B2 7/2010 Viswanathan et al.
7,766,894 B2 8/2010 Weitzner et al.
7,789,874 B2 9/2010 Yu et al.
D626,250 S 10/2010 Wenderow et al.
7,818,076 B2 10/2010 Viswanathan
7,831,294 B2 11/2010 Viswanathan
7,850,640 B2 12/2010 Williams et al.
7,850,642 B2 12/2010 Moll et al.
7,853,306 B2 12/2010 Viswanathan et al.
7,884,727 B2 2/2011 Tran
7,886,743 B2 2/2011 Cooper et al.
7,887,549 B2 2/2011 Wenderow et al.
7,909,798 B2 3/2011 Osypka
7,951,243 B2 5/2011 Boyle, Jr. et al.
7,955,316 B2 6/2011 Weitzner et al.
7,963,288 B2 6/2011 Rosenberg et al.
D641,797 S 7/2011 Chen
8,004,229 B2 8/2011 Nowlin et al.
8,021,326 B2 9/2011 Moll et al.
RE42,804 E 10/2011 Dedig et al.
8,052,636 B2 11/2011 Moll et al.
8,083,753 B2 12/2011 Solar et al.
8,108,069 B2 1/2012 Stahler et al.
8,114,032 B2 2/2012 Ferry et al.
8,123,726 B2 2/2012 Searfoss et al.
8,131,379 B2 3/2012 Hauck
8,137,317 B2 3/2012 Osypka
8,146,874 B2 4/2012 Yu
8,165,684 B2 4/2012 Putz et al.
8,190,238 B2 5/2012 Moll et al.
8,220,468 B2 7/2012 Cooper et al.
8,242,972 B2 8/2012 Garibaldi et al.
8,244,824 B2 8/2012 Garibaldi et al.
8,257,302 B2 9/2012 Beyar et al.
8,262,671 B2 9/2012 Osypka
8,281,807 B2 10/2012 Trombley et al.
8,307,693 B2 11/2012 Uram et al.
D674,484 S 1/2013 Murphy et al.
8,343,096 B2 1/2013 Kirschenman et al.
8,343,098 B2 1/2013 Nystrom et al.
8,377,077 B2 2/2013 Reis
8,390,438 B2 3/2013 Olson et al.
8,399,871 B2 3/2013 Beyar et al.
8,403,909 B2 3/2013 Spohn et al.
D680,645 S 4/2013 Murphy et al.
8,409,172 B2 4/2013 Moll et al.
8,467,853 B2 6/2013 Hunter et al.
D685,468 S 7/2013 Murphy et al.
8,480,618 B2 7/2013 Wenderow et al.
8,498,691 B2 7/2013 Moll et al.
8,506,555 B2 8/2013 Morales
8,521,331 B2 8/2013 Itkowitz
8,529,582 B2 9/2013 Devengenzo et al.
8,540,698 B2 9/2013 Spohn et al.
8,551,084 B2 10/2013 Hauck et al.
8,603,068 B2 12/2013 Weitzner et al.
8,613,730 B2 12/2013 Hieb et al.
8,617,102 B2 12/2013 Moll et al.
8,620,473 B2 12/2013 Diolaiti et al.
8,671,817 B1 3/2014 Bogusky
8,672,880 B2 3/2014 Cohen et al.
8,679,150 B1 3/2014 Janardhan
8,684,953 B2 4/2014 Cabiri
8,684,962 B2 4/2014 Kirschenman et al.
8,694,157 B2 4/2014 Wenderow et al.
8,740,840 B2 6/2014 Foley et al.
8,747,358 B2 6/2014 Trombley et al.
8,790,297 B2 7/2014 Bromander et al.
8,799,792 B2 8/2014 Garibaldi et al.
8,800,881 B2 8/2014 Biseta et al.
8,801,661 B2 8/2014 Moll et al.
8,806,359 B2 8/2014 Garibaldi et al.
8,827,948 B2 9/2014 Romo
8,828,021 B2 9/2014 Wenderow et al.
8,833,293 B2 9/2014 Horn
8,840,628 B2 9/2014 Green et al.
8,852,162 B2 10/2014 Williams et al.
8,852,167 B2 10/2014 Trombley et al.
8,852,184 B2 10/2014 Kucklick
8,876,726 B2 11/2014 Amit et al.
8,894,610 B2 11/2014 Macnamara et al.
8,905,969 B2 12/2014 Nystrom et al.
8,939,963 B2 1/2015 Rogers et al.
8,961,491 B2 2/2015 Uber et al.
8,968,333 B2 3/2015 Yu et al.
8,974,408 B2 3/2015 Wallace et al.
8,974,420 B2 3/2015 Searfoss et al.
8,979,871 B2 3/2015 Tye
8,986,246 B2 3/2015 Foley et al.
9,005,271 B2 4/2015 Ivancev
9,056,200 B2 6/2015 Uber et al.
9,066,740 B2 6/2015 Carlson et al.
9,070,486 B2 6/2015 Guerrera et al.
9,095,681 B2 8/2015 Wenderow et al.
9,101,379 B2 8/2015 Au et al.
9,111,016 B2 8/2015 Besson et al.
9,132,949 B2 9/2015 Bidet et al.
9,138,566 B2 9/2015 Cabiri
9,168,356 B2 10/2015 Wenderow et al.
9,186,046 B2 11/2015 Ramamurthy et al.
9,199,033 B1 12/2015 Cowan et al.
9,205,227 B2 12/2015 Cohen et al.
9,206,309 B2 12/2015 Appleby
9,220,568 B2 12/2015 Bromander et al.
9,233,225 B2 1/2016 Hebert
9,241,768 B2 1/2016 Sandhu et al.
9,242,252 B2 1/2016 Eberle et al.
9,259,526 B2 2/2016 Barron et al.
9,295,527 B2 3/2016 Kirschenman et al.
9,314,306 B2 4/2016 Yu
9,314,307 B2 4/2016 Richmond et al.
9,314,310 B2 4/2016 Kirschenman et al.
9,314,311 B2 4/2016 Wenderow et al.
9,314,594 B2 4/2016 Kirschenman
9,315,663 B2 4/2016 Appleby
9,320,479 B2 4/2016 Wenderow et al.
9,320,573 B2 4/2016 Sandhu et al.
9,333,324 B2 5/2016 Cohen et al.
9,345,859 B2 5/2016 Blacker
9,351,735 B2 5/2016 Nagano et al.
9,375,729 B2 6/2016 Eberle et al.
9,402,977 B2 8/2016 Wenderow et al.
9,408,669 B2 8/2016 Kokish et al.
9,427,515 B1 8/2016 Nystrom
9,427,562 B2 8/2016 Blacker

(56) References Cited

U.S. PATENT DOCUMENTS

D766,902 S 9/2016 Bellinghausen
9,439,736 B2 9/2016 Olson
9,447,890 B2 9/2016 Jennings et al.
9,452,276 B2 9/2016 Duindam et al.
9,452,277 B2 9/2016 Blacker
9,474,857 B2 10/2016 Riley et al.
9,480,797 B1 11/2016 Swantner et al.
9,488,971 B2 11/2016 Yip et al.
9,498,291 B2 11/2016 Balaji et al.
9,510,912 B2 12/2016 Bencteux et al.
9,517,305 B2 12/2016 Uram et al.
9,532,840 B2 1/2017 Wong et al.
9,533,121 B2 1/2017 Pacheco et al.
9,545,497 B2 1/2017 Wenderow et al.
9,549,783 B2 1/2017 Zirps
9,566,201 B2 2/2017 Yu
9,566,414 B2 2/2017 Wong et al.
9,572,481 B2 2/2017 Duindam et al.
9,585,806 B2 3/2017 Herrig
9,586,029 B2 3/2017 Shekalim et al.
9,603,573 B2 3/2017 Leininger et al.
9,623,209 B2 4/2017 Wenderow et al.
9,629,595 B2 4/2017 Walker et al.
9,636,479 B2 5/2017 Bencteux et al.
9,687,304 B2 6/2017 Bencteux et al.
9,700,698 B2 7/2017 Pacheco et al.
9,707,377 B2 7/2017 Cohen et al.
9,717,552 B2 8/2017 Cosman
9,744,305 B2 8/2017 Cowan et al.
9,750,576 B2 9/2017 Murphy et al.
9,750,953 B2 9/2017 Kalafut
9,764,114 B2 9/2017 Murphy et al.
9,770,301 B2 9/2017 Bencteux et al.
9,782,130 B2 10/2017 Hauck et al.
9,782,564 B2 10/2017 Zirps et al.
9,789,285 B1 10/2017 Blacker
D803,837 S 11/2017 Kumar
9,814,534 B2 11/2017 Wenderow et al.
9,825,455 B2 11/2017 Sandhu et al.
9,827,410 B2 11/2017 Cowan et al.
9,828,157 B2 11/2017 Roesler
9,833,293 B2 12/2017 Wenderow et al.
9,839,481 B2 12/2017 Blumenkranz et al.
9,855,101 B2 1/2018 Wenderow et al.
9,943,321 B2 4/2018 Nita
9,943,958 B2 4/2018 Blacker et al.
9,949,799 B2 4/2018 Hingwe et al.
9,962,229 B2 5/2018 Blacker et al.
9,981,109 B2 5/2018 Blacker et al.
9,993,614 B2 6/2018 Pacheco et al.
9,993,615 B2 6/2018 Blacker
9,999,751 B2 6/2018 Pacheco et al.
10,010,699 B2 7/2018 Cohen et al.
10,029,072 B2 7/2018 Hebert
10,046,140 B2 8/2018 Kokish et al.
10,052,761 B2 8/2018 Langenfeld et al.
10,071,224 B2 9/2018 Hebert
10,071,225 B2 9/2018 Hebert
10,085,805 B1 10/2018 Blacker
10,086,167 B2 10/2018 Hebert
10,105,486 B2 10/2018 Trombley et al.
10,111,703 B2 10/2018 Cosman, Jr.
10,123,843 B2 11/2018 Wong et al.
10,123,844 B2 11/2018 Nowlin et al.
10,124,149 B2 11/2018 Hebert
10,130,427 B2 11/2018 Tanner et al.
10,138,025 B2 11/2018 Nakamura
10,145,747 B1 12/2018 Lin et al.
10,149,698 B2 12/2018 Wulfman et al.
10,178,995 B2 1/2019 Cragg
10,183,147 B2 1/2019 Yang et al.
10,201,314 B2 2/2019 Frederick et al.
10,207,315 B2 2/2019 Appleby
10,231,788 B2 3/2019 Olson et al.
10,238,456 B2 3/2019 Murphy et al.
10,245,112 B2 4/2019 Kottenstette et al.
10,258,285 B2 4/2019 Hauck et al.
10,271,910 B2 4/2019 Wenderow et al.
10,299,867 B2 5/2019 Wenderow et al.
D850,447 S 6/2019 Fulghum
10,307,061 B2 6/2019 Cohen
10,307,570 B2 6/2019 Blacker
10,322,277 B2 6/2019 Nystrom
10,342,606 B2 7/2019 Cosman
10,342,953 B2 7/2019 Wenderow et al.
10,363,062 B2 7/2019 Spencer et al.
10,363,109 B2 7/2019 Dachs, II et al.
10,368,951 B2 8/2019 Moll et al.
10,391,234 B2 8/2019 Sams et al.
10,420,537 B2 9/2019 Salahieh et al.
10,426,557 B2 10/2019 Amiri et al.
10,426,559 B2 10/2019 Graetzel et al.
10,426,926 B2 10/2019 Blacker et al.
10,449,007 B2 10/2019 Deboeuf et al.
10,456,556 B2 10/2019 Cabiri
10,512,514 B2 12/2019 Nowlin et al.
10,522,250 B2 12/2019 Spohn et al.
10,531,883 B1 1/2020 Deville et al.
10,531,929 B2 1/2020 Widenhouse et al.
10,537,400 B2 1/2020 Dachs, II et al.
10,539,478 B2 1/2020 Lin et al.
10,549,071 B2 2/2020 Falb et al.
10,549,084 B2 2/2020 Sokolov et al.
10,555,780 B2 2/2020 Tanner et al.
10,556,092 B2 2/2020 Yu et al.
10,561,821 B2 2/2020 Wenderow et al.
10,568,539 B2 2/2020 Kowshik et al.
10,568,700 B2 2/2020 Donhowe et al.
10,583,276 B2 3/2020 Zirps
10,588,656 B2 3/2020 Trosper et al.
10,589,018 B2 3/2020 Uber et al.
D881,234 S 4/2020 Capela
10,611,391 B1 4/2020 Klem et al.
10,639,098 B2 5/2020 Cosman
10,647,007 B2 5/2020 Cordoba et al.
10,653,863 B1 5/2020 Blacker et al.
10,660,814 B2 5/2020 Soundararajan et al.
10,661,453 B2 5/2020 Koenig et al.
10,687,903 B2 6/2020 Lewis et al.
10,695,140 B2 6/2020 Overmyer et al.
10,695,533 B2 6/2020 Deboeuf et al.
10,695,536 B2 6/2020 Weitzner et al.
10,709,510 B2 7/2020 Kottenstette
10,709,512 B2 7/2020 Bajo et al.
10,716,726 B2 7/2020 Bergman et al.
10,722,253 B2 7/2020 Deville et al.
10,729,825 B2 8/2020 Boyle, Jr. et al.
10,736,706 B2 8/2020 Scheib
10,737,061 B2 8/2020 Parmar
10,744,302 B2 8/2020 Pacheco et al.
10,765,303 B2 9/2020 Graetzel et al.
10,765,486 B2 9/2020 Bajo et al.
10,779,775 B2 9/2020 Bergman et al.
10,779,895 B2 9/2020 Wenderow et al.
10,783,993 B2 9/2020 Spohn et al.
10,799,305 B2 10/2020 Murphy et al.
10,806,905 B2 10/2020 Asmus
10,813,713 B2 10/2020 Koch et al.
10,814,102 B2 10/2020 Laby et al.
D901,018 S 11/2020 Swen
10,820,951 B2 11/2020 Soundararajan et al.
10,820,954 B2 11/2020 Marsot et al.
10,827,913 B2 11/2020 Ummalaneni et al.
10,828,463 B2 11/2020 Blacker
10,835,153 B2 11/2020 Rafii-Tari et al.
10,835,329 B2 11/2020 Wenderow et al.
10,835,668 B2 11/2020 Novickoff et al.
10,849,702 B2 12/2020 Hsu et al.
10,864,629 B2 12/2020 Guerrera et al.
10,874,468 B2 12/2020 Wallace et al.
10,881,472 B2 1/2021 Sen et al.
10,881,474 B2 1/2021 Blacker et al.
10,881,765 B2 1/2021 Igarashi
10,898,082 B2 1/2021 Sandgaard

(56) References Cited

U.S. PATENT DOCUMENTS 10,898,288 B2 1/2021 Dachs, II et al.
10,900,771 B2 1/2021 Kottenstette et al.
10,912,624 B2 2/2021 Prentakis et al.
10,912,924 B2 2/2021 Park et al.
10,945,904 B2 3/2021 de Jesus Ruiz et al.
10,953,206 B2 3/2021 Blacker
10,959,789 B2 3/2021 Yi et al.
10,959,792 B1 3/2021 Huang et al.
10,987,179 B2 4/2021 Ummalaneni et al.
10,987,491 B2 4/2021 Wenderow et al.
10,994,102 B2 5/2021 Blacker
11,007,118 B2 5/2021 Cowan et al.
11,007,348 B2 5/2021 Blacker
11,040,147 B2 6/2021 Wagner
11,045,274 B2 6/2021 Dachs, II et al.
11,052,226 B2 7/2021 Salahieh et al.
11,058,508 B2 7/2021 Scheib et al.
11,076,924 B2 8/2021 Kim et al.
11,078,945 B2 8/2021 Grout et al.
11,083,842 B2 8/2021 Chassot
11,083,873 B2 8/2021 Hebert
11,083,882 B2 8/2021 Schrauder et al.
11,096,712 B2 8/2021 Teigen et al.
11,104,012 B2 8/2021 Cordoba et al.
11,109,919 B2 9/2021 Murphy et al.
11,109,920 B2 9/2021 Al-Jadda et al.
11,109,921 B2 9/2021 Kottenstette et al.
11,110,217 B2 9/2021 O'Brien et al.
11,114,918 B2 9/2021 Zirps
11,129,602 B2 9/2021 Wong et al.
11,141,566 B2 10/2021 Cabiri
11,147,950 B2 10/2021 Destrebecq et al.
11,179,213 B2 11/2021 Huang et al.
11,179,546 B2 11/2021 Martin
11,185,455 B2 11/2021 Cagle et al.
11,191,893 B2 12/2021 Capone et al.
11,197,683 B1 12/2021 Teigen et al.
11,207,147 B2 12/2021 Diamond et al.
11,209,300 B2 12/2021 Johnson
11,213,356 B2 1/2022 Tanner et al.
11,213,362 B2 1/2022 Sharon et al.
11,213,654 B2 1/2022 Murphy et al.
11,234,779 B2 2/2022 Fuerst et al.
11,234,781 B2 2/2022 Penny et al.
11,234,784 B2 2/2022 Alden
11,241,291 B2 2/2022 Sharon et al.
11,259,881 B2 3/2022 Garcia Kilroy et al.
11,266,424 B2 3/2022 Hofmann et al.
11,291,515 B2 4/2022 Sharon et al.
11,298,198 B2 4/2022 Fournier et al.
11,304,668 B2 4/2022 Wenderow et al.
11,318,618 B2 5/2022 Desai
11,331,157 B2 5/2022 Russell et al.
11,337,712 B2 5/2022 Teigen et al.
11,337,764 B2 5/2022 Deboeuf et al.
11,357,586 B2 6/2022 Huang et al.
11,357,597 B2 6/2022 Jhaveri et al.
11,359,156 B2 6/2022 Long et al.
11,376,086 B2 7/2022 McGrogan et al.
11,389,360 B2 7/2022 Koenig et al.
11,395,665 B2 7/2022 Yang et al.
11,400,214 B2 8/2022 Porter
11,406,402 B2 8/2022 Deville et al.
11,413,101 B2 8/2022 Sen et al.
11,413,431 B2 8/2022 Blacker
11,419,977 B2 8/2022 Cowan et al.
11,426,246 B2 8/2022 Asadian et al.
11,432,835 B2 9/2022 Shaffer et al.
11,432,840 B2 9/2022 Grothe et al.
11,448,327 B2 9/2022 Heffner et al.
11,464,587 B2 10/2022 Yu et al.
11,464,589 B1 10/2022 Roh et al.
11,472,030 B2 10/2022 Ho et al.
11,478,329 B2 10/2022 Gee et al.
11,490,911 B2 11/2022 Panian
11,491,313 B2 11/2022 Fischel
11,497,481 B2 11/2022 Penny et al.
11,497,523 B2 11/2022 Trosper et al.
11,497,568 B2 11/2022 Ho et al.
11,510,736 B2 11/2022 Rafii-Tari et al.
D976,399 S 1/2023 Carmi
11,547,426 B2 1/2023 Deville et al.
11,547,511 B2 1/2023 Asadian et al.
11,564,649 B2 1/2023 Kedmi-Shahar et al.
11,571,267 B2 2/2023 Gonenc et al.
11,576,743 B2 2/2023 Venkataraman et al.
11,577,382 B2 2/2023 Cagle et al.
11,589,931 B2 2/2023 Desai et al.
11,607,108 B2 3/2023 Yu et al.
11,628,024 B2 4/2023 Kapadia
11,633,247 B2 4/2023 Johnson et al.
11,642,181 B2 5/2023 Nobles et al.
11,653,905 B2 5/2023 Wong et al.
11,660,151 B2 5/2023 Schena
11,660,437 B2 5/2023 Verma
11,672,602 B2 6/2023 Monteverde et al.
11,678,943 B2 6/2023 Zhou et al.
11,678,948 B2 6/2023 Vargas et al.
11,684,759 B2 6/2023 Hayzelden
11,690,985 B2 7/2023 Calhoun et al.
11,696,808 B2 7/2023 Blacker et al.
11,696,810 B2 7/2023 Asadian et al.
11,701,196 B2 7/2023 Scheib et al.
11,703,604 B2 7/2023 Dissertori et al.
11,712,805 B2 8/2023 Zhou et al.
11,713,376 B2 8/2023 Leroux et al.
11,717,356 B2 8/2023 Amiri et al.
11,717,640 B2 8/2023 Fantuzzi et al.
11,723,739 B2 8/2023 Asadian et al.
11,723,744 B2 8/2023 Ergueta Tejerina et al.
11,730,499 B1 8/2023 Thio et al.
11,737,821 B2 8/2023 Algawi et al.
11,744,989 B2 9/2023 Blacker
11,759,269 B2 9/2023 Zhou et al.
11,764,873 B2 9/2023 Burla et al.
11,765,360 B2 9/2023 Schroers et al.
11,766,786 B2 9/2023 Cordoba et al.
11,780,092 B2 10/2023 Desai et al.
11,785,938 B2 10/2023 Clavien et al.
11,786,329 B2 10/2023 Fuerst et al.
11,789,315 B1 10/2023 Yu et al.
11,793,500 B2 10/2023 Vargas
11,793,597 B2 10/2023 Vargas et al.
11,801,365 B2 10/2023 Blacker et al.
11,813,203 B2 11/2023 Timm et al.
11,819,295 B2 11/2023 Wenderow et al.
11,832,904 B2 12/2023 Wenderow et al.
11,844,580 B2 12/2023 Sen et al.
11,844,732 B2 12/2023 Klem et al.
11,883,119 B2 1/2024 Sen et al.
11,883,245 B2 1/2024 Fathollahi Ghezelghieh et al.
11,890,024 B2 2/2024 Panian
11,890,432 B2 2/2024 Awad et al.
11,896,325 B2 2/2024 Clark et al.
11,903,669 B2 2/2024 Cope et al.
11,906,009 B2 2/2024 Klem
11,910,997 B2 2/2024 Fuerst et al.
11,911,120 B2 2/2024 Freiin von Kapri et al.
11,911,910 B2 2/2024 Gonenc et al.
11,918,240 B2 3/2024 Deville et al.
11,918,312 B2 3/2024 Yu
11,918,423 B2 3/2024 Kottenstette et al.
11,931,901 B2 3/2024 Murphy et al.
D1,021,103 S 4/2024 Swen
11,998,290 B2 6/2024 Murphy et al.
12,004,829 B2 6/2024 Searfoss et al.
12,005,589 B2 6/2024 Rea et al.
12,035,989 B2 7/2024 Clark et al.
12,046,363 B2 7/2024 Shrivastava et al.
D1,038,990 S 8/2024 Inwood
12,059,161 B2 8/2024 Deville et al.
12,059,225 B2 8/2024 Zhou et al.
D1,043,739 S 9/2024 Hernandez
12,076,036 B2 9/2024 Baron et al.

(56) References Cited

U.S. PATENT DOCUMENTS

| | | | |
|---|---|---|---|
| 12,076,099 | B2 | 9/2024 | Shrivastava et al. |
| 12,076,497 | B2 | 9/2024 | Fantuzzi et al. |
| 12,076,505 | B2 | 9/2024 | Haubert |
| 12,082,982 | B2 | 9/2024 | Jhaveri et al. |
| 12,087,024 | B2 | 9/2024 | Djelouah et al. |
| 12,102,290 | B2 | 10/2024 | Sharon et al. |
| 12,114,940 | B2 | 10/2024 | Garcia Kilroy et al. |
| 12,117,624 | B2 | 10/2024 | Fuerst et al. |
| 12,133,700 | B2 | 11/2024 | Miller et al. |
| 12,133,702 | B2 | 11/2024 | Nowlin et al. |
| 12,133,965 | B2 | 11/2024 | Chassot et al. |
| 12,137,990 | B2 | 11/2024 | Walker et al. |
| 12,138,004 | B2 | 11/2024 | Cone et al. |
| 12,138,130 | B2 | 11/2024 | Garbus et al. |
| 12,144,564 | B2 | 11/2024 | Barbagli et al. |
| 12,144,569 | B2 | 11/2024 | Cone et al. |
| 12,144,575 | B2 | 11/2024 | Torabi |
| 12,150,660 | B1 | 11/2024 | Teigen et al. |
| 12,150,796 | B2 | 11/2024 | Wenderow et al. |
| 12,156,666 | B2 | 12/2024 | Trosper et al. |
| 12,156,667 | B2 | 12/2024 | Trosper et al. |
| 12,156,711 | B2 | 12/2024 | Liao et al. |
| 12,157,238 | B2 | 12/2024 | Fredrickson et al. |
| 12,161,419 | B2 | 12/2024 | Fuerst et al. |
| 12,171,505 | B2 | 12/2024 | Barbagli et al. |
| 12,171,543 | B2 | 12/2024 | Duindam et al. |
| 12,177,411 | B2 | 12/2024 | Culman |
| 12,178,387 | B2 | 12/2024 | McDowall et al. |
| 12,178,399 | B2 | 12/2024 | Itkowitz et al. |
| 12,178,526 | B2 | 12/2024 | McKenney et al. |
| 12,178,534 | B2 | 12/2024 | Asadian et al. |
| 12,185,947 | B2 | 1/2025 | Hart |
| 12,191,031 | B2 | 1/2025 | Azizian et al. |
| 12,201,484 | B2 | 1/2025 | Itkowitz et al. |
| 12,201,485 | B2 | 1/2025 | McDowall et al. |
| 12,212,240 | B2 | 1/2025 | Schulz |
| 12,232,838 | B2 | 2/2025 | Lau et al. |
| D1,072,942 | S | 4/2025 | Yu |
| 12,329,397 | B2 | 6/2025 | Bartholomew |
| 12,350,415 | B2 | 7/2025 | Kumar et al. |
| 12,376,928 | B2 | 8/2025 | Lau et al. |
| 12,377,206 | B2 | 8/2025 | Bartholomew et al. |
| 12,383,668 | B2 | 8/2025 | Batarilo et al. |
| 12,396,741 | B2 | 8/2025 | Blacker |
| 12,397,099 | B2 | 8/2025 | Aaron et al. |
| 12,419,501 | B2 | 9/2025 | Canale et al. |
| 12,419,703 | B2 | 9/2025 | Yang et al. |
| 12,433,702 | B2 | 10/2025 | Lau et al. |
| 12,440,289 | B2 | 10/2025 | Lau et al. |
| 12,446,979 | B2 | 10/2025 | Yang et al. |
| 12,447,317 | B2 | 10/2025 | Lau et al. |
| D1,102,447 | S | 11/2025 | Bartholomew et al. |
| 12,508,093 | B2 | 12/2025 | Lee et al. |
| 12,558,175 | B2 | 2/2026 | Lau et al. |
| D1,119,865 | S | 3/2026 | Shad |
| 2002/0019608 | A1 | 2/2002 | Mason |
| 2002/0091372 | A1 | 7/2002 | Cragg et al. |
| 2002/0113501 | A1 | 8/2002 | Doi |
| 2002/0192113 | A1 | 12/2002 | Uffenheimer et al. |
| 2003/0071285 | A1 | 4/2003 | Tsukernik |
| 2003/0100849 | A1 | 5/2003 | Jang |
| 2003/0105451 | A1 | 6/2003 | Westlund et al. |
| 2003/0114739 | A1 | 6/2003 | Fuimaono et al. |
| 2003/0125673 | A1 | 7/2003 | Houde et al. |
| 2004/0068248 | A1 | 4/2004 | Mooney et al. |
| 2004/0097805 | A1 | 5/2004 | Verard et al. |
| 2004/0143225 | A1 | 7/2004 | Callan |
| 2005/0027236 | A1 | 2/2005 | Douk |
| 2005/0077225 | A1 | 4/2005 | Usher et al. |
| 2005/0107667 | A1 | 5/2005 | Danitz |
| 2005/0165276 | A1 | 7/2005 | Belson et al. |
| 2005/0277912 | A1 | 12/2005 | John |
| 2006/0000864 | A1 | 1/2006 | Yoshie |
| 2006/0009737 | A1 | 1/2006 | Whiting |
| 2006/0011501 | A1 | 1/2006 | Itou et al. |
| 2006/0095022 | A1 | 5/2006 | Moll et al. |
| 2006/0146010 | A1 | 7/2006 | Schneider |
| 2006/0200026 | A1 | 9/2006 | Wallace et al. |
| 2006/0200191 | A1 | 9/2006 | Zadno-Azizi |
| 2007/0060879 | A1 | 3/2007 | Weitzner |
| 2007/0060915 | A1 | 3/2007 | Kucklick |
| 2007/0106208 | A1 | 5/2007 | Uber et al. |
| 2007/0142824 | A1 | 6/2007 | Devengenzo |
| 2007/0179473 | A1 | 8/2007 | Masters et al. |
| 2007/0270639 | A1 | 11/2007 | Long |
| 2008/0027464 | A1 | 1/2008 | Moll et al. |
| 2008/0086051 | A1 | 4/2008 | Voegele |
| 2008/0234631 | A1 | 9/2008 | Reis |
| 2008/0255505 | A1 | 10/2008 | Carlson et al. |
| 2008/0262513 | A1 | 10/2008 | Stahler et al. |
| 2008/0319387 | A1 | 12/2008 | Amisar et al. |
| 2009/0012464 | A1 | 1/2009 | Martin |
| 2009/0076445 | A1 | 3/2009 | Furnish |
| 2009/0082722 | A1 | 3/2009 | Munger et al. |
| 2009/0131955 | A1 | 5/2009 | Wenderow et al. |
| 2009/0137985 | A1 | 5/2009 | Tanghoej |
| 2009/0153374 | A1 | 6/2009 | Maw et al. |
| 2009/0171332 | A1 | 7/2009 | Bonneau |
| 2009/0204078 | A1 | 8/2009 | Mitchell et al. |
| 2009/0247943 | A1 | 10/2009 | Kirschenman et al. |
| 2009/0247993 | A1 | 10/2009 | Kirschenman et al. |
| 2009/0254083 | A1 | 10/2009 | Wallace et al. |
| 2009/0259200 | A1 | 10/2009 | Lampropoulos |
| 2009/0264785 | A1 | 10/2009 | Causevic et al. |
| 2010/0069833 | A1 | 3/2010 | Wenderow et al. |
| 2010/0175701 | A1 | 7/2010 | Reis et al. |
| 2010/0204712 | A1 | 8/2010 | Mallaby |
| 2010/0204713 | A1 | 8/2010 | Ruiz Morales |
| 2010/0280363 | A1 | 11/2010 | Skarda et al. |
| 2010/0286756 | A1 | 11/2010 | Dorn |
| 2010/0305502 | A1 | 12/2010 | Ferry et al. |
| 2011/0004223 | A1 | 1/2011 | Leeflang |
| 2011/0015484 | A1 | 1/2011 | Alvarez et al. |
| 2011/0028894 | A1 | 2/2011 | Foley et al. |
| 2011/0144658 | A1 | 6/2011 | Wenderow et al. |
| 2011/0152882 | A1 | 6/2011 | Wenderow |
| 2011/0166447 | A1 | 7/2011 | Windolf |
| 2011/0238010 | A1 | 9/2011 | Kirschenman |
| 2011/0288544 | A1 | 11/2011 | Verin et al. |
| 2011/0313318 | A1 | 12/2011 | Rule et al. |
| 2012/0071822 | A1 | 3/2012 | Romo |
| 2012/0071895 | A1 | 3/2012 | Stahler et al. |
| 2012/0154431 | A1 | 6/2012 | Fram |
| 2012/0172798 | A1 | 7/2012 | Miller et al. |
| 2012/0179032 | A1 | 7/2012 | Bromander et al. |
| 2012/0232476 | A1 | 9/2012 | Bhat |
| 2012/0245595 | A1 | 9/2012 | Kesavadas et al. |
| 2012/0316458 | A1 | 12/2012 | Rahmanv |
| 2013/0030408 | A1 | 1/2013 | Piferi |
| 2013/0035537 | A1 | 2/2013 | Wallace |
| 2013/0053704 | A1 | 2/2013 | Bernak et al. |
| 2013/0096551 | A1 | 4/2013 | Govari et al. |
| 2013/0131499 | A1 | 5/2013 | Chan et al. |
| 2013/0214912 | A1 | 8/2013 | Beyar et al. |
| 2013/0231678 | A1 | 9/2013 | Wenderow |
| 2014/0058321 | A1 | 2/2014 | Wenderow et al. |
| 2014/0066900 | A1 | 3/2014 | Blacker |
| 2014/0081113 | A1 | 3/2014 | Cohen |
| 2014/0088411 | A1 | 3/2014 | Suehara |
| 2014/0150782 | A1 | 6/2014 | Vazales |
| 2014/0163364 | A1 | 6/2014 | Perers |
| 2014/0216250 | A1 | 8/2014 | Meyer |
| 2014/0228762 | A1 | 8/2014 | Capone |
| 2014/0243742 | A1 | 8/2014 | Pacheco et al. |
| 2014/0276016 | A1 | 9/2014 | Stigall |
| 2014/0276233 | A1 | 9/2014 | Murphy |
| 2014/0276389 | A1 | 9/2014 | Walker |
| 2014/0276948 | A1 | 9/2014 | Zirps |
| 2014/0318702 | A1 | 10/2014 | Tegg |
| 2015/0005738 | A1 | 1/2015 | Blacker |
| 2015/0005745 | A1 | 1/2015 | Bergman et al. |
| 2015/0073391 | A1 | 3/2015 | Hutchins et al. |
| 2015/0088002 | A1 | 3/2015 | Podhajsky |
| 2015/0157252 | A1 | 6/2015 | Sabesan |

(56) References Cited

U.S. PATENT DOCUMENTS

2015/0265807 A1 9/2015 Park
2015/0272683 A1 10/2015 Yang et al.
2015/0314105 A1 11/2015 Gasparyan
2015/0320478 A1 11/2015 Cosman, Jr.
2015/0320479 A1 11/2015 Cosman, Jr.
2015/0320480 A1 11/2015 Cosman, Jr.
2015/0320481 A1 11/2015 Cosman, Jr.
2015/0327875 A1 11/2015 Look
2015/0374483 A1 12/2015 Janardhan
2016/0058513 A1 3/2016 Giorgi
2016/0067448 A1 3/2016 Blacker et al.
2016/0074057 A1 3/2016 Jezierski et al.
2016/0082502 A1 3/2016 Appleby
2016/0178519 A1 6/2016 Zupkofska
2016/0184032 A1 6/2016 Romo
2016/0310702 A1 10/2016 Cabiri
2016/0331944 A1 11/2016 Tai
2016/0354582 A1 12/2016 Yu et al.
2016/0367214 A1 12/2016 Myklebust
2016/0374590 A1 12/2016 Wong et al.
2017/0000576 A1 1/2017 Zirps
2017/0014998 A1 1/2017 Langenfeld et al.
2017/0020627 A1 1/2017 Tesar et al.
2017/0027653 A1 2/2017 Kirschenman
2017/0080141 A1 3/2017 Lauer
2017/0135773 A1 5/2017 Lohmeier et al.
2017/0143416 A1 5/2017 Guler et al.
2017/0224224 A1 8/2017 Yu
2017/0252025 A1 9/2017 Cabiri et al.
2017/0281054 A1 10/2017 Stever et al.
2017/0281288 A1 10/2017 Au
2017/0311908 A1 11/2017 Kariv et al.
2017/0317937 A1 11/2017 Dillon
2017/0333000 A1 11/2017 Nystrom et al.
2017/0348060 A1 12/2017 Blacker
2017/0348511 A1 12/2017 Burkholz
2018/0126122 A1 5/2018 Cabiri
2018/0153477 A1 6/2018 Nagale et al.
2018/0161001 A1 6/2018 Seip
2018/0168751 A1 6/2018 Yi et al.
2018/0185104 A1 7/2018 Olson et al.
2018/0199916 A1 7/2018 Sugihara et al.
2018/0250086 A1 9/2018 Grubbs
2018/0360398 A1 12/2018 Wenderow et al.
2019/0008360 A1 1/2019 Peh et al.
2019/0008591 A1 1/2019 Desai
2019/0030324 A1 1/2019 Grace et al.
2019/0076640 A1 3/2019 Bhatnagar et al.
2019/0111237 A1 4/2019 Cabiri et al.
2019/0133666 A1 5/2019 Johnson
2019/0167367 A1 6/2019 Walker et al.
2019/0209026 A1 7/2019 Han et al.
2019/0231373 A1 8/2019 Quick
2019/0254690 A1 8/2019 Cabiri et al.
2019/0254754 A1 8/2019 Johnson
2019/0255297 A1 8/2019 Fischell et al.
2019/0269368 A1 9/2019 Hauck et al.
2019/0274809 A1 9/2019 Kapec
2019/0301913 A1 10/2019 Johnson
2019/0304108 A1 10/2019 Carrell et al.
2019/0336227 A1 11/2019 Murphy et al.
2019/0336674 A1 11/2019 Schermeier
2019/0365485 A1 12/2019 Kottenstette et al.
2019/0380825 A1 12/2019 Perkins et al.
2020/0008891 A1 1/2020 Wenderow et al.
2020/0008896 A1 1/2020 Cone et al.
2020/0009354 A1 1/2020 Wenderow et al.
2020/0016371 A1 1/2020 Blacker
2020/0028181 A1 1/2020 Arugula et al.
2020/0054399 A1 2/2020 Duindam
2020/0054403 A1 2/2020 Zhou et al.
2020/0085528 A1 3/2020 Olson et al.
2020/0129740 A1 4/2020 Kottenstette et al.
2020/0163726 A1 5/2020 Tanner et al.
2020/0170630 A1 6/2020 Wong et al.
2020/0242767 A1 7/2020 Zhao et al.
2020/0282186 A1 9/2020 Blacker et al.
2020/0289219 A1 9/2020 Denlinger et al.
2020/0297444 A1 9/2020 Camarillo et al.
2020/0297973 A1 9/2020 Blacker et al.
2020/0306064 A1 10/2020 Perkins et al.
2020/0316340 A1 10/2020 Wenderow et al.
2020/0324084 A1 10/2020 Falb et al.
2020/0338308 A1 10/2020 Saber et al.
2020/0345979 A1 11/2020 Loh et al.
2020/0352494 A1 11/2020 Gable et al.
2020/0368494 A1 11/2020 Parmar
2020/0375671 A1 12/2020 Wenderow et al.
2020/0376249 A1 12/2020 Lockhart
2020/0390503 A1 12/2020 Casas et al.
2020/0397451 A1 12/2020 Feltyberger et al.
2020/0405405 A1 12/2020 Shelton, IV
2020/0405408 A1 12/2020 Shelton, IV et al.
2020/0405410 A1 12/2020 Shelton, IV et al.
2020/0405950 A1 12/2020 Burren
2021/0007816 A1 1/2021 Huang et al.
2021/0022816 A1 1/2021 DeBuys et al.
2021/0030492 A1 2/2021 Wenderow et al.
2021/0031007 A1 2/2021 Alexander
2021/0045622 A1 2/2021 Petroff et al.
2021/0046284 A1 2/2021 Mauch
2021/0060767 A1 3/2021 Guerrera et al.
2021/0068852 A1 3/2021 Spence
2021/0077211 A1 3/2021 Blacker et al.
2021/0093406 A1 4/2021 Blacker et al.
2021/0100627 A1 4/2021 Soper
2021/0100980 A1 4/2021 Blacker
2021/0106346 A1 4/2021 Wallace
2021/0106393 A1 4/2021 Simi et al.
2021/0145532 A1 5/2021 Tucker et al.
2021/0178032 A1 6/2021 Hsu et al.
2021/0178036 A1 6/2021 Nazarifar et al.
2021/0186534 A1 6/2021 Hunt et al.
2021/0192759 A1 6/2021 Lang
2021/0196242 A1 7/2021 Perez
2021/0196413 A1 7/2021 Inoue
2021/0212792 A1 7/2021 Shelton et al.
2021/0220064 A1 7/2021 Kottenstette et al.
2021/0228841 A1 7/2021 Falb et al.
2021/0244434 A1 8/2021 Popa et al.
2021/0247396 A9 8/2021 Penny et al.
2021/0251472 A1 8/2021 Baez
2021/0259884 A1 8/2021 Heeren et al.
2021/0282863 A1 9/2021 Rafii-Tari et al.
2021/0282867 A1 9/2021 Tegg et al.
2021/0282875 A1 9/2021 Sharon et al.
2021/0282893 A1 9/2021 Leo et al.
2021/0290310 A1 9/2021 Laby et al.
2021/0290320 A1 9/2021 Mao et al.
2021/0290324 A1 9/2021 Mintz et al.
2021/0290327 A1 9/2021 Yates et al.
2021/0298847 A1 9/2021 Mao et al.
2021/0298850 A1 9/2021 Huang et al.
2021/0298857 A1 9/2021 Zheng et al.
2021/0298954 A1 9/2021 Alvarez et al.
2021/0305639 A1 9/2021 Ho et al.
2021/0315596 A1 10/2021 Buck et al.
2021/0353129 A1 11/2021 Roelle et al.
2021/0361366 A1 11/2021 Murphy et al.
2021/0369370 A1 12/2021 Malanoski
2021/0378696 A1 12/2021 Yang et al.
2021/0393338 A1 12/2021 Graetzel et al.
2021/0393361 A1 12/2021 Keim
2021/0401527 A1 12/2021 Hassan
2022/0031415 A1 2/2022 Vargas et al.
2022/0040450 A1 2/2022 Haubert
2022/0047344 A1 2/2022 Stepanauskas
2022/0047849 A1 2/2022 Yee et al.
2022/0096120 A1 3/2022 Bajo et al.
2022/0125533 A1 4/2022 Falb
2022/0167984 A1 6/2022 Shelton, IV
2022/0168000 A1 6/2022 Naglretter et al.
2022/0168001 A1 6/2022 Naglretter et al.
2022/0168002 A1 6/2022 Naglretter et al.

(56) References Cited

U.S. PATENT DOCUMENTS

| | | | |
|---|---|---|---|
| 2022/0168049 A1 | 6/2022 | Tanner et al. | |
| 2022/0211452 A1 | 7/2022 | Clark et al. | |
| 2022/0233263 A1 | 7/2022 | Canale et al. | |
| 2022/0233264 A1 | 7/2022 | Klem | |
| 2022/0233820 A1 | 7/2022 | Clark et al. | |
| 2022/0241490 A1 | 8/2022 | Marass | |
| 2022/0313375 A1 | 10/2022 | Zhang et al. | |
| 2022/0323096 A1 | 10/2022 | Naglretter et al. | |
| 2022/0331509 A1 | 10/2022 | Buck et al. | |
| 2022/0370161 A1 | 11/2022 | Yu | |
| 2022/0370706 A1 | 11/2022 | Meganck | |
| 2022/0378522 A1 | 12/2022 | Zemlok et al. | |
| 2023/0000563 A1 | 1/2023 | Bell et al. | |
| 2023/0035508 A1 | 2/2023 | Clark et al. | |
| 2023/0035946 A1 | 2/2023 | Kapadia | |
| 2023/0043432 A1 | 2/2023 | Kapadia | |
| 2023/0048388 A1 | 2/2023 | Lau et al. | |
| 2023/0052862 A1* | 2/2023 | Lau | A61B 34/37 |
| 2023/0061728 A1 | 3/2023 | Davis et al. | |
| 2023/0098497 A1 | 3/2023 | Laby | |
| 2023/0107693 A1 | 4/2023 | Walker et al. | |
| 2023/0116327 A1 | 4/2023 | Walker et al. | |
| 2023/0116700 A1 | 4/2023 | Yu et al. | |
| 2023/0117715 A1 | 4/2023 | Ho et al. | |
| 2023/0126545 A1 | 4/2023 | Liu et al. | |
| 2023/0202040 A1 | 6/2023 | Lin et al. | |
| 2023/0209018 A1 | 6/2023 | Alexanderson et al. | |
| 2023/0218816 A1 | 7/2023 | Germain et al. | |
| 2023/0218861 A1 | 7/2023 | Altshuler | |
| 2023/0310100 A1 | 10/2023 | Wenderow et al. | |
| 2023/0347110 A1 | 11/2023 | Wenderow et al. | |
| 2023/0355299 A1 | 11/2023 | Cosman | |
| 2023/0380914 A1 | 11/2023 | Meglan et al. | |
| 2023/0380915 A1 | 11/2023 | Hundertmark | |
| 2023/0380919 A1 | 11/2023 | DeBuys et al. | |
| 2024/0000524 A1 | 1/2024 | Gregory | |
| 2024/0001101 A1 | 1/2024 | Wallin et al. | |
| 2024/0016557 A1 | 1/2024 | Hung et al. | |
| 2024/0016560 A1 | 1/2024 | Canale et al. | |
| 2024/0019042 A1 | 1/2024 | Lim | |
| 2024/0032949 A1 | 2/2024 | Yang et al. | |
| 2024/0033017 A1 | 2/2024 | Yang et al. | |
| 2024/0041480 A1 | 2/2024 | Bartholomew | |
| 2024/0042124 A1 | 2/2024 | Bartholomew | |
| 2024/0042142 A1 | 2/2024 | Bartholomew | |
| 2024/0130809 A1 | 4/2024 | Scheunert et al. | |
| 2024/0138862 A1 | 5/2024 | Beach | |
| 2024/0138946 A1 | 5/2024 | Swoyer | |
| 2024/0148458 A1* | 5/2024 | Bailey | A61B 34/30 |
| 2024/0165415 A1 | 5/2024 | Grosskopf et al. | |
| 2024/0180635 A1 | 6/2024 | Lau et al. | |
| 2024/0180640 A1 | 6/2024 | Lau et al. | |
| 2024/0180641 A1 | 6/2024 | Lau et al. | |
| 2024/0180642 A1 | 6/2024 | Lau et al. | |
| 2024/0180650 A1 | 6/2024 | Lau et al. | |
| 2024/0180651 A1 | 6/2024 | Lau et al. | |
| 2024/0180652 A1 | 6/2024 | Lau et al. | |
| 2024/0180653 A1 | 6/2024 | Lau et al. | |
| 2024/0180654 A1 | 6/2024 | Lau et al. | |
| 2024/0180658 A1 | 6/2024 | Lau et al. | |
| 2024/0180659 A1 | 6/2024 | Lau et al. | |
| 2024/0181207 A1 | 6/2024 | Lau et al. | |
| 2024/0181208 A1 | 6/2024 | Lau et al. | |
| 2024/0181213 A1 | 6/2024 | Lau et al. | |
| 2024/0181214 A1 | 6/2024 | Lau et al. | |
| 2024/0181224 A1 | 6/2024 | Lau et al. | |
| 2024/0181298 A1 | 6/2024 | Lau et al. | |
| 2024/0183382 A1 | 6/2024 | Lau et al. | |
| 2024/0197416 A1 | 6/2024 | Gonzalez | |
| 2024/0197418 A1 | 6/2024 | Jourdan | |
| 2024/0198039 A1 | 6/2024 | Wainwright et al. | |
| 2024/0198051 A1 | 6/2024 | Jourdan | |
| 2024/0207570 A1 | 6/2024 | Mar | |
| 2024/0277356 A1 | 8/2024 | Vale | |
| 2024/0407794 A1 | 12/2024 | Ray et al. | |
| 2025/0032201 A1 | 1/2025 | Bartholomew et al. | |
| 2025/0032700 A1 | 1/2025 | Burion et al. | |
| 2025/0099089 A1 | 3/2025 | Chookhach Izadeh Moghada | |
| 2025/0177692 A1 | 6/2025 | Yee et al. | |
| 2025/0195835 A1 | 6/2025 | Totten | |
| 2025/0261956 A1 | 8/2025 | Ray et al. | |
| 2025/0319243 A1 | 10/2025 | Mar | |
| 2025/0352717 A1 | 11/2025 | Bartholomew | |
| 2025/0375256 A1 | 12/2025 | Berry | |
| 2025/0375592 A1 | 12/2025 | Dan | |
| 2026/0041414 A1 | 2/2026 | Schorr | |

FOREIGN PATENT DOCUMENTS

| | | |
|---|---|---|
| CN | 103976766 | 8/2014 |
| CN | 104042259 | 9/2014 |
| CN | 203935213 | 11/2014 |
| CN | 204428157 | 7/2015 |
| CN | 105534599 | 5/2016 |
| CN | 105616008 | 6/2016 |
| CN | 105640648 | 6/2016 |
| CN | 105662586 | 6/2016 |
| CN | 105662588 | 6/2016 |
| CN | 105662589 | 6/2016 |
| CN | 105796179 | 7/2016 |
| CN | 205598007 | 9/2016 |
| CN | 106691414 | 5/2017 |
| CN | 107307909 | 11/2017 |
| CN | 107349514 | 11/2017 |
| CN | 107374737 | 11/2017 |
| CN | 107374738 | 11/2017 |
| CN | 107374739 | 11/2017 |
| CN | 107374740 | 11/2017 |
| CN | 107374741 | 11/2017 |
| CN | 107550570 | 1/2018 |
| CN | 107684459 | 2/2018 |
| CN | 107744405 | 3/2018 |
| CN | 107744406 | 3/2018 |
| CN | 107744616 | 3/2018 |
| CN | 107811624 | 3/2018 |
| CN | 108158656 | 6/2018 |
| CN | 108175504 | 6/2018 |
| CN | 207970143 | 10/2018 |
| CN | 207979770 | 10/2018 |
| CN | 207979771 | 10/2018 |
| CN | 207980153 | 10/2018 |
| CN | 109567947 | 4/2019 |
| CN | 208693445 | 4/2019 |
| CN | 109730779 A | 5/2019 |
| CN | 109821137 A | 5/2019 |
| CN | 208989133 | 6/2019 |
| CN | 209136865 | 7/2019 |
| CN | 209137698 | 7/2019 |
| CN | 110151310 A | 8/2019 |
| CN | 110236679 | 9/2019 |
| CN | 209713130 | 12/2019 |
| CN | 211271130 | 12/2019 |
| CN | 210056225 | 2/2020 |
| CN | 111035453 | 4/2020 |
| CN | 111110353 | 5/2020 |
| CN | 111110354 | 5/2020 |
| CN | 111407416 | 7/2020 |
| CN | 111437033 | 7/2020 |
| CN | 111449752 | 7/2020 |
| CN | 210962301 | 7/2020 |
| CN | 111658154 | 9/2020 |
| CN | 111772801 | 10/2020 |
| CN | 211610046 | 10/2020 |
| CN | 211723416 U | 10/2020 |
| CN | 111916214 | 11/2020 |
| CN | 111931626 | 11/2020 |
| CN | 111933268 | 11/2020 |
| CN | 112017516 | 12/2020 |
| CN | 212089719 | 12/2020 |
| CN | 212089720 | 12/2020 |
| CN | 112546396 | 3/2021 |
| CN | 112546397 | 3/2021 |
| CN | 112587241 | 4/2021 |
| CN | 213465314 | 6/2021 |

(56) References Cited

FOREIGN PATENT DOCUMENTS

| | | |
|---|---|---|
| CN | 113303913 | 8/2021 |
| CN | 113304393 | 8/2021 |
| CN | 113693733 | 11/2021 |
| EP | 1 776 057 | 11/2009 |
| EP | 2 124 705 | 5/2019 |
| FR | 3118406 | 7/2022 |
| WO | WO 2000/18290 | 4/2000 |
| WO | WO 2007/102134 | 9/2007 |
| WO | WO 2008/057887 | 10/2008 |
| WO | WO 2009/137410 | 11/2009 |
| WO | WO 2011/109282 | 9/2011 |
| WO | WO 2012/050877 | 4/2012 |
| WO | WO 2013/103885 | 7/2013 |
| WO | WO 2016/191307 | 12/2016 |
| WO | WO 2017/220010 | 12/2017 |
| WO | WO 2019/197673 | 10/2019 |
| WO | WO 2019/222641 | 11/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2021/011551 | 7/2020 |
| WO | WO 2020/167749 | 8/2020 |
| WO | WO 2020/263630 | 12/2020 |
| WO | WO 2021/011533 | 1/2021 |
| WO | WO 2021/011554 | 1/2021 |
| WO | WO 2021/015990 | 1/2021 |
| WO | WO 2021/126698 | 6/2021 |
| WO | WO 2021/127426 | 6/2021 |
| WO | WO 2021/148797 | 7/2021 |
| WO | WO 2021/183444 | 9/2021 |
| WO | WO 2021/184444 | 9/2021 |
| WO | WO 2022/048984 | 3/2022 |
| WO | WO 2022/115717 | 6/2022 |
| WO | WO 2022/154979 | 7/2022 |
| WO | WO 2023/019118 | 2/2023 |
| WO | WO 2023/110598 | 6/2023 |

OTHER PUBLICATIONS

US 12,108,960 B1, 10/2024, Teigen et al. (withdrawn)

Bao et al., Apr. 2018, Operation evaluation in-human of a novel remote-controlled vascular interventional robot, Biomedical Microdevices, 20(2):34.

Bao et al., Feb. 2018, A cooperation of catheters and guidewires-based novel remote-controlled vascular interventional robot, Biomedical Microdevices, 20(1):20.

Bell, Apr. 4, 2019, Coding for Empathy, https://www.youtube.com/watch?v=13tzbxofDVc, screenshot of video.

Bency et al., Apr. 25, 2019, Neural Path Planning: Fixed Time, Near-Optimal Path Generation via Oracle Imitation, arXiv:1904.11102v1 [cs.RO], 8 pp.

Bergman et al., 2020, Robotic assisted percutaneous coronary interventions, in Handbook of Robotic and Image Guided Surgery, Elsevier Inc., pp. 341-362.

BMC Oppthalmology, 2024, Microinterventional system for robot-assisted gonioscopic, posted Aug. 5, 2024 [online], https://bmcophthalmol.biomedcentral.com/articles/10.1186/s12886-024-03595-3/figures/1.

Chen et al., Feb. 14, 2020, Deep learning robotic guidance for autonomous vascular access, Nature Machine Intelligence, https://doi.org/10.1038/s42256-020-0148-7, 12 pp.

Das et al., Feb. 21, 2019, Learning-Based Proxy Collision Detection for Robot Motion Planning Applications, arXiv:1902.08164v1 [cs.RO], 19 pp.

Das et al., May 29, 2020, Stochastic Modeling of Distance to Collision for Robot Manipulators, arXiv:2005.14391v1 [cs.RO], 8 pp.

Evard, Jun. 2018, Catheter localization utilizing a sensor-enabled guidewire design of a proof-of-concept system, Masters Thesis, California Polytechnic State University, San Luis Obispo, 186 pp.

Fagogenis et al., Apr. 2019, Autonomous Robotic Intracardiac Catheter Navigation Using Haptic Vision, Science Robotics, 4(29):1-12.

Guo et al., Apr. 13, 2018, Study on real-time force feedback for a master-slave interventional surgical robotic system, Biomedical Microdevices, 20(2):37, 12 pp.

Guo et al., May 20, 2020, Machine learning-based operation skills assessment with vascular difficulty index for vascular intervention surgery, Medical & Biological Engineering & Computing, https://doi.org/10.1007/s11517-020-02195-9, 15 pp.

Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

Jiang et al., 2018, Initial clinical trial of robot of endovascular treatment with force feedback and cooperating of catheter and guidewire, Applied Bionics and Biomechanics, vol. 2018, Article ID 9735979, 10 pp.

Johnson et al., Aug. 12, 2020, Dynamically Constrained Motion Planning Networks for Non-Holonomic Robots, arXiv:2008.05112v1 [cs.RO}, 7 pp.

Kagiyama et al., Jul. 31, 2019, First experience of robotic-assisted percutaneous coronary intervention in Japan, Intern Med Advance Publication, doi: 10/2016/internalmedicine.3272-19.

Kuang et al., Apr. 2020, Vibration-Based Multi-Axis Force Sensing: Design, Characterization, and Modeling, IEEE Robotics and Automation Letters, 5(2):3082-3089.

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.

Liu et al., 2021, Animal experiment of a novel neurointerventional surgical robotic system with master-slave mode, Applied Bionics and Biomechanics, vol. 2021, Article ID 8836268, 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv:1809.05645v1 [cs.CV], 7 pp.

Sganga, May 22, 2020, Webinar: Autonomous Surgical Robots, https://www.youtube.com/watch?v=QRO2KnfGlgo, screenshot of video.

Wang et al., Feb. 3, 2018, Online measuring and evaluation of guidewire inserting resistance for robotic interventional surgery systems, Microsystem Technologies, https://doi/org/10.1007/s00542-018-03750-4.

Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),:1750002-1-1750002-13.

(56) References Cited

OTHER PUBLICATIONS

Yip et al., Jul. 10, 2017, Robot Autonomy for Surgery, https://arxiv.org/pdf/1707.03080.pdf, 33 pp.
Zhao et al., Apr. 2, 2018, Operating force information on-line acquisition of a novel slave manipulator for vascular interventional surgery, Biomedical Microdevices, 20(2):33, 13 pp.
Zhou et al., 2021, ADRC-based control method for the vascular intervention master-slave surgical robotic system, Micromachines, 12:1439.

* cited by examiner

MAGNETIC COUPLING THROUGH A STERILE FIELD BARRIER

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application is a continuation-in-part of U.S. patent application Ser. No. 18/678,766, filed May 30, 2024, entitled MAGNETIC COUPLING THROUGH A STERILE FIELD BARRIER which claims priority to, and the benefit of U.S. Provisional Application No. 63/470,115, filed May 31, 2023, entitled MAGNETIC COUPLING FOR TORQUE TRANSMISSION THROUGH A STERILE BARRIER. The present application also claims priority to, and the benefit of, U.S. Provisional Patent Application No. 63/727,544, filed Dec. 3, 2024, titled MAGNETIC COUPLING THROUGH A STERILE FIELD BARRIER, the entirety of which is incorporated by reference herein for all purposes and forms a part of this specification.

BACKGROUND

Field

The present application relates to neurovascular procedures, and more particularly, to catheter assemblies and robotic control systems for neurovascular site access.

Description of the Related Art

A variety of neurovascular procedures can be accomplished via a transvascular access, including thrombectomy, diagnostic angiography, embolic coil deployment and stent placement. However, the delivery of neurovascular care is limited or delayed by a variety of challenges. For example, there are not enough trained interventionalists and centers to meet the current demand for neuro interventions. Neuro interventions are difficult, with complex set up requirements and demands on the surgeon's dexterity. With two hands, the surgeon must exert precise control over 3-4 coaxial catheters plus manage the fluoroscopy system and patient position. Long, tortuous anatomy, requires delicate, precise maneuvers. Inadvertent catheter motion can occur due to energy storage and release caused by frictional interplay between coaxial shafts and the patient's vasculature. Supra-aortic access necessary to reach the neurovasculature is challenging to achieve, especially Type III arches. Once supra-aortic access is achieved, adapting the system for neurovascular treatments is time consuming and requires guidewire and access catheter removal and addition of a procedure catheter (and possibly one or more additional catheters) to the stack.

Thus, there remains a need for a supra-aortic access and neurovascular site access system that addresses some or all these challenges and increases the availability of neurovascular procedures. Preferably, the system is additionally capable of driving devices further distally through the supra-aortic access to accomplish procedures in the intracranial vessels.

SUMMARY

Disclosed herein are innovations and embodiments of a robotic drive system for interventional treatments. Some embodiments of the robotic drive system disclosed herein can use a hub adapter (also referred to herein as a carriage) to move a hub (also referred to herein as a puck or instrument coupler) positioned on a sterile side of a sterile barrier, wherein one or more surgical instruments are coupled with the hub. In some embodiments, a magnetic field can be created between the hub adapter and the hub such that a movement of the hub adapter results in a movement of the hub as a result of the magnetic field between the hub and hub adapter. This is one solution for controlling a movement of the hubs of the robotic surgical system through the sterile barrier. Stated another way, magnetic coupling can be used in any embodiments of the robotic surgical systems disclosed herein so that a movement of a driving device on a non-sterile side of a sterile barrier can cause a movement of at least one device on the sterile side of the sterile barrier in any desired direction of movement (e.g., in the direction of insertion and/or withdrawal of an instrument relative to a port going into a patient's body) so as to move an instrument on the sterile side of the sterile barrier.

Also disclosed herein are innovations and embodiments of a magnetic torque transfer unit or system that can be used to transfer a torque load through a sterile barrier to rotate an instrument (e.g., without limitation, a catheter, a guidewire, or other device) that is configured to be inserted into a body during a medical procedure. In some embodiments, a magnetic field can be created between an active torque element or torque master element and a passive torque element (also referred to herein as a sterile side torque device). Such devices can be configured such that a rotation of the active torque element on the non-sterile side of a sterile barrier will cause the passive torque element and an instrument coupled therewith to generally simultaneously rotate. Because of the arrangement of the active torque element relative to the passive torque element, the passive torque element will rotate in an opposite direction that the active torque element rotates in, similar to a pair of meshed gears. In any embodiment, a sterile barrier can separate the active torque element from the passive torque element. In some embodiments, the active torque element and the passive torque element can each have a magnet element that has a plurality of opposite poles. The magnet element can include a single magnet with a plurality of different poles (e.g., without limitation, 4, 6, or 12) or a plurality of individual magnets of opposite poles in an alternating arrangement, so that a north pole of a magnet or a portion of a magnet on the active torque element attracts the south pole of a magnet or a portion of a magnet on the passive torque element. A magnetic force in a shear direction will cause the magnet element of the passive torque element to rotate as the magnet element of the active torque element rotates. This arrangement can significantly reduce a complexity and a cost of the instrument drivers and the overall robotic drive system.

Embodiments of a robotic drive system are disclosed herein. Some embodiments of the robotic drive system can include a torque transfer system that can include an active torque element positioned on a nonsterile side of a sterile barrier and a passive torque element positioned on a sterile side of the sterile barrier. The active torque element can include at least one magnet and the passive torque element can include at least one magnet and can be configured to couple with an interventional device. The active torque element can be configured to rotate to exert a torque on the passive torque element to cause the passive torque element and the interventional device to rotate.

Any embodiments of the robotic drive system, devices thereof, and/or methods of using any embodiments of the robotic drive systems disclosed herein can but are not required to include, in additional embodiments, one or more of the following features, components, steps, and/or details, in any combination with any of the other features, components, steps, and/or details, of any other embodiments disclosed herein: wherein the active torque element includes a plurality of magnets arranged about a periphery of the active torque element; wherein the passive torque element includes a plurality of magnets arranged about a periphery of the passive torque element; wherein the robotic drive system includes a motor coupled with the active torque element and configured to rotate the active torque element; wherein the robotic drive system includes a microcontroller electronically coupled with the motor; wherein the robotic drive system includes a hub configured to be positioned on the sterile side of the sterile barrier, wherein the passive torque element is coupled with the hub; wherein the robotic drive system includes a hub adapter configured to be positioned on a non-sterile side of the sterile barrier, wherein the active torque element is coupled with the hub adapter; wherein the interventional device is a guidewire, an access catheter, a guide catheter, or a procedure catheter; wherein the at least one magnet of the passive torque element can be configured to rotate around an axis transverse to an axis of rotation of the interventional device; wherein the active torque element can be configured to rotate around an axis transverse to an axis of rotation of the interventional device; wherein the passive torque element includes a plurality of disc shaped magnets; wherein the active torque element includes a plurality of disc shaped magnets; wherein the active torque element includes a plurality of arc segment shaped magnets arranged about a periphery of the active torque element; wherein the active torque element includes a plurality of magnets arranged about a periphery of the active torque element and wherein the plurality of magnets alternate in a polarity of a magnetic field projecting radially away from each of the plurality of magnets; wherein the passive torque element includes a plurality of arc segment shaped magnets arranged about a periphery of the passive torque element; wherein the passive torque element includes a plurality of magnets arranged about a periphery of the passive torque element and wherein the plurality of magnets alternate in a polarity of a magnetic field projecting radially away from each of the plurality of magnets; wherein the at least one magnet of the active torque element includes a plurality of magnetic poles extending away from a periphery of the active torque element; wherein the plurality of magnetic poles alternate between north and south poles around the periphery of the at least one magnet of the active torque element; wherein the at least one magnet of the passive torque element includes a plurality of magnetic poles extending away from a periphery of the passive torque element; wherein the plurality of magnetic poles alternate between north and south poles around the periphery of the at least one magnet of the passive torque element; wherein the passive torque element can be configured to rotate around an axis parallel to an axis of rotation of the interventional device; and/or wherein the active torque element can be configured to rotate around an axis parallel to an axis of rotation of the interventional device.

In any embodiments of the robotic drive system disclosed herein, the active torque element can include a plurality of positive magnetic fields projecting radially away from a periphery of the active torque element and a plurality of negative magnetic fields projecting radially away from the periphery of the active torque element, wherein each of the plurality of negative magnetic fields of the active torque element is positioned between two positive magnetic fields of the active torque element, wherein the passive torque element includes a plurality of positive magnetic fields extending away from a periphery of the passive torque element and a plurality of negative magnetic fields extending away from the periphery of the passive torque element, and wherein each of the plurality of negative magnetic fields of the passive torque element is positioned between two positive magnetic fields of the passive torque element.

Also disclosed herein are embodiments of a torque transfer system. In some embodiments, the torque transfer system can include an active torque element configured to be positioned on a nonsterile side of a sterile barrier and a passive torque element configured to be positioned on a sterile side of the sterile barrier. The passive torque element can include a shaft configured to rotate about a longitudinal centerline axis of the shaft and the passive torque element can include at least a first magnet coupled with the shaft of the passive torque element. In any embodiments disclosed herein, the active torque element can include a shaft configured to rotate about a longitudinal centerline axis of the shaft and the active torque element can include at least a first magnet coupled with the shaft of the active torque element. The torque transfer system can be configured such that the first magnet of the passive torque element is magnetically coupleable with the first magnet of the active torque element. The torque transfer system can be configured such that, when the first magnet of the passive torque element is magnetically coupled with the first magnet of the active torque element, a rotation of the shaft of the active torque element about the axis of the shaft of the active torque element will cause a torque to be exerted on the shaft of the passive torque element that will bias the passive torque element to rotate about the axis of the shaft of the passive torque element.

Any embodiments of the torque transfer system, devices thereof, and/or methods of using any embodiments of the torque transfer system disclosed herein can but are not required to include, in additional embodiments, one or more of the following features, components, steps, and/or details, in any combination with any of the other features, components, steps, and/or details, of any other embodiments disclosed herein: wherein the first magnet of the passive torque element has an opposite polarity as compared to the first magnet of the active torque element so that the first magnet of the passive torque element is attracted to the first magnet of the active torque element; wherein the active torque element further includes a second magnet spaced apart from the first magnet of the active torque element and spaced apart from the centerline axis of the shaft of the active torque element; wherein the passive torque element further includes a second magnet spaced apart from the first magnet of the passive torque element and spaced apart from the centerline axis of the shaft of the passive torque element; wherein the torque transfer system is configured such that the second magnet of the passive torque element is magnetically coupleable with the second magnet of the active torque element; wherein the second magnet of the active torque element has an opposite polarity as compared to the first magnet of the active torque element and the second magnet of the passive torque element has an opposite polarity as compared to the first magnet of the passive torque element; wherein the second magnet of the passive torque element has an opposite polarity as compared to the second magnet of the active torque element so that the second magnet of the passive torque element is attracted to the second magnet of the active torque element; wherein the active torque element includes a plurality of magnets each spaced radially apart from one another and radially spaced apart from the centerline axis of the shaft of the active torque element, wherein the passive torque element includes a plurality of magnets each spaced radially apart from one another and radially spaced apart from the centerline axis of the shaft of the passive torque element, and each of the plurality of magnets of the active torque element can be configured to be alignable with and magnetically coupleable with each of the plurality of magnets of the passive torque element; wherein the active torque element further includes a second magnet and a third magnet spaced apart from one another and spaced apart from the first magnet of the active torque element and spaced apart from the centerline axis of the shaft of the active torque element, wherein the passive torque element further includes a second magnet and a third magnet spaced apart from one another and spaced apart from the first magnet of the passive torque element and spaced apart from the centerline axis of the shaft of the passive torque element, and wherein the torque transfer system can be configured such that the second magnet of the passive torque element is magnetically coupleable with the second magnet of the active torque element and the third magnet of the passive torque element is magnetically coupleable with the third magnet of the active torque element; wherein the active torque element further includes a fourth magnet spaced apart from the first magnet, the second magnet, and the third magnet of the active torque element and spaced apart from the centerline axis of the shaft of the active torque element, wherein the passive torque element further includes a fourth magnet spaced apart from the first magnet, the second magnet, and the third magnet of the passive torque element and spaced apart from the centerline axis of the shaft of the passive torque element, and wherein the torque transfer system is further configured such that the fourth magnet of the passive torque element is magnetically coupleable with the fourth magnet of the active torque element; wherein the active torque element includes a magnet support element coupled with a distal end of the shaft of the active torque element, the magnet support element of the active torque element configured to support a plurality of magnets in a planar arrangement radially about the centerline axis of the shaft of the active torque element, and wherein the passive torque element includes a magnet support element coupled with a distal end of the shaft of the passive torque element, the magnet support element of the passive torque element configured to support a plurality of magnets in a planar arrangement radially about the centerline axis of the shaft of the passive torque element, and wherein each of the plurality of magnets of the active torque element can be configured to be alignable with and magnetically coupleable with each of the plurality of magnets of the passive torque element; wherein the magnet support element of the active torque element includes a disc shaped body and plurality of recesses formed in the disc shaped body; wherein each of the plurality of recesses formed in the disc shaped body of the active torque element can be configured to receive therein each of the magnets of the active torque element; and wherein the disc shaped body of the magnet support element of the active torque element has a longitudinal centerline axis that is coincident with the centerline axis of the shaft of the active torque element; wherein the magnet support element of the active torque element includes a disc shaped body that includes a first recess formed in the disc shaped body configured to receive the first magnet of the active torque element and a second recess formed in the disc shaped body configured to receive the second magnet of the active torque element; and/or wherein the disc shaped body of the magnet support element of the active torque element has a longitudinal centerline axis that is coincident with the centerline axis of the shaft of the active torque element.

Any embodiments of the torque transfer system, devices thereof, and/or methods of using any embodiments of the torque transfer system disclosed herein can but are not required to include, in additional embodiments, one or more of the following features, components, steps, and/or details, in any combination with any of the other features, components, steps, and/or details, of any other embodiments disclosed herein: wherein the magnet support element of the passive torque element has a disc shaped body and plurality of recesses formed in the disc shaped body; wherein each of the plurality of recesses formed in the disc shaped body of the passive torque element can be configured to receive therein each of the magnets of the passive torque element; wherein the disc shaped body of the magnet support element of the passive torque element has a longitudinal centerline axis that is coincident with the centerline axis of the shaft of the passive torque element; wherein the magnet support element of the passive torque element includes a disc shaped body that includes a first recess formed in the disc shaped body configured to receive the first magnet of the passive torque element and a second recess formed in the disc shaped body configured to receive the second magnet of the passive torque element, wherein the disc shaped body of the magnet support element of the passive torque element has a longitudinal centerline axis that is coincident with the centerline axis of the shaft of the passive torque element; wherein the first magnet of the active torque element is spaced apart from the axis of the shaft of the active torque element such that a center of the first magnet of the active torque element is eccentric to the axis of the shaft of the active torque element, wherein the first magnet of the active torque element can be configured to rotate in an orbit around the axis of the shaft of the active torque element, wherein the first magnet of the passive torque element is spaced apart from the axis of the shaft of the passive torque element such that a center of the first magnet of the passive torque element is eccentric to the axis of the shaft of the passive torque element, and wherein the first magnet of the passive torque element can be configured to rotate in an orbit around the axis of the shaft of the passive torque element; wherein the active torque element and the passive torque element each comprise only two magnets coupled with the shaft of the active torque element and the passive torque element, respectively; wherein the robotic drive system includes a motor coupled with the active torque element and configured to rotate the active torque element; wherein the active torque element further includes a clutch plate between the shaft and the motor, the clutch plate configured to limit a magnitude of a torque transferred from the motor to the shaft; wherein the robotic drive system includes a controller in electrical communication with the motor of the active torque element, the controller configured to control an operation of the motor in response to an input to the controller; wherein the active torque element further includes a ball bearing around a portion of the shaft of the active torque element and the passive torque element further includes a ball bearing around a portion of the shaft of the passive torque element; wherein the active torque element is coupled with a housing that can be configured to at least translate axially; wherein the passive torque element further includes a first gear coupled with the shaft of the passive torque element, the first gear being configured to couple with and rotate a second gear when the shaft of the passive torque element is rotated;

wherein the first gear and the second gear are miter gears; wherein the second gear is rotationally and axially coupled with an interventional device, the interventional device configured to rotate when the second gear rotates; wherein the passive torque element can be configured to be coupled with an interventional device; wherein the interventional device is a guidewire, a guide catheter, an access catheter or a procedure catheter; wherein the procedure catheter is an aspiration catheter, an embolic deployment catheter, a stent deployment catheter, a flow diverter deployment catheter, a diagnostic angiographic catheter, a stent retriever catheter, a clot retriever, a balloon catheter, a catheter to facilitate percutaneous valve repair or replacement, or an ablation catheter; wherein the passive torque element can be configured to be coupled with a valve and the passive torque element can be configured to rotate the valve between an open and a closed positioned; wherein the valve is rotating hemostatic valve or a stopcock valve; wherein the first magnet of the active torque element is spaced apart from the centerline axis of the shaft of the active torque element by 0.4 inch or approximately 0.4 inch and the first magnet of the passive torque element is spaced apart from the centerline axis of the shaft of the passive torque element by 0.4 inch or approximately 0.4 inch; wherein the first magnet of the active torque element is spaced apart from the centerline axis of the shaft of the active torque element from 0.25 inch or approximately 0.25 inch to 1 inch or approximately 1 inch and the first magnet of the passive torque element is spaced apart from the centerline axis of the shaft of the passive torque element from 0.25 inch or approximately 0.25 inch to 1 inch or approximately 1 inch; and/or wherein the first magnet of the active torque element and the first magnet of the passive torque element each has a diameter of 0.25 inch or approximately 0.25 inch, or 0.375 inch or approximately 0.375 inch, or 0.5 inch or approximately 0.5 inch;

Also disclosed herein are embodiments of a robotic drive system. Any embodiments of the robotic drive system disclosed herein can include a hub adapter configured to be positioned on a non-sterile side of a sterile barrier and configured to move axially based on an input provided by a user of the robotic drive system, a hub configured to be positioned on a sterile side of the sterile barrier and configured move axially in response to axial movement of the hub adapter to adjust an axial position of an interventional device coupled thereto, and one or more torque transfer systems configured as in of the torque transfer system embodiments disclosed herein. In some embodiments, the active torque element of each of the one or more torque transfer system can be coupled with the hub adapter and the passive torque element of each of the one or more torque transfer systems can be coupled with the hub.

In some embodiments, the one or more torque transfer systems can include a plurality of torque transfer systems. Additionally, some embodiments of the robotic drive system can include a drive magnet coupled with the hub adapter and configured to couple with a driven magnet coupled with the hub such that the driven magnet moves in response to movement of the drive magnet when the driven magnet is coupled with the drive magnet to move the hub axially.

Also disclosed herein are embodiments of a method of rotating a surgical device on a sterile side of a sterile barrier, that can include magnetically coupling an active torque element positioned on a non-sterile side of the sterile barrier with a passive torque element positioned on a sterile side of the sterile barrier, wherein the passive torque element is coupled with the surgical device and rotating the active torque element, thereby causing the passive torque element magnetically coupled with the active torque element and the surgical device coupled with the passive torque element to rotate. In some embodiments, the surgical device can be a catheter. In some embodiments, the method can further include rotating the passive torque element to move a seal around a catheter between an open and a closed position.

Also disclosed herein are embodiments of a method of performing a neurovascular procedure, that can include providing a multi-catheter assembly including an access catheter, wherein the access catheter is coupled to a first passive torque element positioned on a sterile side of a sterile barrier, magnetically coupling a first active torque element with the first passive torque element, and rotating the access catheter by rotating the first active torque element. In some embodiments, the multi-catheter assembly can further include a guidewire coupled to a second passive torque element, wherein the method further can include magnetically coupling a second active torque element with the second passive torque element and rotating the guidewire by rotating the second active torque element. In some embodiments, the first active torque element and the second active torque element can each be independently movably carried by a hub adapter. In some embodiments, the multi-catheter assembly further can include a guide catheter and a procedure catheter. The procedure catheter can be an aspiration catheter, an embolic deployment catheter, a stent deployment catheter, a flow diverter deployment catheter, a diagnostic angiographic catheter, a stent retriever catheter, a clot retriever, a balloon catheter, a catheter to facilitate percutaneous valve repair or replacement, or an ablation catheter.

Also disclosed herein are embodiments of a robotic drive system, that can include an active torque element configured to be positioned on a nonsterile side of a sterile barrier, the active torque element including a plurality of magnets configured to rotate about a central axis, and a passive torque element configured to be positioned on a sterile side of the sterile barrier, the passive torque element including a plurality of magnets configured to rotate about a central axis. Each of the plurality of magnets of the active torque element can be coupled to one of the plurality of magnets of the active torque element such that the plurality of magnets of the passive torque element rotate in response to rotation of the plurality of magnets of the active torque element. Some embodiments can include an interventional device coupled with the passive torque element such that the interventional device rotates in response to rotation of the plurality of magnets of the passive torque element. The interventional device can be configured to move axially along an axis transverse to the central axis of the plurality of magnets of the passive torque element. In some embodiments, the interventional device can be configured to move axially along an axis transverse to the central axis of the plurality of magnets of the passive torque element. The central axis of the plurality of magnets of the active torque element can be coaxial with the central axis of the plurality of magnets of the passive torque element. In some embodiments, the passive torque element can be coupled to a hub. In some embodiments, the active torque element can be coupled to a hub adapter.

Also disclosed herein are embodiments of a method of rotating a surgical instrument on a sterile side of a sterile barrier without passing any electrical cables through the sterile barrier. Also disclosed herein are embodiments of a method of rotating a surgical instrument on a sterile side of a sterile barrier with a rotating hub without any electrical cables coupled with the rotating hub.

Also disclosed herein are embodiments of a hub assembly for a robotically driven interventional device, that can include an interventional device hub having an interventional device and at least one magnet. The hub assembly is configured to be positioned on a sterile side of a sterile field barrier and magnetically couple to a hub adapter on a non-sterile side of the sterile field barrier so that hub assembly moves axially in response to axial movement of the hub adapter and the at least one magnet of the hub assembly rotates in response to rotation of at least one magnet of the hub adapter. In some embodiments, the at least one magnet of the hub assembly is configured to operatively couple with the interventional device so that rotation of the at least one magnet of the hub assembly causes rotation of the interventional device. In some embodiments, the at least one magnet is configured to rotate around an axis transverse to an axis of rotation of the interventional device. In some embodiments, the at least one magnet of the hub assembly is configured to couple with a valve of a fluidics subsystem of the hub assembly. In some embodiments, the valve is a hemostatic valve, wherein rotation of the at least one magnet of the hub assembly is configured to cause the hemostatic valve to move between an opened and a closed configuration. In some embodiments, the valve is configured to selectively facilitate the flow of fluid to or from the interventional device. In some embodiments, the valve is a three-way valve coupled to a first flow path for vacuum and a second flow path for saline and contrast. In some embodiments, the at least one magnet comprises a polymagnet having a plurality of magnetic regions. In some embodiments, the hub assembly is configured to move axially in response to a magnetic force applied to the at least one magnet of the hub assembly by the at least one magnet of the hub adapter. In some embodiments, the at least one magnet of the hub assembly includes a plurality of magnets, wherein the at least one magnet of the hub adapter includes a plurality of magnets, wherein each of the plurality of magnets of the hub assembly is configured to rotate in response to rotation of one of the plurality of magnets of the hub adapter. In some embodiments, the plurality of magnets of the hub assembly includes a first magnet coupled with the interventional device so that rotation of the first magnet causes rotation of the interventional device and a second magnet coupled to a valve of a fluidics subsystem. In some embodiments, the hub assembly includes one or more detectable objects configured to be detected by one or more sensors on the non-sterile side of the sterile field barrier. In some embodiments, the hub assembly includes a passive torque element, the passive torque element comprising the at least one magnet of the hub assembly and a magnet support, wherein the at least one magnet of the hub assembly is attached to the magnet support, wherein the passive torque element is configured to rotate in response to rotation of the at least one magnet of the hub adapter. In some embodiments, the magnet support is formed of a ferrous material. In some embodiments, the at least one magnet of the hub assembly and the magnet support are each disc shaped. In some embodiments, the hub assembly includes a mount and an interventional device hub removably coupled to the mount. In some embodiments, the at least one magnet of the hub assembly is attached to the mount. In some embodiments, the at least one magnet of the hub assembly is configured to rotate around an axis of rotation, wherein the hub assembly is configured to move axially along an axis transverse to the axis of rotation of the at least one magnet of the hub assembly. In some embodiments, the hub assembly includes a plurality of rollers configured to contact a drive surface. In some embodiments, the plurality of rollers are configured to space the at least one magnet of the hub assembly apart from the drive surface.

Also disclosed herein are embodiments of a robotic drive system, that can include a hub adapter positioned on a non-sterile side of a sterile field barrier and configured to move axially. The hub adapter includes at least one magnet. The hub adapter is configured to couple with a hub assembly on a sterile side of the sterile field barrier so that axial movement of the hub adapter causes axial movement of the hub assembly and rotational movement of the at least one magnet of the hub adapter causes rotational movement of at least one magnet of the hub assembly. In some embodiments, the hub adapter is configured to translate axially along a first axis, wherein the hub adapter comprises a frame configured to translate axially along a second axis transverse to the first axis. In some embodiments, the at least one magnet of the hub adapter is configured to rotate around a third axis, wherein the third axis is parallel with the second axis. In some embodiments, the hub adapter is configured to move axially along a drive surface, the hub adapter further includes a spring assembly, wherein the spring assembly comprises one or more springs configured to bias the at least one magnet of the hub adapter to maintain an air gap between the at least one magnet and the drive surface. In some embodiments, the at least one magnet of the hub adapter includes a polymagnet having a plurality of magnetic regions. In some embodiments, the at least one magnet of the hub adapter includes a plurality of magnets, wherein the at least one magnet of the hub assembly includes a plurality of magnets, wherein each of the plurality of magnets of the hub adapter is configured to rotate to cause rotation of one of the plurality of magnets of the hub assembly. In some embodiments, the hub adapter includes an active torque element, the active torque element including the at least one magnet of the hub adapter and a magnet support, wherein the at least one magnet of the hub adapter is attached to the magnet support, wherein the active torque element is configured to rotate so as to cause rotation of the at least one magnet of the hub assembly. In some embodiments, the magnet support is formed of a ferrous material. In some embodiments, the magnet of the hub adapter and the magnet support are each disc shaped. In some embodiments, the hub adapter includes a plurality of rollers configured to contact a drive surface. In some embodiments, the plurality of rollers are configured to space the at least one magnet of the hub adapter apart from the drive surface. In some embodiments, the at least one magnet of the hub adapter is configured to rotate around an axis of rotation, wherein the hub adapter is configured to move axially along an axis transverse to the axis of rotation of the at least one magnet of the hub adapter. In some embodiments, the robotic drive system further includes the hub assembly. In some embodiments, the at least one magnet of the hub assembly is configured to couple to an interventional device of the hub assembly, so that rotation of the at least one magnet of the hub assembly causes rotation of the interventional device. In some embodiments, the at least one magnet of the hub assembly is configured to couple with a valve of a fluidics subsystem of the hub assembly. In some embodiments, the valve is a hemostatic valve, wherein rotation of the at least one magnet of the hub assembly is configured to cause the hemostatic valve to move between an opened and a closed configuration. In some embodiments, the valve is configured to selectively facilitate the flow of fluid to or from the interventional device. In some embodiments, the hub assembly is configured to move axially in response to a magnetic force applied to the at least one magnet of the hub assembly by the at least one magnet of the hub adapter. In some embodiments, the hub assembly includes one or more detectable objects, wherein the hub adapter includes one or more sensors configured to detect the one or more detectable objects. In some embodiments, the hub assembly includes a mount and an interventional device hub removably coupled to the mount.

Also disclosed herein are embodiments of a robotic drive system, that can include at least one magnet positioned on a non-sterile side of a sterile field barrier and a frame. The at least one magnet is coupled to the frame. The frame is configured to move from a retracted position to an extended position, wherein the one or more magnets are positioned closer to the sterile field barrier in the extended position than in the retracted position. In some embodiments, the robotic drive system further includes a hub adapter. The hub adapter includes the at least one magnet and the frame, wherein the hub adapter is configured to move axially along a drive surface. In some embodiments, the hub adapter includes a spring assembly, wherein the spring assembly includes one or more springs configured to bias the at least one magnet to maintain an air gap between the at least one magnet and the drive surface when the frame is in the extended position. In some embodiments, the hub adapter is configured to translate axially along a first axis, wherein the frame is configured to translate axially along a second axis transverse to the first axis between the retracted position and the extended position. In some embodiments, the at least one magnet of the hub adapter is configured to rotate around a third axis, wherein the third axis is parallel with the second axis. In some embodiments, the hub adapter includes a support assembly configured to maintain a minimum air gap between the at least one magnet and the drive surface. In some embodiments, the support assembly includes a plurality of rollers.

Also disclosed herein are embodiments of a robotic drive system, that can include a torque transfer system. The torque transfer system can include an active torque element positioned on a nonsterile side of a sterile field barrier and a passive torque element positioned on a sterile side of the sterile field barrier. The active torque element includes at least one magnet and the passive torque element includes at least one magnet. The passive torque element is configured to couple with an interventional device. The active torque element is configured to rotate to exert a torque on the passive torque element to cause the passive torque element and the interventional device to rotate. In some embodiments, the robotic drive system further includes a hub assembly configured to be positioned on the sterile side of the sterile field barrier, wherein the passive torque element is coupled with the hub. In some embodiments, the passive torque element is configured to rotate around an axis of rotation perpendicular to an axis of rotation of the interventional device.

Also disclosed herein are embodiments of a method of rotating a surgical device on a sterile side of a sterile field barrier, that can include magnetically coupling an active torque element positioned on a non-sterile side of the sterile field barrier with a passive torque element positioned on a sterile side of the sterile field barrier, wherein the passive torque element is coupled with the surgical device, and rotating the active torque element, thereby causing the passive torque element magnetically coupled with the active torque element and the surgical device coupled with the passive torque element to rotate.

Also disclosed herein are embodiments of a method of performing a vascular procedure, that can include providing a multi-catheter assembly, magnetically coupling a first active torque element with the first passive torque element, and rotating the access catheter by rotating the first active torque element. The multi-catheter assembly includes an access catheter, wherein the access catheter is coupled to a first passive torque element positioned on a sterile side of a sterile field barrier.

Also disclosed herein are embodiments of a method of performing a vascular procedure, that can include magnetically coupling a hub assembly having an interventional device on a sterile side of a sterile field barrier to a hub adapter on a non-sterile side of a sterile filed barrier and rotating at least one magnet of the hub adapter to cause rotation of at least one magnet of the hub assembly.

Also disclosed herein are embodiments of a hub assembly for a robotically driven interventional device. The hub assembly includes an interventional device hub having an interventional device, at least one magnet, wherein the hub assembly is configured to be positioned on a sterile side of a sterile field barrier, wherein the at least one magnet is configured to magnetically couple to a hub adapter on a non-sterile side of the sterile field barrier so that the hub assembly moves axially in response to axial movement of the hub adapter, and a plurality of detection components having either a plurality of sensors configured to detect a plurality of detectable objects of the hub adapter or a plurality of detectable objects configured to be detected by a plurality of sensors of the hub adapter.

The plurality of detection components can include the plurality of sensors configured to detect the plurality of detectable objects of the hub adapter. The plurality of sensors can be hall sensors. The plurality of sensors can include a first sensor positioned on a proximal side of the hub assembly and a second sensor positioned on a distal side of the hub assembly. The plurality of detection components can include a plurality of detectable objects. Each of the plurality of detectable objects can include a detectable magnet. The plurality of detectable objects can include two detectable objects. Each of the plurality of detectable objects can be a binary device. Each of the plurality of detectable objects can be a trinary device. The hub assembly can be configured to move axially in response to a magnetic force applied to the at least one magnet of the hub assembly by the at least one magnet of the hub adapter. The at least one magnet of the hub assembly can include a plurality of magnets, wherein the at least one magnet of the hub adapter includes a plurality of magnets, wherein each of the plurality of magnets of the hub assembly is configured to rotate in response to rotation of one of the plurality of magnets of the hub adapter. The hub assembly can include a mount and an interventional device hub removably coupled to the mount. The plurality of detection components can be attached to the mount. The hub assembly can include a plurality of rollers configured to contact a drive surface.

Also disclosed herein are embodiments of a robotic medical system for performing a vascular procedure. The system includes a plurality of hub assemblies positioned on a sterile side of a sterile field barrier, wherein the plurality of hub assemblies includes a first hub assembly having a first plurality of detectable objects having a first combination of detectable outputs or states, and a second hub assembly having a second plurality of detectable objects having a second combination of detectable outputs or states, the second combination of detectable outputs or states being different than the first combination of detectable outputs or states. The system includes a plurality of hub adapters positioned on a non-sterile side of a sterile field barrier, wherein the plurality of hub adapters includes a first hub adapter having a first plurality of sensors configured to detect one or more detectable objects of one or more of the plurality of hub assemblies; and a second hub adapter having a second plurality of sensors configured to detect one or more detectable objects of one or more of the plurality of hub assemblies. The system includes a control system configured to axially drive the first hub adapter and the second hub adapter to align the first hub adapter with the first hub assembly based on detection of the first plurality of detectable objects by the first plurality of sensors and align the second hub adapter with the second hub assembly based on detection of the second plurality of detectable objects by the second plurality of sensors.

The first plurality of detectable objects can include a first magnet having a first polarity in a direction of the sterile field barrier and a second magnet having a second polarity in the direction of the sterile field barrier, wherein the second plurality of detectable objects includes a first magnet having a first polarity in the direction of the sterile field barrier and a second magnet having a second polarity in the direction of the sterile field barrier, wherein the second polarity of the second magnet of the second plurality of detectable objects is different than the second polarity of the second magnet of the first plurality of detectable objects.

Also disclosed herein are embodiments of a robotic medical system for performing a vascular procedure includes a plurality of hub adapters positioned on a non-sterile side of a sterile field barrier, a plurality of hub assemblies positioned on a sterile side of the sterile field barrier, a plurality of sensors disposed on each of either the plurality of hub adapters or the plurality of hub assemblies, wherein the plurality of sensors face the sterile field barrier, a plurality of detectable objects disposed on each of the other of the plurality of hub adapters or the plurality of hub assemblies different from the plurality of sensors, wherein the plurality of detectable objects face the sterile field barrier, and a control system configured to axially drive the plurality of hub adapters. Each of the plurality of hub adapters are configured to couple to a corresponding one of the plurality of hub assemblies so that the corresponding one of the plurality of hub assemblies moves axially in response to axial movement of the corresponding hub adapter. The plurality of sensors are configured to detect the presence of the detectable objects across the sterile field barrier. The control system is configured to align each of the plurality of hub adapters with the corresponding one of the plurality of hub assemblies based on the detection of the detectable objects.

DETAILED DESCRIPTION

In certain embodiments, a system is provided for advancing a guide catheter from a femoral artery or radial artery access into the ostium of one of the great vessels at the top of the aortic arch, thereby achieving supra-aortic access. A surgeon can then take over and advance interventional devices into the cerebral vasculature via the robotically placed guide catheter.

In some implementations, the system may additionally be configured to robotically gain intra-cranial vascular access and to perform an aspiration thrombectomy or other neuro vascular procedure.

A drive table can be positioned over or alongside the patient, and configured to axially advance, retract, and in some cases rotate and/or laterally deflect two or three or more different (e.g., concentrically or side by side oriented) intravascular devices.

A hub or hub assembly can be moveable along a path along the surface of the drive table to advance or retract the interventional device as desired. Each hub (or hub assembly) may also contain mechanisms to rotate or deflect the device as desired, and is connected to fluid delivery tubes (not shown) of the type conventionally attached to a catheter hub. Each hub (or hub assembly) can be in electrical communication with an electronic control system, either via hard wired connection, RF wireless connection or a combination of both.

Each hub (or hub assembly) can be independently movable across the surface of a sterile field barrier membrane carried by the drive table. Each hub (or hub assembly) can be releasably magnetically coupled to a unique drive carriage on the table side of the sterile field barrier. A drive carriage may also be referred to as a hub adapter. The drive system can independently move each hub (or hub assembly) in a proximal or distal direction across the surface of the barrier, to move the corresponding interventional device proximally or distally within the patient's vasculature.

The carriages or hub adapters on the drive table, which magnetically couple with the hubs to provide linear motion actuation, can be universal. Functionality of the catheters/guidewire can be provided based on what is contained in the hub and the shaft designs. This allows flexibility to configure the system to do a wide range of procedures using a wide variety of interventional devices on the same drive table. Additionally, the interventional devices and methods disclosed herein can be readily adapted for use with any of a wide variety of other drive systems (e.g., any of a wide variety of robotic surgery drive systems).

Figure 1:
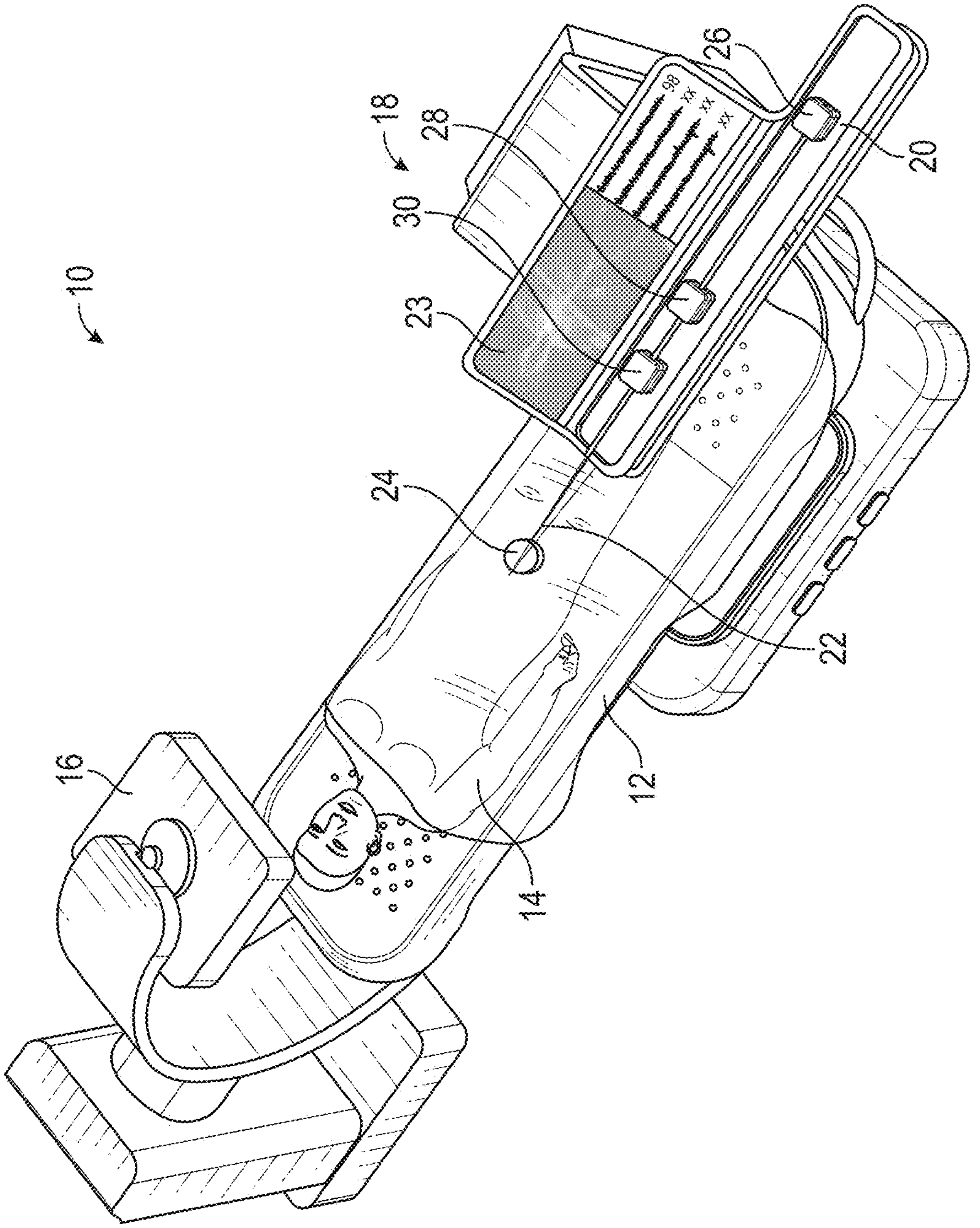
FIG. 1 is a schematic perspective view of an interventional setup having an imaging system, a patient support table, and a robotic drive system in accordance with the present disclosure.

FIG. 1 is a schematic perspective view of an interventional setup 10 having a patient support table 12 for supporting a patient 14. An imaging system 16 may be provided, along with a robotic interventional device drive system 18 in accordance with the present disclosure.

The drive system 18 may include a support table 20 for supporting, for example, a guidewire hub 26, an access catheter hub 28 and a guide catheter hub 30. In the present context, the term 'access' catheter can be any catheter having a lumen with at least one distally facing or laterally facing distal opening, that may be utilized to aspirate thrombus, provide access for an additional device to be advanced therethrough or therealong, or to inject saline or contrast media or therapeutic agents.

More or fewer interventional device hubs may be provided depending upon the desired clinical procedure. For example, in certain embodiments, a diagnostic angiogram procedure may be performed using only a guidewire hub 26 and an access catheter hub 28 for driving a guidewire and an access catheter (in the form of a diagnostic angiographic catheter), respectively. Multiple interventional devices 22 extend between the support table 20 and (in the illustrated example) a femoral access point 24 on the patient 14. Depending upon the desired procedure, access may be achieved by percutaneous or cut down access to any of a variety of arteries or veins, such as the femoral artery or radial artery. Although disclosed herein primarily in the context of neuro vascular access and procedures, the robotic drive system and associated interventional devices can readily be configured for use in a wide variety of additional medical interventions, in the peripheral and coronary arterial and venous vasculature, gastrointestinal system, lymphatic system, cerebral spinal fluid lumens or spaces (such as the spinal canal, ventricles, and subarachnoid space), pulmonary airways, treatment sites reached via trans ureteral or urethral or fallopian tube navigation, or other hollow organs or structures in the body (for example, in intra-cardiac or structural heart applications, such as valve repair or replacement, or in any endoluminal procedures).

A display 23 such as for viewing fluoroscopic images, catheter data (e.g., fiber Bragg grating fiber optics sensor data or other force or shape sensing data) or other patient data may be carried by the support table 20 and or patient support 12. Alternatively, the physician input/output interface including display 23 may be remote from the patient, such as behind radiation shielding, in a different room from the patient, or in a different facility than the patient.

In the illustrated example, a guidewire hub 26 is carried by the support table 20 and is moveable along the table to advance a guidewire into and out of the patient 14. An access catheter hub 28 is also carried by the support table 20 and is movable along the table to advance the access catheter into and out of the patient 14. The access catheter hub may also be configured to rotate the access catheter in response to manipulation of a rotation control, and may also be configured to laterally deflect a deflectable portion of the access catheter, in response to manipulation of a deflection control.

Figure 2:
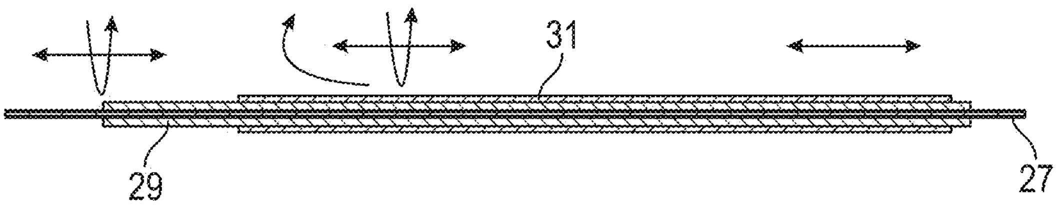
FIG. 2 is a longitudinal cross section showing the concentric relationship between a guidewire having two degrees of freedom, an access catheter having 3 degrees of freedom and a guide catheter having one degree of freedom.

FIG. 2 is a longitudinal cross section schematically showing the motion relationship between a guidewire 27 having two degrees of freedom (axial and rotation), an access catheter 29 having three degrees of freedom (axial, rotational and lateral deflection) and a guide catheter 31, having one degree of freedom (axial).

Figure 3A:
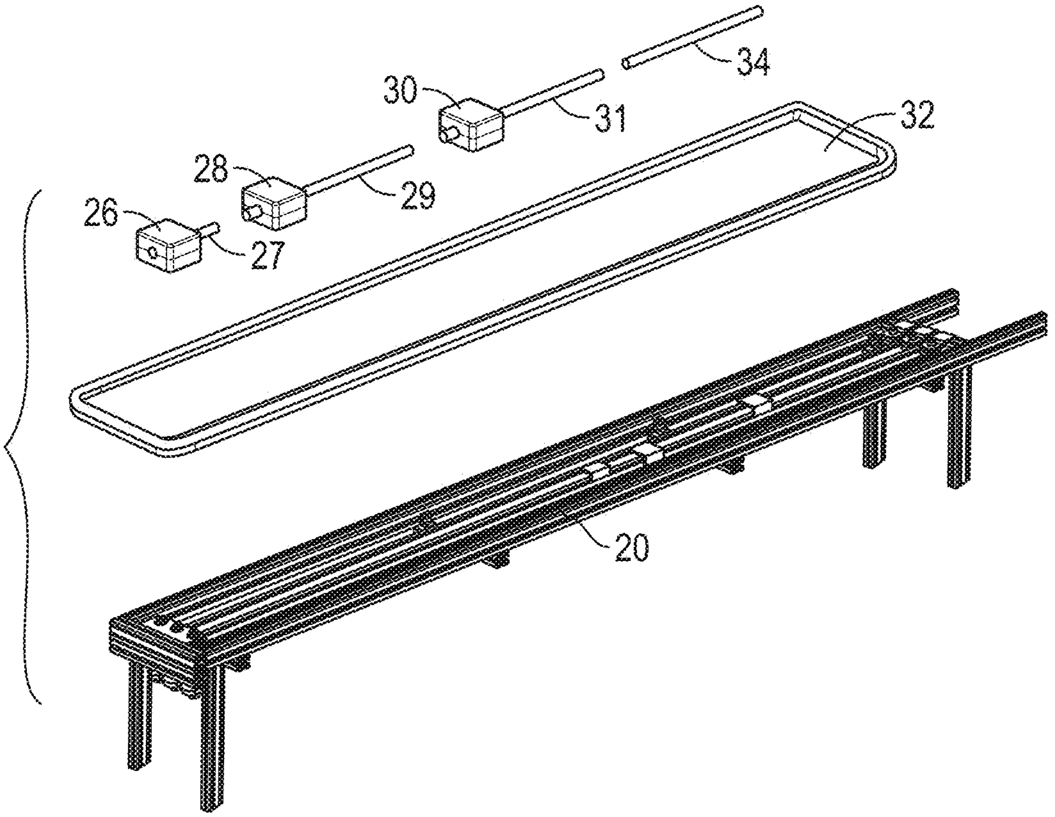
FIG. 3A is an exploded schematic view of interventional device hubs separated from a support table by a sterile barrier.

Referring to FIG. 3A, the support table 20 includes a drive mechanism described in greater detail below, to independently drive the guidewire hub 26, access catheter hub 28, and guide catheter hub 30. An anti-buckling feature 34 may be provided in a proximal anti-buckling zone for resisting buckling of the portion of the interventional devices spanning the distance between the support table 20 and the femoral artery access point 24. The anti-buckling feature 34 may include a plurality of concentric telescopically axially extendable and collapsible tubes through which the interventional devices extend.

Alternatively, a proximal segment of one or more of the device shafts may be configured with enhanced stiffness to reduce buckling under compression. For example, a proximal reinforced segment may extend distally from the hub through a distance of at least about 5 centimeters or 10 centimeters but typically no more than about 120 centimeters or 100 centimeters to support the device between the hub and the access point 24 on the patient. Reinforcement may be accomplished by using metal or polymer tubing or embedding at least one or two or more axially extending elements into the wall of the device shafts, such as elongate wires or ribbons. In some implementations, the extending element may be hollow and protect from abrasion, buckling, or damage at the inputs and outputs of the hubs. In some embodiments, the hollow extending element may be a hollow and flexible coating attached to a hub. The hollow, extending element (e.g., a hollow and flexible coating) may cover a portion of the device shaft when threaded through the hubs. In some embodiments in which the hollow extending element is a coating, the coating may be attached to a portion of a hub such that threading the catheter device through the hub 26, 28, or 30 threads the catheter device through the coating as well. In some implementations, an anti-buckling device may be installed on or about or surrounding a device shaft to avoid misalignment or insertion angle errors between hubs or between a hub and an insertion point. The anti-buckling device may be a laser cut hypotube, a spring, telescoping tubes, tensioned split tubing, or the like.

In some implementations, a number of deflection sensors may be placed along a catheter length to identify buckling. Identifying buckling may be performed by sensing that a hub is advancing distally, while the distal tip of the catheter or interventional device has not moved. In some implementations, the buckling may be detected by sensing that an energy load (e.g., due to friction) has occurred between catheter shafts.

Alternatively, thin tubular stiffening structures can be embedded within or carried over the outside of the device wall, such as a tubular polymeric extrusion or length of hypo-tube. Alternatively, a removable stiffening mandrel may be placed within a lumen in the proximal segment of the device, and proximally removed following distal advance of the hub towards the patient access site, to prevent buckling of the proximal shafts during distal advance of the hub. Alternatively, a proximal segment of one or more of the device shafts may be constructed as a tubular hypo tube, which may be machined (e.g., with a laser) so that its mechanical properties vary along its length. This proximal segment may be formed of stainless steel, nitinol, and/or cobalt chrome alloys, optionally in combination with polymer components which may provide for lubricity and hydraulic sealing. In some embodiments, this proximal segment may be formed of a polymer, such as polyether ether ketone (PEEK). Alternatively, the wall thickness or diameter of the interventional device can be increased in the anti-buckling zone.

In certain embodiments, a device shaft having advanced stiffness (e.g., axially and torsionally) may provide improved transmission of motion from the proximal end of the device shaft to the distal end of the device shaft. For example, the device shafts may be more responsive to motion applied at the proximal end. Such embodiments may be advantageous for robotic driving in the absence of haptic feedback to a user.

In some embodiments, a flexible coating can be applied to a device shaft and/or hub to reduce frictional forces between the device shaft and/or hub and a second device shaft when the second device shaft passes therethrough.

The interventional device hubs may be separated from the support table 20 by sterile barrier 32, which may also be referred to as a sterile field barrier. Sterile barrier 32 may include a thin plastic membrane such as polyethylene terephthalate (PET), polyethylene terephthalate glycol (PETG), polyethylene terephthalate (PETE), high-density polyethylene (HDPE), polyvinyl chloride (PVC), low-density polyethylene (LDPE), polypropylene (PP), polystyrene (PS), or styrene. This allows the support table 20 and associated drive system to reside on a non-sterile (lower) side of sterile barrier 32. The guidewire hub 26, access catheter hub 28, guide catheter hub 30 and the associated interventional devices are all on a sterile (top) side of the sterile barrier 32. The sterile barrier is preferably waterproof and can also serve as a tray used in the packaging of the interventional devices, discussed further below. The interventional devices can be provided individually or as a coaxially preassembled kit that is shipped and stored in the tray and enclosed within a sterile packaging.

FIGS. 3B-3F schematically illustrate an alternate sterile barrier in the form of a dual function sterile barrier for placement on the support table during the interventional procedure, and shipping tray, having one or more storage channels for carrying sterile interventional devices. The sterile barrier may also act as a sterile work surface for preparation of catheters or other devices during a procedure.

Figure 3B:
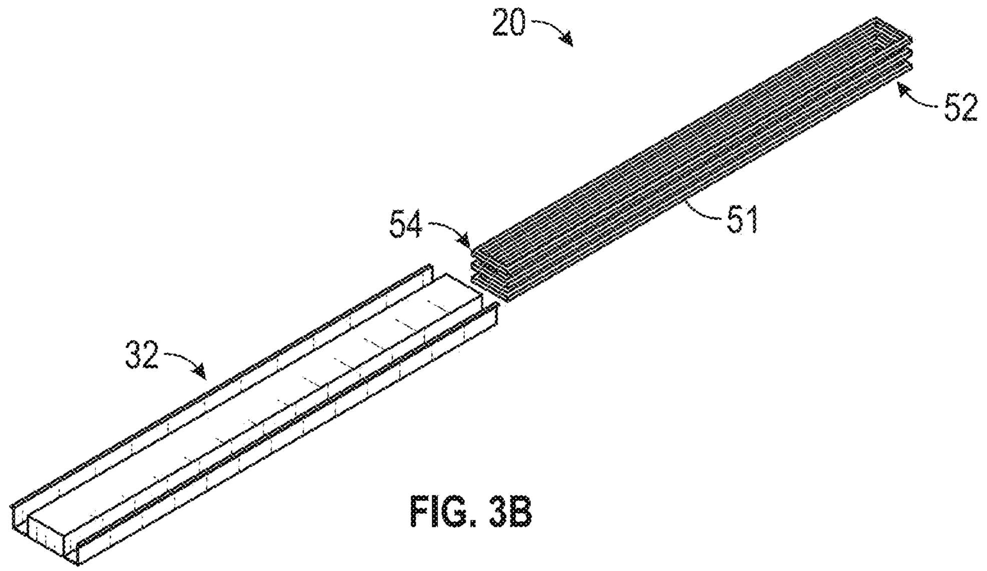
FIGS. 3B-3F show an alternate sterile barrier in the form of a shipping tray having one or more storage channels for carrying interventional devices.
Figure 3C:
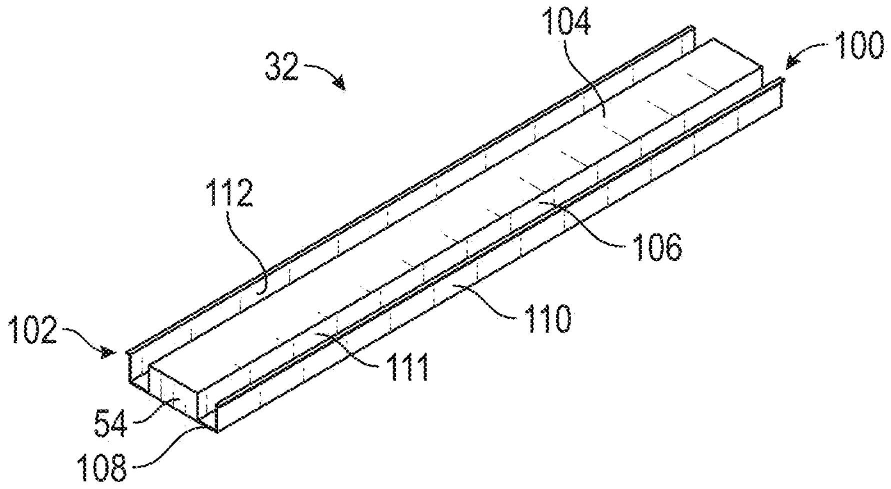

Referring to FIGS. 3B and 3C, there is illustrated a sterile barrier 32 in the form of a pre-shaped tray, for fitting over an elongate support table 20. In use, the elongate support table 20 would be positioned below the sterile barrier 32. The sterile barrier 32 extends between a proximal end 100 and a distal end 102 and includes an upper support surface 104 for supporting the interventional device hubs. In one implementation, the support surface 104 has an axial length greater than the length of the intended interventional devices, in a linear drive configuration.

The length of support surface 104 will typically be at least about 100 centimeters and within the range of from about 100 centimeters to about 2.7 meters. Shorter lengths may be utilized in a system configured to advance the drive couplers along an arcuate path. In some embodiments, two or more support surfaces may be used instead of a single support surface 104. The two or more support surfaces may have a combined length between 100 centimeters to about 2.7 meters. The width of the linear drive table is preferably no more than about 30 to about 80 centimeters.

At least a first channel 106 may be provided, extending axially at least a portion of the length of the support table 20. In the illustrated implementation, first channel 106 extends the entire length of the support table 20. Preferably, the first channel 106 has a sufficient length to hold the interventional devices, and sufficient width and depth to hold the corresponding hubs (for example, by providing lateral support to prevent dislodgment of the hubs when forces are applied to the hubs). First channel 106 is defined within a floor 108, outer side wall 110 and inner side wall 111, forming an upwardly facing concavity. Optionally, a second channel 112 may be provided. Second channel 112 may be located on the same side or the opposite side of the upper support surface 104 from the first channel 106. Two or three or more additional recesses such as additional channels or wells may be provided, to hold additional medical devices or supplies that may be useful during the interventional procedure as well as to collect fluids and function as wash basins for catheters and related devices.

Figure 3D:
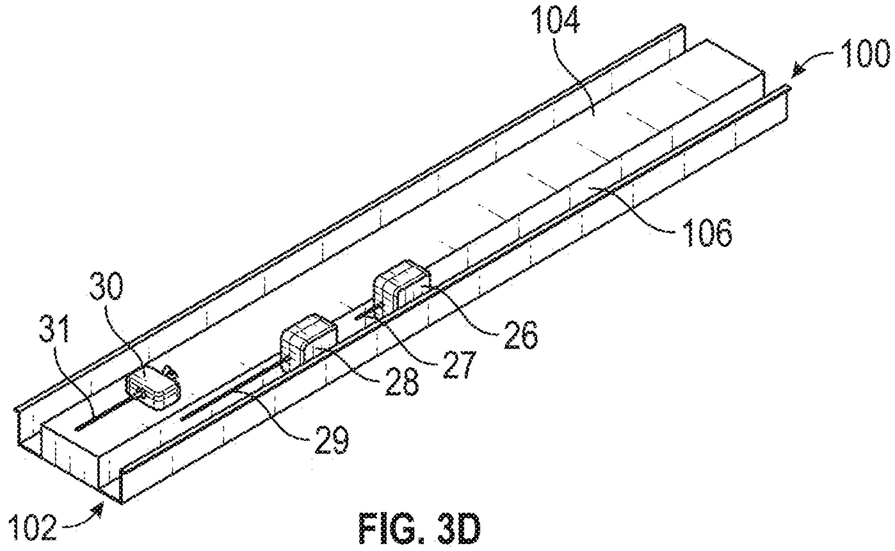

Referring to FIG. 3D, the guide catheter hub 30 is shown positioned on the upper support surface 104, and magnetically coupled to the corresponding coupler holding the drive magnets, positioned beneath the sterile barrier 32. The access catheter hub 28 and access catheter 29, and guidewire hub 26 and guidewire 27 are illustrated residing within the first channel 106 such as before introduction through the guide catheter 31 or following removal from the guide catheter 31.

The interventional devices may be positioned within the channel 106 and enclosed in a sterile barrier for shipping. At the clinical site, an upper panel of the sterile barrier may be removed, or a tubular sterile barrier packaging may be opened and axially removed from the support table 20 and sterile barrier 32 assembly, exposing the sterile top side of the sterile barrier tray and any included interventional devices. The interventional devices may be separately carried in the channel, or preassembled into an access assembly or procedure assembly, discussed in additional detail below.

Figure 3E:
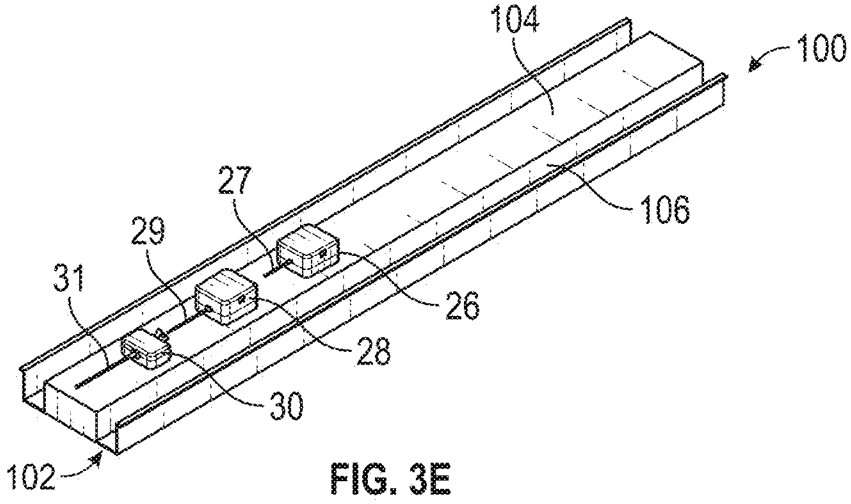
Figure 3F:
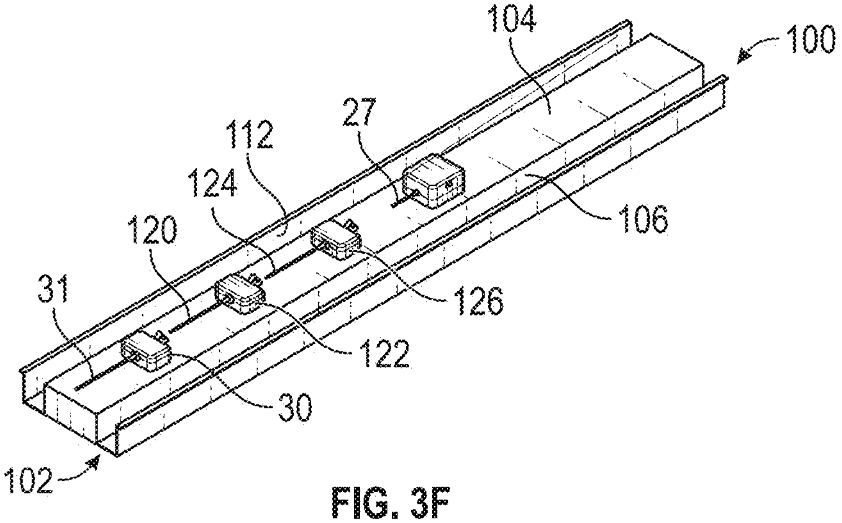

FIGS. 3D-3F illustrate the support table with sterile barrier in place, and in FIG. 3E, the interventional devices configured in an access assembly for aortic access, following coupling of the access assembly to the corresponding carriages beneath the sterile barrier. The access assembly may be preassembled with the guidewire fully advanced through the access catheter which is in turn fully advanced through the guide catheter. In embodiments in which the access catheter or other catheters are pre-shaped (i.e., pre-curved or not straight), the guidewire and/or outer catheters may be positioned so that relatively stiff sections are not superimposed with curved stiffer sections of the pre-shaped catheter, for example, to avoid creep or straightening of the pre-shaped catheter and/or introduction of a curve into an otherwise straight catheter. This access assembly may be lifted out of the channel 106 and positioned on the support surface 104 for coupling to the respective drive magnets and introduction into the patient. The guide catheter hub 30 is the distal most hub. Access catheter hub 28 is positioned proximally of the guide catheter hub, so that the access catheter 29 can extend distally through the guide catheter. The guidewire hub 26 is positioned most proximally, in order to allow the guidewire 27 to advance through the access catheter 29 and guide catheter 31.

A procedure assembly is illustrated in FIG. 3F following introduction of the procedure assembly through the guide catheter 31 that was used to achieve supra-aortic access. In this implementation, guide catheter 31 remains the distal most of the interventional devices. A first procedure catheter 120 and corresponding hub 122 is illustrated extending through the guide catheter 31. An optional second procedure catheter 124 and corresponding hub 126 is illustrated extending through the first procedure catheter 120. The guidewire 27 extends through at least a portion of the second procedure catheter 124 in a rapid exchange version of second procedure catheter 124, or the entire length of second procedure catheter 124 in an over the wire implementation.

As is discussed in greater detail in connection with FIG. 17, the multi catheter stack may be utilized to achieve both access and the intravascular procedure without the need for catheter exchange. This may be accomplished in either a manual or a robotically driven procedure. In one example, the guide catheter 31 may include a catheter having an inner diameter of at least about 0.08 inches and in one implementation about 0.088 inches. The first procedure catheter 120 may include a catheter having an inner diameter within the range of from about 0.065 inches to about 0.075 inches and in one implementation catheter 120 has an inner diameter of about 0.071 inches. The second procedure catheter 124 may be an access catheter having an OD sized to permit advance through the first procedure catheter 120. The second procedure catheter maybe steerable, having a deflection control 2908 configured to laterally deflect a distal end of the catheter. The second procedure (access) catheter may also have an inner lumen sized to allow an appropriately sized guidewire to remain inside the second procedure catheter while performing contrast injections through the second procedure catheter.

In certain embodiments, the catheter 31 may be a 'large bore' access catheter or guide catheter having a diameter of at least about 0.075 or at least about 0.080 inches in diameter. The catheter 120 may be an aspiration catheter having a diameter within the range of from about 0.060 to about 0.075 inches. The catheter 124 may be a steerable catheter with a deflectable distal tip, having a diameter within the range of from about 0.025 to about 0.050 inches. The guidewire 27 may have a diameter within the range of from about 0.014 to about 0.020 inches. In one example, the catheter 31 may have a diameter of about 0.088 inches, the catheter 120 about 0.071 inches, the catheter 124 about 0.035 inches, and the guidewire 27 may have a diameter of about 0.018 inches.

In one commercial execution, a preassembled access assembly (guide catheter, access catheter and guidewire) may be carried within a first channel on the sterile barrier tray and a preassembled procedure assembly (one or two procedure catheters and a guidewire) may be carried within the same or a different, second channel on the sterile barrier tray. One or two or more additional catheters or interventional tools may also be provided, depending upon potential needs during the interventional procedure.

Figures 3G, 3H, 3I, 3J, 3K, 3L, 3M:
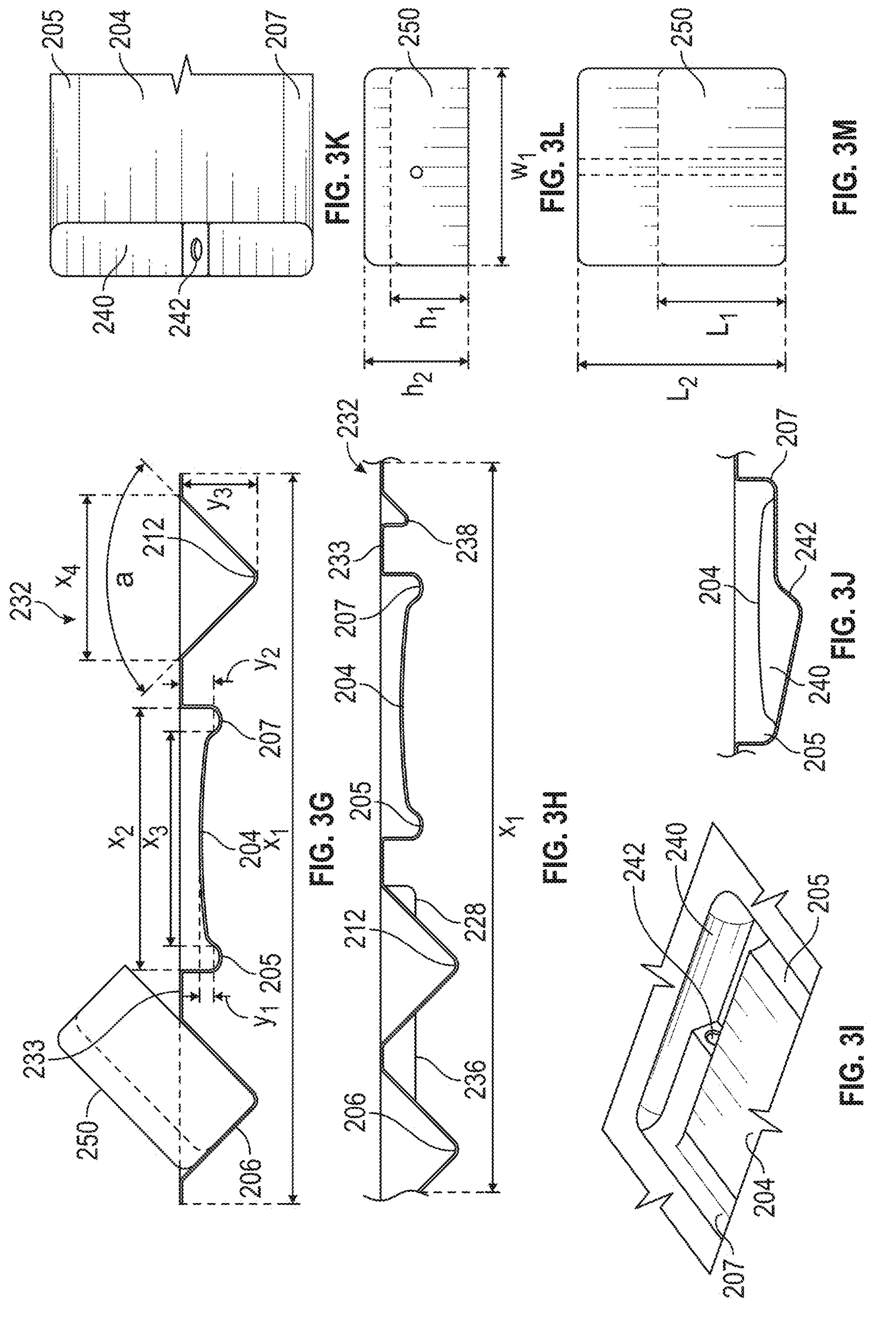
FIGS. 3G-3K show embodiments of an alternate sterile barrier having a convex drive surface.
FIGS. 3L and 3M depict an example of a hub that may be used with the sterile barriers of FIGS. 3G-3K.

FIGS. 3G-3K illustrate embodiments of an alternate sterile barrier having a convex drive surface (e.g., a convex, crowned road like drive surface). FIG. 3G is a cross-sectional view of a sterile barrier 232. The sterile barrier 232 includes a convex upper support surface 204. Fluid channels 205 and 207 are positioned laterally of and below the support surface 204 for self-clearing or draining of fluids from the support surface 204 (for example, during an interventional procedure). The fluid channels 205 and 207 may extend axially at least a portion of the length of the sterile barrier.

FIGS. 3I, 3J, and 3K illustrate a sectional perspective view, a cross-sectional view, and a top sectional view, respectively, of a proximal end of the sterile barrier 232. As shown, in FIGS. 3I-3K, the sterile barrier 232 can include a trough 240 in communication with the fluid channels 205 and 207. The trough 240 can receive fluids from the channels 205 and 207 (for example, during an interventional procedure). The trough 240 may be positioned at least partially below the fluid channels 205 and 207 so that fluid within the channels 205 and 207 flows into the trough 240. In certain embodiments, the fluid channels 205 and 207 may be angled relative to a horizontal plane (for example, may decline from an end of the channel furthest from the trough 240 to the trough 240) so that fluid within the channels 205 and 207 is directed to the trough 240. For example, the channels 205 and 207 may increase in depth from an end of the channels furthest from the trough 240 to the trough 240. Alternatively, the sterile barrier 232 and/or support table may be positioned at an angle relative to a horizontal plane, during part of or an entirety of an interventional procedure, such that the end of the channels 205 and 207 furthest from the trough 240 is positioned higher than the trough 240. For example, the sterile barrier 232 and/or support table may be constructed or arranged in an angled arrangement so that an end of the sterile barrier 232 and/or support table opposite the trough 240 is positioned higher than the trough 240. Alternatively or additionally, a drive mechanism may temporarily tilt the sterile barrier 232 and/or support table so that an end of the sterile barrier 232 and/or support table opposite the trough 240 is positioned higher than the trough 240 (for example, by lifting an end of the sterile barrier and/or support table opposite the trough 240 or lowering an end of the sterile barrier 232 and/or support table at which the trough 240 is positioned) so that fluids within the channels 205 and 207 flow into the trough 240.

The trough 240 can include a drain hole 242. The trough 240 can be shaped, dimensioned, and/or otherwise configured so that fluid within the trough 240 empties to the drain hole 242. The drain hole 242 can include tubing, a barb fitting, and/or an on-off valve for removal of fluids from the trough 240. As shown in FIGS. 3I-3K, the trough 240 can be positioned at the proximal end of the sterile barrier 232. In alternate embodiments, the trough 240 may be positioned at a distal end of the sterile barrier 232. In some embodiments, the sterile barrier 232 can include a first trough 240 at the proximal end and a second trough 240 at the distal end. In some embodiments, the trough 240 can also be used as a wash basin.

A first channel 206 may extend axially at least a portion of the length of the sterile barrier 232. The channel 206 can have a sufficient length to hold the interventional devices, and sufficient width and depth to hold the corresponding hubs (for example, by providing support to prevent dislodgement of the hubs when forces are applied to the hubs). Optionally, a second channel 212 may be provided. The second channel 212 may be located on the same side or the opposite side of the upper support surface 204 from the first channel 206. FIG. 3G illustrates the channel 212 located on the opposite side of the support surface 204 from the channel 206. FIG. 3H is a cross-sectional view illustrating an alternate embodiment of the sterile barrier 232 in which the channel 212 is on the same side of the support surface 204 as the channel 206.

As shown in FIGS. 3G and 3H, the channels 206 and 212 can have generally triangular, wedge-shaped, or otherwise angled cross-sections, so as to hold the hubs at an angle relative to a horizontal plane. Holding the hubs at an angle relative to the horizontal plane can allow for smaller width of the sterile barrier 232.

Two or three or more additional recesses such as additional channels or wells may be provided, to hold additional medical devices or supplies that may be useful during the interventional procedure as well as to collect fluids and function as wash basins for catheters and related devices.

In some embodiments, the sterile barrier 232 can include one or more structural ribs 236. The sterile barrier 232 can further include one or more frame support bosses 228 and 238.

In the embodiment of the sterile barrier 232 shown in FIG. 3G, a width $x_1$ can be 14 in, about 14 in, between 12 in and 16 in, between 10 in and 18 in, or any other suitable width. In the embodiment of the sterile barrier 232 shown in FIG. 3H, the width $x_1$ can be 15 in, about 15 in, between 13 in and 17 in, between 11 in and 19 in, or any other suitable width. A height $y_1$ of the support surface 204 can be 0.125 in, about 0.125 in, between 0.1 and 0.15 in, or any other suitable height. In some embodiments, the support surface 204 can be recessed from a top surface 233 of the sterile barrier 232. A height $y_2$ between a bottom of the support surface 204 and the top surface 233 can be 0.5 in, about 0.5 in, between 0.25 in and 0.75 in, or any other suitable height. A width $x_2$ from a lateral edge of the channel 205 to a lateral edge of the channel 207 can be 5 in, about 5 in, between 4 in and 6 in, or any other suitable width. A width $x_3$ of the support surface 204 can be 4 in, about 4 in, between 3 in and 5 in, or any other suitable width. A height $y_3$ of the channel 206 and/or channel 212 can be 1.5 in, about 1.5 in, between 1 in and 2 in, or any other suitable height. A width $x_4$ of the channel 206 and/or channel 212 can be 3 in, about 3 in, between 2 in and 4 in, or any other suitable width. The channel 206 and/or channel 212 can be defined by an arc angle $\alpha$ of 90°, about 90°, between 80° and 100°, or any other suitable angle, and a radius of curvature of 0.125 in, about 0.125 in, between 0.1 and 0.15 in, or any other suitable radius of curvature. In certain embodiments, an arc angle $\alpha$ of 90° or about 90° may be used to hold a hub having a rectangular or generally rectangular cross-section. The support surface 204 can be defined by a radius of curvature of 13 in, about 13 in, between 11 in and 15 in, or any other suitable radius of curvature. The channel 205 and/or channel 207 can be defined by a radius of curvature of 0.25 in, about 0.25 in, between 0.15 in and 0.35 in, or any other suitable radius of curvature.

FIGS. 3L and 3M depict example dimensions of a hub 250 that may be used with the sterile barrier 232 as shown in FIGS. 3G-3K. The hub 250 may be any of the hubs described herein. In certain embodiments, the hub 250 can have a width $w_1$ of 3.75 in, about 3.75 in, between 3.25 in and 4.25 in, or any other suitable width. The hub 250 can have a height $h_1$ of 1.5 in, about 1.5 in, between 1.25 in and 1.75 in, or any other suitable height. Alternatively, the hub 250 can have a height $h_2$ of 2 in, about 2 in, between 1.75 in and 2.25 in, or any other suitable height. In some embodiments, the hub 250 can have a length $L_1$ of 2.5 in, about 2.5 in, between 2 in and 3 in or any other suitable length. Alternatively, the hub 250 can have a length $L_2$ of 4 in, about 4 in, between 3.25 in and 4.75 in, or any other suitable length.

In some embodiments, a top surface of the support table can include surface features that generally correspond to those of the sterile barrier 232. For example, the support table can include a convex surface configured to correspond to the shape, size, and location of the support surface 204 and/or one or more recesses configured to correspond to the shape, size, and location of the channels 205 and 207.

In alternate embodiments, a planar support surface (for example, support surface 104 of sterile barrier 32) can be positioned at an angle to a horizontal plane to facilitate the draining of fluids. In some embodiments, the sterile barrier and/or support table may be positioned, during part of or the entirety of an interventional procedure, at an angle to a horizontal plane to facilitate the draining of fluids. For example, the sterile barrier and/or support table may be constructed or arranged in an angled arrangement (for example, so that one lateral side of the planar support surface is positioned higher than the other lateral side of the planar support surface, the proximal end is higher than the distal end, or the distal end Is higher than the proximal end) to facilitate the drainage of fluids. Alternatively or additionally, a drive mechanism may temporarily tilt the sterile barrier and/or support table (for example, so that one lateral side of the planar support surface is positioned higher than the other lateral side of the planar support surface, the proximal end is higher than the distal end, or the distal end is higher than the proximal end) to facilitate the drainage of fluids. For example, the drive mechanism may raise or lower one lateral side of the sterile barrier and/or support table, the proximal end of the sterile barrier and/or support table, and/or the distal end of the sterile barrier and/or support table.

In certain embodiments, a support surface (for example, support surface 104 of sterile barrier 32) can be positioned in a vertical configuration instead in the horizontal configuration shown, for example, in FIGS. 3A-3F. For example, the support surface 104 can be positioned at about 90 degrees (or any other suitable angle) from a horizontal plane (e.g., rotated 90 degrees about a long axis—such as longitudinal axis A1 shown in FIG. 3C—of the support surface 104 relative to the embodiment shown in of FIGS. 3A-3F). A vertical configuration may provide for easier interaction with the drive system 18 by a physician. A vertical configuration may also provide for a lower axis of catheter travel closer to a patient without adding standoff height to the drive system 18.

In some embodiments, the drive system 18 may be positioned, during part of or the entirety of an interventional procedure, at an angle to a horizontal plane to facilitate the draining of fluids. For example, the drive system 18 may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or additionally, a drive mechanism may temporarily tilt the drive system 18 (for example, so that one lateral side of the drive system 18 is positioned higher than the other lateral side of the drive system 18, the proximal end is higher than the distal end, or the distal end is higher than the proximal end) to facilitate the drainage of fluids. For example, the drive mechanism may raise or lower one lateral side of the system 18, the proximal end of the drive system 18, and/or the distal end of the drive system 18. In some embodiments, the drive system 18 may be angled so that it extends at an angle away from axis point 24 (for example, so that the proximal end is higher than the distal end), for example, to allow for clearance of a patient's feet.

Figure 4:
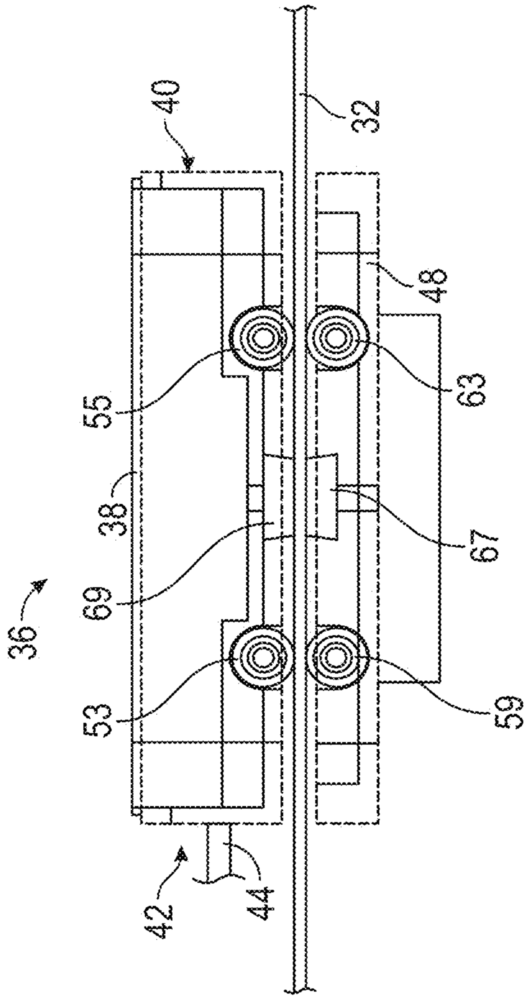
FIG. 4 is a schematic elevational cross section through a hub adapter having a drive magnet separated from an interventional device hub and driven magnet by a sterile barrier.

Referring to FIG. 4, hub 36 may represent any of the hubs previously described. Hub 36 includes a housing 38 which extends between a proximal end 40 and a distal end 42. An interventional device 44, which could be any of the interventional devices disclosed herein, extends distally from the hub 36 and into the patient 14 (not illustrated). A hub adapter 48 or carriage acts as a shuttle by advancing proximally or distally along a track in response to operator instructions or controller manipulations. The hub adapter 48 includes at least one drive magnet 67 configured to couple with a driven magnet 69 carried by the hub 36. This provides a magnetic coupling between the drive magnet 67 and driven magnet 69 through the sterile barrier such that the hub 36 is moved across the top of the sterile barrier 32 in response to movement of the hub adapter 48 outside of the sterile field. Movement of the hub adapter is driven by a drive system carried by the support table and described in additional detail below. The hub adapter may act as a robotic drive for an interventional device coupled thereto.

To reduce friction in the system, the hub 36 may be provided with at least a first roller 53 and a second roller 55 which may be in the form of wheels or rotatable balls or drums. The rollers space the sterile barrier apart from the surface of the driven magnet 69 by at least about 0.02 centimeters (about 0.008 inches) and generally no more than about 0.08 centimeters (about 0.03 inches). In some implementations, the space is within the range of from about 0.03 centimeters (about 0.010 inches) and about 0.041 centimeters (about 0.016 inches). The space between the drive magnet 67 and driven magnet 69 is generally no more than about 0.38 centimeters (about 0.15 inches) and in some implementations is no more than about 0.254 centimeters (about 0.10 inches) such as within the range of from about 0.216 centimeters (about 0.085 inches) to about 0.229 centimeters (about 0.090 inches). The hub adapter 48 may similarly be provided with at least a first hub adapter roller 59 and the second hub adapter roller 63, which may be positioned opposite the respective first roller 53 and second roller 55 as illustrated in FIG. 4.

Figure 6:
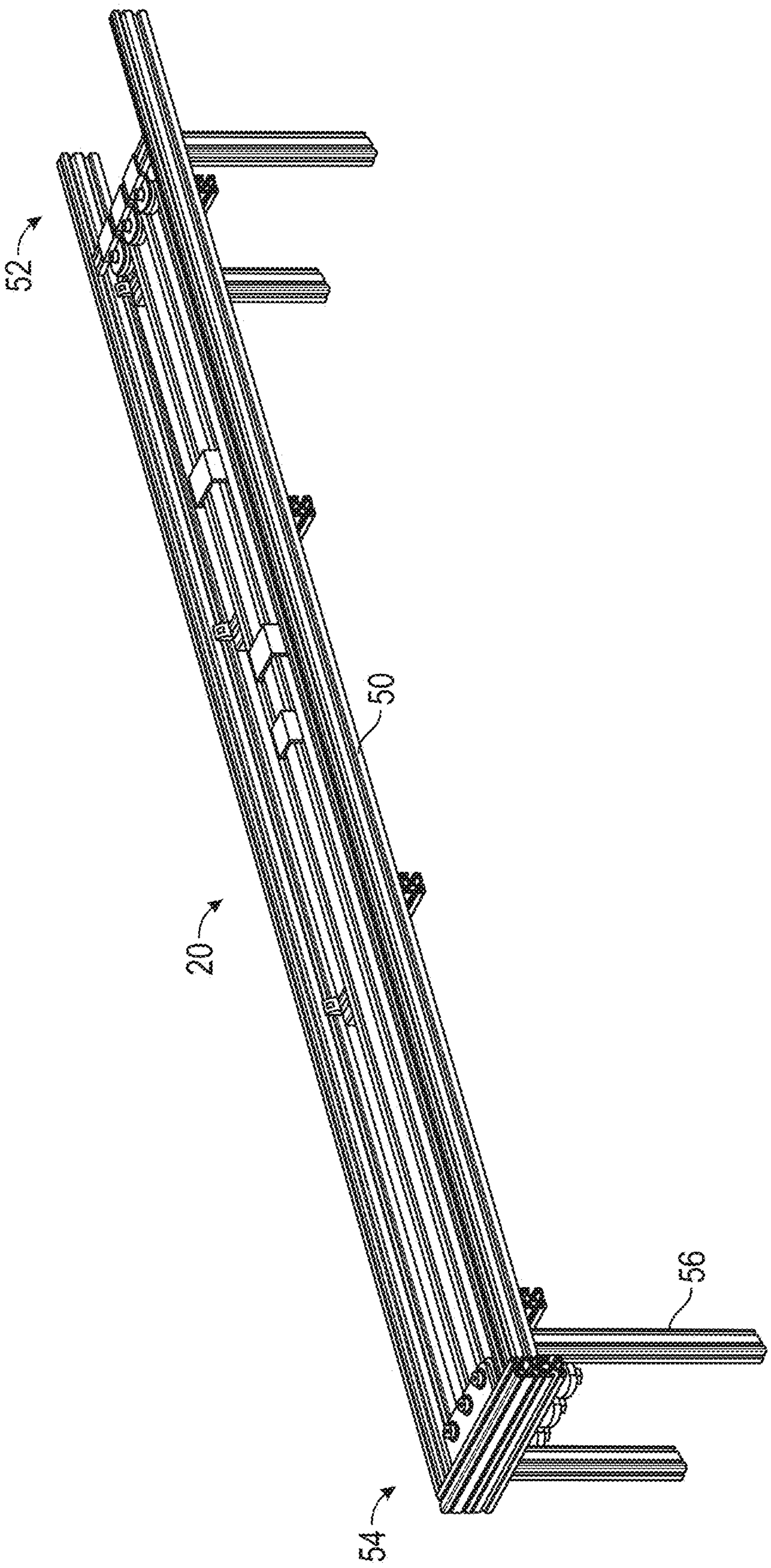
FIG. 6 is a perspective view of a support table.

Referring to FIG. 6, there is schematically illustrated one example of a low-profile linear drive support table 20. Support table 20 includes an elongated frame 51 extending between a proximal end 52 and a distal end 54. At least one support table support 56 is provided to stabilize the support table 20 with respect to the patient (not illustrated). Support 56 may include one or more legs or preferably an articulating arm configured to allow movement and positioning of the frame 51 over or adjacent to the patient.

Figure 7:
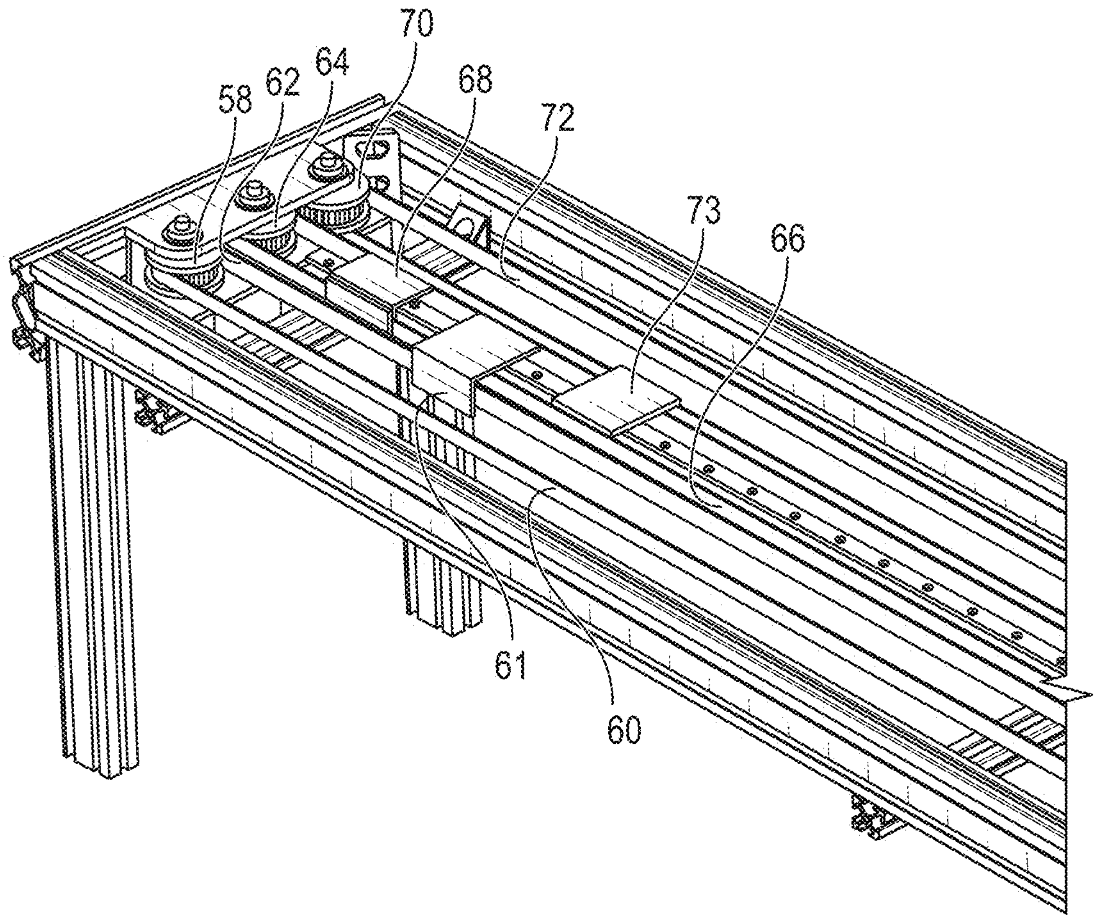
FIG. 7 is a close-up view of the motor drive end of a support table.

One example of a linear drive table 20 illustrated in FIG. 7 includes three distinct drives. However, two drives or four or more drives (e.g., up to eight drives) may be included depending upon the desired clinical performance. A first drive pulley 58 engages a first drive belt 60. A first carriage bracket 61 is secured to the first drive belt 60 such that rotation of the first drive pulley 58 causes rotation of the first drive belt 60 through an elongate closed loop path. The first carriage bracket 61 may be advanced in a proximal or distal direction along a longitudinal axis (e.g., longitudinal axis A2 shown in FIG. 7) of the support table 20 depending upon the direction of rotation of the drive pully 58. In the illustrated implementation, the drive pulley 58 is provided with surface structures such as a plurality of drive pulley teeth 62 for engaging complementary teeth on the first drive belt 60.

A second drive pulley 64 may engage a second drive belt 66 configured to axially move a second carriage bracket 68 along an axial path on the support table 20. A third drive pulley 70 may be configured to drive a third drive belt 72, to advance a third carriage bracket 73 axially along the support table 20. Each of the carriage brackets may be provided with a drive magnet assembly discussed previously but not illustrated in FIG. 7, to form couplers for magnetically coupling to a corresponding driven magnet within the hub of an interventional device as has been discussed.

Figure 8:
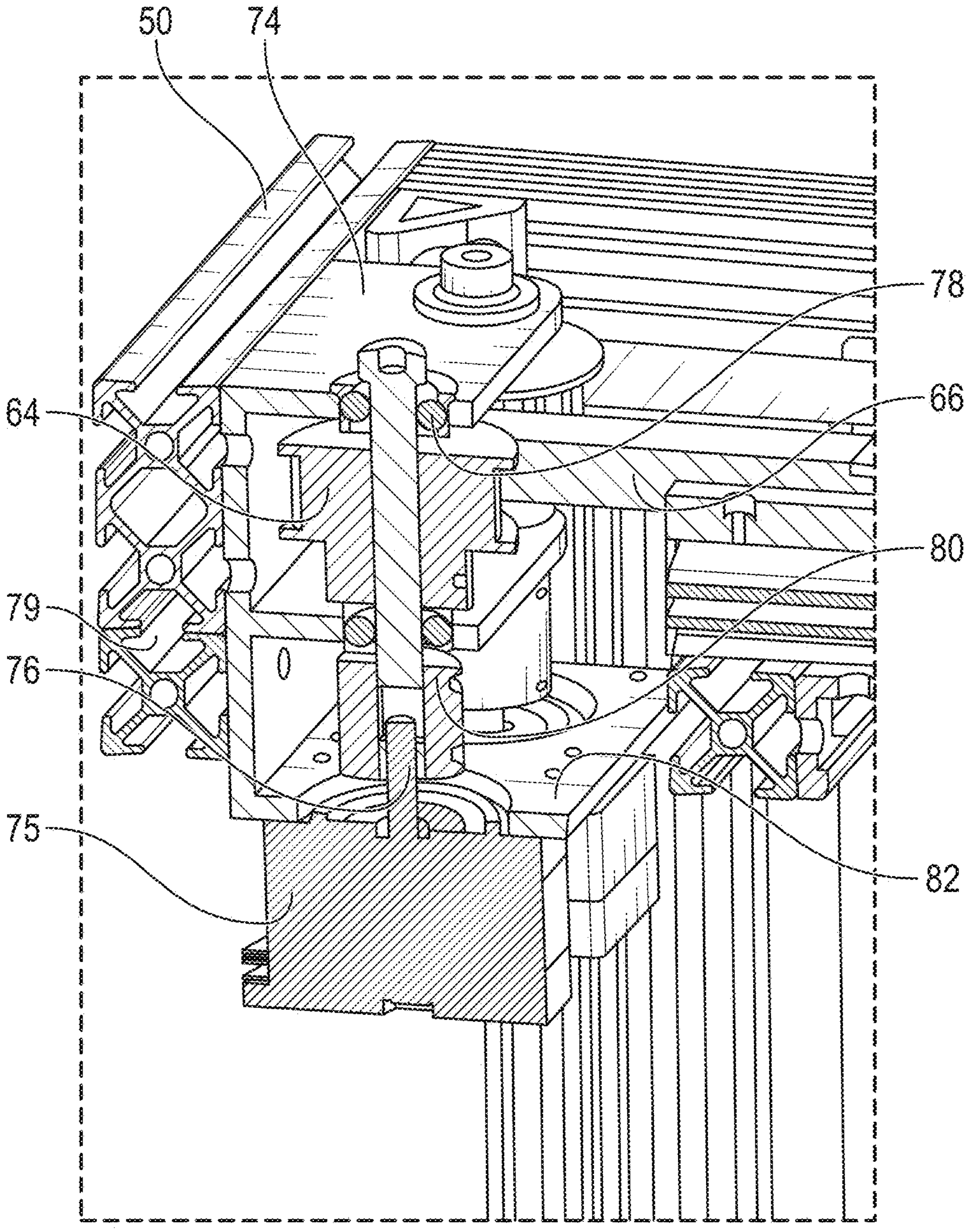
FIG. 8 is an elevational cross section through a motor and belt drive assembly.

A detailed view of a drive system is shown schematically in FIG. 8. A drive support 74 may be carried by the frame 51 for supporting the drive assembly. The second drive pulley 64 is shown in elevational cross section as rotationally driven by a motor 75 via a rotatable shaft 76. The rotatable shaft 76 may be rotatably carried by the support 74 via a first bearing 78, a shaft coupling 80 and second bearing 79. Motor 75 may be stabilized by a motor bracket 82 connected to the drive support 74 and or the frame 51. The belt drive assemblies for the first drive belt 60 and third drive belt 72 maybe similarly constructed and are not further detailed herein. In some embodiments, the drive systems described herein may be a rack and pinion drive table system that is foldable. In such embodiments, motors 75 may be attached to and move with the carriages.

Figure 9:
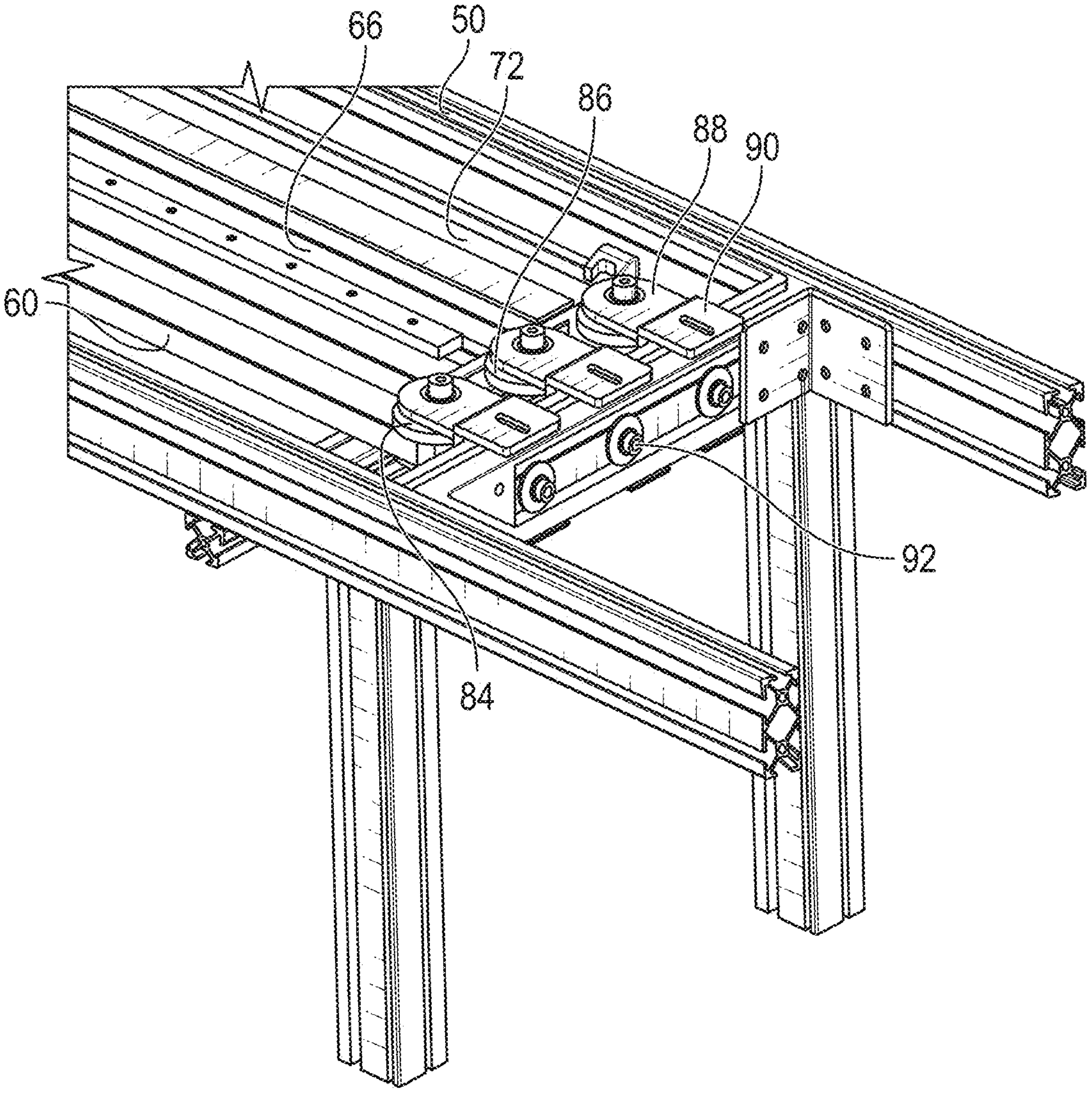
FIG. 9 is a close-up view of a pulley end of the support table.
Figure 10:
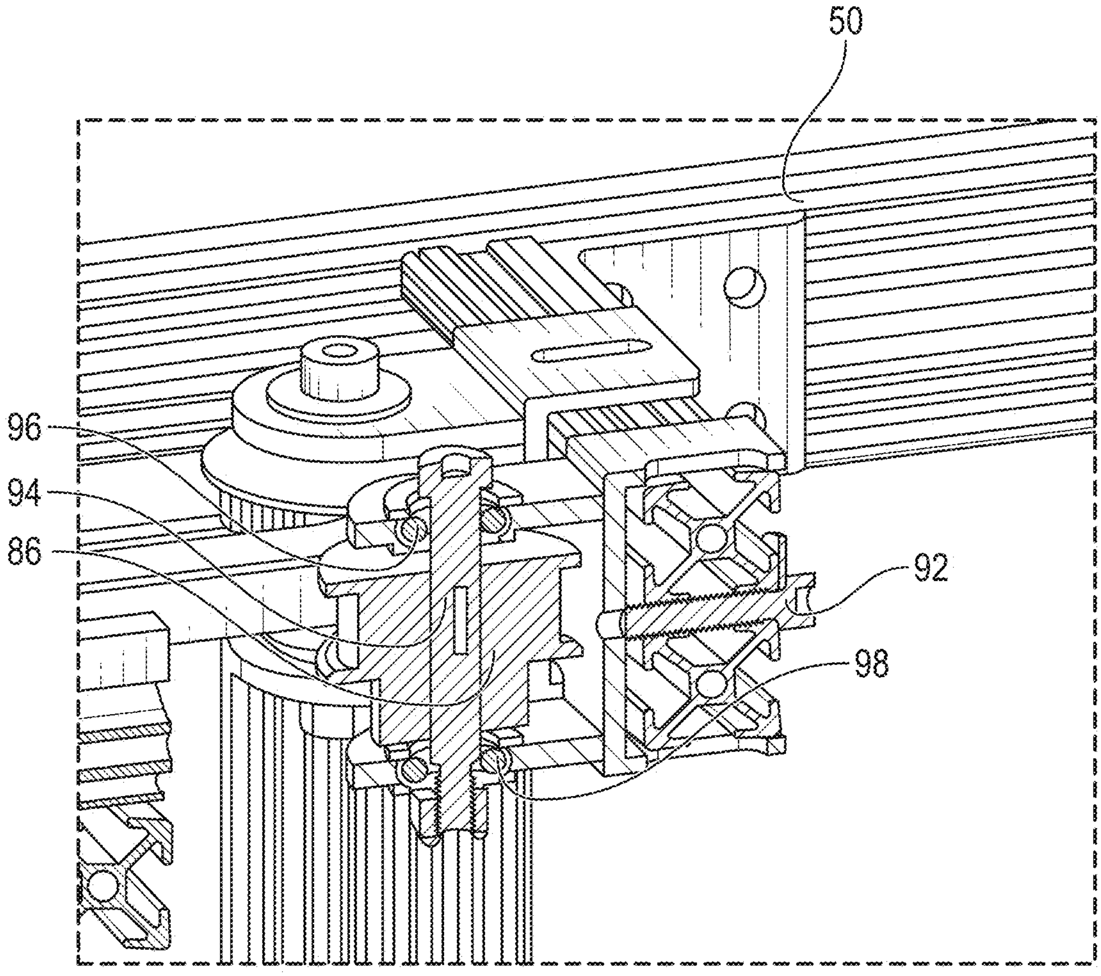
FIG. 10 is an elevational cross section through a belt pully.

Referring to FIGS. 9 and 10, each of the first second and third drive belts extends around a corresponding first idler pulley 84 second idler pulley 86 and third idler pulley 88. Each idler pulley may be provided with a corresponding tensioning bracket 90, configured to adjust the idler pulleys in a proximal or distal direction in order to adjust the tension of the respective belt. Each tensioning bracket 90 is therefore provided with a tensioning adjustment 92 such as a rotatable screw.

As seen in FIG. 10, the second idler pulley 86, for example, may be carried by a rotatable shaft 94, rotatably secured with respect to the mounting bracket by a first bearing 96 and second bearing 98.

Figure 5A:
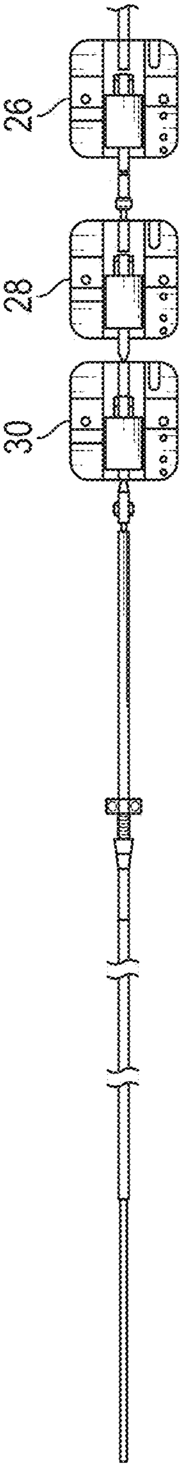
FIGS. 5A and 5B schematically illustrate a three interventional device and a four interventional device assembly.
Figure 5B:
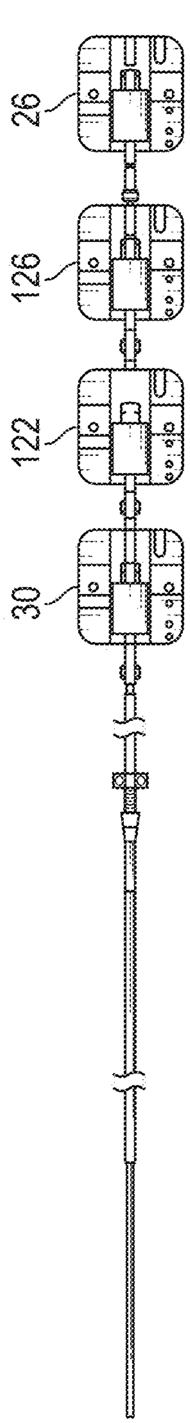
Figure 11:
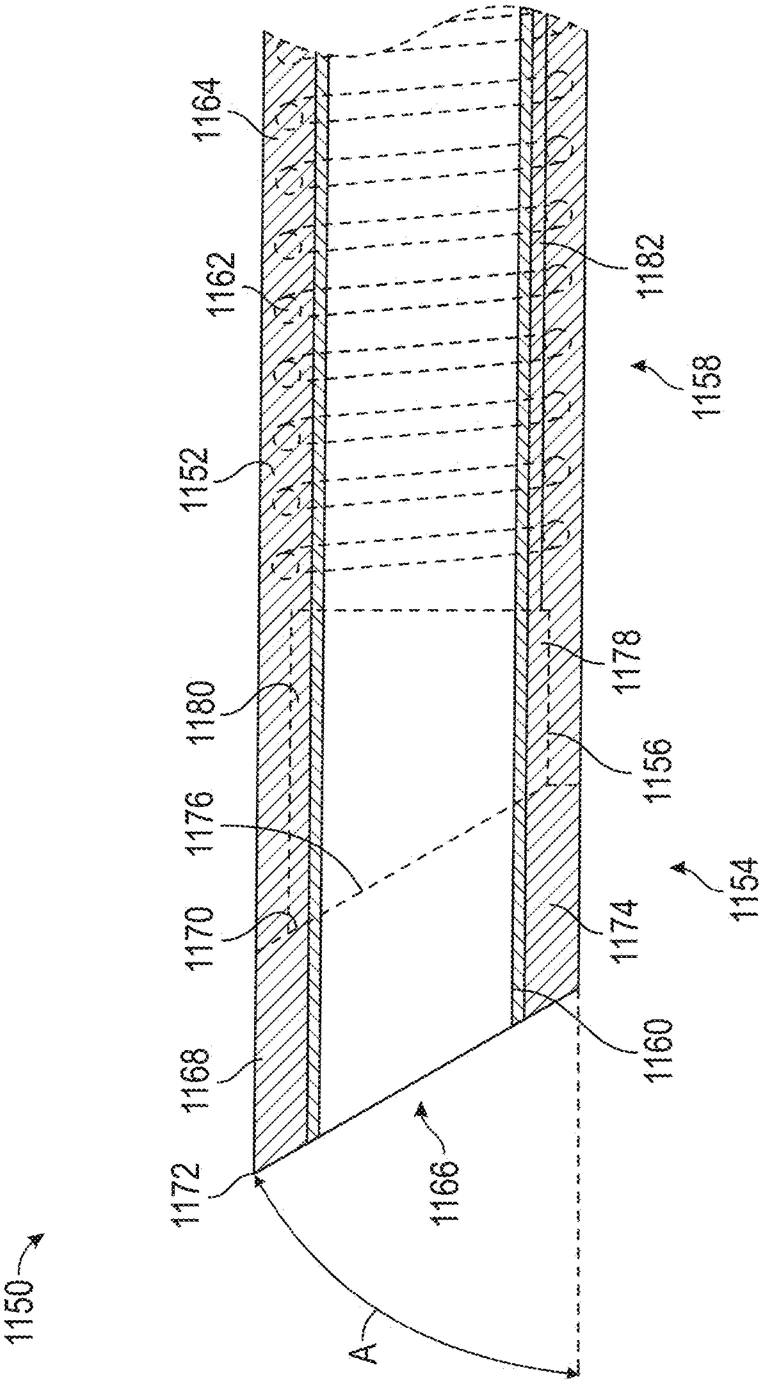
FIG. 11 is a side elevational cross-section through a distal portion of a catheter such as any of those shown in FIGS. 5A and 5B.

Any of the catheters illustrated, for example, in FIG. 5A, 5B or 11 generally include an elongate tubular body extending between a proximal end and a distal functional end. The length and diameter of the tubular body depends upon the desired application. For example, lengths in the area of from about 90 centimeters to about 195 centimeters or more are typical for use in femoral access percutaneous transluminal coronary applications. Intracranial or other applications may call for a different catheter shaft length depending upon the vascular access site.

Any of the catheters disclosed herein may be provided with an inclined distal tip. Referring to FIG. 11, distal catheter tip 1150 includes a tubular body 1152 which includes an advance segment 1154, a marker band 1156 and a proximal segment 1158. An inner tubular liner 1160 may extend throughout the length of the distal catheter tip 1150, and may include dip coated or extruded PTFE or other lubricious material.

A reinforcing element 1162 such as a braid and/or spring coil is embedded in an outer jacket 1164 which may extend the entire length of the catheter.

The advance segment 1154 terminates distally in an angled face 1166, to provide a leading side wall portion 1168 having a length measured between the distal end 130 of the marker band 1156 and a distal tip 1172. In some embodiments, the entire distal tip may be shaped to avoid snagging the tip in areas of arterial bifurcation. A trailing side wall portion 1174 of the advance segment 1154, has an axial length in the illustrated embodiment of approximately equal to the axial length of the leading side wall portion 1168 as measured at approximately 180 degrees around the catheter from the leading side wall portion 1168. The leading side wall portion 1168 may have an axial length within the range of from about 0.1 millimeters to about 5 millimeters and generally within the range of from about 1 to 3 millimeters. The trailing side wall portion 1174 may be equal to or at least about 0.1 or 0.5 or 1 millimeter or 2 millimeters or more shorter than the axial length of the leading side wall portion 1168, depending upon the desired performance.

The angled face 1166 inclines at an angle A within the range of from about 45 degrees to about 80 degrees from the longitudinal axis (represented by A3 in FIG. 11) of the catheter. For certain implementations, the angle is within the range of from about 55 degrees to about 65 degrees from the longitudinal axis (e.g., longitudinal axis A3 shown in FIG. 11) of the catheter. In one implementation, the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105 percent, and no more than about 130 percent, in some implementations within the range of from about 110 percent and about 125 percent, and in one example is about 115 percent of the area of the corresponding circular port (angle A is 90 degrees).

In the illustrated embodiment, the axial length of the advance segment is substantially constant around the circumference of the catheter, so that the angled face 1166 is approximately parallel to the distal surface 1176 of the marker band 1156. The marker band 1156 has a proximal surface approximately transverse to the longitudinal axis of the catheter, producing a marker band 1156 having a right trapezoid configuration inside elevational view. A short sidewall 1178 is rotationally aligned with the trailing side wall portion 1174, and has an axial length within the range of from about 0.2 millimeters to about 4 millimeters, and typically from about 0.5 millimeters to about 2 millimeters. An opposing long sidewall 1180 is rotationally aligned with the leading side wall portion 1168. Long sidewall 1180 of the marker band 1156 is generally at least about 10 percent or 20 percent longer than short sidewall 1178 and may be at least about 50 percent or 70 percent or 90 percent or more longer than short sidewall 1178, depending upon desired performance. Generally, the long sidewall 1180 will have a length of at least about 0.5 millimeters or 1 millimeter and less than about 5 millimeters or 4 millimeters.

The marker band may be a continuous annular structure, or may have at least one and optionally two or three or more axially extending slits throughout its length. The slit may be located on the short sidewall 1178 or the long sidewall 1180 or in between, depending upon desired bending characteristics. The marker band may include any of a variety of radiopaque materials, such as a platinum/iridium alloy, with a wall thickness preferably no more than about 0.003 inches and in one implementation is about 0.001 inches.

The fluoroscopic appearance of the marker bands may be unique or distinct for each catheter size or type when a plurality of catheters is utilized so that the marker bands can be distinguishable from one another by a software algorithm. Distinguishing the marker bands of a plurality of catheters may be advantageous when the multiple catheters are used together, for example, in a multi catheter assembly or stack as described herein. In some embodiments, the marker band of a catheter may be configured so that a software algorithm can detect motion of the catheter tip.

The marker band zone of the assembled catheter may have a relatively high bending stiffness and high crush strength, such as at least about 50 percent or at least about 100 percent less than proximal segment 18 but generally no more than about 200 percent less than proximal segment 1158. The high crush strength may provide radial support to the adjacent advance segment 1154 and particularly to the leading side wall portion 1168, to facilitate the functioning of distal tip 1172 as an atraumatic bumper during transluminal advance and to resist collapse under vacuum. The proximal segment 1158 preferably has a lower bending stiffness than the marker band zone, and the advance segment 1154 preferably has even a lower bending stiffness and crush strength than the proximal segment 1158.

The advance segment 1154 may include a distal extension of the outer tubular jacket 1164 and optionally the inner liner 1160, without other internal supporting structures distally of the marker band 1156. Outer jacket 1164 may include extruded polyurethane, such as Tecothane®. The advance segment 1154 may have a bending stiffness and radial crush stiffness that is no more than about 50 percent, and in some implementations no more than about 25 percent or 15 percent or 5 percent or less than the corresponding value for the proximal segment 1158.

The catheter may further include an axial tension element or support such as a ribbon or one or more filaments or fibers for increasing the tension resistance and/or influencing the bending characteristics in the distal zone. The tension support may include one or more axially extending mono strand or multi strand filaments. The one or more tension element 1182 may be axially placed inside the catheter wall near the distal end of the catheter. The one or more tension element 1182 may serve as a tension support and resist tip detachment or elongation of the catheter wall under tension (e.g., when the catheter is being proximally retracted through a kinked outer catheter or tortuous or narrowed vasculature).

At least one of the one or more tension element 1182 may proximally extend along the length of the catheter wall from within about 1.0 centimeters from the distal end of the catheter to less than about 10 centimeters from the distal end of the catheter, less than about 20 centimeters from the distal end of the catheter, less than about 30 centimeters from the distal end of the catheter, less than about 40 centimeters from the distal end of the catheter, or less than about 50 centimeters from the distal end of the catheter.

The one or more tension element 1182 may have a length greater than or equal to about 40 centimeters, greater than or equal to about 30 centimeters, greater than or equal to about 20 centimeters, greater than or equal to about 10 centimeters, or greater than or equal to about 5 centimeters.

At least one of the one or more tension element 1182 may extend at least about the most distal 50 centimeters of the length of the catheter, at least about the most distal 40 centimeters of the length of the catheter, at least about the most distal 30 centimeters or 20 centimeters or 10 centimeters of the length of the catheter.

In some implementations, the tension element extends proximally from the distal end of the catheter along the length of the coil 24 and ends proximally within about 5 centimeters or 2 centimeters or less either side of a transition between a distal coil and a proximal braid. The tension element may end at the transition without overlapping with the braid.

The one or more tension element 1182 may be placed near or radially outside the inner liner 1160. The one or more tension element 1182 may be placed near or radially inside the braid and/or the coil. The one or more tension element 1182 may be carried between the inner liner 1160 and the helical coil, and may be secured to the inner liner or other underlying surface by an adhesive prior to addition of the next outer adjacent layer such as the coil. Preferably, the tension element 1182 is secured to the marker band 1156 such as by adhesives or by mechanical interference. In one implementation, the tension element 1182 extends distally beyond the marker band on a first (e.g., inside) surface of the marker band, then wraps around the distal end of the marker band and extends along a second (e.g., outside) surface in either or both a proximal inclined or circumferential direction to wrap completely around the marker band.

When more than one tension element 1182 or filament bundles are spaced circumferentially apart in the catheter wall, the tension elements 1182 may be placed in a radially symmetrical manner. For example, the angle between two tension elements 1182 with respect to the radial center of the catheter may be about 180 degrees. Alternatively, depending on desired clinical performances (e.g., flexibility, trackability), the tension elements 1182 may be placed in a radially asymmetrical manner. The angle between any two tension elements 1182 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 1182 may include materials such as Vectran®, Kevlar®, Polyester®, Spectra®, Dyneema®, Meta-Para-Aramide®, or any combinations thereof. At least one of the one or more tension element 1182 may include a single fiber or a multi-fiber bundle, and the fiber or bundle may have a round or rectangular (e.g., ribbon) cross section. The terms fiber or filament do not convey composition, and they may include any of a variety of high tensile strength polymers, metals or alloys depending upon design considerations such as the desired tensile failure limit and wall thickness. The cross-sectional dimension of the one or more tension element 1182, as measured in the radial direction, may be no more than about 2 percent, 5 percent, 8 percent, 15 percent, or 20 percent of that of the catheter 10.

The cross-sectional dimension of the one or more tension element 1182, as measured in the radial direction, may be no more than about 0.03 millimeters (about 0.001 inches), no more than about 0.0508 millimeters (about 0.002 inches), no more than about 0.1 millimeters (about 0.004 inches), no more than about 0.15 millimeters (about 0.006 inches), no more than about 0.2 millimeters (about 0.008 inches), or about 0.38 millimeters (about 0.015 inches).

The one or more tension element 1182 may increase the tensile strength of the distal zone of the catheter before failure under tension (e.g., marker band detachment) to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 12A:
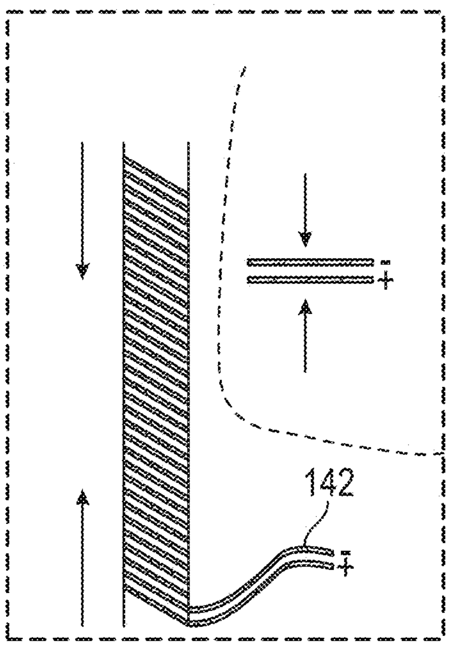
FIGS. 12A and 12B schematically illustrate a force sensor integrated into the sidewall of the catheter.

Any of a variety of sensors may be provided on any of the catheters, hubs, carriages, or table, depending upon the desired data. For example, in some implementations, it may be desirable to measure axial tension or compression force applied to the catheter such as along a force sensing zone. The distal end of the catheter would be built with a similar construction as illustrated in FIG. 11, with a helical coil distal section. But instead of using a single helical coil of nitinol wire, a first conductor 140 and second conductor 142 are wrapped into intertwined helical coils and electrically isolated from each other such as by the plastic/resin of the tubular body. See FIG. 12A. Each coil is in electrical communication with the proximal hub by a unique electrical conductor such as a conductive trace or proximal extension of the wire.

Figure 12B:
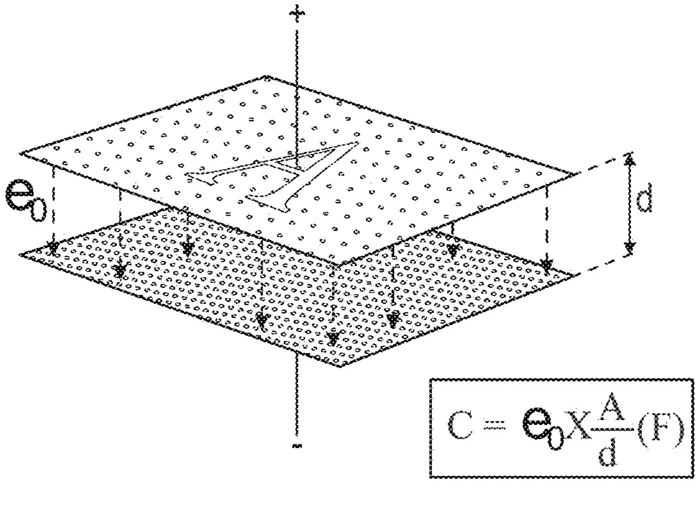

This construction of double, electrically isolated helical coils creates a capacitor. This is roughly equivalent to two plates of nitinol with a plastic layer between them, illustrated in FIG. 12B. The capacitance is inversely proportional to the distance between wires. The only variable that would be changing would be d, the distance between the plates. If an axial compressive force is applied to the catheter, the wires (e.g., conductor 140 and conductor 142) will move closer together, thus increasing the capacitance. If an axial tensile force is applied, the wires will get further apart, decreasing the capacitance. This capacitance can be measured at the proximal end of the catheter, giving a measurement of the force at the helical capacitor. Although referred to as a capacitor, this sensor is measuring the electrical interaction between the two coils of wire. There may be a measurable change in inductance or other resulting change due to applied axial forces.

At least a first helical capacitor may have at least one or five or ten or more complete revolutions of each wire. A capacitor may be located within the distal most 5 or 10 or 20 centimeters of the catheter body to sense forces experienced at the distal end. At least a second capacitor may be provided within the proximal most 5 or 10 or 20 centimeters of the catheter body, to sense forces experienced at the proximal end of the catheter.

Figure 13A:
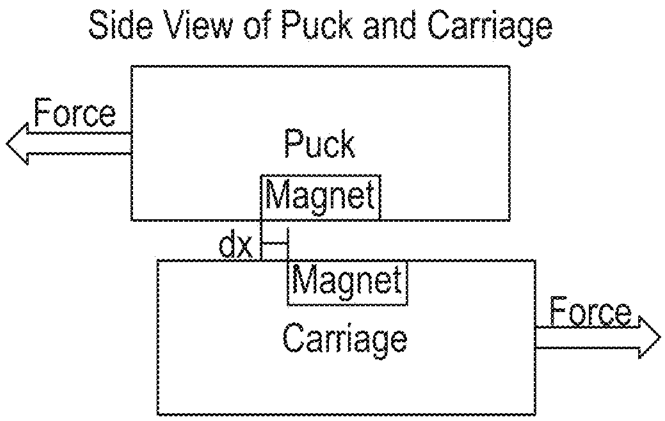
FIGS. 13A and 13B schematically illustrate a sensor for measuring elastic forces at the magnetic coupling between the hub and corresponding hub adapter.
Figure 13B:
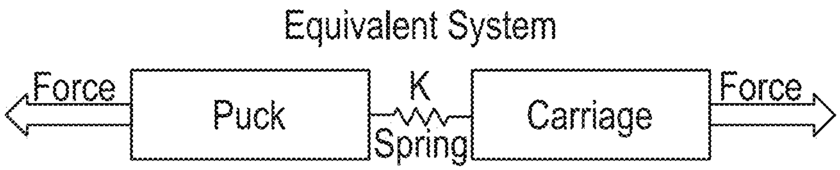

It may also be desirable to measure elastic forces across the magnetic coupling between the hub and corresponding carriage, using the natural springiness (compliance) of the magnetic coupling to measure the force applied to the hub. The magnetic coupling between the hubs and carriages creates a spring. When a force is applied to the hub, the hub will move a small amount relative to the carriage. See FIG. 13A. In robotics, this is called a series elastic actuator. This property can be used to measure the force applied from the carriage to the hub. To measure the force, the relative distance between the hub and the carriage (dx shown in FIG. 13A) is determined and characterize some effective spring constant k between the two components. See FIG. 13B.

The relative distance could be measured in multiple different ways. One method for measuring the relative distance between the hub and carriage is a magnetic sensor (e.g., a Hall effect Sensor between hub and carriage). A magnet is mounted to either the hub or carriage, and a corresponding magnetic sensor is mounted on the other device (carriage or hub). The magnetic sensor might be a hall effect sensor, a magnetoresistive sensor, or another type of magnetic field sensor. Generally, multiple sensors may be used to increase the reliability of the measurement. This reduces noise and reduces interference from external magnetic fields.

Other non-contact distance sensors can also be used. These include optical sensors, inductance sensors, and capacitance sensors. Optical sensors would preferably be configured in a manner that avoids accumulation of blood or other fluid in the interface between the hubs carriages. In some implementations, wireless (i.e., inductive) power may be used to translate movement and/or transfer information across the sterile barrier between a drive carriage and a hub, for example.

The magnetic coupling between the hub and the carriage has a shear or axial break away threshold which may be about 300 grams or 1000 grams or more. The processor can be configured to compare the axial force applied to the catheter to a preset axial trigger force which if applied to the catheter is perceived to create a risk to the patient. If the trigger force is reached, the processor may be configured to generate a response such as a visual, auditory or tactile feedback to the physician, and/or intervene and shut down further advance of the catheter until a reset is accomplished. An override feature may be provided so the physician can elect to continue to advance the catheter at forces higher than the trigger force, in a situation where the physician believes the incremental force is warranted.

Force and or torque sensing fiber optics (e.g., Fiber Bragg Grating (FBG) sensors) may be built into the catheter side wall to measure the force and/or torque at various locations along the shaft of a catheter or alternatively may be integrated into a guidewire. The fiber measures axial strain, which can be converted into axial force or torque (when wound helically). At least a first FBG sensor can be integrated into a distal sensing zone, proximal sensing zone and/or intermediate sensing zone on the catheter or guidewire, to measure force and or torque in the vicinity of the sensor.

It may also be desirable to understand the three-dimensional configuration of the catheter or guidewire during and/or following transvascular placement. Shape sensing fiber optics such as an array of FBG fibers to sense the shape of catheters and guidewires. By using multiple force sensing fibers that are a known distance from each other, the shape along the length of the catheter/guidewire can be determined.

A resistive strain gauge may be integrated into the body of the catheter or guidewire to measure force or torque. Such as at the distal tip and/or proximal end of the device.

Measurements of force and/or torque applied to the catheter or guidewire shafts can be used to determine applied force and/or torque above a safety threshold. When an applied force and/or torque exceeds a safety threshold, a warning may be provided to a user. Applied force and/or torque measurements may also be used to provide feedback related to better catheter manipulation and control. Applied force and/or torque measurements may also be used with processed fluoroscopic imaging information to determine or characterize distal tip motion.

Absolute position of the hubs (and corresponding catheters) along the length of the table may be determined in a variety of ways. For example, a non-contact magnetic sensor may be configured to directly measure the position of the hubs through the sterile barrier. The same type of sensor can also be configured to measure the position of the carriages. Each hub may have at least one magnet attached to it. The robotic table would have a linear array of corresponding magnetic sensors going the entire length of the table. A processor can be configured to determine the location of the magnet along the length of the linear sensor array, and display axial position information to the physician.

The foregoing may alternatively be accomplished using a non-contact inductive sensor to directly measure the position of the hubs through the sterile barrier. Each hub or carriage may be provided with an inductive "target" in it. The robotic table may be provided with an inductive sensing array over the entire working length of the table. As a further alternative, an absolute linear encoder may be used to directly measure the linear position of the hubs or carriages. The encoder could use any of a variety of different technologies, including optical, magnetic, inductive, and capacitive methods.

In one implementation, a passive (no electrical connections) target coil may be carried by each hub. A linear printed circuit board (PCB) may run the entire working length of the table (e.g., at least about 1.5 meters to about 1.9 meters) configured to ping an interrogator signal which stimulates a return signal from the passive coil. The PCB is configured to identify the return signal and its location.

Axial position of the carriages may be determined using a multi-turn rotary encoder to measure the rotational position of the pulley, which directly correlates to the linear position of the carriage. Direct measurement of the location of the carriage may alternatively be accomplished by recording the number of steps commanded to the stepper motor to measure the rotational position of the pulley, which directly correlates to the linear position of the carriage.

The location of the catheters and guidewires within the anatomy may also be determined by processing the fluoroscopic image with machine vision, such as to determine the distal tip position, distal tip orientation, and/or guidewire shape. Comparing distal tip position or movement or lack thereof to commanded or actual proximal catheter or guidewire movement at the hub, may be used to detect a loss of relative motion, which may be indicative of a device shaft buckling, prolapse, kinking, or a similar outcome (for example, along the device shaft length inside the body (e.g., in the aorta) or outside the body between hubs. The processing may be done in real time to provide position/orientation data at up to 30 Hertz, although this technique would only provide data while the fluoroscopic imaging is turned on. In some embodiments, machine vision algorithms can be used to generate and suggest optimal catheter manipulations to access or reach anatomical landmarks, similar to driver assist. The machine vision algorithms may utilize data to automatically drive the catheters depending on the anatomy presented by fluoroscopy.

Figure 14:
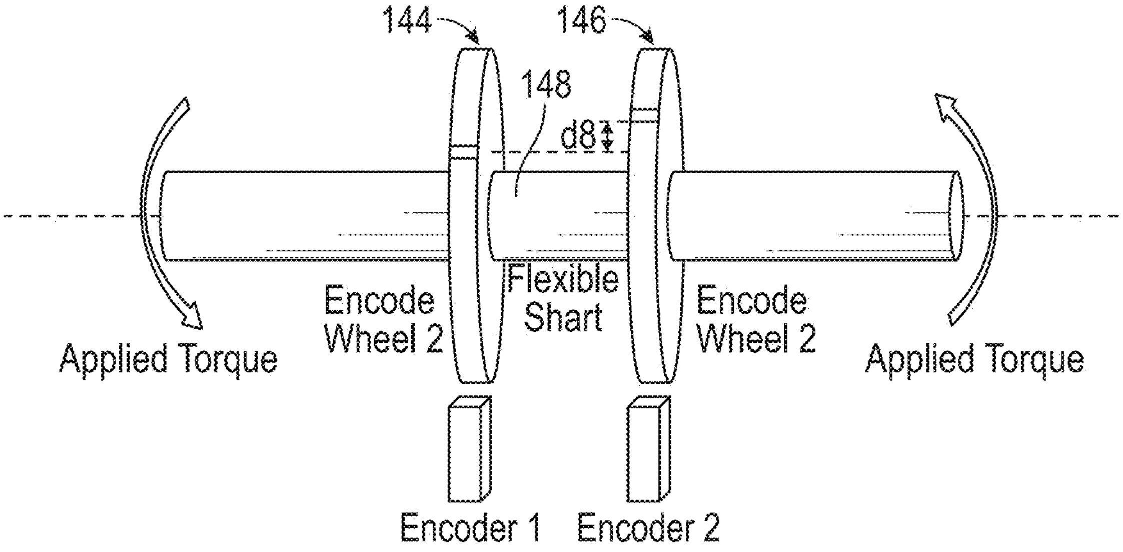
FIG. 14 schematically illustrates a dual encoder torque sensor for use with a catheter of the present disclosure.

Proximal torque applied to the catheter or guidewire shaft may be determined using a dual encoder torque sensor. Referring to FIG. 14, a first encoder 144 and a second encoder 146 may be spaced axially apart along the shaft 148, for measuring the difference in angle over a length of flexible catheter/tube. The difference in angle is interpolated as a torque, since the catheter/tube has a known torsional stiffness. As torque is applied to the shaft, the slightly flexible portion of the shaft will twist. The difference between the angles measured by the encoders ($d\theta$) tells us the torque. $T=k*d\theta$, where k is the torsional stiffness.

Confirming the absence of bubbles in fluid lines may also be accomplished using bubble sensors, particularly where the physician is remote from the patient. This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub. To detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Preferably, a bubble removal system is automatically activated upon detection of in line bubbles. A processor may be configured to activate a valve positioned in the flow path downstream of the bubble detector, upon the detection of bubbles. The valve diverts a column of fluid out of the flow path to the patient and into a reservoir. Once bubbles are no longer detected in the flow path and after the volume of fluid in the flow path between the detector and the valve has passed through the valve, the valve may be activated to reconnect the source of fluid with the patient through the flow path. In other embodiments, the bubble removal system can include a pump and control system upstream of the bubble detector for removal of in line bubbles. A processor may be configured to activate the pump upon detection of bubbles to reverse the fluid flow and clear the bubbles into a waste reservoir before reestablishing bubble free forward flow.

Figure 15:
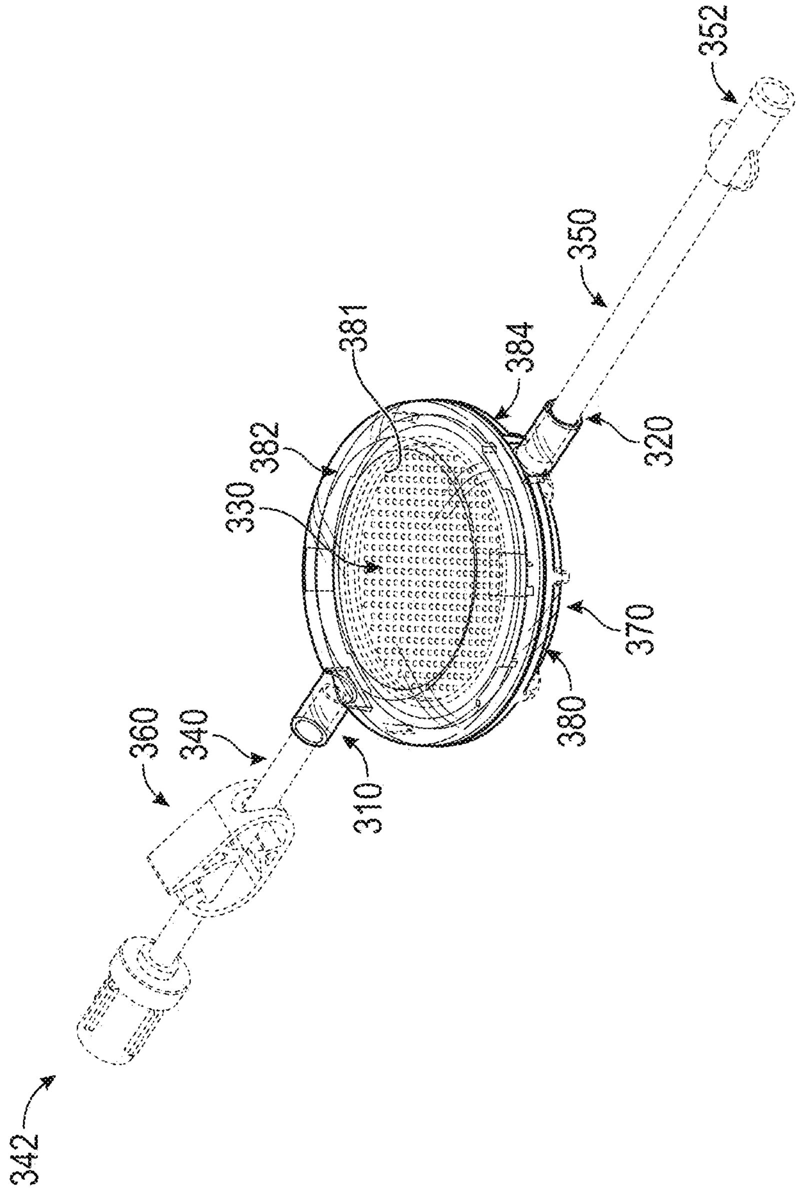
FIG. 15 illustrates a clot capture and visualization device that can be integrated into a hub and/or connected to an aspiration line.

It may additionally be desirable for the physician to be able to view aspirated clot at a location within the sterile field and preferably as close to the patient as practical for fluid management purposes. This may be accomplished by providing a clot retrieval device mounted on the hub, or in an aspiration line leading away from the hub in the direction of the pump. Referring to FIG. 15, one example of a clot retrieval device 370 can include a body 380 enclosing a chamber 381 which communicates with a first port 310 and a second port 320.

In some embodiments, the body 380 includes a housing having a top portion 382 and a bottom portion 384. The body 380 may include a filter 330 positioned in the chamber 381 between the top portion 382, and the bottom portion 384. In some examples, the first port 310 is configured to connect to a first end of a first tube 340 that is fluidly connected to a proximal end of an aspiration catheter.

In an embodiment that is configured to be connected downstream from the hub, the first tube 340 includes a connector 342 positioned at a second end of the first tube 340 that is configured to engage or mate with a corresponding connector on or in communication with the hub. The first port 310 directly communicates with the chamber on the upstream (e.g., top side) of the filter, and the second port 320 directly communicates with the chamber on the downstream (e.g., bottom side) of the filter to facilitate direct visualization of material caught on the upstream side of the filter.

In an implementation configured for remote operation, any of a variety of sensors may be provided to detect clot passing through the aspiration line and/or trapped in the filter, such as an optical sensor, pressure sensor, flow rate sensor, ultrasound sensor or others known in the art.

In some embodiments, the second port 320 is configured to connect to a first end of a second tube 350 that is fluidly connected to an aspiration source (e.g., a pump). In some embodiments, the second tube 350 includes a connector 352 positioned at a second end of the second tube 350 that is configured to engage or mate with a corresponding connector on the pump.

In some examples, the system 300 can include an on-off valve 360 such as a clamp 360. The clamp 360 can be positioned in between the filter 330 and the patient, such as over the first tube 340 to allow the user to engage the clamp and provide flow control by isolating the patient from the clot retrieval device 370. Closing the valve 360 and operating the remote vacuum pump (not illustrated) causes the canister associated with the vacuum pump and the chamber 381 to reach the same low pressure. Due to the short distance and small line volume of the lumen between the chamber 381 end the distal end of the catheter, a sharp negative pressure spike is experienced at the distal end of the catheter rapidly following opening of the valve 360. Additional details are disclosed in U.S. Pat. No. 11,259,821 issued Mar. 1, 2022 to Buck et al., entitled Aspiration System with Accelerated Response, the entirety of which is hereby expressly incorporated by reference herein. In some embodiments, a vacuum may be cycled against a clot to retrieve the clot. The vacuum may be automatically and robotically controlled to remove the clot.

The body 380 can have a top surface spaced apart from a bottom surface by a tubular side wall. In the illustrated implementation, the top and bottom surfaces are substantially circular, and spaced apart by a cylindrical side wall. The top surface may have a diameter that is at least about three times, or five times or more than the axial length (transverse to the top and bottom surfaces) of the side wall, to produce a generally disc shaped housing. Preferably at least a portion of the top wall is optically transparent to improve clot visualization once it is trapped in the clot retrieval device 370. Additional details may be found in U.S. Patent Application No. 63/256,743, the entirety of which is hereby expressly incorporated by reference herein.

In some examples, the body 380 can include a flush port (not illustrated) that is configured to allow the injection of an optically transparent media such as air, saline or other fluid into the chamber 381 to clear an optical path between the window and the filter to improve clot visualization once it is trapped in the filter 330.

The foregoing represents certain specific implementations of a drive table and associated components and catheters. A wide variety of different drive table constructions can be made, for supporting and axially advancing and retracting two or three or four or more drive magnet assemblies to robotically drive interventional devices, fluid elements, and electrical umbilical elements for communicating electrical signals and fluids to the catheter hubs, as will be appreciated by those of skill in the art in view of the disclosure herein. Additional details may be found in U.S. patent application Ser. No. 17/527,393, the entirety of which is hereby expressly incorporated by reference herein.

While the foregoing describes robotically driven interventional devices and manually driven interventional devices, the devices may be manually driven, robotically driven, or a combination of both manually and robotically driven interventional devices, as will be appreciated by those of skill in the art in view of the disclosure herein.

Figure 16A:
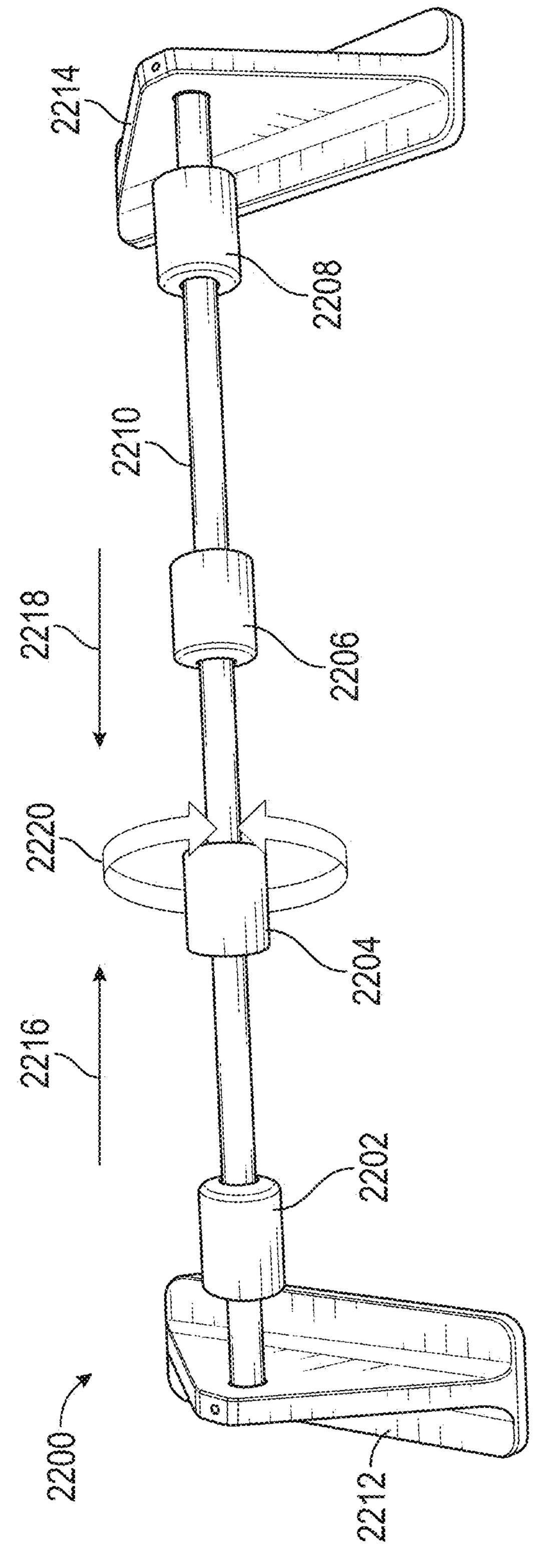
FIGS. 16A-16C illustrate an example control mechanism for manipulating interventional devices driven by respective hubs.
Figure 16B:
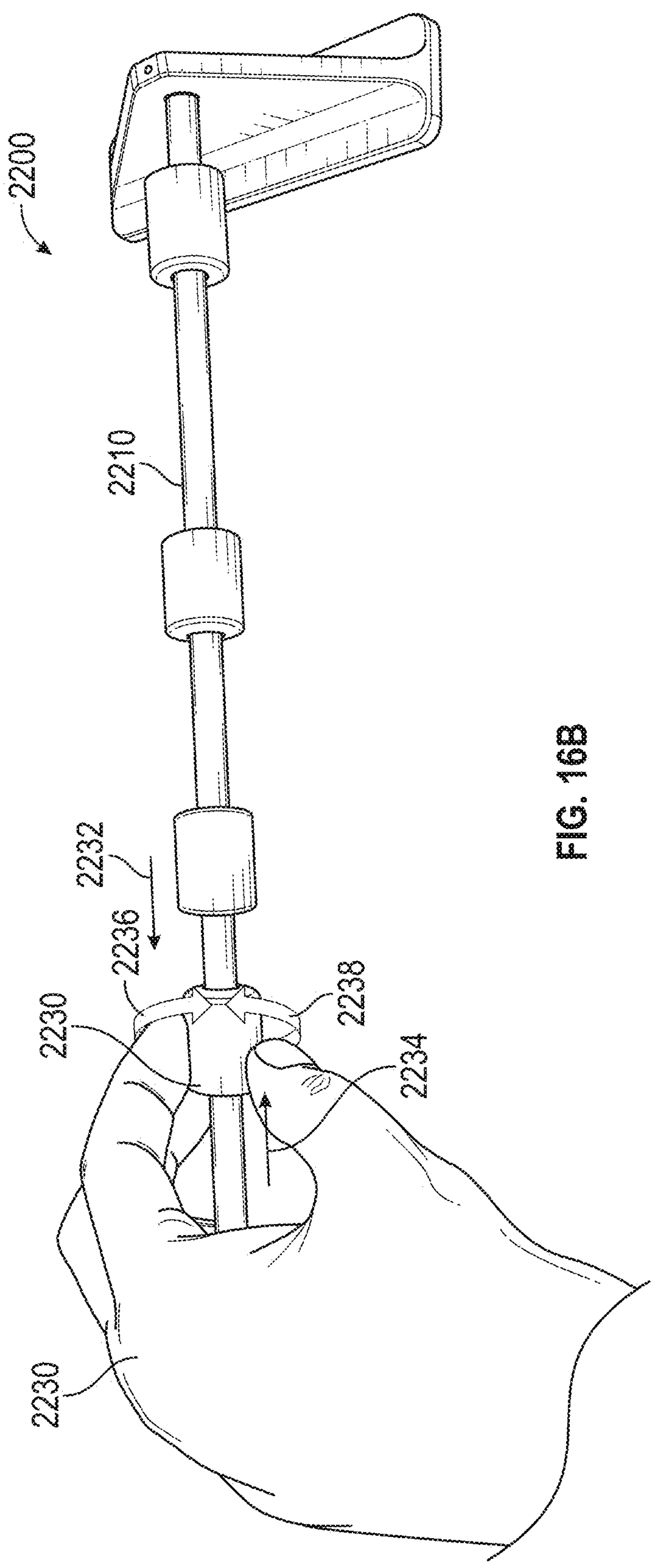
Figure 16C:
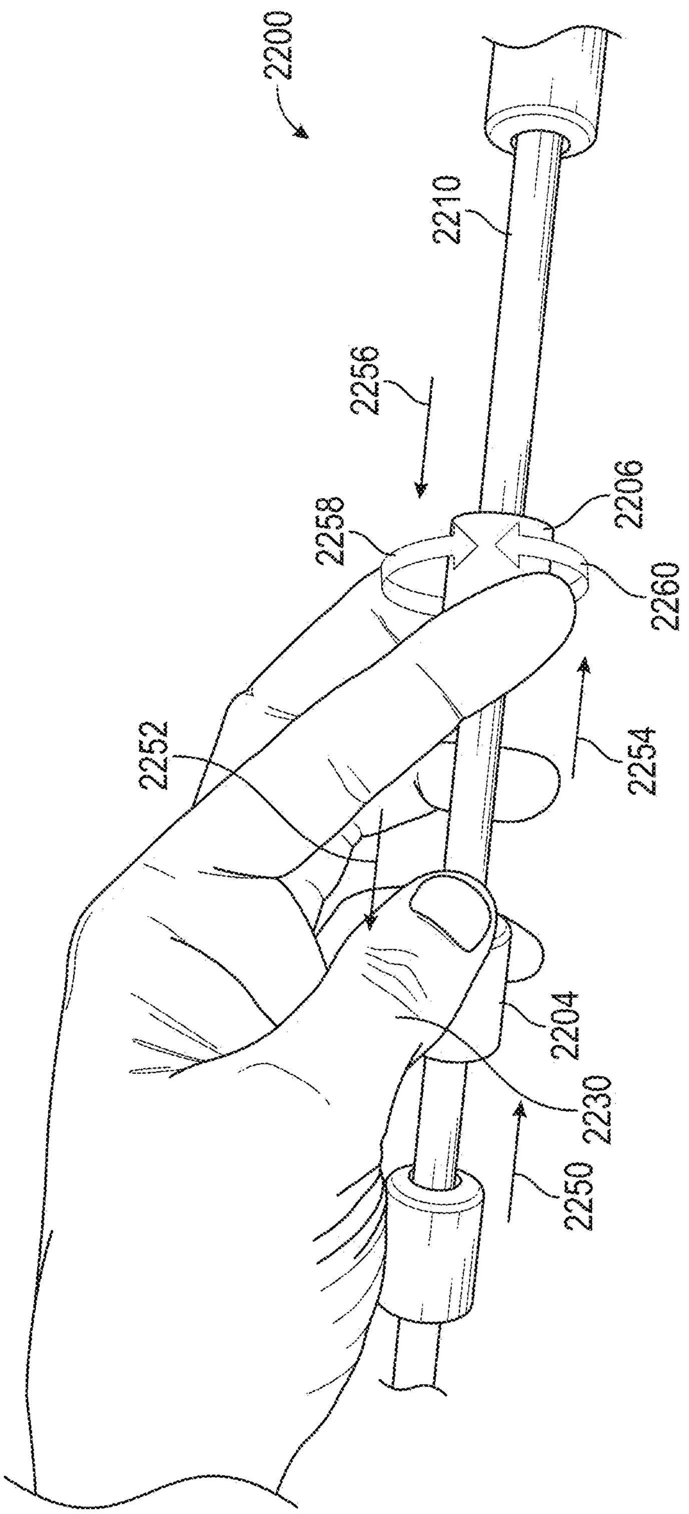

FIGS. 16A-16C illustrate an example control mechanism 2200 for manipulating interventional devices driven by (or otherwise associated with) respective hubs. For example, each hub may be manipulated and/or otherwise moved using at least one control installed in control mechanism 2200. Each control may be adapted to move a unique hub and associated interventional device during an interventional procedure.

As shown in FIG. 16A, the control mechanism 2200 include a first control 2202, a second control 2204, a third control 2206, and a fourth control 2208. More or fewer controls may be provided, depending upon the intended interventional devices configuration. Each control 2202-2208 is movably carried on a shaft 2210 that is coupled to a distal bracket 2212 and to a proximal bracket 2214. The controls 2202-2208 may advance distally or retract proximally on the shaft 2210, as indicated by arrow 2218 and arrow 2216. In addition, each control 2202-2208 may also be rotated about the shaft 2210, as indicated by arrow 2220. Each control movement may trigger a responsive movement in a corresponding carriage on the support table, which may in turn drive movement of a corresponding hub as has been discussed.

The control mechanism 2200 may be positioned on or near to a patient support table having a set of hubs and catheters/interventional devices. In some implementations, the control mechanism 2200 may be positioned remote from the support table such as behind a radiation shield or in a different room or different geographical location in a telemedicine implementation.

Each control 2202-2208 may correspond to and drive movement of a hub and/or a hub and interventional device combination. For example, the control 2202 may be configured to drive hub 30 (FIG. 3F) to move an interventional device such as an 0.088 inch guide catheter corresponding to the hub 30. Similarly, the control 2204 may be configured to drive hub 28 (122) to move an interventional device such as an 0.071 inch procedure catheter. The control 2206 may be configured to drive hub 126 to move an interventional device such as a steerable access catheter. The control 2208 may be configured to drive hub 26 to axially and rotationally move an interventional device such as a guidewire.

FIG. 16B illustrates an example of manually manipulating the control 2202 on control mechanism 2200. In operation, if the user 2230 moves the control 2202 axially along shaft 2210 and distally, as shown by arrow 2232, a corresponding coupled hub and/or interventional device may move responsively in the same direction by a same or scaled amount. If the user 2230 rotates the control 2202 about the shaft 2210 and advances the control proximally, as shown by arrow 2234, a corresponding coupled interventional device will responsively move rotationally and proximally by a same or scaled amount. If the user 2230 moves the control 2202 rotationally about the shaft 2210, as shown by arrow 2236 or arrow 2238, a corresponding coupled hub will drive the corresponding interventional device rotationally in the same direction and/or by a same or scaled amount.

Other axes and degrees of freedom may be defined to enable control 2202 to perform movements that may be translated to movement of hubs and/or interventional devices. For example, the control mechanism may be provided with one or more deflection controls configured to initiate a lateral deflection in a deflection zone on the corresponding interventional device.

Axial movement of a control may be configured to move the coupled hub on a 1:1 basis, or on a non 1:1 scaled basis. For example, if the user 2230 advances the control 2022 about 5 millimeters distally along the shaft 2210, then the corresponding hub may responsively move 5 millimeters in the distal direction.

If the user 2230 rotates the control 2022 about its rotational axis (represented by A4 in FIG. 16B) by 5 degrees, the coupled hub will cause the corresponding interventional device to rotate on a 1:1 basis or on a non 1:1 scaled basis. The scaled amount may be selected to reduce or increase the amount of distance and rotation that a hub and/or interventional device moves in accordance with the control movement.

In some implementations, the scaled amount described herein may be determined using a scale factor. The scale factor may apply to one or both translational and rotational movement. In some implementations, a first scale factor is selected for translational movement and a second scale factor, different than the first scale factor, is selected for rotational movement. The axial scaling factor may drive proximal catheter movement at a faster speed than distal catheter movement for a given proximal or distal manipulation of the control.

The rotational scale factor may be 1:1 while the axial scale factor may move the hub by a greater distance than movement of the control such that hub travel to control travel is at least about 2:1 or 5:1 or 10:1 or more depending upon the desired axial length of the control assembly.

The control mechanism 2200 may be configured to enable the clinician to adjust the scale factor for different parts of the procedure. For example, distal advance of the procedure catheter and access catheter through the guide catheter and up to the selected ostium may desirably be accomplished in a 'fast' mode. But more distal travel into the neuro vasculature may desirably be accomplished in a relatively slow mode by actuation of a speed control.

In another implementation, one or more controls may be configured to progressively drive advance or retraction speeds of the corresponding hub and associated catheter. For example, distal control 2202 may drive the guide catheter. A slight distal movement of the control 2202 may advance the guide catheter distally at a slow speed, while advancing the control 2202 by a greater distance distally increases the rate of distal travel of the guide catheter.

Controlling the speed of the corresponding hubs either axially or both axially and rotationally may enhance the overall speed of the procedure. For example, advance of the various devices from the femoral access point up to the aortic arch may desirably be accomplished at a faster rate than more distal navigation closer to the treatment site. Also proximal retraction of the various devices, particularly the guidewire, access catheter and procedure catheter may be desirably accomplished at a relatively higher speeds than distal advance.

FIG. 16C illustrates another example of manually manipulating a control on the control mechanism 2200 to move hubs and/or other interventional devices. In some implementations, two or more controls 2202-2208 may be moved in combination to trigger movement of one or more hubs and/or related interventional devices. In the depicted example, the user 2230 moves control 2204 and control 2206 in combination (e.g., sequentially, simultaneously) such as to simultaneously move the 0.088 guide catheter and the 0.071 aspiration catheter as a unit. Example movement of control 2204 may include axial proximal movement in the directions shown by arrows 2250. Sequentially or simultaneously, the user 2230 may move control 2206 axially in either of the directions shown by arrows 2254 and 2256 while also moving control 2206 rotationally in either of the directions shown by arrows 2258 and 2260.

In some implementations, each control mechanism and/or additional controls (not shown) may be color coded, shaped coded, tactile coded, or other coding to indicate to the user 2230 which color is configured to move which hub or interventional device. In some implementations, the control color coding may also be applied to the hubs and/or interventional devices such that a user may visually match a particular hub/device with a particular control.

In some implementations, other control operations beyond translational movement and rotational movement may be carried out using controls 2202-2208. For example, controls 2202-2208 may be configured to drive a shape change and/or stiffness change of a corresponding interventional device. Controls 2202-2208 may be toggled between different operating modes. For example, controls 2202-2208 may be toggled between movement driven by acceleration and velocity to movement that reflects actual linear displacement or rotation.

In some implementations, the control mechanism 2200 may be provided with a visual display or other indicator of the relative positions of the controls which may correspond the relative positions of the interventional devices. Such displays may depict any or all movement directions, instructions, percentage of movements performed, and/or hub and/or catheter indicators to indicate which device is controlled by a particular control. In some implementations, the display may depict applied force or resistance encountered by the catheter or other measurement being detected or observed by a particular hub or interventional component.

In some implementations, the control mechanism 2200 may include haptic components to provide haptic feedback to a user operating the controls. For example, if the control 2202 is triggering movement of a catheter and the catheter detects a large force at the tip, the control 2202 may generate haptic feedback to indicate to the user to stop or reverse a performed movement. In some implementations, haptic feedback may be generated at the control to indicate to the user to slow or speed a movement using the control. In some implementations, haptics may provide feedback on a large torsional strain buildup that might precede an abrupt rotation, or a large axial force buildup that may be a prelude to buckling of the catheter.

The systems described herein may compare an actual fluoroscopic image position to an input displacement from the controller. A static fluoroscopic image of the patient may be captured in which the patient's vasculature is indexed relative to bony landmarks or one or more implanted soft tissue fiducial markers. Then a real time fluoroscopic image may be displayed as an overlay, aligned with the static image by registration of the fiducial markers. Visual observation of conformance of the real time movement with the static image, assisted by detected force data can help confirm proper navigation of the associated catheter or guidewire. The systems described herein can also display a comparison of an input proximal mechanical translation of a catheter or guidewire and a resulting distal tip output motion or lack thereof. A loss of relative motion at the distal tip may indicate shaft buckling, prolapse, kinking, or a similar outcome, either inside or outside the body. Such a comparison may be beneficial when the shaft buckling, prolapse, kinking, or similar outcome occurs outside of a current fluoroscopic view.

Figure 17:
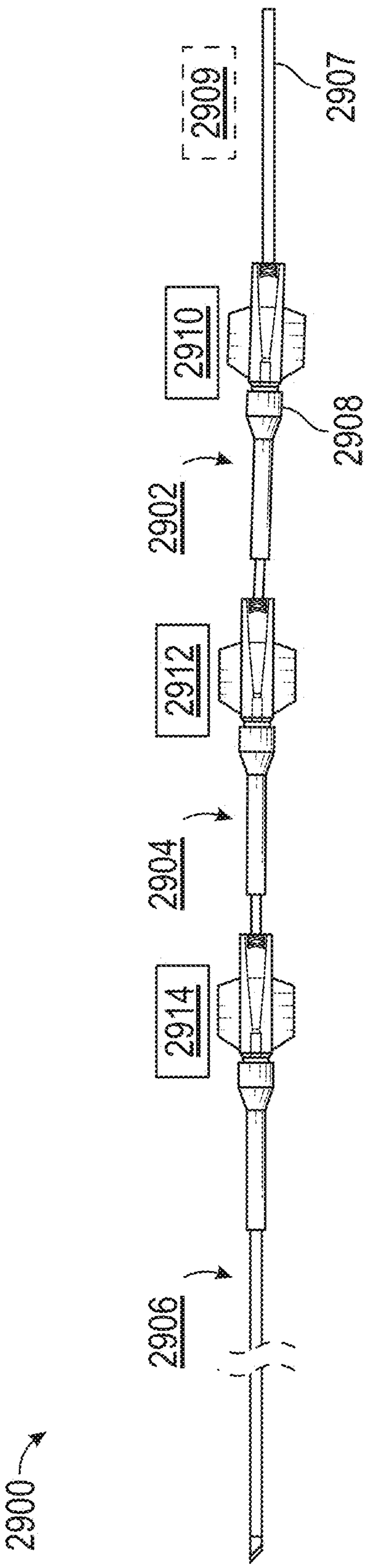
FIG. 17 illustrates a side elevational schematic view of an interventional device assembly for supra-aortic access and neuro-interventional procedures.

FIG. 17 illustrates a side elevational schematic view of a multi catheter interventional device assembly 2900 for combined supra-aortic access and/or neurovascular site access and procedure (e.g., aspiration), as described herein. The multi catheter assembly 2900 may be configured for either a manual or a robotic procedure.

The interventional device assembly 2900 includes an insert or access catheter 2902, a procedure catheter 2904, and a guide catheter 2906. Other components are possible including, but not limited to, one or more guidewires (e.g., optional guidewire 2907), one or more guide catheters, an access sheath and/or one or more other procedure catheters and/or associated catheter (control) hubs. In some embodiments, the assembly 2900 may also be configured with an optional deflection control 2908 for controlling deflection of one or more catheters of assembly 2900.

In operation, the multi-catheter assembly 2900 may be used without having to exchange hub components. For example, in the two stage procedure disclosed previously, a first stage for achieving supra-aortic access includes mounting an access catheter, guide catheter and guidewire to the support table. Upon gaining supra aortic access, the access catheter and guidewire were typically removed from the guide catheter. Then, a second catheter assembly is introduced through the guide catheter after attaching a new guidewire hub and a procedure catheter hub to the corresponding drive carriage on the support table.

The single multi catheter assembly 2900 of FIG. 17 is configured to be operated without having to remove hubs and catheters and without the addition of additional assemblies and/or hubs. Thus, the multicomponent access and procedure configuration of assembly 2900 may utilize a guidewire 2907 manufactured to function as an access guidewire and a navigation guidewire to allow for sufficient access and support, and navigation to the particular distal treatment site. In a non-limiting example configured for robotic implementation, a catheter assembly may include a guidewire hub (e.g., guidewire hub 2909 or guidewire hub 26 positioned on a drive table and to the right of catheter 2902), an insert or access catheter hub 2910, a procedure catheter hub 2912, a guide catheter hub 2914 and corresponding catheters. In certain embodiments, one or more of the hubs may include or be coupled to a hemostasis valve (e.g., a rotating hemostasis valve) to accommodate introduction of interventional devices therethrough. Additional details regarding hemostasis valves are included in U.S. patent application Ser. No. 17/879,614, entitled Multi Catheter System With Integrated Fluidics Management, filed Aug. 2, 2022, which is hereby expressly incorporated by reference in its entirety herein Once access above the aortic arch has been achieved, the insert or access catheter 2902 (associated with insert or access catheter hub 2910) may be parked in the vicinity of a carotid artery ostia and the remainder or a subset of the catheter assembly may be guided more distally toward a particular site (e.g., a clot site, a surgical site, a procedure site, etc.).

In some embodiments, other smaller procedure catheters may also be added and used at the site. As used herein for catheter assembly 2900, in a robotic configuration of assembly 2900, the guide catheter 2906 may function as a guide catheter. The procedure catheter 2904 may function as a procedure (e.g., aspiration) catheter. In some embodiments, the guide catheter 2906 may function to perform aspiration in addition to functioning as a guide catheter, either instead of or in addition to the procedure catheter 2904. The access catheter 2902 may have a distal deflection zone and can function to access a desired ostium. One of skill in the art will appreciate from FIGS. 18A-18E that either manual manipulation or robotic manipulation of the multi catheter stack are contemplated herein.

In some embodiments, the catheter assembly 2900 (or other combined catheter assemblies described herein) may be driven as a unit to a location. However, each catheter (or guidewire) component may instead be operated and driven independent of one another to the same or different locations.

In a non-limiting example, the catheter assembly 2900 may be used for a diagnostic angiogram procedure. In some embodiments, the assembly 2900 may include only the guidewire 2907 and access catheter 2902 (in the form of a diagnostic angiographic catheter) for performing the diagnostic angiogram procedure or only the guidewire 2907 and the access catheter 2902 may be utilized during the procedure. Alternatively, the guide catheter 2906 and procedure catheter 2904 may be retracted proximally to expose the distal end of the access catheter 2902 (e.g., a few centimeters of the distal end of the access catheter) to perform the diagnostic angiography.

As shown in FIG. 17, the guide catheter 2906, procedure catheter 2904, access catheter 2902, and guidewire 2907 can be arranged concentrically. In certain embodiments, the guide catheter 2906 may be a 'large bore' guide catheter or access catheter having a diameter of at least about 0.075 or at least about 0.080 inches in diameter. The procedure catheter 2904 may be an aspiration catheter having a diameter within the range of from about 0.060 to about 0.075 inches. The access catheter 2902 may be a steerable catheter with a deflectable distal tip, having a diameter within the range of from about 0.025 to about 0.050 inches. The guidewire 2907 may have a diameter within the range of from about 0.014 to about 0.020 inches. In one example, the guide catheter 2906 may have a diameter of about 0.088 inches, the procedure catheter 2904 about 0.071 inches, the access catheter 2902 about 0.035 inches, and the guidewire 2907 may have a diameter of about 0.018 inches.

FIGS. 18A-18E depict an example sequence of steps of introducing a multi-catheter assembly configured to achieve access all the way to the clot, either manually or robotically. FIGS. 18A-18E may be described using the interventional device assembly of FIG. 17. Other combinations of catheters may be substituted for the interventional device assembly, as will be appreciated by those of skill in the art in view of the disclosure herein.

Figure 18A:
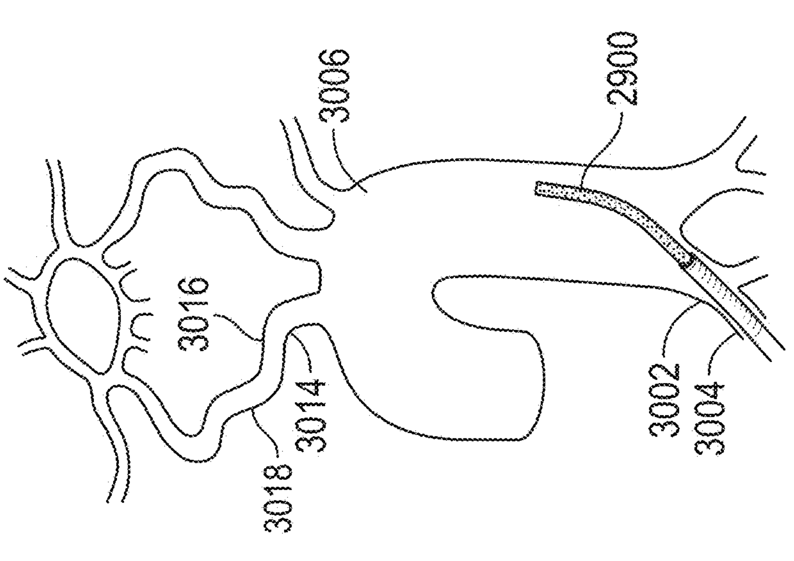
FIGS. 18A-18E depict an example sequence of steps of introducing a catheter assembly configured to achieve supra-aortic access and neurovascular site access.
Figure 18B:
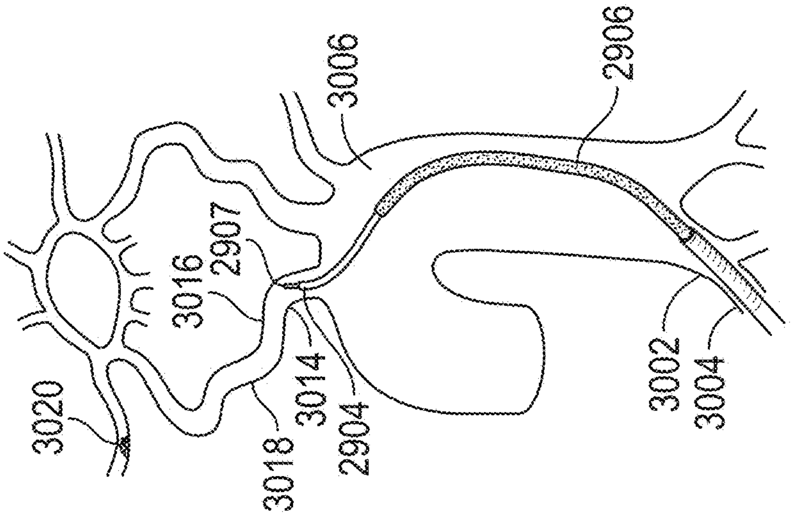

Referring to FIG. 18A, the three catheter interventional device assembly 2900 is shown driven through an introducer sheath 3002, up through the iliac artery 3004 and into the descending aorta. Next, the access catheter 2902, the procedure catheter 2904 (e.g., 0.071 inch) and the guide catheter 2906 (e.g., 0.088 inch) are tracked up to the aortic arch 3006, as shown in FIG. 18B. Here, the distal end of the guide catheter 2906 may be parked below the aortic arch 3006 and the procedure catheter 2904, access catheter 2902 (positioned within the procedure catheter 2904 and not visible in FIG. 18B), and a guidewire 2907 can be driven into the ostium (e.g., simultaneously or separately). In some embodiments, the access catheter 2902 is advanced out of the procedure catheter 2904 and the guide catheter 2906 to engage the ostium first. After the distal end of the access catheter 2902 is positioned within the desired ostium, the guidewire 2907 can be advanced distally into the ostium to secure access. After the access catheter 2902 and guidewire 2907 are positioned within the desired ostium, the procedure catheter 2904 and/or guide catheter 2906 can be advanced into the ostium (and, in some embodiments, beyond), while using the support of the access catheter 2902 and/or guidewire 2907 to maneuver through the aorta and into the ostium. In the embodiment shown in FIG. 18B, the procedure catheter 2904 has been advanced into the ostium while the guide catheter 2906 has remained parked below the aortic arch 3006.

Figure 18C:
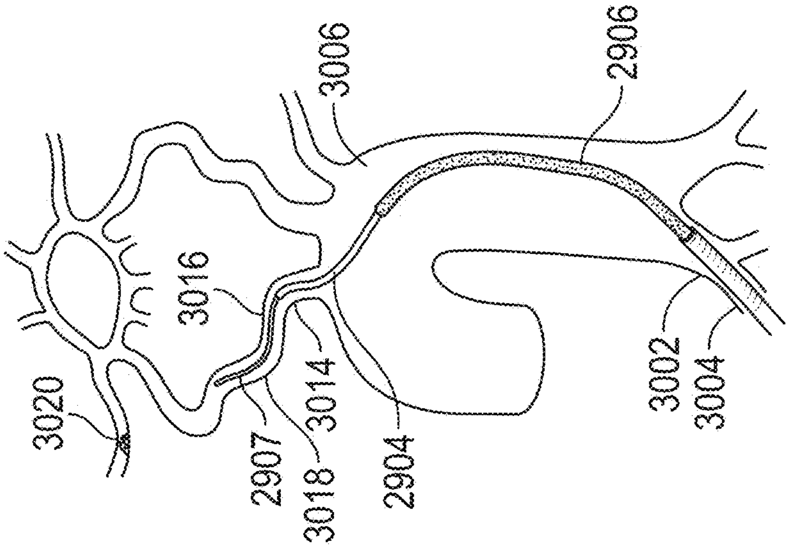

Referring to FIG. 18C, the guidewire 2907 may be distally advanced and the radiopacity of the guidewire 2907 may be used to confirm under fluoroscopic imaging that access through the desired ostia has been attained. The guidewire 2907 engages the origin of the brachiocephalic artery 3014. The guidewire 2907 is then advanced up to the petrous segment 3018 of the internal carotid artery 3016.

Figure 18E:
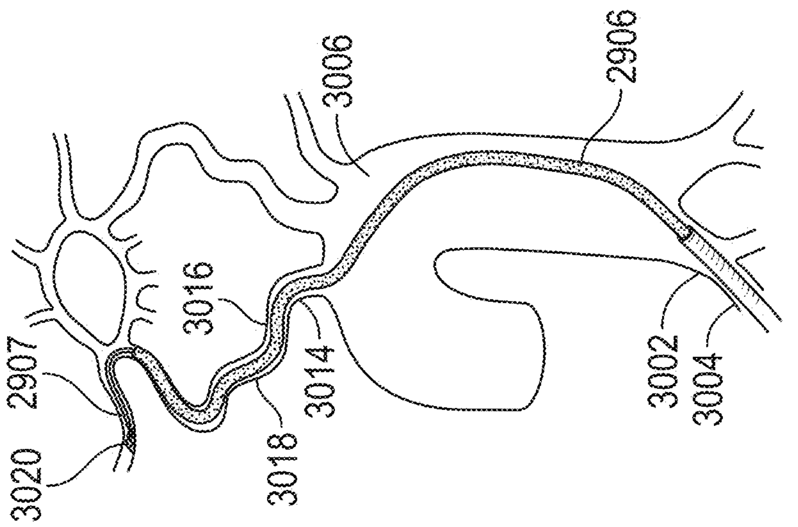
Figure 18D:
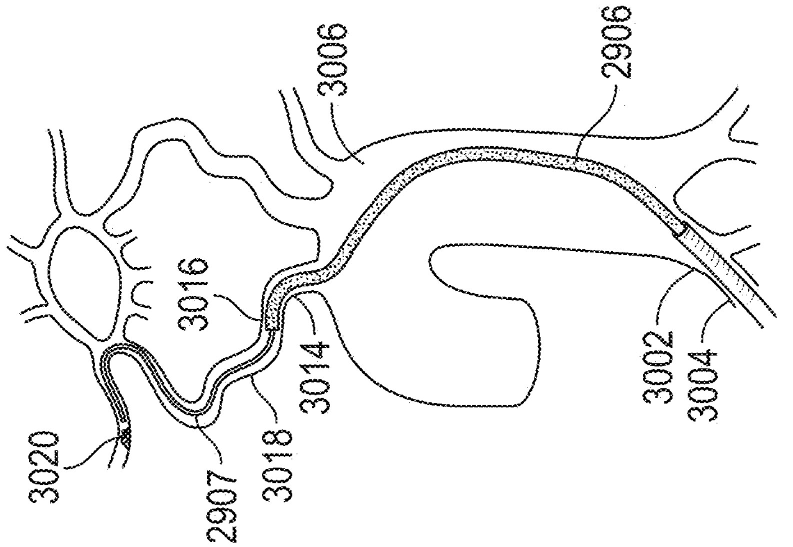

Referring to FIG. 18D, the guide catheter 2906 and the procedure catheter 2904 (positioned within the guide catheter 2906 and not visible in FIG. 18D) are both advanced (e.g., simultaneously or sequentially) over the guidewire 2907 and over the insert or access catheter 2902 (positioned within the procedure catheter 2904 and not visible in FIG. 18D) while the access catheter 2902 remains at the ostium for support. The guidewire 2907 may be further advanced past the petrous segment 3018 to the site of the clot 3020, such as the M1 segment.

Referring to FIG. 18E, the guide catheter 2906 and the procedure catheter 2904 (positioned within the guide catheter 2906 and not visible in FIG. 18E) are advanced (e.g., simultaneously or sequentially) to position the distal tip of the procedure catheter 2904 at the procedure site, for example on the face of the clot 3020. The guidewire 2907 and access catheter 2902 (positioned within the procedure catheter 2904 and not visible in FIG. 18E) are removed, and aspiration of the clot 3020 commences through the procedure catheter 2904. That is, the guidewire 2907 and the access catheter 2902 are proximally retracted to allow aspiration through the procedure catheter 2904. After aspiration of the clot, the procedure catheter 2904 and guide catheter 2906 can be removed (e.g., simultaneously or sequentially). For example, in some embodiments, the procure catheter 2904 may be removed before removing the guide catheter 2906.

The catheter assembly 2900 may be used to perform a neurovascular procedure, as described in FIGS. 18A-18E. For example, the neurovascular procedure may be a neurovascular thrombectomy. The steps of the procedure may include providing an assembly that includes at least a guidewire, an access catheter, a guide catheter, and a procedure catheter. For example, the catheter assembly 2900 includes a guidewire 2907, an access (e.g., insert) catheter 2902, a guide catheter 2906, and at least one procedure catheter 2904. The procedure catheter 2904 may include an aspiration catheter, an embolic deployment catheter, a stent deployment catheter, a flow diverter deployment catheter, a diagnostic angiographic catheter, a stent retriever catheter, a clot retriever catheter, a balloon catheter, a catheter to facilitate percutaneous valve repair or replacement, an ablation catheter, and/or an RF ablation catheter or guidewire.

The neurovascular procedure may further include steps of coupling the assembly to a non-robotic or a robotic drive system, and driving the assembly to achieve supra-aortic access. The steps may further include driving a subset of the assembly to a neurovascular site, and performing the neurovascular procedure using a subset of the assembly. The subset of the assembly may include the guidewire, the guide catheter, and the procedure catheter.

Each of the guidewire 2907, the access catheter 2902, the guide catheter 2906, and the procedure catheter 2904 is configured to be adjusted by a respective hub. For example, the guidewire 2907 may include (or be coupled to) a hub installed on one of the tray assemblies described herein. Similarly, the access catheter 2902 may be coupled to insert or access catheter hub 2910. The guide catheter 2906 may be coupled to the guide catheter hub 2914. The procedure catheter 2904 may be coupled to the procedure catheter hub 2912.

In general coupling of the assembly may include magnetically coupling a first hub such as a guidewire hub 2909 coupled to the guidewire 2907 to a first drive magnet, magnetically coupling a second hub such as an insert or access catheter hub 2910 coupled to the access catheter 2902 to a second drive magnet, magnetically coupling a third hub such as a procedure catheter hub 2912 coupled to the procedure catheter 2904 to a third drive magnet, and magnetically coupling a fourth hub such as a guide catheter hub 2914 coupled to the guide catheter 2906 to a fourth drive magnet. In general, the first drive magnet, the second drive magnet, the third drive magnet, and the fourth drive magnet are each independently movably carried by a drive table, as described with respect to tray assemblies and controls described herein. In some embodiments, the first drive magnet, the second drive magnet, the third drive magnet, and the fourth drive magnet are coupled (e.g., to their respective catheter hubs) through a sterile barrier (e.g., a sterile and fluid barrier) and independently movably carried by a drive table having a plurality of driven magnets. In some embodiments, two or more drive magnets can be tethered or otherwise coupled together to move as a unit in response to commands from a single controller tethered or otherwise coupled to one of the drive magnets.

In some implementations, the steps of performing the neurovascular procedure may include driving the assembly in response to movement of each of the hub adapters along a support table until the assembly is positioned to achieve supra-aortic vessel access. The hub adapters may include, for example, a coupler/carriage that acts as a shuttle by advancing proximally or distally along a track in response to operator instructions. The hub adapters described herein may each include at least one drive magnet configured to couple with a driven magnet carried by the respective hub. This provides a magnetic coupling between the drive magnet and driven magnet through the sterile barrier such that the respective hub is moved across the top of the sterile barrier in response to movement of the hub adapter outside of the sterile field (as described in detail in FIG. 4). Movement of the hub adapter is driven by a drive system carried by the support table in which the guidewire hub 2909, the guide catheter hub 2914, the procedure catheter hub 2912, and the insert or access catheter hub 2910 are installed upon.

The steps may further include driving a subset of the assembly in response to movement of each of the hub adapters along the support table until the subset of the assembly is positioned to perform a neurovascular procedure at a neurovascular treatment site. The subset of the assembly may include the guidewire 2907, the guide catheter 2906, and the procedure catheter 2904.

In some embodiments, the guidewire 2907, the guide catheter 2906 and the procedure catheter 2904 are advanced as a unit through (with respect to the guidewire 2907) and over (with respect to the guide catheter 2906 and the procedure catheter 2904) at least a portion of a length of the access (e.g., insert) catheter 2902 after supra-aortic access is achieved.

In some embodiments, the catheter assembly 2900 may be part of a robotic control system for achieving supra-aortic access and neurovascular treatment site access, as described in FIGS. 18A-18E. In some embodiments, the catheter assembly 2900 may be part of a manual control system for achieving supra-aortic access and neurovascular treatment site access. In some embodiments, the catheter assembly 2900 may be part of a hybrid control system (with manual and robotic components) for achieving supra-aortic access and neurovascular treatment site access. For example, in such hybrid systems, supra-aortic access may be robotically driven while neurovascular site access and embolectomy or other procedures may be manual. Alternatively, in such hybrid systems, supra-aortic access may be manual while neurovascular site access may be robotically achieved. Still further, in such hybrid systems, any one or more of: the guidewire, access catheter, guide catheter, or procedure catheter may be robotically driven or manually manipulated.

An example robotic control system may include at least a guidewire hub (e.g., guidewire hub 2909) configured to adjust each of an axial position and a rotational position of a guidewire 2907. The robotic control system may also include an insert access catheter hub 2910 configured to adjust axial and rotational movement of an access catheter 2902. The robotic control system may also include a guide catheter hub 2914 configured to control axial movement of a guide catheter 2906. The robotic control system may also include a procedure catheter hub 2912 configured to adjust an axial position and a rotational position of a procedure catheter 2904.

In some embodiments, the procedure catheter hub 2912 is further configured to laterally deflect a distal deflection zone of the procedure catheter 2904.

In some embodiments, the guidewire hub 2909 is configured to couple to a guidewire hub adapter by magnetically coupling the guidewire hub to a first drive magnet. The insert or access catheter hub 2910 is configured to couple to an access catheter hub adapter by magnetically coupling the insert or access catheter hub 2910 to a second drive magnet. The procedure catheter hub 2912 is configured to couple to a procedure catheter hub adapter by magnetically coupling the procedure catheter hub 2912 to a third drive magnet. The guide catheter hub 2914 is configured to couple to a guide catheter hub adapter by magnetically coupling the guide catheter hub 2914 to a fourth drive magnet. In some embodiments, the first drive magnet, the second drive magnet, the third drive magnet, and the fourth drive magnet are independently movably carried by a drive table.

In some embodiments, the robotic control system includes a first driven magnet on the guidewire hub 2909. The first driven magnet may be configured to cooperate with the first drive magnet such that the first driven magnet is configured to move in response to movement of the first drive magnet. In some embodiments, the first drive magnet is configured to move outside of a sterile field separated from the first driven magnet by a barrier while the first driven magnet is within the sterile field. In some embodiments, a position of the first driven magnet is movable in response to manipulation of a procedure drive control on a control console associated with the drive table. Drive magnets and driven magnet interactions are described in detail with respect to FIG. 4 above.

In some embodiments, the robotic control system includes a second driven magnet on the insert or access catheter hub 2910. The second driven magnet may be configured to cooperate with the second drive magnet such that the second driven magnet is configured to move in response to movement of the second drive magnet. In some embodiments, the second drive magnet is configured to move outside of a sterile field separated from the second driven magnet by a barrier while the second driven magnet is within the sterile field.

In some embodiments, the robotic control system includes a third driven magnet on the procedure catheter hub 2912. The third driven magnet may be configured to cooperate with the third drive magnet such that the third driven magnet is configured to move in response to movement of the third drive magnet. In some embodiments, the third drive magnet is configured to move outside of a sterile field separated from the third driven magnet by a barrier while the third driven magnet is within the sterile field.

In some embodiments, the robotic control system includes a fourth driven magnet on the guide catheter hub 2914. The fourth driven magnet may be configured to cooperate with the fourth drive magnet such that the fourth driven magnet is configured to move in response to movement of the fourth drive magnet. In some embodiments, the fourth drive magnet is configured to move outside of a sterile field separated from the fourth driven magnet by a barrier while the fourth driven magnet is within the sterile field. In some embodiments, there may be more than four driven magnets and corresponding catheter hubs for control of additional catheters.

In some embodiments, devices (e.g., hubs, hub adapters, interventional devices, and/or trays) described herein may be used during a robotically driven procedure. For example, in a robotically driven procedure, one or more of the interventional devices may be driven through vasculature and to a procedure site. Robotically driving such devices may include engaging electromechanical components that are controlled by user input. In some implementations, users may provide the input at a control system that interfaces with one or more hubs and hub adapters.

In some embodiments, the hubs, hub adapters, interventional devices, and trays described herein may be used during a non-robotic (e.g., manually driven) procedure. Manually driving such devices may include engaging manually with the hubs to affect movement of the interventional devices.

In some embodiments, the devices described herein may be used to carry out a method of performing an intracranial procedure at an intracranial site. The method of performing the intracranial procedure may include any of the same steps as described herein for performing a neurovascular procedure. The procedure may be robotically performed, manually performed, or a hybridized combination of both.

While the foregoing describes magnetic coupling of hubs to drive magnets, in other embodiments, any of the interventional devices and/or hubs may be mechanically coupled to a drive system. Any of the methods described herein may include steps of mechanically coupling one or more interventional devices (e.g., the guidewire 2907, the access catheter 2902, the procedure catheter 2904, and/or the guide catheter 2906) and/or one or more hubs (e.g., the guidewire hub 2909, the insert or access catheter hub 2910, the procedure catheter hub 2912, and/or the guide catheter hub 2914) with one or more drive mechanisms.

Figure 19:
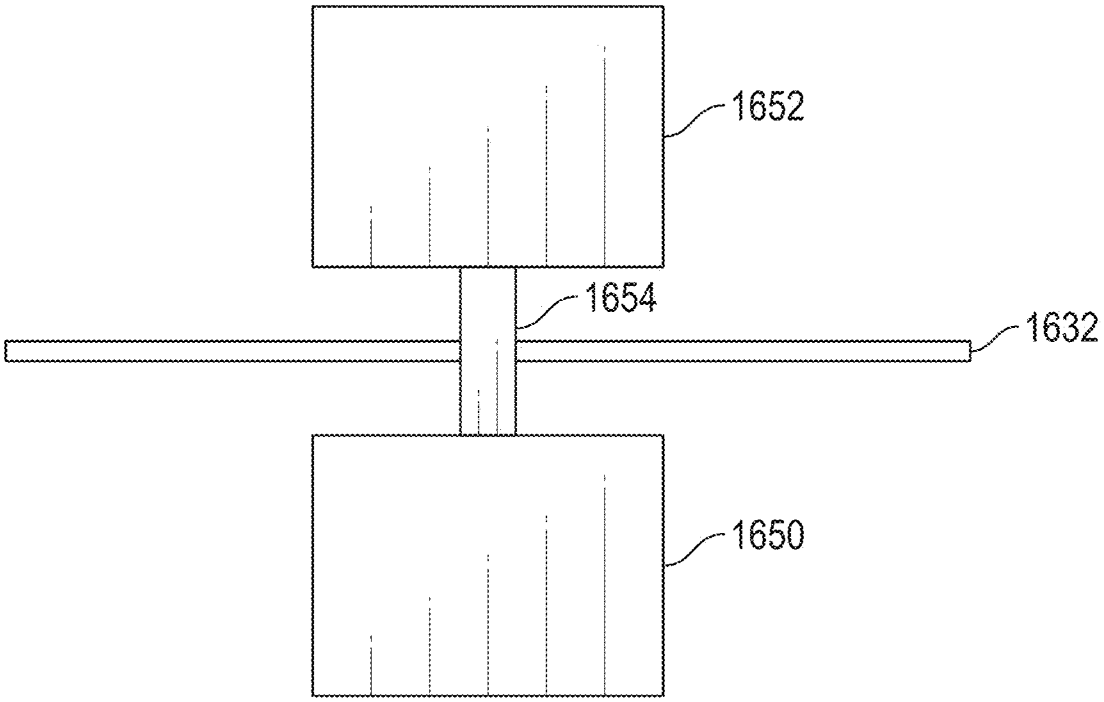
FIG. 19 schematically illustrates an embodiment of a mechanical coupling between a drive mechanism and a driven mechanism.

FIG. 19 illustrates a mechanical coupling mechanism 1654 between a drive mechanism 1650 and a driven mechanism 1652. Drive mechanism 1650 and driven mechanism 1652 may have any of the same or similar features or functions as the drive magnet 67 and driven magnet 69, respectively, except as otherwise described herein. The drive mechanism 1650 may be part of or coupled to a hub adapter (e.g., the hub adapter 48). The driven mechanism 1652 may be part of or coupled to a hub (e.g., the hub 36, the guidewire hub 2909, the insert or access catheter hub 2910, the procedure catheter hub 2912, or the guide catheter hub 2914). In some instances, the mechanical coupling mechanism 1654 may include a structural support (e.g., a support rod or support strut) extending transversely through a seal in a sterile barrier 1632. The seal may permit the structural support to be advanced along a length of the sterile barrier 1632, while still maintaining a seal with the structural support to maintain the sterile field, as the drive mechanism 1650 and driven mechanism 1652 are advanced and/or retracted as described herein. For example, the seal may include a tongue and groove closure mechanism along the sterile barrier 1632 that is configured to close on either side of the structural support while permitting passage of the structural support through the sterile barrier 1632 and maintaining a seal against the structural support as the structural support is advanced along the length of the sterile barrier 1632.

In some embodiments, the structural support can extend through an elongate self closing seal between two adjacent coaptive edges of flexible material (e.g., similar in shape to a duckbill valve) that extends along an axis. As the structural support advances along the axis between the coaptive edges, the coaptive edges may permit the structural support to advance, and then may be biased back into a sealing engagement with each other as the structural support passes any given point along the axis.

In some embodiments, the drive mechanism may be a splined drive shaft (e.g., a non-sterile splined drive shaft). The mechanical coupling mechanism 1654 can include a pulley within a plate that serves as the sterile barrier 1632 and a sterile splined shaft configured to couple to the driven mechanism 1652. The driven mechanism 1652 can be a sterile pulley that receives the sterile splined shaft from the sterile barrier. In some embodiments, one or more splined drive shafts can engage and turn corresponding pulleys in the plate that serves as the sterile barrier. Each hub can have a sterile pulley that is configured to receive a sterile splined shaft from the sterile barrier plate. Rotation of the splined drive shaft can turn the pulley in the sterile barrier plate which can in turn the sterile pulley in the hub via the sterile splined shaft.

It will be understood by one having skill in the art that any embodiment as described herein may be modified to incorporate a mechanical coupling mechanism, for example, as shown in FIG. 19.

The interventional devices described herein may be provided individually or at least some of the interventional devices can be provided in a preassembled (e.g., nested or stacked) configuration. For example, the interventional devices may be provided in the form of an interventional device assembly, such as interventional device assembly 2900, in a concentric nested or stacked configuration. If provided individually, each catheter (and in some embodiments, each corresponding catheter hub) can be unpackaged and primed to remove air from its inner lumen, for example, by flushing the catheter (and in some embodiments, the corresponding catheter hub) to remove air by displacing it with a fluid, such as saline, contrast media, or a mixture of saline and contrast media. After priming, the interventional devices can be manually assembled into a stacked configuration so that they are ready for introduction into the body for a surgical procedure, for example, via an introducer sheath.

Assembling the devices into a stacked configuration can include individually inserting interventional devices into one another by order of size. For example, an interventional device having a second largest diameter can be inserted into the lumen of an interventional device having a largest diameter. An interventional device having a third largest diameter can then be inserted into the interventional device having the second largest diameter and so on.

For example, with respect to FIG. 17, assembly can be performed by first inserting a distal end of the procedure catheter 2904 through the guide catheter hub 2914 and into the guide catheter 2906. The procedure catheter 2904 can be advanced through the guide catheter 2906 until the distal tip of the procedure catheter 2904 is flush with or extends beyond the distal tip of the guide catheter 2906, and/or until the procedure catheter 2904 cannot be inserted any further. Then, the distal end of the catheter 2902 can be inserted through the procedure catheter hub 2912 and into the procedure catheter 2904. The catheter 2902 can be advanced through the procedure catheter 2904 until the distal tip of the catheter 2902 is flush with or extends beyond the distal tip of the procedure catheter 2904, and/or until the catheter 2902 cannot be inserted any further. Then, the distal end of the guidewire 2907 can be inserted through the insert or access catheter hub 2910 and into the catheter 2902. The guidewire 2907 can be advanced through the catheter 2902 until the distal tip of the guidewire 2907 is flush with or extends beyond the distal tip of the catheter 2902, and/or until the guidewire 2907 cannot be inserted any further.

Embodiments in which two or more of the interventional devices are packaged together as a single unit in an assembled (e.g., nested or stacked) configuration may provide efficient unpackaging and preparation prior to use and efficient assembly within a robotic control system. The interventional devices may be pre-mounted to their respective hubs prior to packaging. In certain embodiments, two or three or more interventional devices may be packaged in a fully nested (i.e., fully axially inserted) configuration or nearly fully nested configuration. In a fully nested configuration, each interventional device is inserted as far as possible into an adjacent distal hub and interventional device. Such a fully nested configuration may minimize a total length of the interventional device assembly and minimize the size of the packaging required to house the interventional device assembly.

In some embodiments, the interventional devices may also be sterilized prior to packaging while in the assembled configuration, for example, using ethylene oxide gas. In some embodiments, the interventional devices may be packaged while in the assembled configuration before sterilization with ethylene oxide gas. For interventional devices in a nested or stacked configuration, ethylene oxide gas can be provided in a space between adjacent interventional devices (for example, an annular lumen between an outer diameter of a first interventional device nested within a second interventional device and the inner diameter of the second interventional device) for sterilization. In some embodiments, the interventional device assembly can be packaged in a thermoformed tray and sealed with an HDPE (e.g., Tyvek®) lid. The interventional device assembly can be unpackaged by removal (e.g., opening or peeling off) of the lid by a user in a non-sterile field. A user in the sterile field can then remove the interventional device assembly and place it on the sterile work surface, for example, of a robotic drive table, as described herein.

Packaging the interventional devices in an assembled configuration and sterilized state can reduce the time associated with unpackaging and assembly of individual interventional devices and facilitate efficient connection to a robotic drive system. Each interventional device and hub combination may further be packaged with a fluidics connection for coupling to a fluid source and/or a vacuum source. In some embodiments, each hub or a hemostasis valve coupled to the hub may include the fluidics connection.

After the interventional device assembly is unpackaged (e.g., after the interventional device assembly is positioned on the robotic drive table), priming can be performed while the devices are concentrically nested or stacked. This is preferably accomplished in each fluid lumen, such as, for example, the annular lumen between the guide catheter 2906 and the procedure catheter 2904 and in between each of the additional concentric interventional devices in the concentric stack. In certain embodiments, the fluid lumen can include a lumen between a distal hub and a proximal interventional device, such as, for example, the lumen between the guide catheter hub 2914 and the procedure catheter 2904. In certain embodiments, priming can be performed while the devices are still in the sterile packaging. The fluidics connections can be connected to a fluidics system for delivering saline and contrast media to the catheters and providing aspiration. In some embodiments, the fluidics connections may be passed outside the sterile field for connection to the fluidics system. Once connected, the fluidics system can perform a priming sequence to flush each catheter of the interventional device assembly with fluid (e.g., saline, contrast media, or a mixture of saline and contrast media). The priming sequence may also include flushing each corresponding catheter hub with fluid. The fluid may be de-aired or de-gassed by the fluidics system prior to priming. In some embodiments, a vacuum source of the fluidics system can also be used to evacuate air from each catheter while flushing with fluid. In certain embodiments, a tip of the catheter can be placed into a container of fluid, such as saline, contrast media, or a mixture of saline and contrast media, during priming so that the fluid in the container, and not air, is aspirated through the tip of the catheter when the vacuum source is applied. In other embodiments, the tip of the catheter may be blocked (for example, using a plug) so that air is not aspirated from the tip of the catheter when the vacuum source is applied. In certain embodiments, the priming process may be automated such that a user can provide a single command and each catheter (and in some embodiments, each corresponding catheter hub) can be primed, sequentially (for example, as described with respect to FIGS. 20A-20C) or simultaneously.

Additional details regarding fluidics systems are disclosed in U.S. patent application Ser. No. 17/879,614, entitled Multi Catheter System With Integrated Fluidics Management, filed Aug. 2, 2022, which is hereby expressly incorporated by reference in its entirety herein.

Fluid resistance within a lumen may be greater when there is a reduction in cross sectional luminal area for flow, for example, when a second interventional device (e.g., a catheter or guidewire) extends within the lumen of a first interventional device. The amount of fluid resistance can be affected by the length of the cross sectional narrowing, for example, due to a depth of axial insertion of the second interventional device within the first interventional device. A second interventional device extending partially through the lumen of a first interventional device will provide a smaller length of cross-sectional narrowing, and accordingly may result in a lower fluid resistance within the lumen of the first catheter, than if the second interventional device were to extend entirely through the lumen of the first interventional device. Thus, fluid resistance can be lowered by at least partially decreasing a depth of axial insertion (i.e., axial overlap) of a second interventional device into the lumen through which fluid is to be injected (e.g., a length of the second interventional device into its concentrically adjacent lumen).

In some embodiments, over certain depths of insertion of a second interventional device within a first interventional device (for example, when the second interventional device is at or near a maximum insertion depth within the first interventional device), the size of the fluid channel between the devices (e.g., the annular lumen between the first interventional device and the second interventional device) can lead to higher than desirable amounts of fluid resistance during a priming procedure. In some embodiments, the depth of insertion of the second interventional device within the first interventional device can be decreased to reduce the pressure needed to prime the catheter and reduce internal interference.

In some embodiments, a catheter in the interventional device assembly can be separated from the other interventional devices for priming to reduce the pressure needed to prime the catheter and reduce internal interference. The catheter being primed may be separated from the interventional devices within the lumen of the catheter by proximally retracting the interventional devices within the lumen of the catheter. For example, the interventional devices within the lumen of the catheter being primed can be proximally retracted from the catheter being primed as far as possible while still maintaining a nested or stacked relationship (e.g., at least about 2 cm or 5 cm or more axial overlap) in order to minimize the pressure needed to prime the catheter and minimize internal interference. In other words, a catheter can be separated from more proximal interventional devices for priming while a distal tip of an adjacent proximal interventional device is still positioned within the lumen of the catheter. Maintaining at least some of the distal tip of an adjacent proximal interventional device within the lumen of the catheter may allow for easier reinsertion and advancement of the proximal interventional device after priming.

In some embodiments, the axial overlap may be between about 2 cm and about 20 cm, between about 2 cm and 10 cm, between about 2 cm and 5 cm, between about 5 cm and 20 cm, between about 5 cm and 10 cm, or any other suitable range. In some embodiments, the axial overlap may be at least about 2 cm, at least about 5 cm, at least about 10 cm, at least about 20 cm, no more than 2 cm, no more than 5 cm, no more than 10 cm, no more than 20 cm, about 2 cm, about 5 cm, about 10 cm, about 20 cm, or any other suitable amount.

In some embodiments, the robotic drive table can be programed to proximally retract the inner interventional device(s) from the catheter being primed as much as possible while still maintaining a nested or stacked relationship. In other embodiments, the robotic drive table can be programmed to separate inner devices from the catheter being primed to a distance sufficient to optimize the length of the unobstructed lumen and result in an amount of fluid resistance lower than a threshold value. After the catheter being primed is separated from the other interventional devices, the catheter can be primed by flushing the catheter with fluid, such as saline, contrast media, or a mixture of saline and contrast media.

After the catheter is primed, it may be returned to an initial position and a next catheter of the interventional device assembly can be separated from the other interventional devices within its lumen for priming. This sequence can be repeated for each catheter of the interventional device assembly. In other embodiments, after a catheter is primed, it may be advanced to a ready or drive position to begin insertion into the patient. While the foregoing describes separating catheters to be primed by retraction of inner interventional devices, an outer catheter may also be separated from inner interventional devices by distally axially advancing the outer catheter relative to the inner interventional devices. An example of a priming process is described with respect to FIGS. 20A-20C.

Figure 20A:
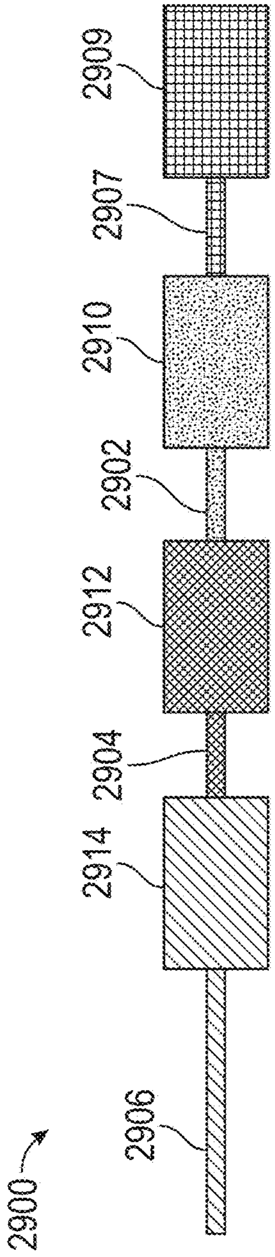
FIGS. 20A-20C depict an example sequence of steps of priming a catheter assembly in a stacked configuration.
Figure 20B:
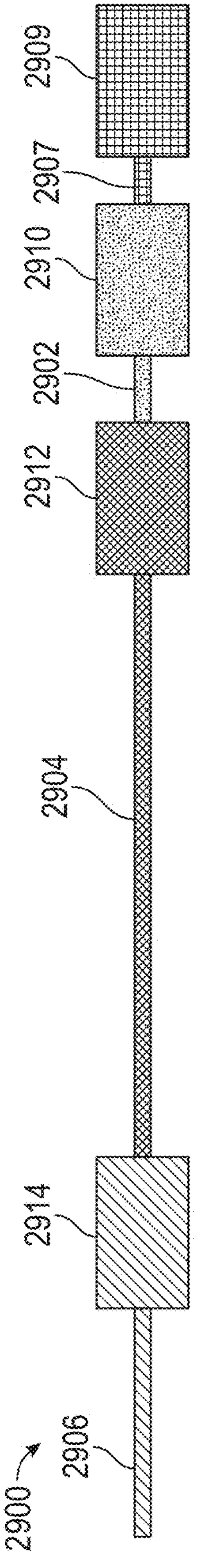

FIG. 20A depicts the interventional device assembly 2900 assembled in a concentric stack and axially compressed configuration. As shown in FIG. 20A, the interventional devices can be fully nested within each other. This may be the configuration following unpackaging of the device assembly 2900 and placement onto the robotic drive table. A priming sequence may begin by distally axially advancing the guide catheter 2906 and guide catheter hub 2914 relative to the procedure catheter 2904, procedure catheter hub 2912, catheter 2902, insert or access catheter hub 2910, guidewire 2907, and guidewire hub 2909, for example, as far as possible while maintaining a distal tip of the procedure catheter 2904 within the lumen of the guide catheter 2906, as shown in FIG. 20B, or to a distance that will result in a desirable amount of fluid resistance for priming. In some embodiments, the guide catheter 2906 is advanced in response to a control signal from a control system. The guide catheter 2906 can then be primed by introducing priming fluid using the fluidics system. In some embodiments, priming fluid is introduced in response to a control signal from a control system. Priming the guide catheter 2906 can include priming the guide catheter hub 2914. For example, in certain embodiments, the guide catheter hub 2914 or a hemostasis valve coupled thereto can include fluidics connections to receive priming fluid from the fluidics system. After priming, the guide catheter 2906 can be returned to its initial position (e.g., the fully axially compressed configuration) as shown in FIG. 20A. In some embodiments, the guide catheter 2906 is returned to its initial position in response to a control signal from a control system.

Figure 20C:
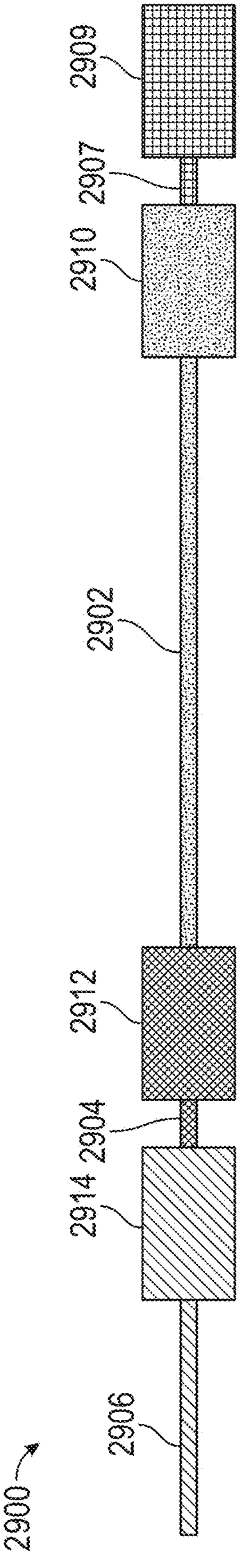

After the guide catheter 2906 is primed and returned to its initial position, the procedure catheter 2904 and procedure catheter hub 2912 can be distally axially advanced relative to the catheter 2902, insert or access catheter hub 2910, guidewire 2907 and guidewire hub 2909 (also distally axially advancing the guide catheter 2906 and guide catheter hub 2914 without changing or minimally changing their relative position with respect to procedure catheter 2904), for example, as far as possible while maintaining a distal tip of the catheter 2902 within the lumen of the procedure catheter 2904, as shown in FIG. 20C, or to a distance that will result in a desirable amount of fluid resistance for priming. In some embodiments, the procedure catheter 2904 and the guide catheter 2906 are advanced in response to a control signal from a control system. The procedure catheter 2904 can then be primed by introducing priming fluid using the fluidics system. In some embodiments, priming fluid is introduced in response to a control signal from a control system. Priming the procedure catheter 2904 can include priming the procedure catheter hub 2912. For example, in certain embodiments, the procedure catheter hub 2912 or a hemostasis valve coupled thereto can include fluidics connections to receive priming fluid from the fluidics system. After priming, the procedure catheter 2904 and guide catheter 2906 can be returned to their initial positions (e.g., the fully axially compressed configuration) as shown in FIG. 20A. In some embodiments, the procedure catheter 2904 and the guide catheter 2906 are returned to their initial position in response to a control signal from a control system.

After the procedure catheter 2904 is primed and returned to its initial position, the catheter 2902 and insert or access catheter hub 2910 can be distally axially advanced relative to the guidewire 2907 and guidewire hub 2909 (also distally axially advancing the guide catheter 2906, guide catheter hub 2914, procedure catheter 2904, and procedure catheter hub 2912 without changing or minimally changing their relative positions with respect to the catheter 2902), for example, as far as possible while maintaining a distal tip of the guidewire 2907 within the lumen of the catheter 2902, or to a distance that will result in a desirable amount of fluid resistance for priming. In some embodiments, the catheter 2902, the procedure catheter 2904, and the guide catheter 2906 are advanced in response to a control signal from a control system. The catheter 2902 can then be primed by introducing priming fluid using the fluidics system. In some embodiments, priming fluid is introduced in response to a control signal from a control system. Priming the catheter 2902 can include priming the insert or access catheter hub 2910. For example, in certain embodiments, the insert or access catheter hub 2910 or a hemostasis valve coupled thereto can include fluidics connections to receive priming fluid from the fluidics system. After priming, the catheter 2902 and catheters 2904 and 2906 can be returned to their initial positions (e.g., the fully axially compressed configuration) shown in FIG. 20A. In some embodiments, the catheter 2902, the procedure catheter 2904, and the guide catheter 2906 are returned to their initial position in response to a control signal from a control system.

In some embodiments, the priming procedure described with respect to FIGS. 20A-20C may be performed in response to a single control signal from a control system. In other embodiments, various steps of the priming procedure may be performed in response to unique control signals. In some embodiments, priming of each unique interventional device can be performed in response to a unique control signal.

In alternative embodiments, each of the catheters can be distally separated from one another simultaneously for priming. For example, the catheter 2902 can be distally separated from the guidewire 2907 while maintaining the distal tip of the guidewire 2907 in the lumen of the catheter 2902, the procedure catheter 2904 can be distally separated from the catheter 2902 while maintaining the distal tip of the catheter 2902 in the lumen of the procedure catheter 2904, and the guide catheter 2906 can be distally separated from the procedure catheter 2904 while maintaining the distal tip of the procedure catheter 2904 in the lumen of the guide catheter 2906 simultaneously. However, an embodiment in which only one set of adjacent hubs is separated at a time, as described with respect to FIGS. 20A-20C, can provide a smaller overall length of the assembly at any particular time, which can allow for use with a smaller robotic drive system. While separation of outer catheters from their inner interventional devices is described as distally axially advancing the catheters relative to their inner interventional devices, separation can include proximally retracting the inner interventional devices from the outer catheters.

In alternative embodiments, one or more of the catheter 2902, the procedure catheter 2904, and the guide catheter 2906 can be advanced to a ready or drive position to begin insertion into the patient after priming (e.g., prior to priming a subsequent catheter). In such embodiments, the catheters may advance to the ready or drive position without returning to their initial position after priming.

As described above, in some embodiments, the catheters 2902, 2904, and 2906 may be assembled into the concentric stack orientation illustrated in FIG. 17 prior to flushing the catheters to remove air by displacing it with a fluid such as saline contrast media, or a mixture of saline and contrast media. This is preferably accomplished in each fluid lumen, such as, for example, the annular lumen between the guide catheter 2906 and the procedure catheter 2904 and in between each of the additional concentric interventional devices in the concentric stack. Infusing fluid (e.g., saline, contrast media, or a mixture of saline and contrast media) under pressure may displace substantially all of the air but some small bubbles may remain, adhering to the inside wall of an outer catheter (e.g., the guide catheter 2906), the outside wall of an inner catheter (e.g., the procedure catheter 2904), or both.

While fluid is being introduced under pressure into the proximal end of the annular lumen (e.g., into a hub of the outer catheter or a hemostasis valve coupled thereto), the inner catheter may be moved with respect to the outer catheter, to disrupt the holding forces between the microbubbles and adjacent wall and allow the bubbles to be carried downstream and out through the distal opening of the lumen or removed via aspiration. The catheters may be moved axially, rotationally or both with respect to each other. In certain embodiments, the catheters may be reciprocated axially, rotationally, or both with respect to each other. In some embodiments, the catheters may be moved intermittently axially, rotationally, or both. In other embodiments, the catheters may be rotated continuously or in a constant direction.

In some implementations, a first catheter is moved reciprocally with respect to an adjacent catheter or guidewire such as axially over a stroke length in a range of from about 1 mm to about 250 mm, from about 10 mm to about 250 mm, from about 5 mm to about 125 mm, from about 25 mm to about 125 mm, from about 10 mm to about 50 mm, from about 15 mm to about 30 mm, from about 5 mm to about 30 mm, from about 15 mm to about 25 mm, from about 20 mm to about 40 mm, or any other suitable range. In some implementations, a first catheter is moved reciprocally with respect to an adjacent catheter or guidewire such as axially over a stroke length of at least 5 mm, at least 10 mm, at least 15 mm, at least 20 mm, at least 25 mm, at least 30 mm, at least 50 mm, no more than 10 mm, no more than 20 mm, no more than 25 mm, no more than 30 mm, no more than 50 mm, no more than 125 mm, no more than 150 mm, about 5 mm, about 10 mm, about 15 mm, about 20 mm, about 25 mm, about 30 mm, about 50 mm, or any other suitable stroke length.

In some implementations, a first catheter is moved reciprocally with respect to an adjacent catheter or guidewire such as axially at a reciprocation frequency in a range of from about 0.5 Hz to about 1 Hz, from about 1 Hz to about 5 Hz, from about 1 Hz to about 10 Hz, from about 1 Hz to about 25 Hz, from about 5 Hz to about 10 Hz, from about 10 Hz to about 25 Hz, or any other suitable range of frequencies. In some implementations, the first catheter is moved reciprocally with respect to an adjacent catheter or guidewire such as axially at a reciprocation frequency of at least 0.5 Hz, at least 1 Hz, at least 2 Hz, at least 5 Hz, at least 10 Hz, at least 25 Hz, no more than 0.5 Hz, no more than 1 Hz, no more than 2 Hz, no more than 5 Hz, no more than 10 Hz, no more than 25 Hz, about 0.5 Hz, about 1 Hz, about 2 Hz, about 5 Hz, about 10 Hz, about 25 Hz or any other suitable frequency.

In one implementation, a first catheter is moved reciprocally with respect to the adjacent catheter or guidewire such as axially over a stroke length in a range of from about 0.5 inches to about 10 inches, or from about one inch to about 5 inches at a reciprocation frequency of no more than about 5 cycles per second or two cycles per second or less.

In some implementations, a first catheter is moved reciprocally with respect to an adjacent catheter or guidewire such as rotationally over an angle of rotation per stroke in a range of from about 5 degrees to about 180 degrees, from about 5 degrees to about 360 degrees, from about 15 degrees to about 180 degrees, from about 15 degrees to about 150 degrees, from about 15 degrees to about 120 degrees, from about 15 degrees to about 90 degrees, form about 15 degrees to about 60 degrees, from about 15 degrees to about 30 degrees, from about 30 degrees to about 180 degrees, from about 30 degrees to about 150 degrees, from about 30 degrees to about 120 degrees, from about 30 degrees to about 90 degrees, form about 30 degrees to about 60 degrees, from about 60 degrees to about 180 degrees, from about 60 degrees to about 150 degrees, from about 60 degrees to about 120 degrees, from about 60 degrees to about 90 degrees, from about 90 degrees to about 180 degrees, from about 90 degrees to about 150 degrees, from about 90 degrees to about 120 degrees, from about 120 degrees to about 180 degrees, from about 120 degrees to about 150 degrees, from about 150 degrees to about 180 degrees or any other suitable range. In some implementations, a first catheter is moved reciprocally with respect to an adjacent catheter or guidewire such as rotationally over an angle of rotation per stroke of at least 5 degrees, at least 15 degrees, at least 30 degrees, at least 60 degrees, at least 90 degrees, at least 120 degrees, at least 150 degrees, at least 180 degrees, at least 360 degrees, no more than 5 degrees, no more than 15 degrees, no more than 30 degrees, no more than 60 degrees, no more than 90 degrees, no more than 120 degrees, no more than 150 degrees, no more than 180 degrees, no more than 360 degrees, about 5 degrees, about 15 degrees, about 30 degrees, about 60 degrees, about 90 degrees, about 120 degrees, about 150 degrees, about 180 degrees, about 360 degrees, or any other suitable angle.

In some implementations, a first catheter is moved reciprocally with respect to an adjacent catheter or guidewire such as rotationally at a reciprocation frequency in a range of from about 0.5 Hz to about 1 Hz, from about 1 Hz to about 5 Hz, from about 1 Hz to about 10 Hz, from about 1 Hz to about 25 Hz, from about 5 Hz to about 10 Hz, from about 10 Hz to about 25 Hz, or any other suitable range of frequencies. In some implementations, the first catheter is moved reciprocally with respect to an adjacent catheter or guidewire such as rotationally at a reciprocation frequency of at least 0.5 Hz, at least 1 Hz, at least 2 Hz, at least 5 Hz, at least 10 Hz, at least 25 Hz, no more than 0.5 Hz, no more than 1 Hz, no more than 2 Hz, no more than 5 Hz, no more than 10 Hz, no more than 25 Hz, about 0.5 Hz, about 1 Hz, about 2 Hz, about 5 Hz, about 10 Hz, about 25 Hz or any other suitable frequency.

In some implementations, a first catheter is moved reciprocally with respect to an adjacent catheter or guidewire for a number of reciprocations between 1 and 200, between 1 and 100, between 1 and 50, between 1 and 25, between 1 and 15, between 1 and 10, between 1 and 5, between 5 and 25, between 5 and 15, between 5 and 10, or any other suitable range. In some implementations, a first catheter is moved reciprocally with respect to an adjacent catheter or guidewire for at least 1 reciprocation, at least 2 reciprocations, at least 5 reciprocations, at least 10 reciprocations, at least 15 reciprocations, at least 25 reciprocations, at least 50 reciprocations, no more than 5 reciprocations, no more than 10 reciprocations, no more than 15 reciprocations, no more than 25 reciprocations, no more 50 than reciprocations, no more than 100 reciprocations, no more than 200 reciprocations, about 1 reciprocation, about 2 reciprocations, about 5 reciprocations, about 10 reciprocations, about 25 reciprocations, about 50 reciprocations, about 100 reciprocations, about 200 reciprocations, or any other suitable number. One reciprocation can include a movement (axially or rotationally) from a first position to a second position followed by a return from the second position to the first position.

In some implementations, a first catheter is moved reciprocally with respect to an adjacent catheter or guidewire over a length of time in a range of from 1 about second to about 60 seconds, from about 1 second to about 45 seconds, from about 1 second to about 30 seconds, from about 1 second to about 20 seconds, from about 1 second to about 15 seconds, from about 1 second to about 10 seconds, from about 5 seconds to about 45 seconds, from about 5 seconds to about 30 seconds, from about 5 seconds to about 20 seconds, from about 5 seconds to about 15 seconds, from about 5 seconds to about 10 seconds, from about 10 seconds to about 30 seconds, form about 10 seconds to about 20 seconds, or any other suitable range. In some implementations, a first catheter is moved reciprocally with respect to an adjacent catheter or guidewire over a length of time of at least 1 second, at least 5 seconds, at least 10 seconds, at least 15 seconds, at least 20 seconds, at least 30 seconds, at least 45 seconds, at least 60 seconds, no more than 5 seconds, no more than 10 seconds, no more than 15 seconds, no more than 20 seconds, no more than 30 seconds, no more than 45 seconds, no more than 60 seconds, about 5 seconds, about 10 seconds, about 15 seconds, about 20 seconds, about 30 seconds, about 45 seconds, about 60 seconds, or any other suitable length of time.

Reciprocation of adjacent catheters to disrupt microbubbles may be accomplished manually by grasping the corresponding catheter hubs and manually moving the catheters axially or rotationally with respect to each other while delivering pressurized fluid (e.g., saline, contrast media, or a mixture of saline and contrast media). Alternatively, such as in a robotically driven system, a processor may be configured to robotically drive at least one of two adjacent catheter hubs (for example, at least one of guide catheter hub 2914 and procedure catheter hub 2912) to achieve relative movement between the adjacent catheters thereby disrupting and expelling microbubbles, such as in response to user activation of a flush control. For example, in certain embodiments, two adjacent interventional devices may be moved relative to one another in response to a control signal from a control system. In certain embodiments, delivery of pressurized fluid may be performed in response to a control signal from a control system.

The reciprocation of adjacent catheters may generate shear forces that dislodge the air bubbles. For example, relative movement of the inner and outer surfaces of adjacent catheters may increase the fluid shear rate between the adjacent catheters during priming in comparison to static surfaces. In some embodiments, the shear force can be increased by increasing the flow rate of the solution (e.g., saline, contrast media, or a mixture of saline and contrast media) being provided by the fluidics system. In certain embodiments, both flow rate and relative movement between adjacent catheters are controlled to dislodge air bubbles.

In some embodiments, after each catheter is primed by the fluidics system, an ultrasound bubble detector may be used to confirm that the catheters are substantially free of air bubbles. For example, an ultrasound chip (such as mounted within a hub adjacent a catheter receiving lumen) may be run along the length of the catheters to confirm that no air bubbles remain in the system.

Figure 21A:
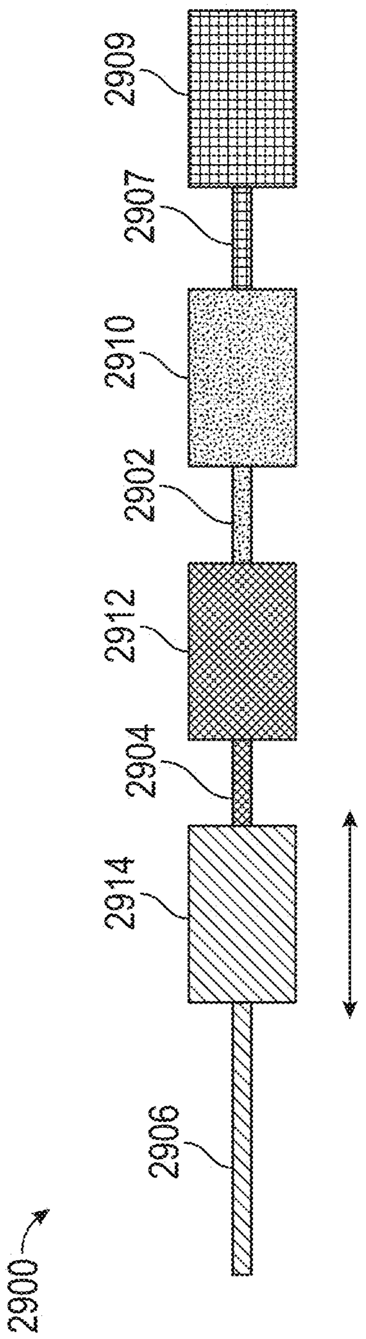
FIGS. 21A-21B depict an example sequence of steps of priming a catheter assembly in a stacked configuration.
Figure 21B:
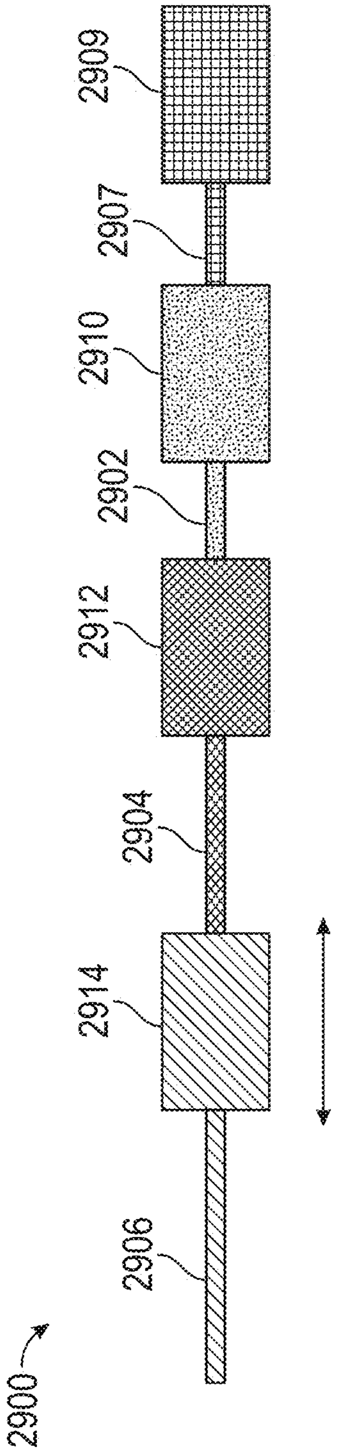

An example of a priming process including reciprocal movement of adjacent catheters is described with respect to FIGS. 21A-21B.

FIG. 21A depicts the interventional device assembly 2900 assembled in a concentric stack configuration. As shown in FIG. 21A, the interventional devices can be fully nested within each other. This may be the configuration following unpackaging of the device assembly 2900 and placement onto the robotic drive table. Alternatively, individual interventional devices of the device assembly 2900 can be assembled into the device assembly 2900 on the drive table.

A priming sequence may begin by priming the guide catheter 2906. In some embodiments, the guide catheter 2906 can be primed by introducing fluid (e.g., saline, contrast media, or a mixture of saline and contrast media) under pressure into the lumen of the guide catheter 2906 while generating reciprocal movement of guide catheter 2906 and/or guide catheter hub 2914, axially, rotationally or both, relative to the procedure catheter 2904. Priming the guide catheter 2906 can include priming the guide catheter hub 2914. For example, in certain embodiments, the guide catheter hub 2914 or a hemostasis valve coupled thereto can include fluidics connections to receive priming fluid from the fluidics system. In certain embodiments, the guide catheter 2906 and/or guide catheter hub 2914 can be axially agitated back and forth along a longitudinal axis (represented by axis A5 in FIGS. 21A and 21B) of the guide catheter 2906 (e.g., between the position of FIG. 21A and the position of FIG. 21B). Axial and/or rotational reciprocal motion of the guide catheter 2906 and/or guide catheter hub 2914 can be performed manually or by a robotic drive table. Reciprocal movement may be generated in response to a control signal from a control system. Introducing fluid under pressure may be performed in response to a control signal from a control system.

In some embodiments, priming of the guide catheter 2906 may be performed by introducing fluid (e.g., saline, contrast media, or a mixture of saline and contrast media) under pressure into the lumen of the guide catheter 2906 while generating reciprocal movement of the procedure catheter 2904 and/or procedure catheter hub 2912, axially, rotationally or both, relative to the guide catheter 2906. Axial and/or rotational reciprocal motion of the procedure catheter 2904 and/or procedure catheter hub 2912 can be performed manually or by a robotic drive table. Reciprocal movement may be generated in response to a control signal from a control system. Introducing fluid under pressure may be performed in response to a control signal from a control system.

In some embodiments, priming of the guide catheter 2906 may be performed by introducing fluid (e.g., saline, contrast media, or a mixture of saline and contrast media) under pressure into the lumen of the guide catheter 2906 while generating reciprocal movement of both the guide catheter 2906 (and/or guide catheter hub 2914) and the procedure catheter 2904 (and/or procedure catheter hub 2912), axially, rotationally or both, relative to one another. Reciprocal movement may be generated in response to a control signal from a control system. Introducing fluid under pressure may be performed in response to a control signal from a control system.

In some embodiments, after priming the guide catheter 2906, the guide catheter 2906 can be returned to an initial position as shown in FIG. 21A. In other embodiments, after priming the guide catheter 2906, the guide catheter 2906 can be advanced to a ready or drive position to begin insertion into the patient.

In some embodiments, after the guide catheter 2906 is primed, the procedure catheter 2904 can be primed. Priming the procedure catheter 2904 can include priming the procedure catheter hub 2912. For example, in certain embodiments, the procedure catheter hub 2912 or a hemostasis valve coupled thereto can include fluidics connections to receive priming fluid from the fluidics system. In some embodiments, the procedure catheter 2904 can be primed by introducing fluid (e.g., saline, contrast media, or a mixture of saline and contrast media) under pressure into the lumen of the procedure catheter 2904 while generating reciprocal movement of the procedure catheter 2904 and/or procedure catheter hub 2912, axially, rotationally or both, relative to the catheter 2902. Reciprocal movement may be generated in response to a control signal from a control system. Introducing fluid under pressure may be performed in response to a control signal from a control system.

In some embodiments, priming of the procedure catheter 2904 may be performed by introducing fluid (e.g., saline, contrast media, or a mixture of saline and contrast media) under pressure into the lumen of the procedure catheter 2904 while generating reciprocal movement of the catheter 2902 and/or insert or access catheter hub 2910, axially, rotationally or both, relative to the procedure catheter 2904. Axial and/or rotational reciprocal motion of the catheter 2902 and/or insert or access catheter hub 2910 can be performed manually or by a robotic drive table. Reciprocal movement may be generated in response to a control signal from a control system. Introducing fluid under pressure may be performed in response to a control signal from a control system.

In some embodiments, priming of the procedure catheter 2904 may be performed by introducing fluid (e.g., saline, contrast media, or a mixture of saline and contrast media) under pressure into the lumen of the procedure catheter 2904 while generating reciprocal movement of both the procedure catheter 2904 (and/or procedure catheter hub 2912) and the catheter 2902 (and/or insert or access catheter hub 2910), axially, rotationally or both, relative to one another. Reciprocal movement may be generated in response to a control signal from a control system. Introducing fluid under pressure may be performed in response to a control signal from a control system.

In some embodiments, after priming the procedure catheter 2904, the procedure catheter 2904 can be returned to an initial position as shown in FIG. 21A. In some embodiments, after priming the procedure catheter 2904, the procedure catheter 2904 can be advanced to a ready or drive position to begin insertion into the patient.

In some embodiments, after the procedure catheter 2904 is primed, the catheter 2902 can be primed. Priming the catheter 2902 can include priming the insert or access catheter hub 2910. For example, in certain embodiments, the insert or access catheter hub 2910 or a hemostasis valve coupled thereto can include fluidics connections to receive priming fluid from the fluidics system. In some embodiments, the catheter 2902 can be primed by introducing fluid (e.g., saline, contrast media, or a mixture of saline and contrast media) under pressure into the lumen of the catheter 2902 while generating reciprocal movement of the catheter 2902 and/or insert or access catheter hub 2910, axially, rotationally or both, relative to the guidewire 2907. Reciprocal movement may be generated in response to a control signal from a control system. Introducing fluid under pressure may be performed in response to a control signal from a control system.

In some embodiments, priming of the catheter 2902 may be performed by introducing fluid (e.g., saline, contrast media, or a mixture of saline and contrast media) under pressure into the lumen of the catheter 2902 while generating reciprocal movement of the guidewire 2907 and/or guidewire hub 2909, axially, rotationally or both, relative to the catheter 2902. Axial and/or rotational reciprocal motion of the guidewire 2907 and/or guidewire hub 2909 can be performed manually or by a robotic drive table. Reciprocal movement may be generated in response to a control signal from a control system. Introducing fluid under pressure may be performed in response to a control signal from a control system.

In some embodiments, priming of the catheter 2902 may be performed by introducing fluid (e.g., saline, contrast media, or a mixture of saline and contrast media) under pressure into the lumen of the catheter 2902 while generating reciprocal movement of both the catheter 2902 (and/or insert or access catheter hub 2910) and the guidewire 2907 (and/or guidewire hub 2909), axially, rotationally or both, relative to one another. Reciprocal movement may be generated in response to a control signal from a control system. Introducing fluid under pressure may be performed in response to a control signal from a control system.

In some embodiments, after priming the catheter 2902, the catheter 2902 can be returned to an initial position as shown in FIG. 21A. In other embodiments, after priming the catheter 2902, the catheter 2902 can be advanced to a ready or drive position to begin insertion into the patient.

In some embodiments, the priming procedure described with respect to FIGS. 21A and 21B may be performed in response to a single control signal from a control system. In other embodiments, various steps of the priming procedure may be performed in response to unique control signals. In some embodiments, priming of each unique interventional device can be performed in response to a unique control signal.

In the priming sequence described herein with respect to FIGS. 21A and 21B, the catheters are primed in order starting with the guide catheter 2906, followed by the procedure catheter 2904, and then followed by the catheter 2902. However, it is contemplated that the catheters may be primed in any order. The catheters may be primed in series as described above with respect to FIGS. 21A and 21B. Alternatively, two or more of the catheters or each of the catheters may be primed in parallel.

In certain embodiments, priming the catheters can include decreasing a depth of axial insertion (i.e., axial overlap) of a second interventional device into the lumen of a first interventional device through which fluid is to be injected (e.g., a length of the second interventional device into its concentrically adjacent lumen), as described with respect. to FIGS. 20A-20C, and also generating relative reciprocal movement, axially, rotationally or both, between first interventional device and the second interventional device during priming, as discussed with respect to FIGS. 21A and 21B.

In some implementations, priming of a catheter can include vibrating at least a portion of the catheter and/or its associated hub when included. Vibration can be induced, for example, by an electric motor incorporated into a hub of the catheter, or by a separate electric motor or source of vibration put against the catheter when priming. In some implementations, at least a portion of the support table on which the catheters and/or their associated hubs are placed upon can vibrate during priming of any one or more catheters to aid in removal of air and/or microbubbles of air. Such vibration can be performed by an electric motor.

EXAMPLES

Additional embodiments are disclosed in further detail in the following examples, which are not in any way intended to limit the scope of the claims.

Figure 22:
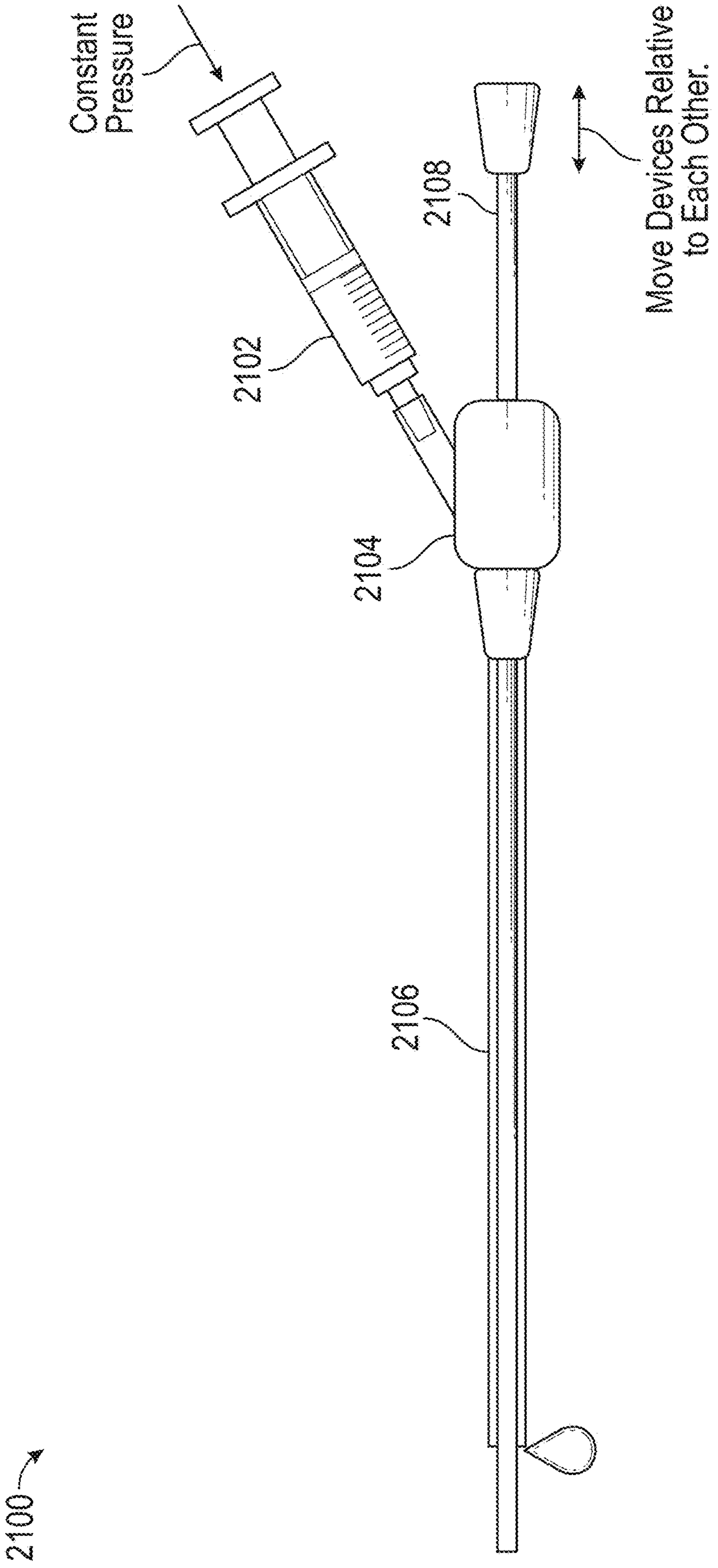
FIG. 22 depicts an example test system for the priming process depicted in FIGS. 21A-21B.
Figure 23A:
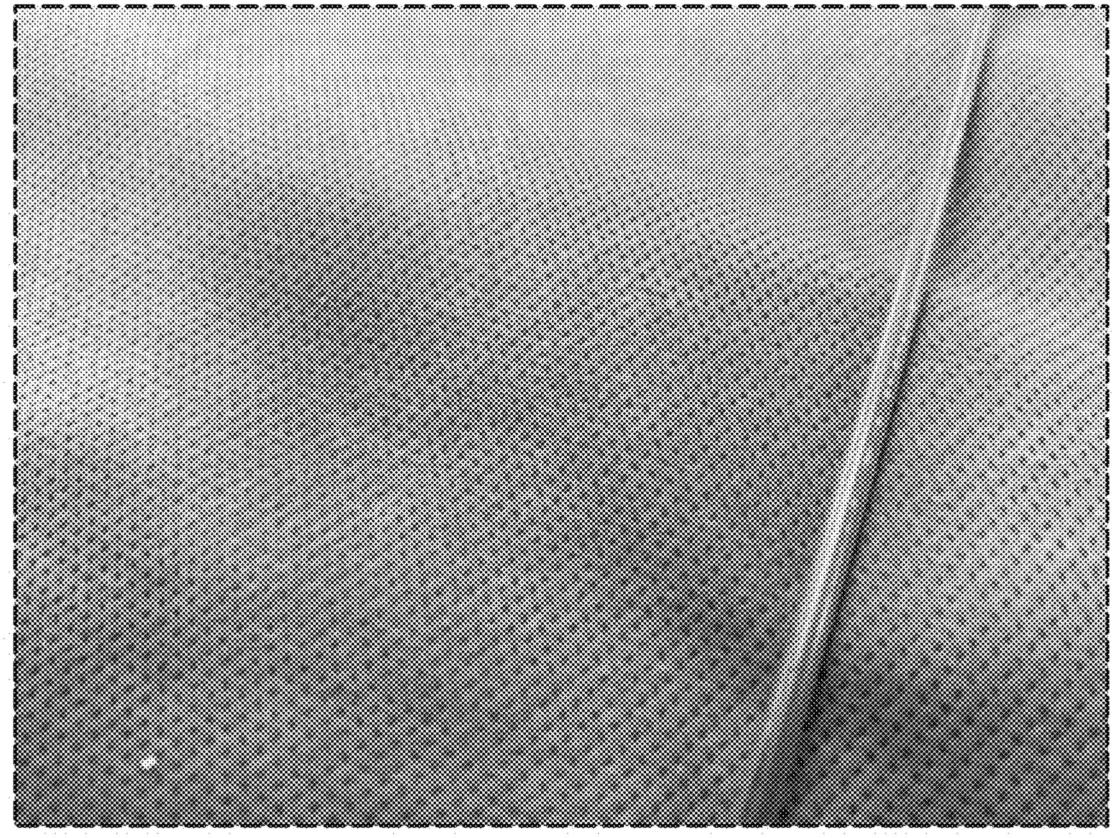
FIG. 23A shows an example of a catheter assembly.
Figure 23B:
FIG. 23B shows an example of a catheter assembly after a priming procedure.
Figure 23C:
FIG. 23C shows an example of a catheter assembly after a priming procedure including relative movement between adjacent catheters.
Figure 23D:
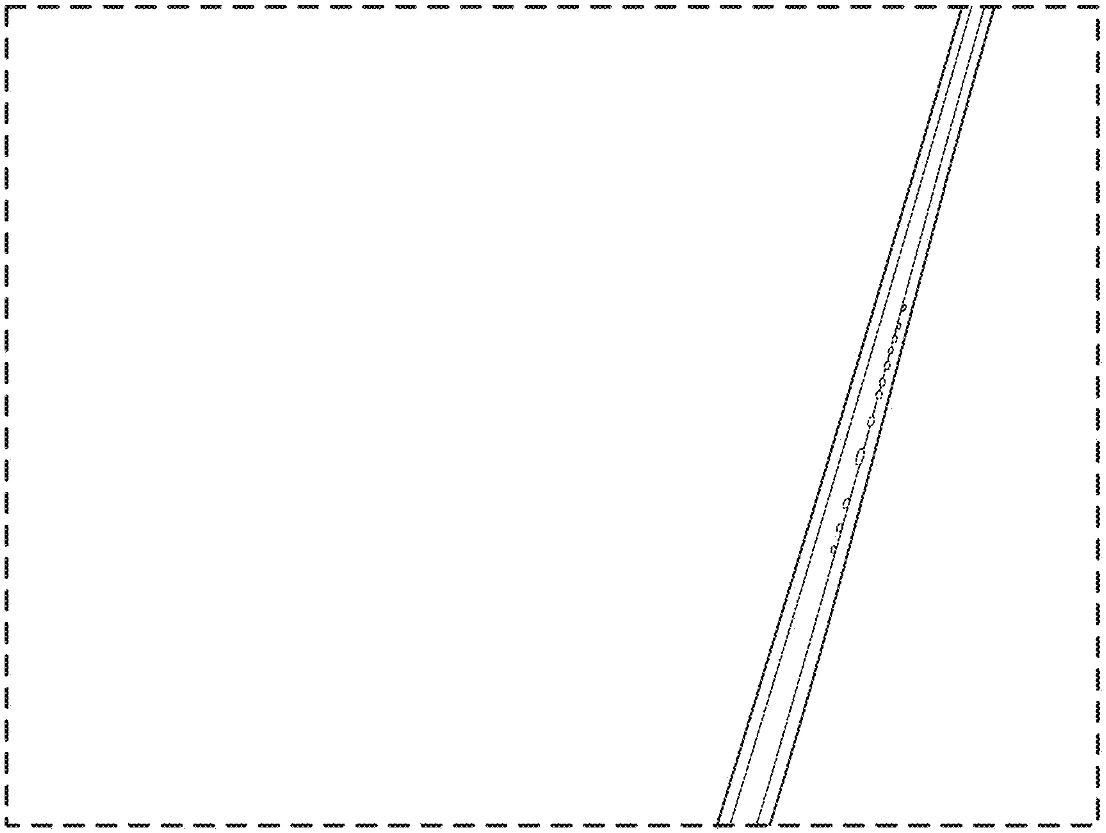
FIGS. 23D-23F illustrate the example catheter assembly of FIGS. 23A-23C.

FIG. 22 is a diagram of a test system that was used for detecting the removal of air bubbles between concentrically stacked catheters. The test system included an inner catheter 2108 positioned within an interior lumen of an outer catheter 2106 in a concentric stack. The outer catheter 2106 was coupled to a rotating hemostasis valve 2104. The hemostasis valve 2104 was coupled to a syringe 2102 so that fluid injected using the syringe would flow through the lumen between the inner catheter 2108 and the outer catheter 2016. In the test system, the inner catheter 2108 had a diameter of about 0.071 inches. The outer catheter 2106 had a diameter of about 0.088 inches. The outer catheter 2106 was transparent to permit visualization of bubbles within the lumen. A distal end of the outer catheter 2108 allowed for small volumes of fluid to exit the outer catheter. FIG. 23A is a photograph showing the catheter 2106 and catheter 2108 in a concentric stack, prior to injection of fluid. FIG. 23D is an illustration thereof.

Example 1

Figure 23E:
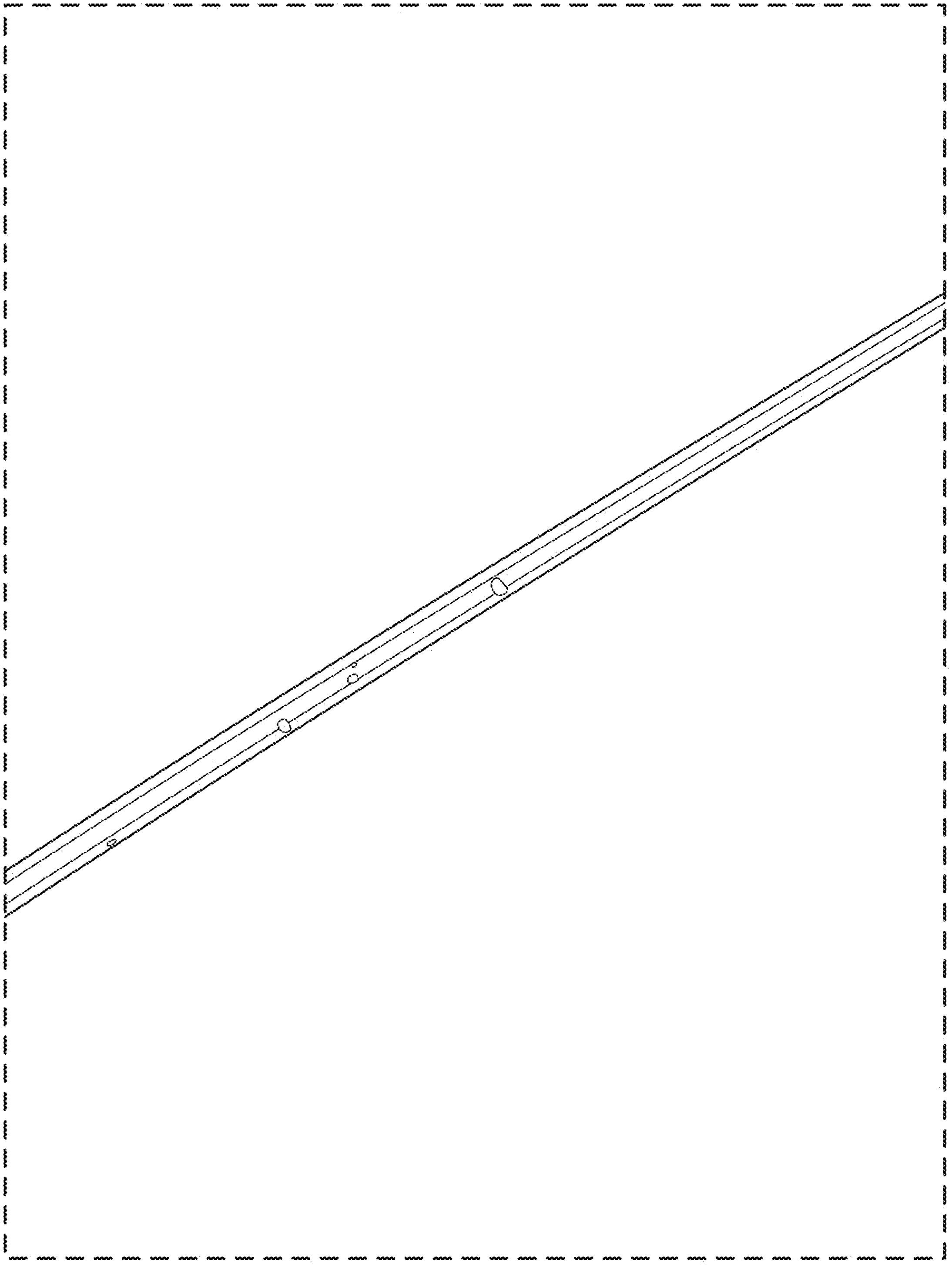

In a first example, the syringe 2102 was used to inject water at a constant pressure of about 150 psi through the hemostasis valve 2104 without moving the catheter 2106 or the catheter 2108. FIG. 23B is a photograph showing the catheter 2106 and catheter 2108 following the injection of water. FIG. 23E is an illustration thereof. As shown in FIG. 23B, bubbles are present within the lumen between the catheter 2106 and the catheter 2108.

Example 2

Figure 23F:
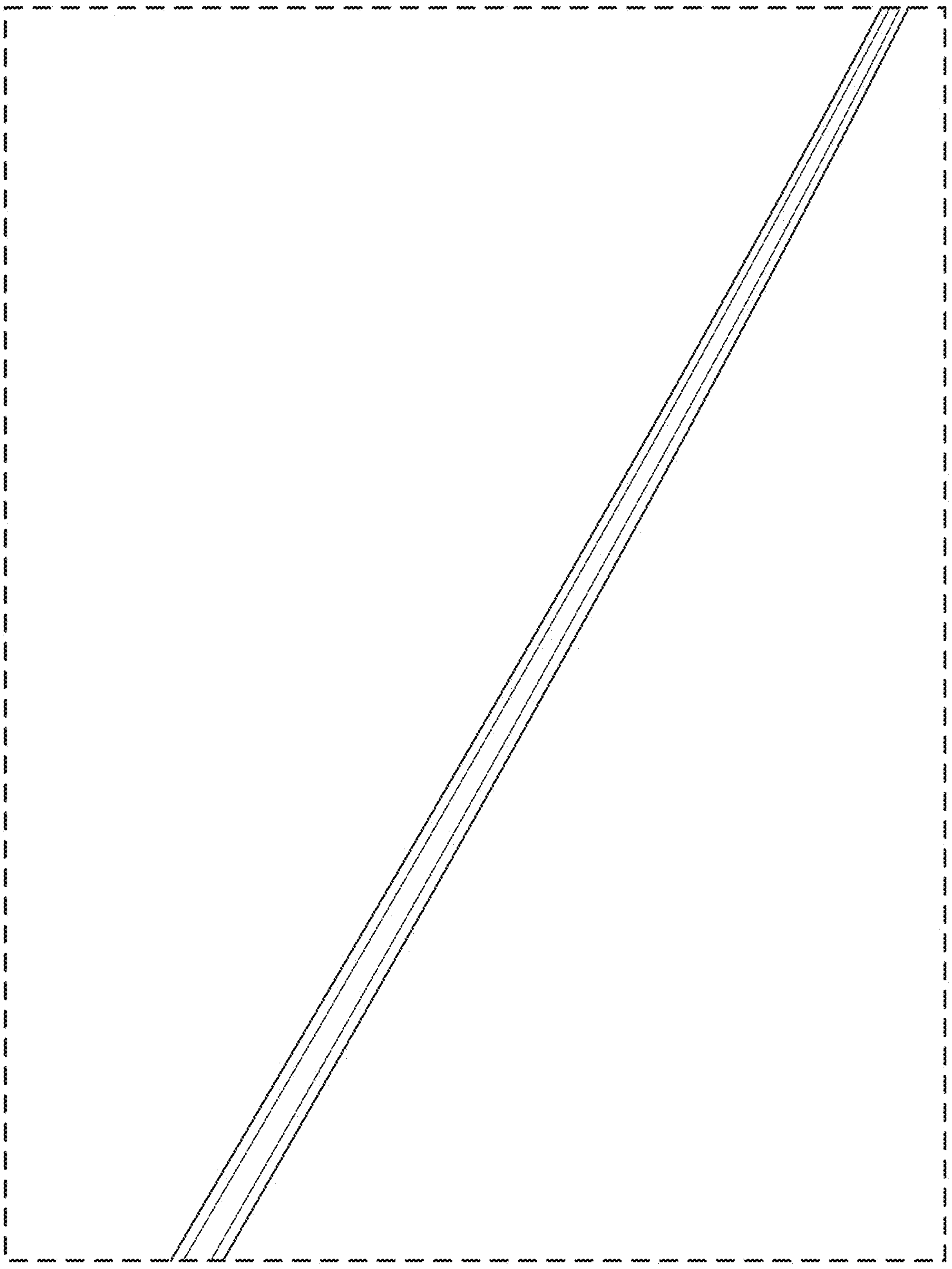

In a second example, the syringe 2102 was used to inject water at a constant pressure of about 150 psi through the hemostasis valve 2104. Shortly after beginning to inject water, axial reciprocal movement of the inner catheter 2108 was performed for about 10 seconds. The reciprocal movement was performed at a frequency of about 1 Hz (or less) and a stroke length of about 20 mm (or more). FIG. 23C is a photograph showing the catheter 2106 and the catheter 2108 following the axial reciprocal movement. FIG. 23F is an illustration thereof. As shown in FIG. 23C, the lumen between the catheter 2106 and the catheter 2108 was substantially free of bubbles.

Example 3

In a third example, an outer catheter having a diameter of about 0.071 inches and an inner catheter having a diameter of about 0.035 inches were used in the test system 2100 instead of the outer catheter 2106 and the inner catheter 2108 described with respect to Examples 1 and 2. A syringe 2102 was used to inject water at a constant pressure of about 150 psi through a hemostasis valve 2104 coupled to the outer catheter. Shortly after beginning to inject water, axial reciprocal movement of the inner catheter was performed for about 10 seconds. The reciprocal movement was performed at a frequency of about 1 Hz (or less) and a stroke length of about 20 mm (or more). Following the axial reciprocal movement, the lumen between the outer and inner catheters was found to be substantially free of bubbles by visual inspection.

Control System

Figure 24:
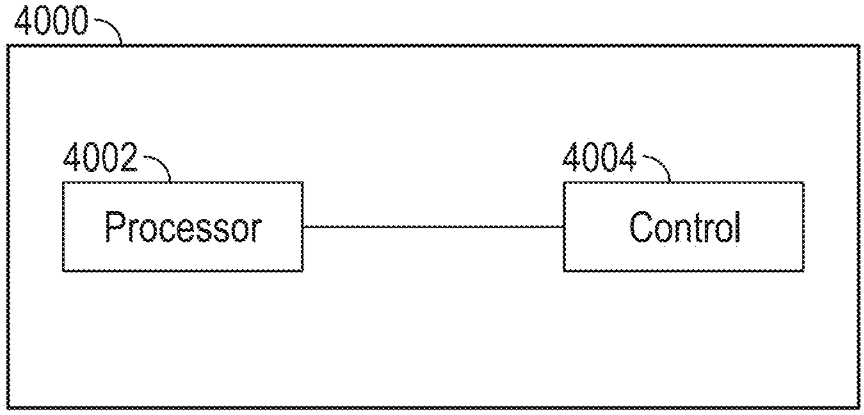
FIG. 24 depicts a schematic of a control system.

FIG. 24 illustrates a schematic view of an example of a control system 4000 that may be used to electronically control the systems and components described herein and/or perform the methods described herein. The control system 4000 may be configured to automatically adjust various motors, hub adapters, hubs, interventional devices, fluidics components (e.g., valves, pumps, etc.), and/or any other components described herein in response to commands input by an operator such as a physician. In response to command inputs by an operator, the control system 4000 may cause a series of responsive events to automatically occur.

In certain embodiments, the control system 4000 can include one or more processors 4002. The one or more processors 4002 can be configured to automatically adjust the various system components described herein in response to commands input by an operator, for example, using one or more controls 4004 of the control system 4000. A single control 4004 is shown in FIG. 24. However, any suitable number of controls may be provided to correspond to various functions of the systems described herein. For example, in certain embodiments, each interventional device may have its own unique control 4004 or set of controls 4004 that can control various functions of the interventional device (e.g., axial movement, rotational movement, supply of fluids (e.g., saline, contrast, etc.), aspiration, etc.).

In certain embodiments, one or more controls 4004 may control priming functions for one or more interventional devices. For example, one or more controls 4004 can be operated to cause the interventional devices to perform a priming procedure, as described for example, with reference to FIGS. 20A-C. For example, one or more controls 4004 can be operated to cause axial movement of one or more interventional devices relative to one or more other interventional devices (e.g., by causing axial movement of corresponding hubs and/or hub adapters). One or more controls 4004 can be operated to cause introduction of fluid into the lumen of an interventional device to prime the interventional device.

In certain embodiments, one or more controls 4004 may be operated to cause the interventional devices to perform a priming procedure, as described for example, with reference to FIGS. 21A-21B. For example, one or more controls 4004 can be operated to cause reciprocal movement (e.g., axial and/or rotational reciprocal movement) of one or more interventional devices relative to one or more other interventional devices (e.g., by causing reciprocal movement of corresponding hubs and/or hub adapters). One or more controls 4004 can be operated to cause introduction of fluid into the lumen of an interventional device to prime the interventional device (e.g., during relative reciprocal movement).

The processor 4002 may receive signals from the one or more controls 4004 and in response, initiate corresponding actions in the components of the systems described herein. For example, the processor 4002 may be configured to generate output signals that cause responsive actions to be performed by the components of the described herein.

While the foregoing describes robotically driven interventional devices and manually driven interventional devices, the devices may be manually driven, robotically driven, or any combination of manually and robotically driven interventional devices, as will be appreciated by those of skill in the art in view of the disclosure herein.

The foregoing represents one specific implementation of a robotic control system. A wide variety of different robotic control system constructions can be made, for supporting and axially advancing and retracting two or three or four or more assemblies to robotically drive interventional devices, as will be appreciated by those of skill in the art in view of the disclosure herein.

While the foregoing describes interventional devices that are driven by a drive table, other suitable robotic drive systems or mechanisms may be used to drive the interventional devices, as will be appreciated by those of skill in the art in view of the disclosure herein.

Various systems and methods are described herein primarily in the context of a neurovascular access or procedure (e.g., neurothrombectomy). However, the catheters, systems (e.g., drive systems), and methods disclosed herein can be readily adapted for any of a wide variety of other diagnostic and therapeutic applications throughout the body, including particularly intravascular procedures such as in the peripheral vasculature (e.g., deep venous thrombosis), central vasculature (pulmonary embolism), and coronary vasculature, as well as procedures in other hollow organs or tubular structures in the body.

Magnetic Coupling for Torque Transmission

In some embodiments, magnets (e.g., neodymium magnets) may be used to transmit torque through a sterile barrier. For example, one or more magnets outside of a sterile field may couple to corresponding magnets within a sterile field so that rotation of the one or more magnets outside of the sterile field can cause a corresponding rotation of the one or more magnets within the sterile field.

A torque transfer system may transmit torque from outside of the sterile field (e.g., from a hub adapter) to within the sterile field (e.g., to a hub). The torque transfer system may also be referred to as a magnetic coupling or a rotational magnetic coupling. In certain embodiments, the hub adapter may be reusable (e.g., part of the capital equipment within an operating room) and the hub may be disposable. In some embodiments, a torque transfer system can facilitate the provision of torque to rotate an interventional device coupled to the hub without a motor and motor control board on the disposable hub, which may greatly reduce equipment and procedure costs. In addition, some embodiments of the torque transfer system disclosed herein eliminate the need for cable management to each hub, increasing simplicity and reducing the cost of the system. In some embodiments, a torque transfer system can facilitate the provision of torque to rotate other instruments of a robotic surgical system (e.g., a robotic surgical system for neurovascular procedures). For example, the torque transfer system can be used to actuate one or more valves, as described herein. Instruments that are used in a robotic surgical procedure or to prepare for a robotic surgical procedure, including interventional devices, may be referred to as surgical instruments herein.

Figure 25:
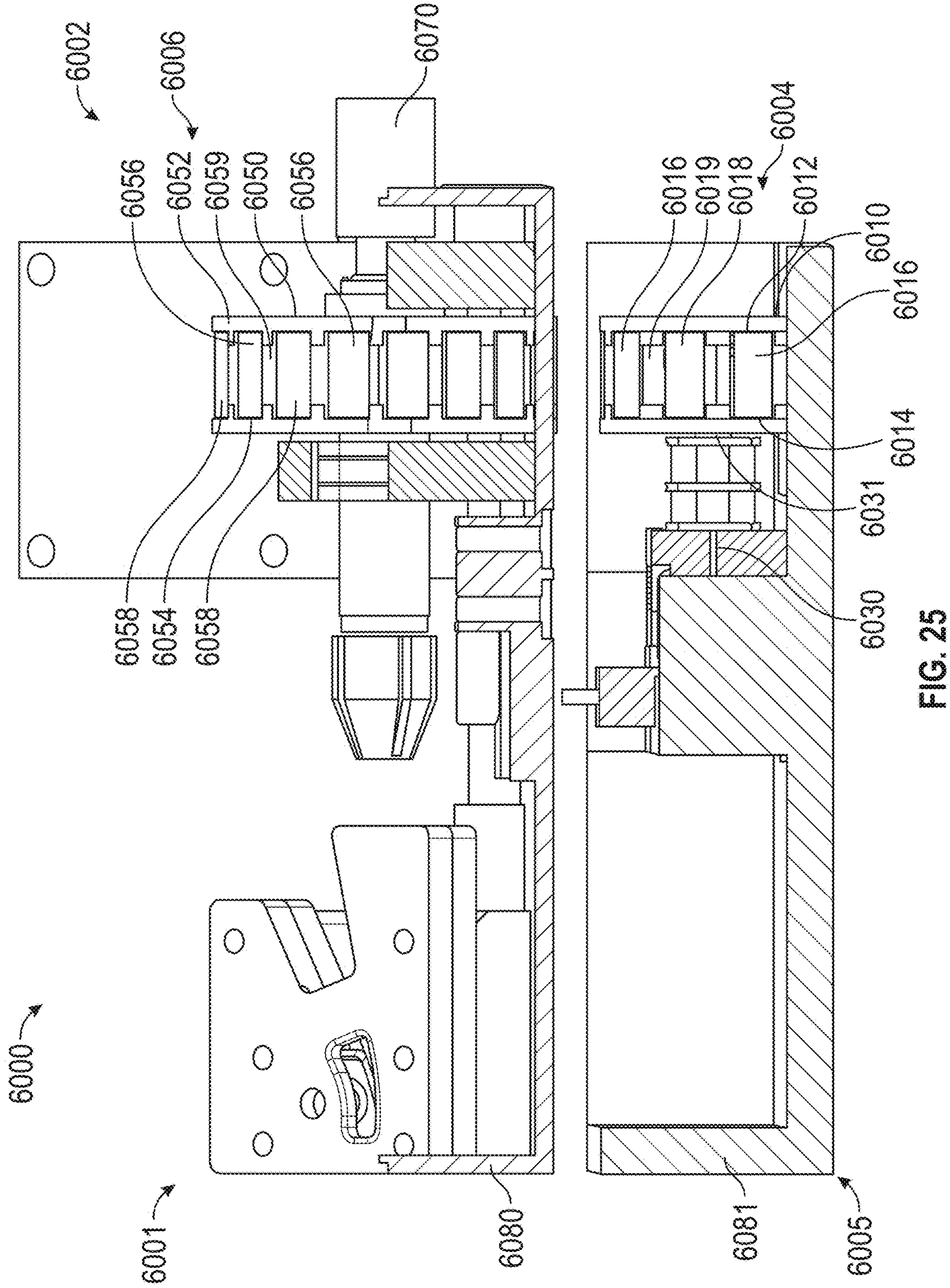
FIG. 25 is a perspective view of a portion of a robotic drive system, showing a passive torque element of a torque transfer system coupled with a hub and an active torque element of the torque transfer system coupled with a hub adapter.

FIG. 25 shows an embodiment of a portion of a robotic drive system 6000 having a hub 6001, a hub adapter 6005, and a torque transfer system 6002 that can be used with any robotic drive system embodiments disclosed herein to support and move an instrument, such as interventional device (e.g., a catheter or guidewire), that is coupled with the hub 6001 and that is configured to be inserted into a body during a medical procedure. In certain embodiments, the torque transfer system 6002 can include a drive side torque transfer element and an instrument side torque transfer element that is not physically in contact with the drive side torque transfer unit. The torque transfer elements may also be referred to as torque transfer units or torque transfer devices. FIGS. 26-30 show additional details of torque transfer system 6002. In some embodiments, increasing a width of the magnets can linearly increase the magnitude of the magnetic coupling force.

In certain embodiments, the torque transfer system 6002 can include a drive side torque transfer element and an instrument side torque transfer element that is not coupled with the drive side torque transfer element with wires or other tangible or physical components. As described herein, the drive side of the robotic drive system 6000 may be separated from the driven side by a sterile barrier. In some embodiments, the drive side of the robotic drive system 6000 may be separated by a section (e.g., a wall) of a drive table and a sterile barrier positioned over section of the drive table. The drive side torque transfer torque transfer element may be a non-sterile side torque transfer element. The driven side torque transfer element may be a sterile side torque transfer element.

As described herein, though the torque transfer system embodiments are not so limited, some embodiments of the torque transfer system disclosed herein can have a plurality of magnets configured to provide a magnetic coupling force or magnetic shear force between the drive side torque transfer element and an instrument side torque transfer element to transfer a torque from the drive side torque transfer element to the instrument side torque transfer element.

In any embodiments disclosed herein, the robotic drive system 6000 and/or any components of the robotic drive system 6000 can have any of the components, features, or other details of any other robotic drive system embodiments disclosed herein and vice versa. The hub 6001 can have any of the components, features, or other details of any other hubs disclosed herein and vice versa. The hub adapter 6005 can have any of the components, features, or other details of any other hub adapters disclosed herein and vice versa.

Some embodiments of the torque transfer system 6002 can have an active torque element 6004 (also referred to herein as an active torque transfer element) and a passive torque element 6006 (also referred to herein as a passive torque transfer element). The active torque element 6004 may be a drive side torque transfer element or a non-sterile side torque transfer element. The passive torque element 6006 may be a drive side torque transfer element or a sterile side torque element.

The active torque element 6004 can be positioned on a non-sterile side of a sterile barrier and the passive torque element 6006 can be positioned on a sterile side of the sterile barrier. In some embodiments, the passive torque element 6006 can be configured to be rotationally coupled with a surgical instrument (e.g., any of the interventional devices described herein) such that a rotation of the passive torque element 6006 will generally cause a rotation (e.g., an equal and simultaneous rotation) of the instrument coupled with the passive torque element 6006, or at least a proximal portion of the instrument coupled with the passive torque element 6006 (e.g., as long as a rotation of the instrument I and the passive torque element 6006 is not inhibited). In some embodiments, the passive torque element 6006 can be configured to be rotated by a rotation of the active torque element 6004 due to a magnetic coupling force between the active torque element 6004 and the passive torque element 6006, as will be described in greater detail herein.

The passive torque element 6006 can be part of, supported by, or otherwise coupled with the hub 6001. The active torque element can be part of, supported by, or otherwise coupled with the hub adapter 6005. A sterile barrier can be positioned between the passive torque element 6006 and the active torque element 6004 so that the active torque element 6004 is positioned on the non-sterile side of the sterile barrier and the passive torque element 6006 is positioned on the sterile side of the sterile barrier. In certain embodiments, there can be a plurality of torque transfer systems 6002, each coupled with separate hubs 6001 or otherwise.

In certain embodiments, a motor 6030 can be coupled with the active torque element 6004, below the sterile barrier. The motor 6030 may cause rotation of the active torque element 6004, which may in turn cause rotation of the passive torque element 6006 due to a magnetic coupling force between the active torque element 6004 and the passive torque element 6006.

In certain embodiments, the hub 6001 can include a support housing 6080. As described herein, the hub 6001 may be provided with rollers, which may be coupled to the support housing 6080. The hub adapter 6005 can include support housing 6081. As described herein, the hub adapter 6005 may be provided with rollers, which may be coupled to the support housing 6081.

The hub 6001 can be configured to move in an axial direction, as described herein, so as to move the passive torque element 6006 and any interventional device coupled thereto in an axial direction. The robotic drive system 6000 can be configured such that the passive torque element 6006 can be rotated so as to move (e.g., rotate) a surgical instrument (e.g., an interventional device) coupled with the hub 6001 without any puncture holes in the sterile barrier. In other words, this can be achieved without any electrical or communication wires, drive components, structural components, or other tangible components connecting the hub with any devices or components on the non-sterile side of the sterile barrier or passing through the sterile barrier.

In certain embodiments, the interventional device coupled with the hub 6001 can be a guidewire, a guide catheter, a procedure catheter, or an access or insert catheter. In certain embodiments, the procedure catheter can be an aspiration catheter, an embolic deployment catheter, a stent deployment catheter, a flow diverter deployment catheter, a diagnostic angiographic catheter, a stent retriever catheter, a clot retriever, a balloon catheter, a catheter to facilitate percutaneous valve repair or replacement, an ablation catheter, or any other suitable or desired device.

Some embodiments of the torque transfer system 6002 can use magnets (e.g., without limitation, neodymium magnets) to transmit torque from an active torque element through a sterile barrier from a non-sterile side of the sterile barrier (e.g., a capital equipment side of the sterile barrier) to the hub 6001 on the sterile side (e.g., a disposable side) of the sterile barrier. This can, in some embodiments, eliminate any penetrations through the sterile barrier and eliminate the need for a motor and motor control board on the disposable hub or hubs, which can greatly increase patient safety and reduce a cost of procedures. In addition, the embodiments disclosed herein can eliminate or reduce the need for cable management to each hub, increasing simplicity of the system.

The magnets in any embodiments of the torque transfer system 6002 disclosed herein can be arranged in a circle or in a cylindrical arrangement (e.g., about a central axis). For example, the active torque transfer element 6004 can include a plurality of magnets arranged in a circle or cylindrical arrangement about a first central axis (such as central axis A6 shown in FIG. 26). The passive torque transfer element 6006 can include a plurality of magnets arranged in a circular or cylindrical arrangement about a second central axis (such as central axis A7 shown in FIG. 27). In some embodiments, the first central axis can be parallel with the second central axis. In some embodiments, the first central axis and/or the second central axis can be parallel with a central axis of an interventional device coupled to the passive torque element.

A magnetic field can be created between the active torque element 6004 and the passive torque element 6006. Such devices can be configured such that a rotation of the active torque element 6004 on the non-sterile side of a sterile barrier will exert a rotational force or torque on the passive torque element 6006 and a surgical instrument (e.g.) interventional device coupled therewith. This torque can cause the passive torque element 6006 and the surgical instrument coupled therewith to rotate in response to a rotation of the active torque element 6004 when the active torque element 6004 and the passive torque element 6006 are magnetically coupled, as long as the passive torque element 6006 and/or the interventional device coupled with the passive torque element 6006 are not prevented from rotating by external force(s). In other words, in some embodiments, the torque that can be exerted by the active torque element 6004 on the passive torque element 6006 can cause the passive torque element 6006 and any interventional device coupled therewith to rotate when the active torque element 6004 and the passive torque element 6006 are magnetically coupled (e.g., as long as any torque load on the passive torque element 6006 and/or the instrument, if any, coupled with the passive torque element 6006 is not greater than the shear force created by the magnetic field between the passive torque element 6006 and active torque element 6004).

In some embodiments, a rotation of the passive torque element 6006 can be delayed in that the passive torque element 6006 may rotate in response to a rotation of the active torque element 6004, but after a short delay of time or lag time. This delay can, in some embodiments and without limitation, result from the elasticity of the shear force between the active torque element 6004 and the passive torque element 6006 and/or from any forces inhibiting a rotation of the passive torque element 6006, such as friction and/or inertial forces in the passive torque element 6006, friction and/or inertial forces or other torque type forces acting on a surgical instrument (e.g., interventional device) coupled with the passive torque element 6006. In some embodiments, for the passive torque element 6006 and an instrument coupled therewith to rotate, the shear or torque force provided by the magnetic field between the active torque element 6004 and passive torque element 6006 must be greater than any force inhibiting rotation acting on the passive torque element 6006 and/or surgical instrument. Because of the arrangement of the active torque element 6004 relative to the passive torque element 6006, the passive torque element 6006 will, in some embodiments, rotate in an opposite direction as compared to the direction that the active torque element 6004 rotates in, similar to a driven gear.

In any embodiment, as mentioned, a sterile barrier can separate the active torque element 6004 from the passive torque element 6006. The magnetic field between the active torque element 6004 and passive torque element 6006 can cause the torque that allows the passive torque element 6006 to rotate in response to a rotation of the active torque element 6004, without requiring any wiring or other connections to pass through the sterile barrier.

With reference to FIG. 25, in some embodiments, the active torque element 6004 can have a magnet element 6010 that has a plurality of opposite poles, typically arranged in alternating positions such that a first magnet 6016 of the magnet element 6010 has a north (or positive) pole facing radially outwardly from the magnet element 6010 and a second magnet 6018 adjacent to the first magnet 6016 has a south (or negative) pole facing radially outwardly. The next magnet in sequence can be another first magnet 6016 having a north pole facing radially outwardly from the magnet element 6010, and so on in this alternating arrangement. In some embodiments, the plurality of first and second magnets 6016, 6018 can be supported between a first support 6012 and a second support 6014.

In some embodiments, the magnet element 6010 can have 8 or less (e.g., without limitation, 4, 6, or 8) different poles or magnets 6016, 6018. In some embodiments, the magnet element 6010 can have from 8 to 20 or more different poles or magnets 6016, 6018, or from 10 to 18 or more different poles or magnets 6016, 6018, or from 12 to 18 or more different poles or magnets 6016, 6018. In some embodiments, the magnet element 6010 can have from 12 to 20 different poles or magnets 6016, 6018, or from 12 to 20 or more different poles or magnets 6016, 6018. In some embodiments, the magnet element 6010 can have 12 or more (e.g., without limitation, 12, 14, 16, 18, 20, 22, 24, or more) different poles or magnets 6016, 6018. A higher number of poles can, in some embodiments, increase a resolution of the rotational control of the instrument to provide a finer level of control for rotating or torquing the instrument to a surgeon.

In any embodiments disclosed herein, the robotic drive system 6000 can have two or more, three or more, four or more torque transfer systems, wherein each torque transfer system, can have an active torque element 6004 and a passive torque element 6006. In any embodiments disclosed herein, the robotic drive system 6000 can have two or more, three or more, four or more torque transfer systems, wherein any of the torque transfer systems can have a different active torque element 6004 and/or passive torque element 6006 than another of the torque transfer systems, in terms of number of magnets, type of magnets, size of the magnets, the active torque element, and/or the passive torque element 6006.

In some embodiments, the first and second magnets 6016, 6018 can have an elongated cuboid shape. The magnet element 6010 can have a space 6019 between each adjacent magnet. In some embodiments, each of the first and second magnets 6016, 6018 can have a wedge shape or arc segment shape so that each of the first and second magnets 6016, 6018 can be tightly fit together to minimize or eliminate all spacing between the first and second magnets 6016, 6018.

Figure 26:
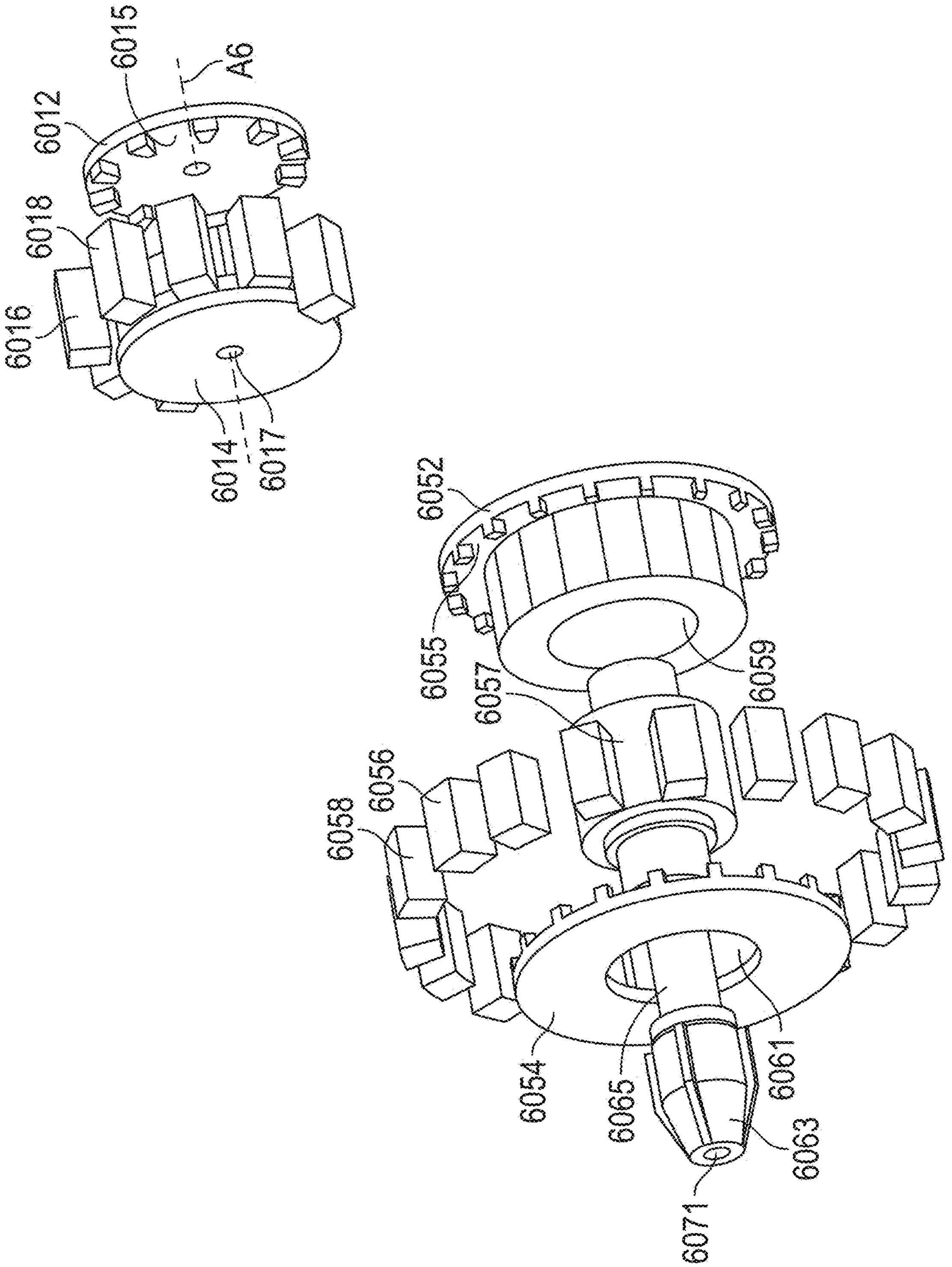
FIG. 26 is an exploded view of the active torque element and the passive torque element of FIG. 25.
Figure 27:
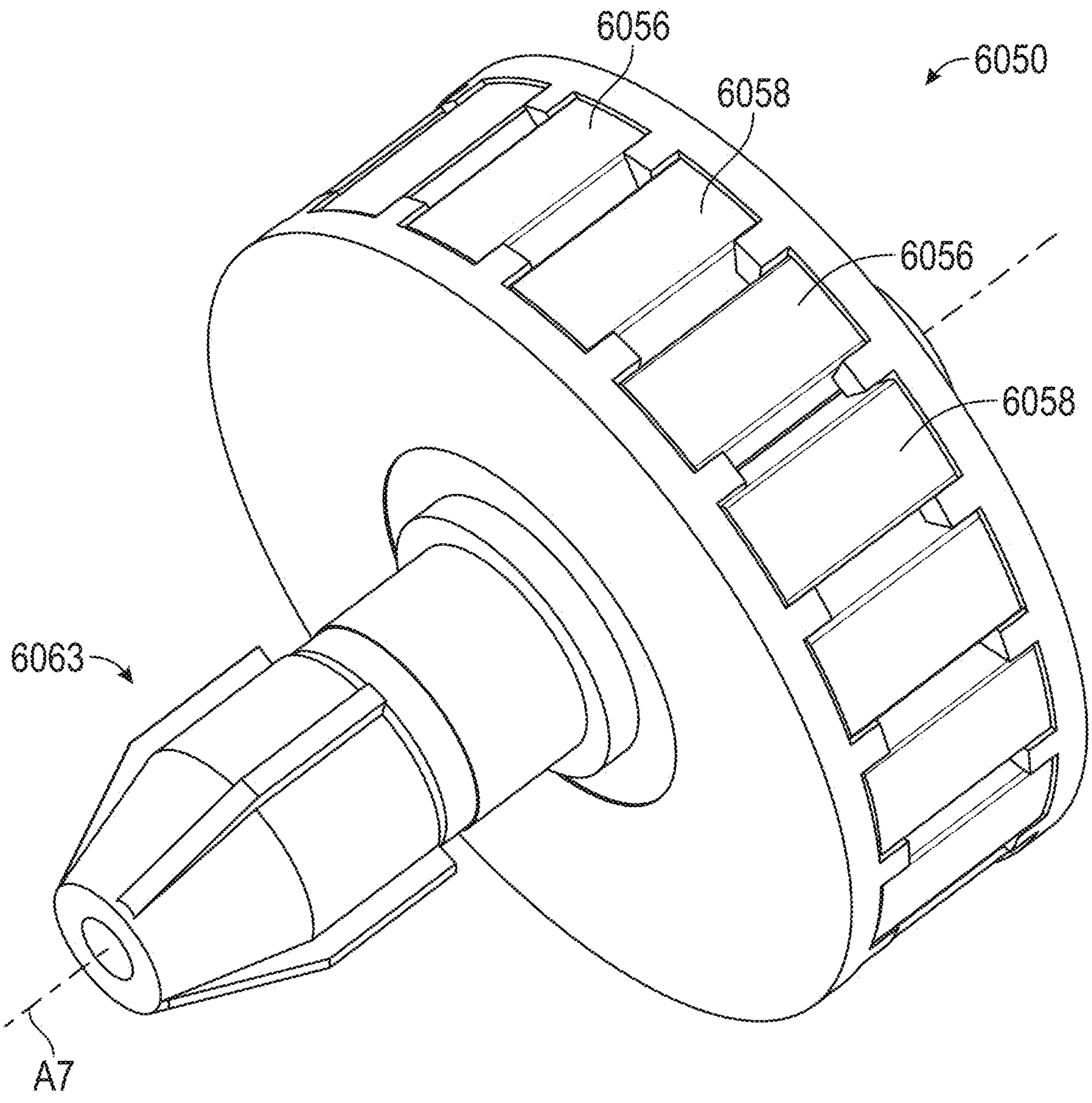
FIG. 27 is a perspective view of the passive torque element of FIG. 25.
Figure 28:
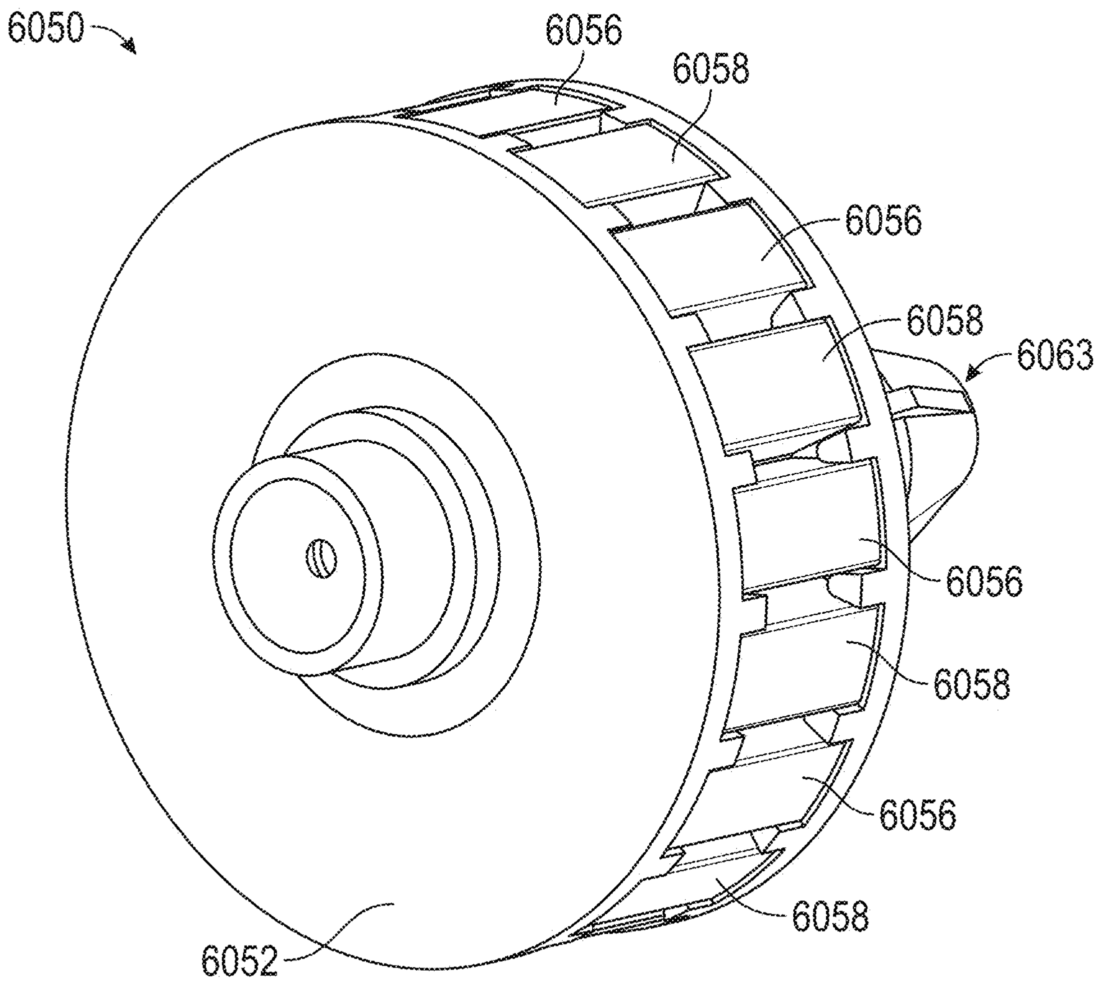
FIG. 28 is a second perspective view of the passive torque element of FIG. 25.

As shown in FIG. 26, the first and second supports 6012, 6014 can have a plurality of grooves or recesses 6015 that are configured to receive and support the first and second magnets 6016, 6018. The first and second supports 6012, 6014 can be coupled together, or can be monolithic or made from a single piece of material. In some embodiments, as shown, the first and second supports 6012, 6014 can have a circular or disclike shape. The magnet element 6010 can be axially and rotationally coupled with the drive motor 6030. The drive motor 6030 can be configured to rotate the magnet element 6010 in response to a user input, for example and without limitation, when a user desires to rotate a catheter, a guidewire, or any other desired interventional device (or other surgical instrument) coupled with the passive torque element 6006. In certain embodiments, the magnets can be coupled with the first and/or second supports or other components of the magnet element with screws, pins, adhesive, slots, grooves, and/or other mechanical fasteners.

Some embodiments of the magnets can have features configured to lock with or secure to complementary features on the first and/or second support. For example and without limitation, some embodiments of the magnets can have T-shaped grooves or other locking grooves or channels in a radially inward portion of the magnet configured to receive and/or engage with complementary shaped projections or features on a radially outwardly facing portion of the first and/or second support. Similarly, for example and without limitation, some embodiments of the magnets can have T-shaped protrusions on a radially inward portion thereof configured to slide into and engage with T-shaped slots on a radially outwardly facing surface of the first and/or second support. In some embodiments, each magnet can have a slot (e.g., a T-slot) on one side and a complementary projection (e.g., a T) on the other, opposite side surface so that the magnets are configured to fit together during assembly and secure to one another to resist movement in a radial direction, once in an assembled state or position.

As shown in FIG. 26, Some embodiments of the magnet element 6010 can have an opening 6017 passing therethrough. The opening 6017 can be configured to receive a shaft 6031 (as shown in FIG. 25) of the motor 6030 therethrough. The opening 6017 can have a flat surface for indexing with the shaft 6031 or to prevent the shaft 6031 from rotating relative to the magnet element 6010 in an assembled state.

In some embodiments, the magnet element 6010 can be formed from a single magnet having a plurality of alternating poles or having a plurality of portions that each has a north pole or a south pole and which are arranged in an alternating arrangement. For example and without limitation, the magnet element 6010 can be formed from a single magnet having 10 alternating poles or regions of alternating polarity (i.e., 5 north poles and 5 south poles, in alternating arrangement), or 12 or more alternating poles or regions of alternating polarity (i.e., 6 north poles and 6 south poles, in alternating arrangement), or 14 or more alternating poles or regions of alternating polarity (i.e., 7 north poles and 7 south poles, in alternating arrangement), or 16 or more alternating poles or regions of alternating polarity (i.e., 8 north poles and 8 south poles, in alternating arrangement), or 18 or more alternating poles or regions of alternating polarity (i.e., 9 north poles and 9 south poles, in alternating arrangement), or 20, 22, or 24 or more alternating poles.

Similarly, in some embodiments, with reference to FIG. 25, the passive torque element 6006 can have a magnet element 6050 that can have a plurality of north and south poles, typically arranged in an alternating fashion such that a first magnet 6056 of the magnet element 6050 has a north (or positive) pole facing radially outwardly from the magnet element 6050 and such that a second magnet 6058 adjacent to the first magnet 6056 has a south (or negative) pole facing radially outwardly. The next magnet in sequence can be another first magnet 6056 having a north pole facing radially outwardly from the magnet element 6050, and so on in this alternating arrangement.

Any embodiments of the magnet element 6050 can be similarly configured as compared to any of the embodiments of the magnet element 6010 described above—e.g., without limitation, any embodiments of the magnet element 6050 can have wedge or truncated pie shaped first and second magnets (e.g., as described with respect to the first and second magnets 6116, 6118 of the magnet element 6110 as shown in FIGS. 36-41). Any embodiments of the magnet element 6050 can have any of the arrangements and numbers of magnets as described above for magnet element 6010.

Figure 29:
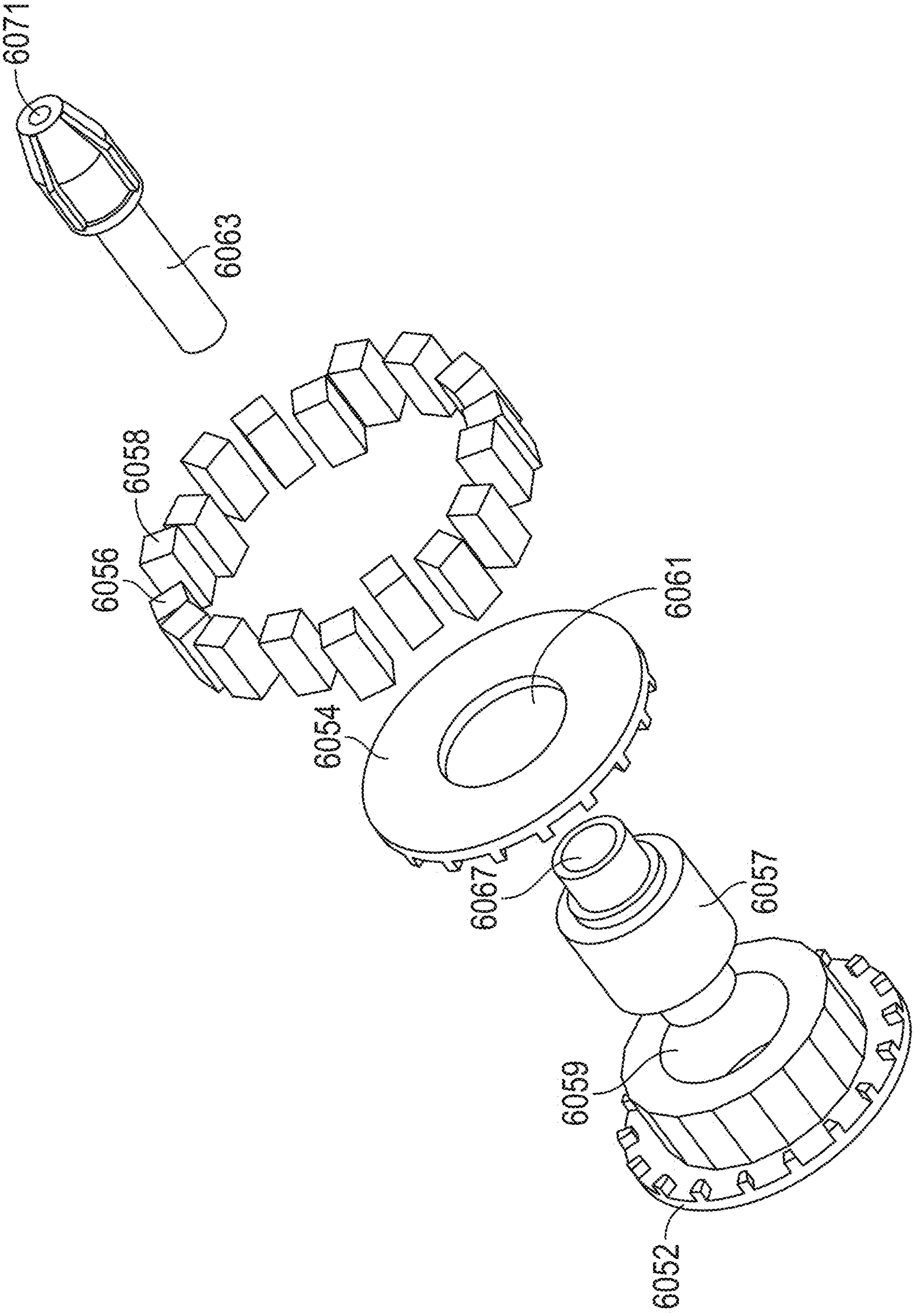
FIG. 29 is an exploded view of the passive torque element of FIG. 25.
Figure 30:
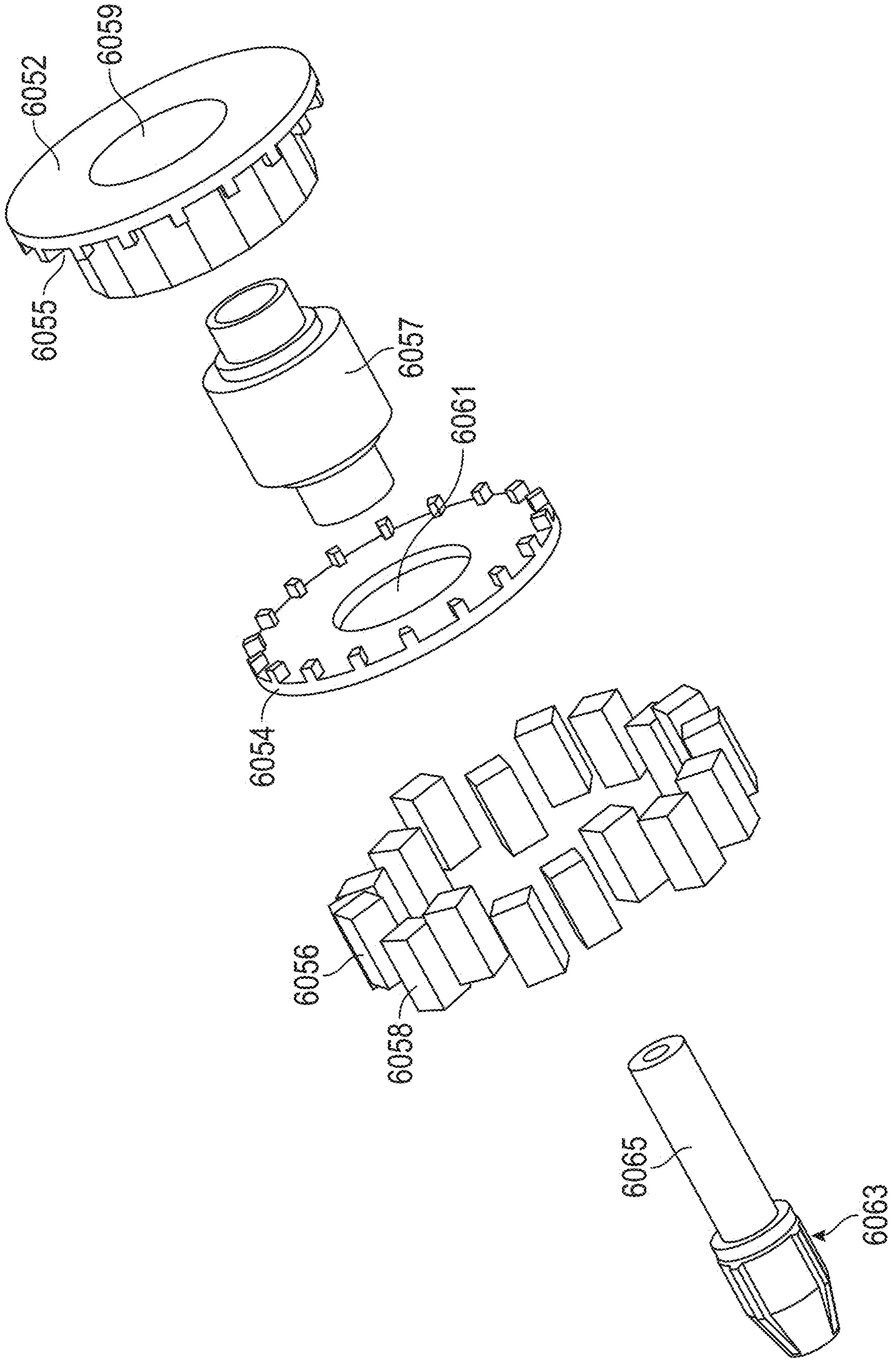
FIG. 30 is a second exploded view of the passive torque element of FIG. 25.

In some embodiments, the first and second magnets 6056, 6058 can have an elongated cuboid shape, as shown in FIGS. 29 and 30. The magnet element 6050 can have a space or an opening 6059 between each adjacent magnet. In some embodiments, each of the first and second magnets 6056, 6058 can have a wedge shape or arc segment shape so that each of the first and second magnets 6056, 6058 can be tightly fit together to minimize or eliminate all spacing between the first and second magnets 6056, 6058.

In some embodiments, the magnet element 6050 can have 8 or less (e.g., without limitation, 4, 6, or 8) different poles or magnets 6056, 6058. In some embodiments, the magnet element 6050 can have from 8 to 12 different poles or magnets 6056, 6058, or from 8 to 14 or more different poles or magnets 6056, 6058. In some embodiments, the magnet element 6050 can have from 12 to 20 different poles or magnets 6056, 6058, or from 12 to 20 or more different poles or magnets 6056, 6058. In some embodiments, the magnet element 6050 can have 12 or more (e.g., without limitation, 12, 14, 16, 18, or 20 or more) different poles (e.g., alternating poles) or magnets 6056, 6058.

In some embodiments, the plurality of first and second magnets 6056, 6058 can be supported between a first support 6052 and a second support 6054. The first and second supports 6052, 6054 can have a plurality of grooves or recesses 6055 that are configured to receive and support the first and second magnets 6056, 6058. The first and second supports 6052, 6054 can be coupled together, or can be monolithic or made from a single piece of material. In some embodiments, as shown, the first and second supports 6052, 6054 can have a circular or disclike shape. The magnet element 6050 can be axially and rotationally coupled with an instrument coupling element 6070 that can be configured to receive an interventional device and to rotate the interventional device in response to a rotation of the magnetic element 6050.

As shown in FIG. 26, some embodiments of the magnet element 6050 can have a hub component 6057 configured to be at least partially received within an opening 6059 of the second support 6054 and an opening 6061 of the first support 6052. The opening 6059 can pass axially through the second support 6054. The opening 6061 can pass axially through the first support 6052. The hub component 6057 can be fixedly coupled with the first and second supports 6052, 6054. In some embodiments, the first support 6052, the second support 6054, and the hub component 6057 can each be fabricated as individual, separate pieces. In some embodiments, the first support 6052, the second support 6054, and the hub component 6057 can be fabricated as combined, single monolithic piece, along with the plurality of grooves or recesses 6055 and the opening 6059.

An instrument coupler 6063 can have a cylindrical body portion 6065 that can be received within an opening 6067 passing axially through the hub component 6057. In some embodiments, the hub component 6057 can include a tapered opening which can be configured to receive the cylindrical body portion 6065. In some embodiments, the cylindrical body portion 6065 can be coupled to the hub component 6057 and biased from becoming disengaged from the hub component 6057 using friction or with an interference fit. In some embodiments, the cylindrical body portion 6065 can be a locking luer component used for guidewires. In some embodiments, the hub component 6057 can include shoulders for bearings to ride along.

An opening 6071 can extend axially through the instrument coupler 6063. The instrument coupler 6063 can be configured to selectively tighten and constrict around an outside surface of a surgical instrument, such as an interventional device (e.g., a guidewire or catheter), extending through the instrument coupler 6063 to prevent the instrument from moving in an axial direction relative to the instrument coupler 6063.

In some embodiments, the magnet element 6050 can be formed from a single magnet having a plurality of alternating poles or having a plurality of portions that each has a north pole or a south pole and which are arranged in an alternating arrangement. For example and without limitation, the magnet element 6050 can be formed from a single magnet having 10 alternating poles or regions of alternating polarity (i.e., 5 north poles and 5 south poles, in alternating arrangement), or more than 10 alternating poles or regions of alternating polarity, or having 12 alternating poles or regions of alternating polarity (i.e., 6 north poles and 6 south poles, in alternating arrangement), or more than 12 alternating poles or regions of alternating polarity. In some embodiments, the magnet element 6050 can be formed from a single magnet having 16 alternating poles or regions of alternating polarity (i.e., 8 north poles and 8 south poles, in alternating arrangement), or more than 16 alternating poles or regions of alternating polarity, or having 18 alternating poles or regions of alternating polarity (i.e., 9 north poles and 9 south poles, in alternating arrangement), or more than 18 alternating poles or regions of alternating polarity.

The magnet element 6050 of the passive torque element 6006 can have a larger radius, in some embodiments, than the magnet element 6010 of the active torque element 6004. This can increase the torque applied to an interventional device coupled with the passive torque element 6006 and also increase a resolution of the rotation of the interventional device coupled with the passive torque element 6006.

A support housing 6080 that the passive torque element 6006 can be supported by or coupled with can be configured to translate in any desired direction (e.g., without limitation, in any axial direction, which is a direction parallel to a centerline axis (represented by axis A8 in FIG. 31) of an interventional device coupled with the passive torque element 6006). The support housing 6080 can have one or more bearings, slides, wheels, or other features to facilitate a movement of the support housing in at least an axial direction.

In some embodiments, as described herein, a hub adapter 6005 on a non-sterile side of the sterile barrier can be used to move the support housing—for example and without limitation, as in any other embodiments disclosed herein using magnets. Any such components can be combined with any of the components of the passive torque element 6006 in any combination to enable such axial movement of the support housing 6080.

In some embodiments, the magnets can be neodymium magnets. Any of the support components that the magnets are coupled with can be made from any suitable or desired plastic material, metal material, or otherwise. In some embodiments, the first support 6012, the second support 6014, the first support 6052, and/or the second support 6054 can be molded plastic or metal, or can be 3D printed plastic or metal.

In some embodiments, as mentioned, the torque elements can use alternating polarity neodymium magnets arranged in a circle. In some embodiments, the torque elements (e.g., the active torque element or the passive torque element) can have 10 magnets arranged in a circle, or any number disclosed herein or desired. The circle of any embodiments of the torque elements disclosed herein can have an outer diameter of 1 inch, or approximately 1 inch, or from 0.5 inch to 2 inches, or of any value or from and to any values disclosed in the foregoing range. In some embodiments, the passive torque element can have 18 magnets arranged in a circle. The circle can have an outer diameter of 1.48 inch or approximately 1.5 inch, or from 0.75 inch to 2.5 inches, or of any value or from and to any values disclosed in the foregoing range. In some embodiments, the passive torque element can have a larger outer diameter than the active torque element to create a gear reduction that can increase the torque exerted on the instrument as compared to a smaller passive torque element. The larger diameter of the passive torque element can also result in the magnet element of the passive torque element being in closer proximity with the sterile barrier, in some embodiments.

In some embodiments, a distance between the active torque element and the passive torque element can be from 0 to 0.35 inches or approximately 0.35 inches, or more than 0.35 inches. A strength of the magnetic field between the active torque element and the passive torque element will decrease as the space between them increases. The strength of the field decreases with distance squared, so the torque transmitted drops off exponentially after a certain distance. At a barrier thickness of 0.185 inches, in some embodiments, the torque transfer system 6002 can transmit a peak torque of 46 mNm or approximately 46 mNm. In some embodiments, a guidewire and insert catheter will experience torque forces that can range from 10 or to 20 mNm. Accordingly, in some embodiments, the torque transfer system 6002 can be configured to transmit torque from 0 to 25 mNm or approximately 25 mNm, or from 0 to 20 mNm or approximately 20 mNm, or to transmit a peak torque of 20 mNm or approximately 20 mNm, or 25 mNm or approximately 25 mNm, or 30 mNm or approximately 30 mNm.

Figure 31:
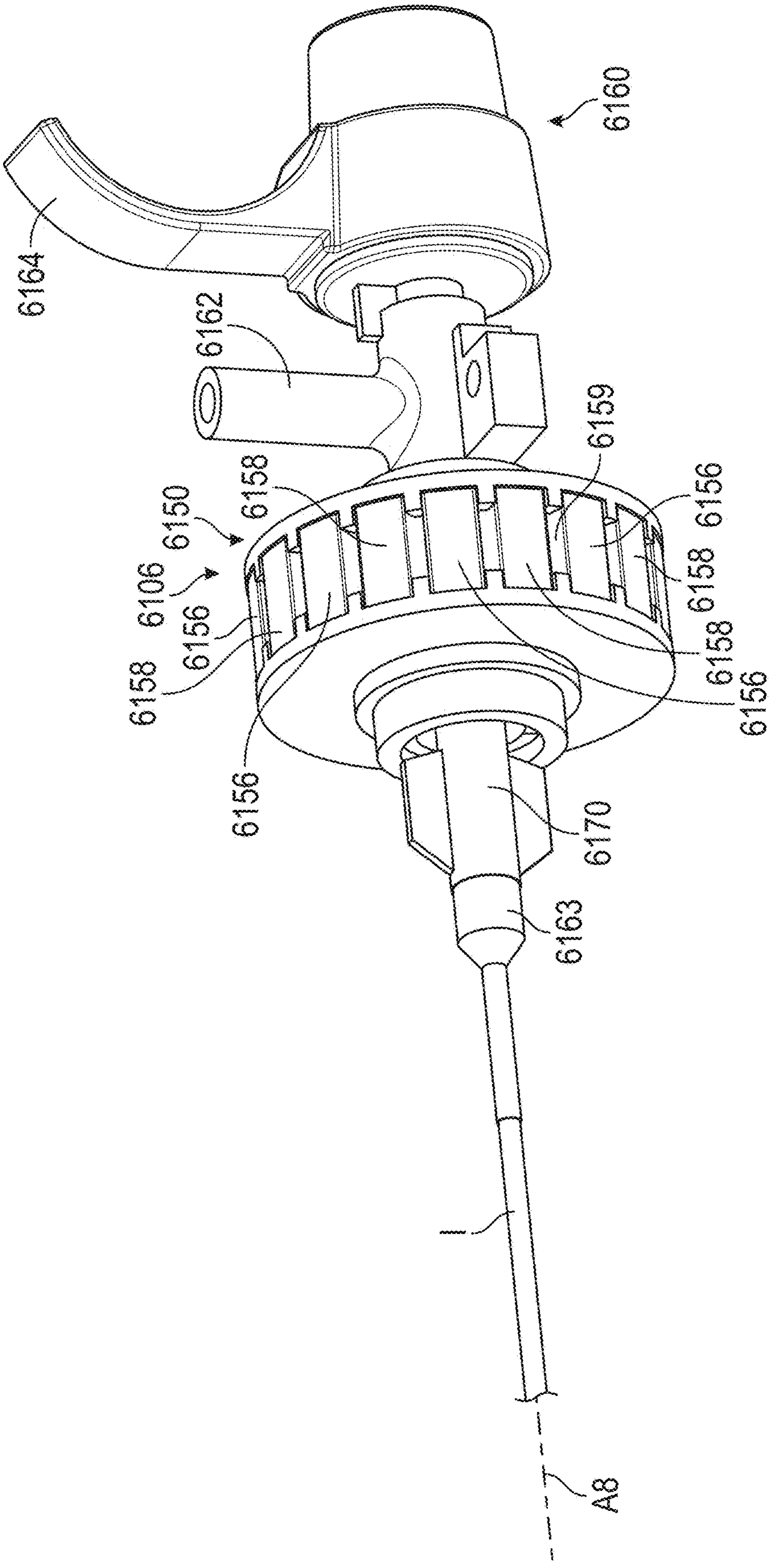
FIG. 31 is a perspective view of an embodiment of a passive torque element coupled with a rotating hemostatic valve.
Figure 32:
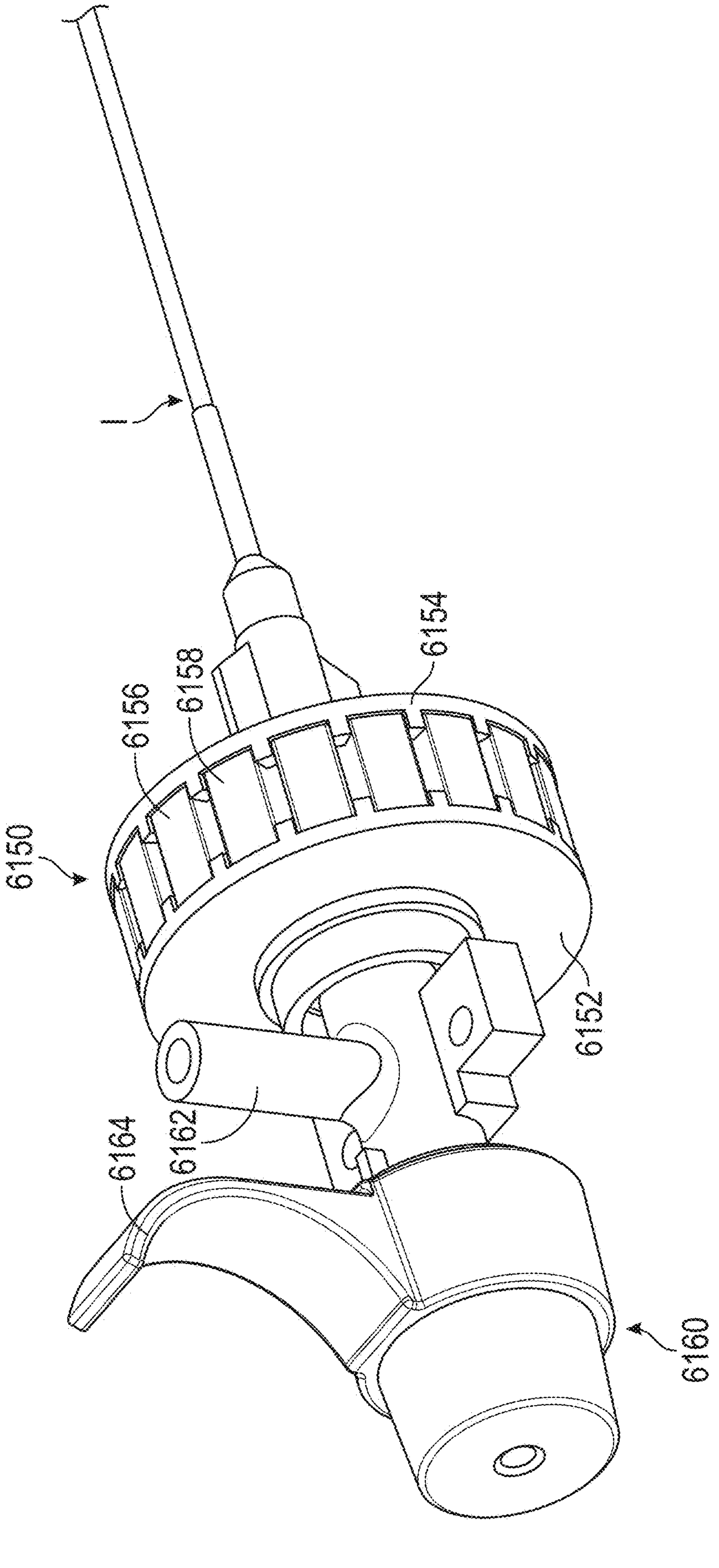
FIG. 32 is a second perspective view of the passive torque element and hemostatic valve of FIG. 31.

FIG. 31 is a perspective view of an embodiment of a passive torque element 6106 coupled with an interventional device I, which may be any of the interventional devices described herein. In any embodiments disclosed herein, the passive torque element 6106 can have any of the components, features, or other details of any other passive torque element embodiments disclosed herein, including without limitation any embodiments of the passive torque element 6006 disclosed herein. Additionally, any embodiments of the passive torque element 6106 can be configured to receive and couple with any desired interventional device I.

For example and without limitation, the passive torque element 6106 can have a magnet element 6150 that has a plurality of opposite poles, typically arranged in an alternating fashion such that a first magnet 6156 of the magnet element 6150 has a north (or positive) pole facing radially outwardly from the magnet element 6150 and such that a second magnet 6158 adjacent to the first magnet 6156 has a south (or negative) pole facing radially outwardly. The next magnet in sequence can be another first magnet 6156 having a north pole facing radially outwardly from the magnet element 6150, and so on in this alternating arrangement.

Figure 33:
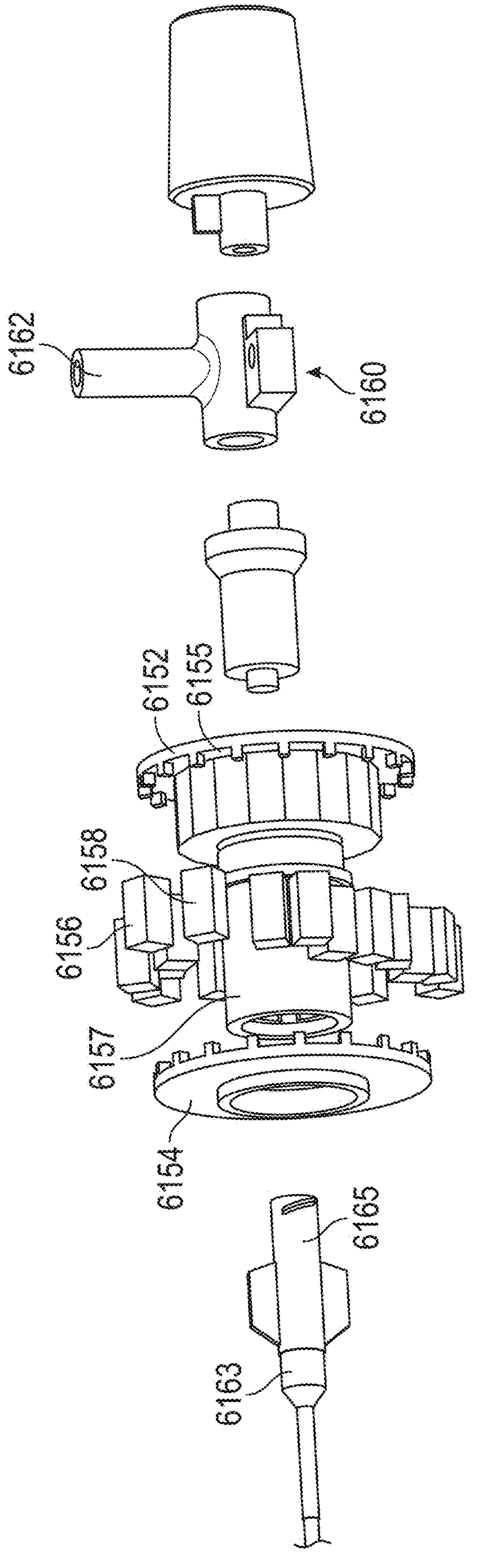
FIG. 33 is an exploded view of the passive torque element and hemostatic valve of FIG. 31.

In some embodiments, the first and second magnets 6156, 6158 can have an elongated cuboid shape, as shown in FIG. 33. The magnet element 6150 can have a space 6159 between each adjacent magnet. In some embodiments, each of the first and second magnets 6156, 6158 can have a wedge shape or arc segment shape so that each of the first and second magnets 6156, 6158 can be tightly fit together to minimize or eliminate all or excess spacing between the first and second magnets 6156, 6158.

In some embodiments, the magnet element 6150 can have 8 or less (e.g., without limitation, 4, 6, or 8) different poles or magnets 6156, 6158. In some embodiments, the magnet element 6150 can have from 8 to 12 different poles or magnets 6156, 6158, or from 8 to 14 or more different poles or magnets 6156, 6158. In some embodiments, the magnet element 6150 can have from 12 to 20 different poles or magnets 6156, 6158, or from 12 to 20 or more different poles or magnets 6156, 6158. In some embodiments, the magnet element 6150 can have 12 or more (e.g., without limitation, 12, 14, 16, 18, or 20 or more) different poles or magnets 6156, 6158.

An instrument coupler 6163 can have a cylindrical body portion 6165 that can be received within an opening passing axially through the hub component 6157. An opening can extend axially through the instrument coupler 6163. The instrument coupler 6163 can be configured to selectively tighten and constrict around an outside surface of an interventional device (e.g., a guidewire or catheter) extending through the instrument coupler 6163 to prevent the instrument from moving in an axial direction relative to the instrument coupler 6163.

As shown in FIG. 31, the instrument coupler 6163 and/or magnet element 6150 can be coupled to a hemostasis valve, such as a rotating hemostasis valve (RHV) 6160. The RHV 6160 can include a fluid port 6162 that can be placed in fluid communication with a fluidics system for the delivery of fluids (e.g., saline and/or contrast media) to the instrument I and/or for aspiration of fluids from the instrument I. The RHV 6160 can include a handle or lever 6164 that can be manually actuated to control the RHV 6160. In other embodiments, the RHV 6160 may be robotically actuated.

The RHV 6160 can be configured to receive a more proximal interventional device therethrough. The RHV 6160 can be actuatable between various states to allow for and/or restrict movement of the interventional device therethrough and to allow for and/or prevent fluid flow therethrough. For example, the RHV 6160 can be actuatable between a first fully open state, a second partially opened (low sealing force state) for sealing around an interventional device but permitting sliding movement of the interventional device, a third state for sealing around an interventional device for high pressure management, and a fourth completely closed state in the absence of any interventional devices extending therethrough.

In some embodiments, the plurality of first and second magnets 6156, 6158 can be supported between a first support 6152 and a second support 6154. The first and second supports 6152, 6154 can have a plurality of grooves or recesses 6155 that are configured to receive and support the first and second magnets 6156, 6158. The first and second supports 6152, 6154 can be coupled together, or can be monolithic or made from a single piece of material. In some embodiments, as shown, the first and second supports 6152, 6154 can have a circular or disclike shape. The magnet element 6150 can be axially and rotationally coupled with an instrument coupling element 6170 that can be configured to receive a surgical instrument I (e.g., an interventional device) and to rotate the surgical instrument I in response to a rotation of the magnetic element 6150.

Figure 34:
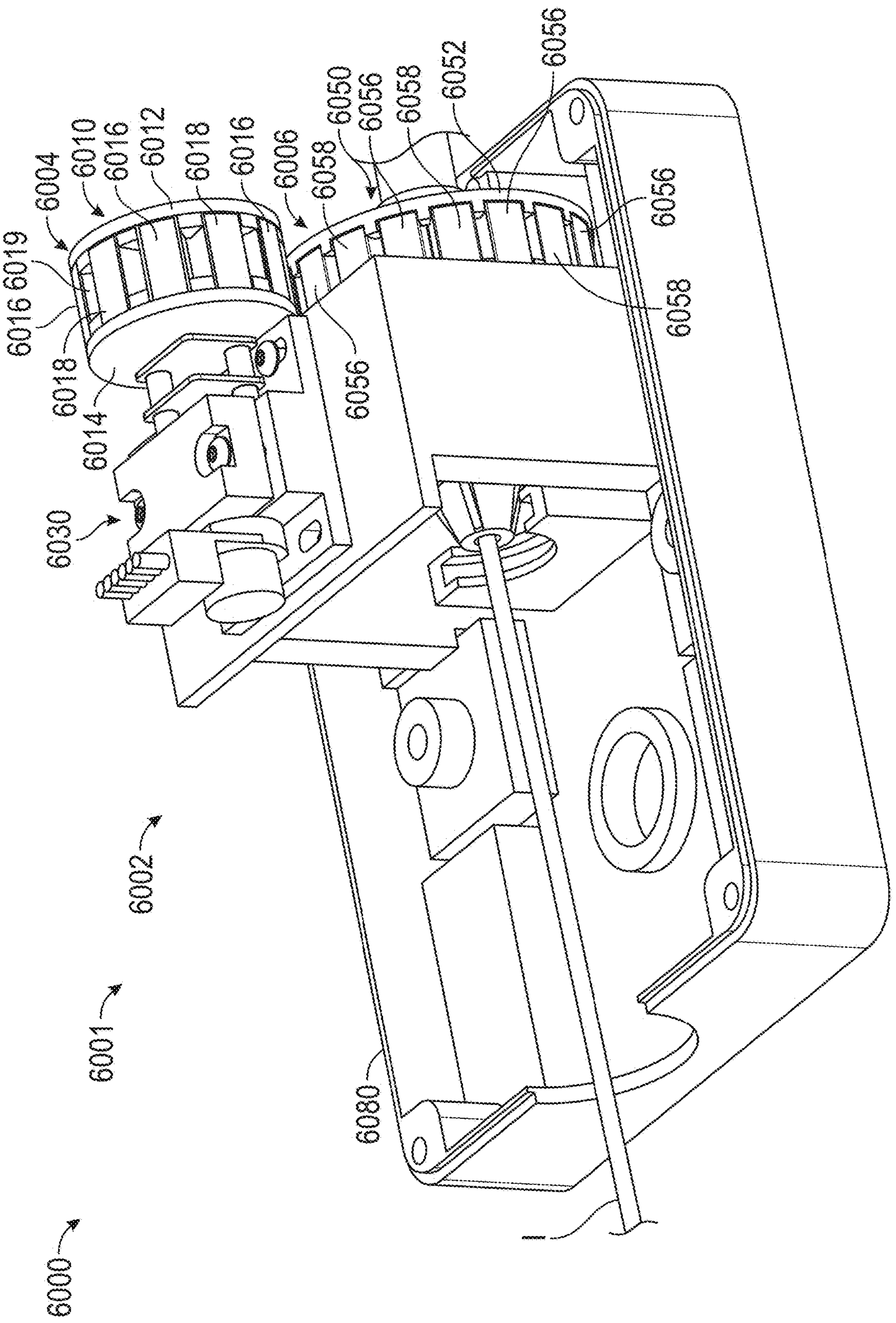
FIG. 34 is a perspective view of a portion of a robotic drive system, showing a passive torque element and an active torque element coupled with a hub.
Figure 35:
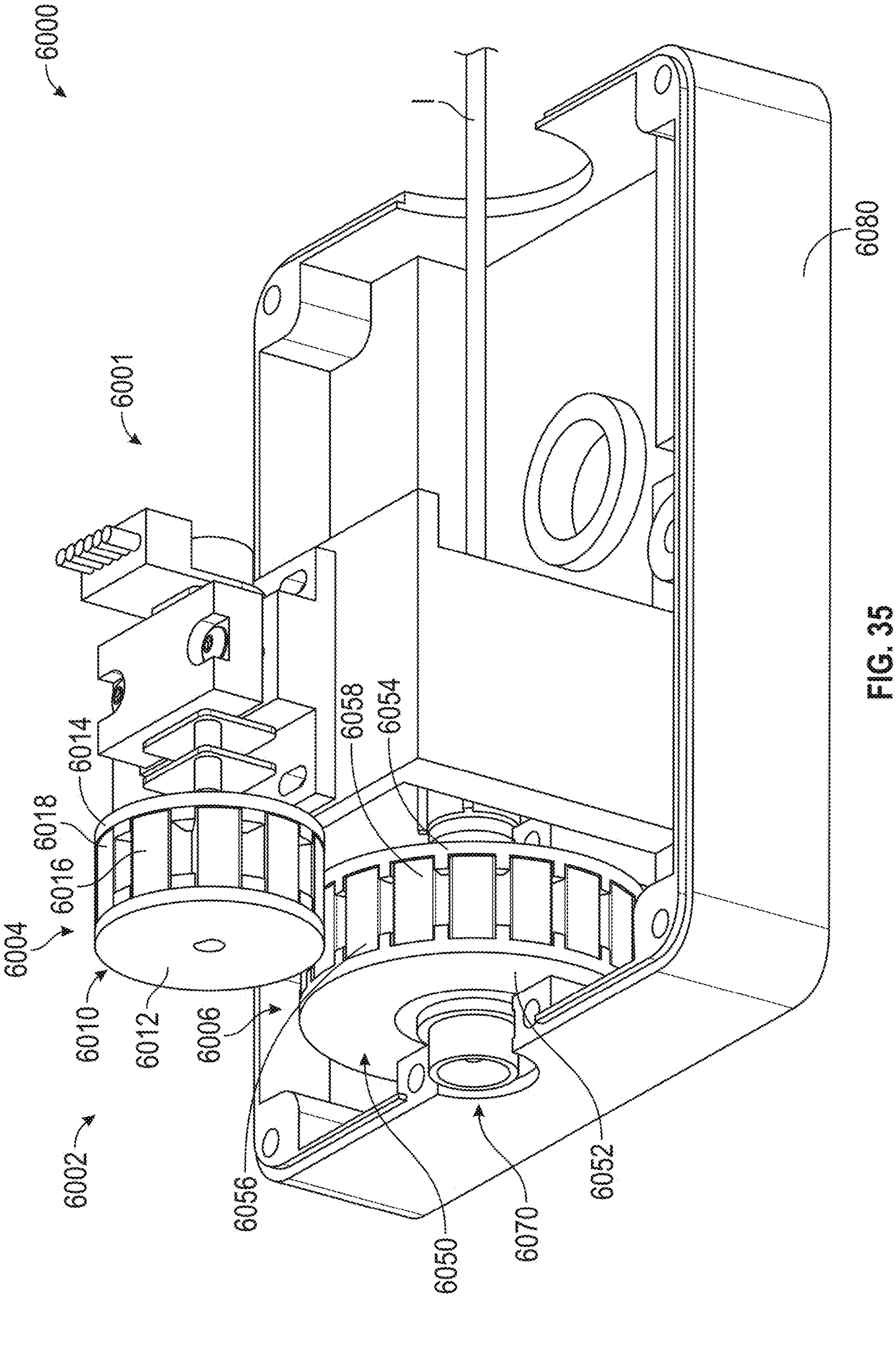
FIG. 35 is a second perspective view of the portion of the robotic control system of FIG. 34.
Figure 36:
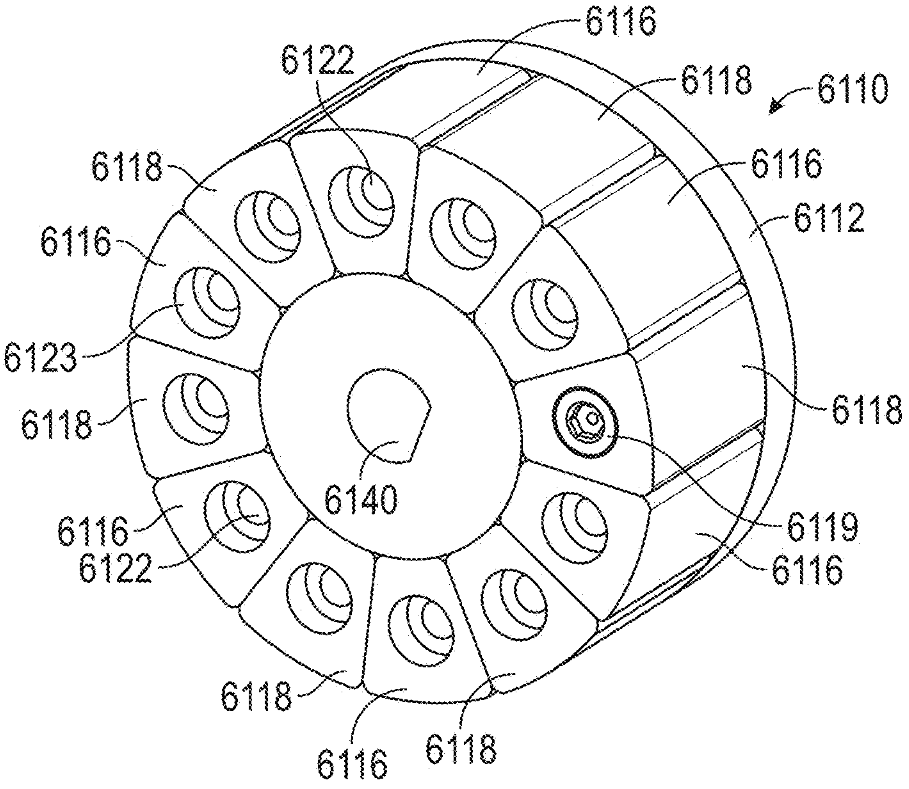
FIG. 36 is a first perspective view of an embodiment of an active torque element.
Figure 37:
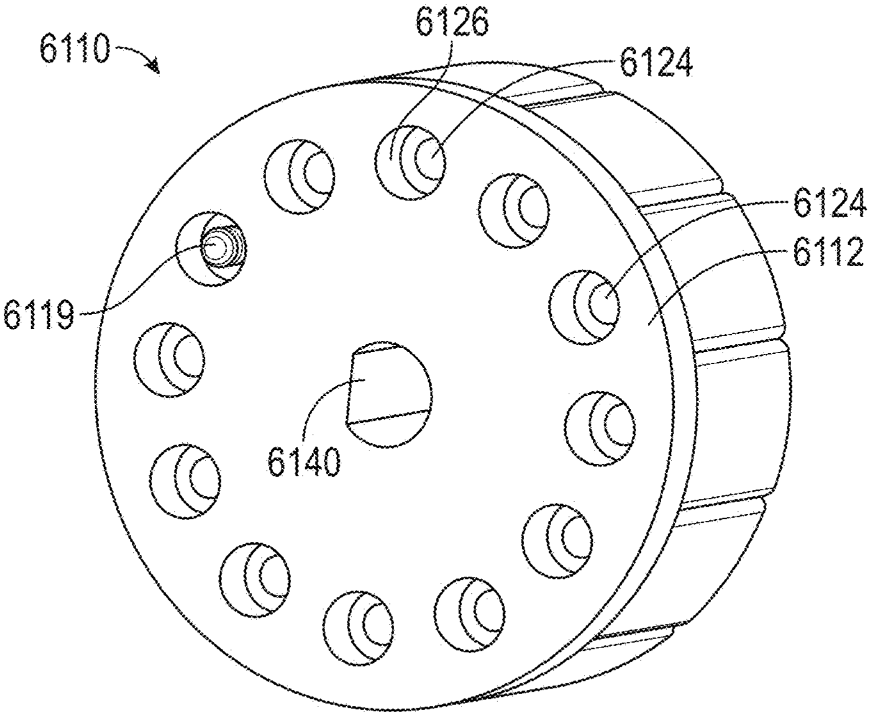
FIG. 37 is a second perspective view of the active torque element of FIG. 36.
Figure 38:
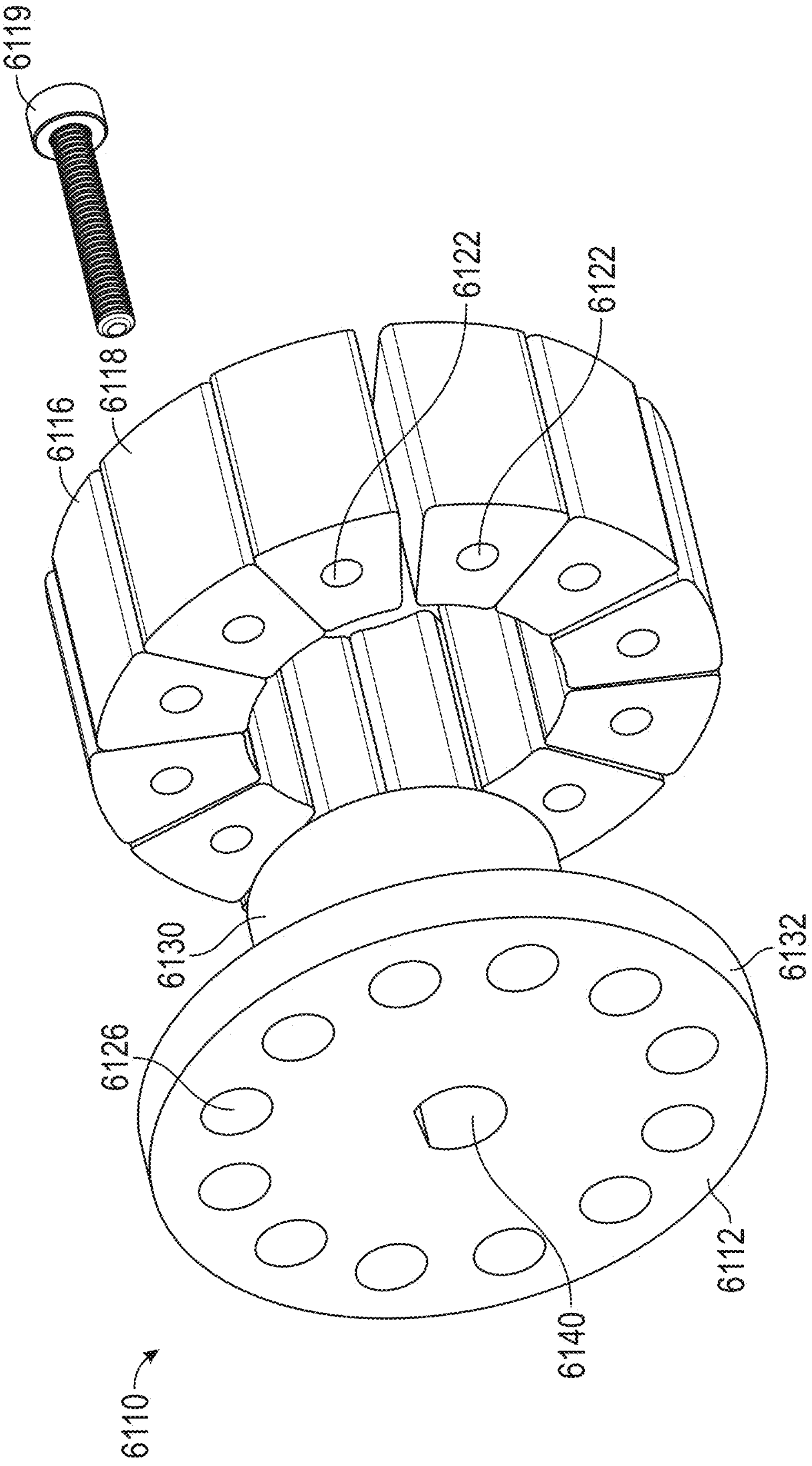
FIG. 38 is an exploded perspective view of the embodiment of the active torque element of FIG. 36.

FIGS. 34-35 shown an alternative embodiment of a robotic drive system 6000*a* in which the active torque element 6004 and the passive torque element 6006 are both positioned on the sterile side (e.g., the disposable side). As shown, in certain embodiments, the active torque element 6004 can be coupled to the hub 6001. For example, the active torque element 6004 and/or motor 6030 may be mounted above the passive torque element 6006.

FIGS. 36-41 show another example embodiment of a magnet element 6110 that has a plurality of first and second magnets 6116, 6118 having opposite outward facing poles and that are arranged in an alternating fashion such that a first magnet 6116 of the magnet element 6110 has a north (or positive) pole facing radially outwardly from the magnet element 6110 and such that a second magnet 6118 adjacent to the first magnet 6116 has a south (or negative) pole facing radially outwardly. In some embodiments, the next magnet in sequence can be another first magnet 6116 having a north pole facing radially outwardly from the magnet element 6110, and so on in this alternating arrangement. In some embodiments, the plurality of first and second magnets 6116, 6118 can be supported by a first support 6112. In some embodiments, a cross-sectional shape of the first and second magnets 6116, 6118 can be pie shaped, or have a truncated pie shape. Any embodiments of the magnet element 6110 can be used with any embodiment of the robotic drive system 6000 disclosed herein.

In some embodiments, a fastener 6119 such as a screw can be used to couple each of the first and second magnets 6116, 6118 to the first support 6112. The fastener 6119 can be advanced through an opening 6122 extending longitudinally through each of the first and second magnets 6116, 6118 and through each of the openings 6124 in the first support 6112. The openings 6124 can be threaded in some embodiments. In some embodiments, a recessed opening 6123 can be formed coaxial with the opening 6122 so that a head of the fastener 6119 can be recessed within each of the first and second magnets 6116, 6118. In some embodiments, a recessed opening such as a recess 6126 can be formed coaxially with each opening 6124 so that a threaded nut can be positioned and be recessed within the first support 6112 for each fastener 6119. In some embodiments, the first support 6112 can have a central portion 6130 extending axially away from a flange portion 6132. The central portion 6130 can provide a support surface for a radial inward facing surface of each first and second magnet. The central portion 6130 can be coaxial with an opening 6140 extending through the magnet element 6110.

Figure 41:
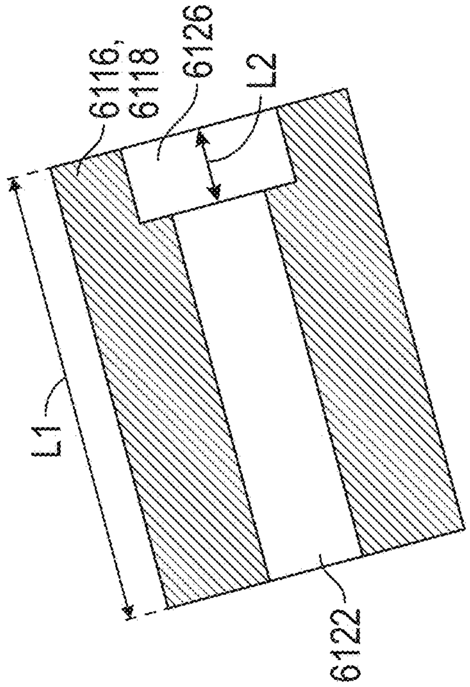
FIG. 41 is a cross-sectional view of the magnet of FIG. 40 taken along line A-A
Figure 40:
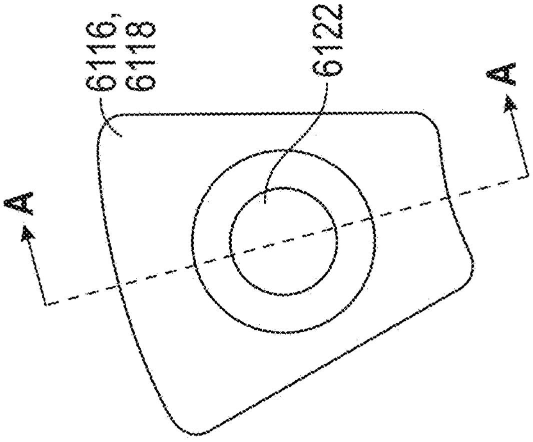
FIG. 40 is a front view of the magnet of FIG. 39.
Figure 39:
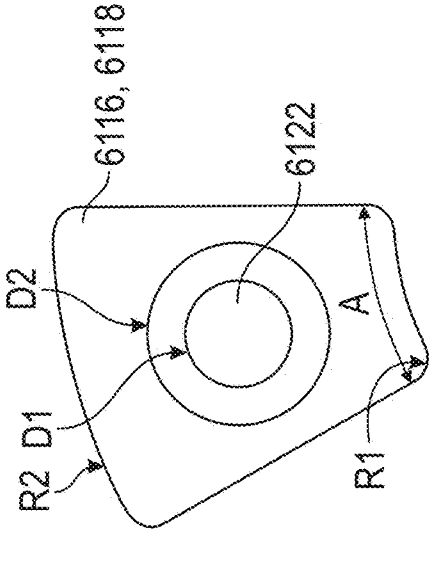
FIG. 39 is a front view of a magnet of the active torque element of FIG. 36.

As shown in FIG. 41, in some embodiments, the arc segment shaped magnet 6116, 6118 can have an overall length L1 of 0.375 in, or approximately 0.375 inch. As shown in FIG. 39, the arc shaped segment can have side walls separated by an angle A of 29 degrees, or approximately 29 degrees. An inner radius R1 of the arc segment shaped magnet 6116, 6118 can be 0.250 in, or approximately 0.250 in, and an outer radius R2 of the arc segment shaped magnet 6116, 6118 can be 0.50 in, or approximately 0.50 in. A diameter D1 of the opening 6122 extending through the arc segment shaped magnet 6116, 6118 can be 0.079 in or approximately 0.079 in. A recess 6126 can have a diameter D2 of 0.134 in or approximately 0.134 in. The recess 6126 can have a length of 0.063 in or about 0.063 in. In other embodiments, any of the foregoing values can be increased or decreased by 10%, or increased or decreased by 20%, or increased or decreased by 30%.

FIGS. 42A-43P illustrate additional embodiments of torque transfer systems in the form of magnetic couplings having magnets (e.g., neodymium magnets) to transmit torque through a sterile barrier from the capital equipment (e.g., a hub adapter) to the disposable side of the surgical robot (e.g., to a hub, also referred to herein as a puck). As previously described, this can have the advantage of eliminating the need for a motor and motor control board on the disposable hubs, greatly reducing cost the of equipment and the cost of procedures. In addition, some embodiments of the magnetic coupler disclosed herein eliminate the need for cable management to each hub, increasing simplicity and reducing the cost of the system.

FIGS. 42A-43P show butted shaft configurations (face magnets) instead of parallel shaft configurations (edge magnets) as shown in FIGS. 25-41. The magnetic torque coupling transmits rotary power without a mechanical attachment. The absence of a mechanical attachment such as a drive shaft allows torque to be transmitted across a sterile barrier without the need of moving components. Though a magnetic couple significantly simplifies workflow, it increases design complexity, and the torque transmission is not well understood. Empirical testing will be used to quantify the magnetic torque and effect of the following factors.

Figure 42A:
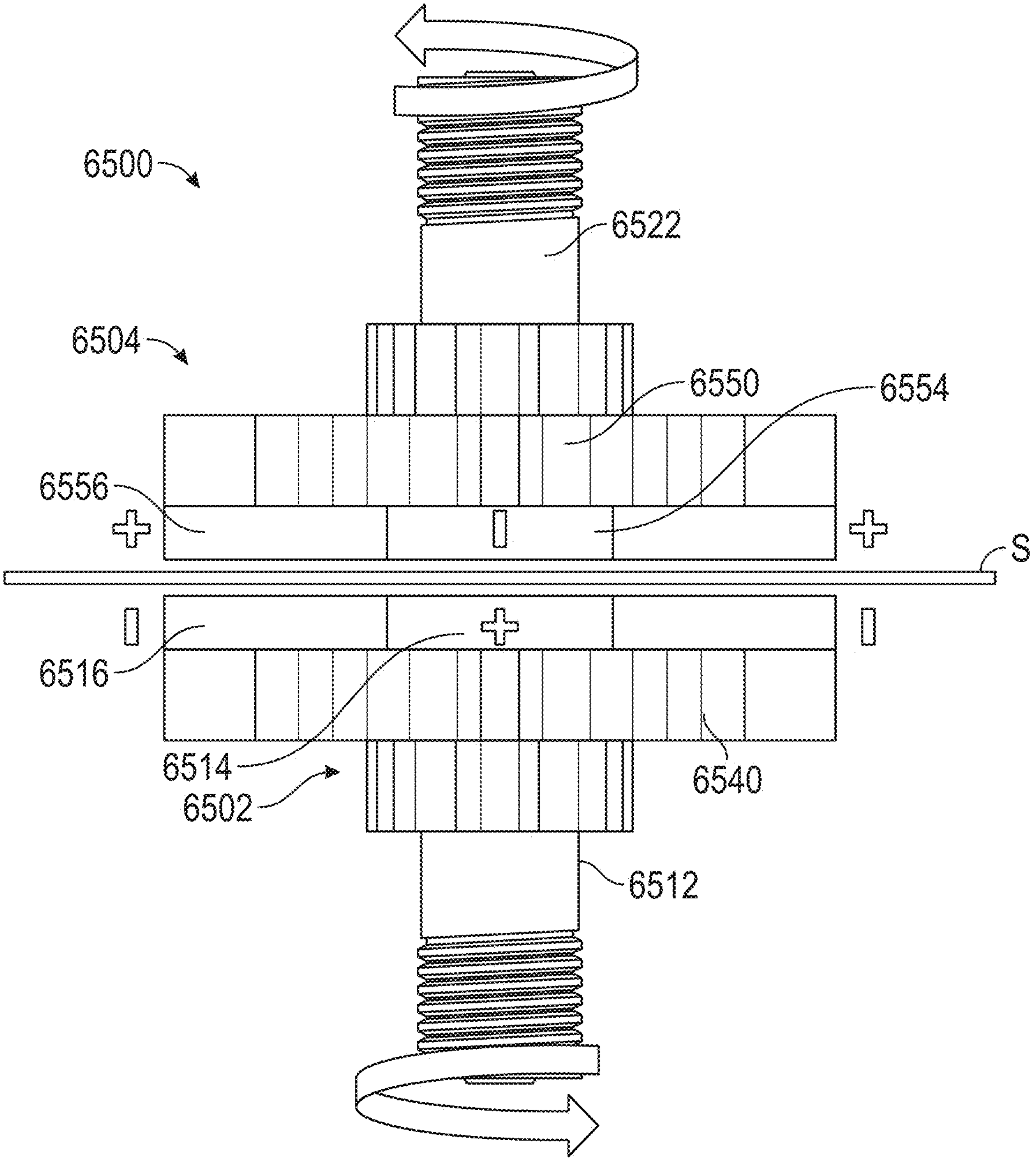
FIG. 42A is a side view of an embodiment of a torque transfer system.
Figure 42B:
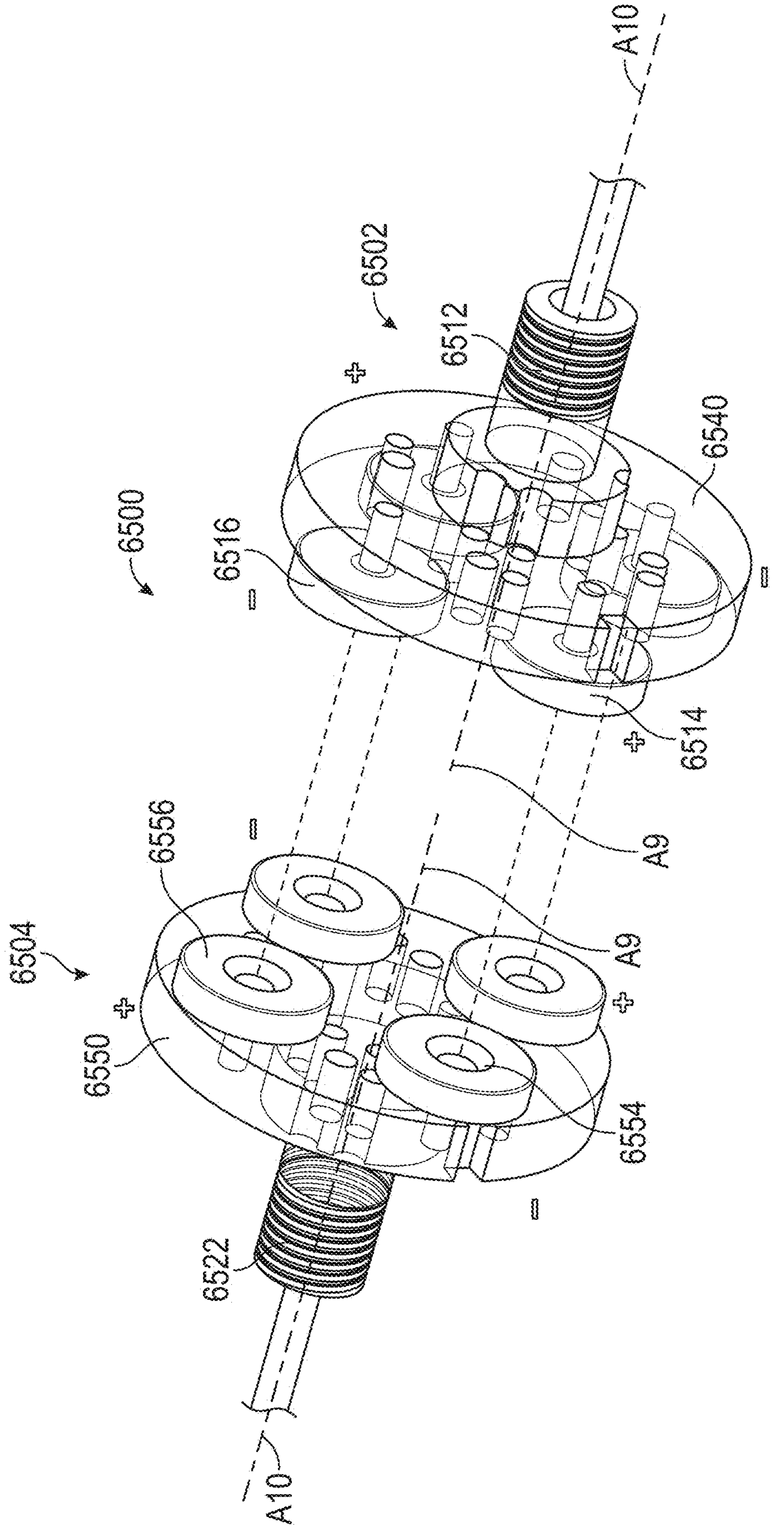
FIG. 42B is a perspective view of the torque transfer system of FIG. 42A.

FIGS. 42A-42B show an embodiment of a torque transfer system 6500 that can be configured to transfer a torque force through a sterile barrier (designated by S in FIG. 42A). In some embodiments, the torque transfer system 6500 can include an active torque element 6502 configured to be positioned on a nonsterile side (e.g., a capital equipment side) of a sterile barrier and a passive torque element 6504 configured to be positioned on a sterile side (e.g., a disposable equipment side) of the sterile barrier.

In some embodiments, the active torque element 6502 can include a plurality of magnets arranged around a central axis (represented by axis A9 in FIG. 42B). The plurality of magnets can include one or more first magnets 6514 and one or more second magnets 6516. The one or more first magnets 6514 can include a north or positive pole facing axially towards the passive torque element 6504. The one or more second magnets 6516 can include a south or negative pole facing axially towards the passive torque element 6504. The magnets 6514 and 6516 can be disc magnets. In some embodiments, the plurality of magnets of the active torque element 6502 can be arranged in a planar arrangement on a plane parallel with or generally parallel with the sterile barrier.

The passive torque element 6504 can include a plurality of magnets arranged around a central axis, such as axis A9. The plurality of magnets can include one or more first magnets 6554 and one or more second magnets 6556. The one or more first magnets 6554 can include a south or negative pole facing axially towards the active torque element 6502. The one or more second magnets 6556 can include a north or positive pole facing axially towards the active torque element 6502. The magnets 6554 and 6556 can be disc magnets. In some embodiments, the plurality of magnets of the passive torque element 6504 can be arranged in a planar arrangement on a plane parallel with or generally parallel with the sterile barrier.

The first magnets 6514 of the active torque element 6502 can be magnetically coupled with the first magnets 6554 of the passive torque element 6504, and the second magnets 6516 of the active torque element 6502 can be coupled with the second magnets 6556 of the passive torque element 6504. Rotation of the plurality of magnets of the active torque element 6502 about the central axis of the plurality of magnets of the active torque element 6502 can cause a corresponding rotation of the plurality of magnets of the passive torque element 6504 about the central axis of the plurality of magnets of the passive torque element 6504.

In some embodiments, the central axis of the plurality of magnets of the active torque element 6502 can be coaxial with or parallel with the central axis of the plurality of magnets of the passive torque element 6504. In some embodiments, the central axis of the plurality of magnets of the active torque element 6502 and/or the central axis of the plurality of magnets of the passive torque element 6504 can be transverse to (e.g., perpendicular to) a direction of axial movement of a hub adapter, hub, and/or interventional device to which components of torque transfer system 6500 are coupled.

In some embodiments, the active torque element can include a shaft 6512 configured to rotate about a longitudinal centerline axis (represented by A10 in FIG. 42B) of the shaft 6512. The longitudinal centerline axis of the shaft 6512 can be coaxial with the central axis (e.g., axis A9) of the plurality of magnets of the active torque element 6502. The one or more first magnets 6514 and one or more second magnets 6516 can be coupled to the shaft 6512. In some embodiments, the active torque element 6502 can include a magnet support element 6540 positioned at (e.g., coupled with or integrally formed with) a distal end of the shaft 6512 of the active torque element 6502.

In some embodiments, the passive torque element 6504 can include a shaft 6522 configured to rotate about a longitudinal centerline axis of the shaft 6522. The longitudinal centerline axis of the shaft 6522 can be coaxial with the central axis of the plurality of magnets of the passive torque element 6504. The one or more first magnets 6554 and one or more second magnets 6556 can be coupled to the shaft 6522. In some embodiments, the passive torque element 6504 can include a magnet support element 6550 positioned at (e.g., coupled with or integrally formed with) a distal end of the shaft 6522 of the passive torque element 6504.

In some embodiments, the shaft 6512 of the active torque element 6502 may be rotated (e.g., by a motor) to cause rotation of the magnet support element 6540 and/or the plurality of magnets of the active torque element 6502. Rotation of the plurality of magnets of the active torque element 6502 can cause rotation of the plurality of magnets of the passive torque element 6504. Rotation of the plurality of magnets of the passive torque element 6504 and/or magnet support element 6550. Rotation of the plurality of magnets of the passive torque element 6504 and/or magnet support element 6550 can cause rotation of the shaft 6522.

The plurality of magnets of the passive torque element 6504, the magnet support element 6550, and/or the shaft 6522 may be coupled with (e.g., directly or indirectly) a surgical instrument (e.g., an interventional device, a valve, etc.) so that rotation of the plurality of magnets of the passive torque element 6504 cause a corresponding movement of the surgical instrument (e.g., rotation of an interventional device, opening and/or closing of a valve, etc.).

Figure 43A:
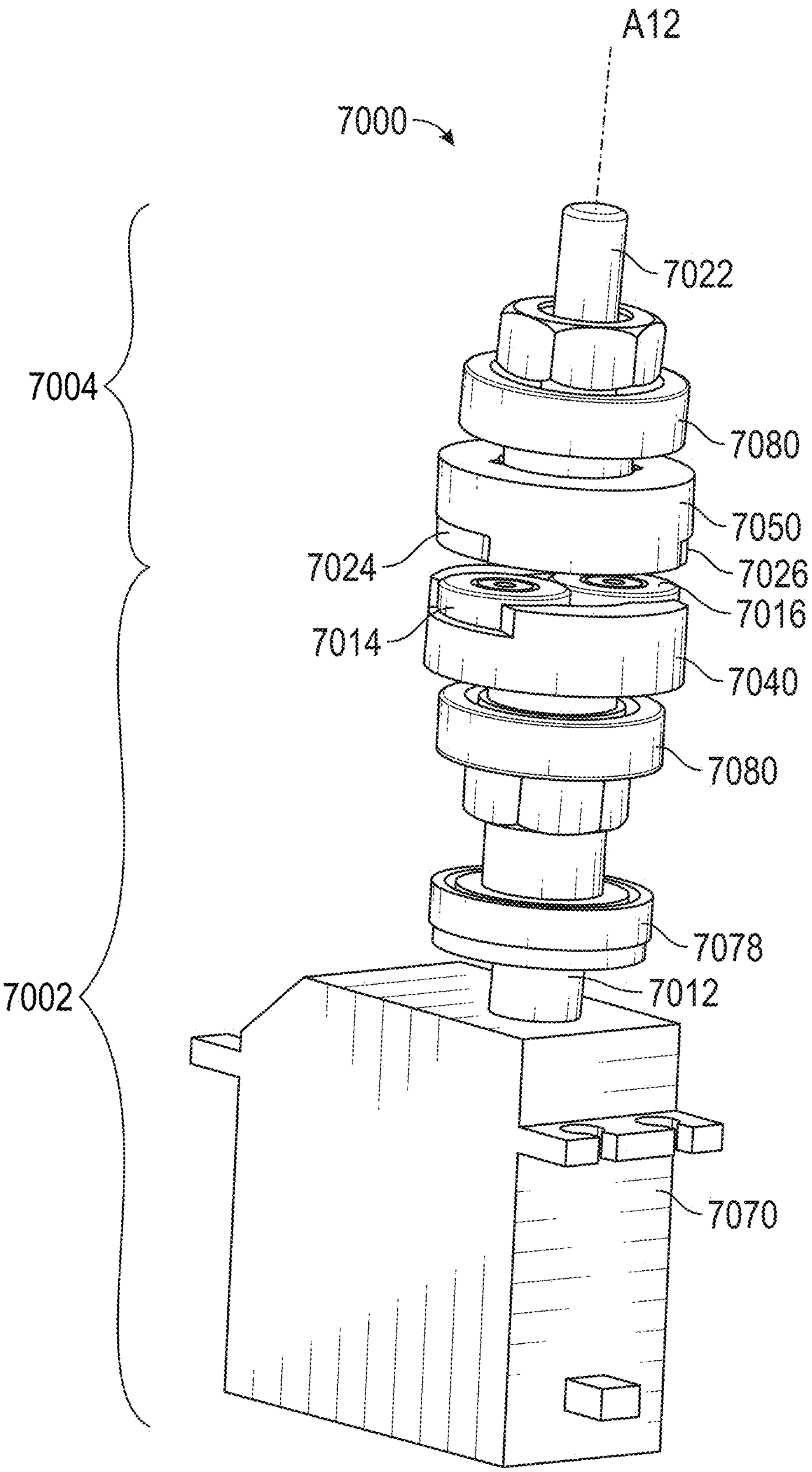
FIG. 43A is a perspective view of an embodiment of a torque transfer system.
Figure 43B:
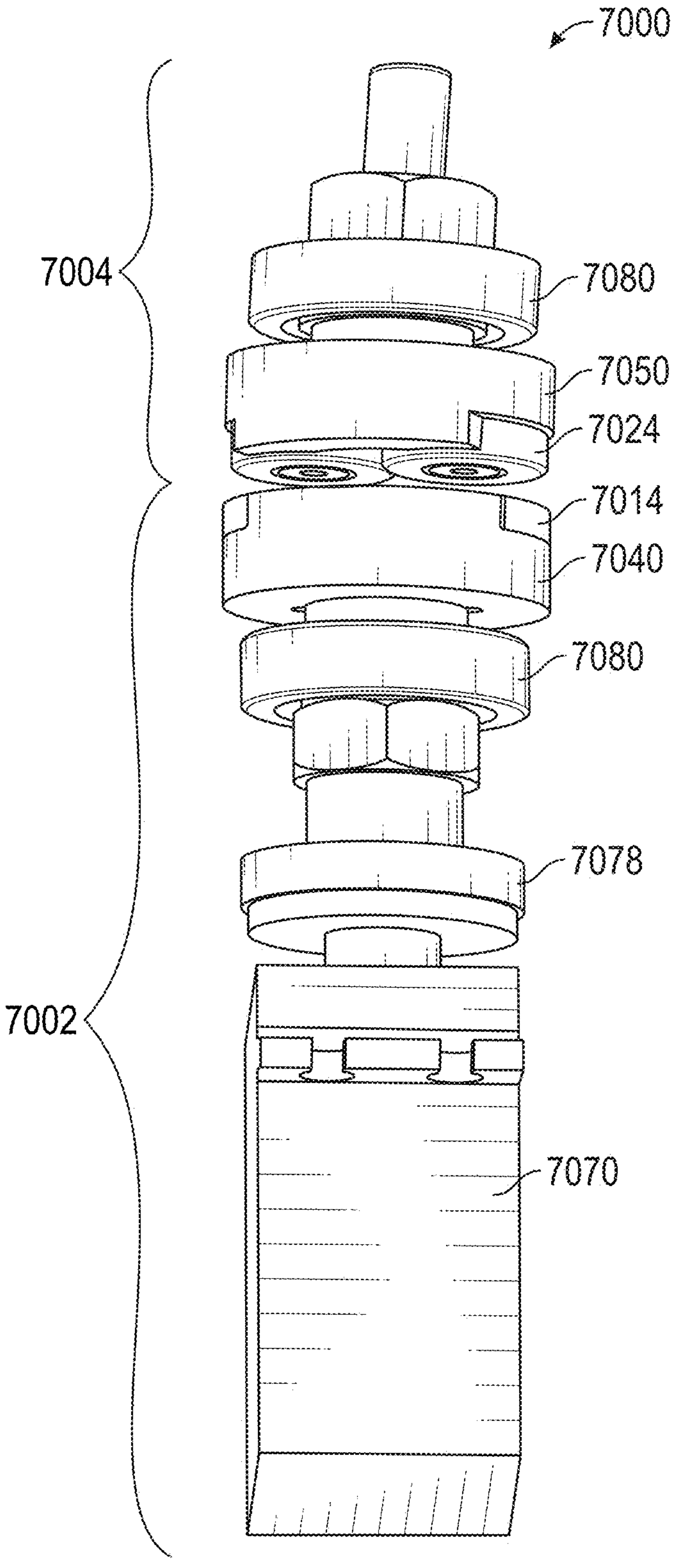
FIG. 43B is a side view of the torque transfer system of FIG. 43A.
Figure 43C:
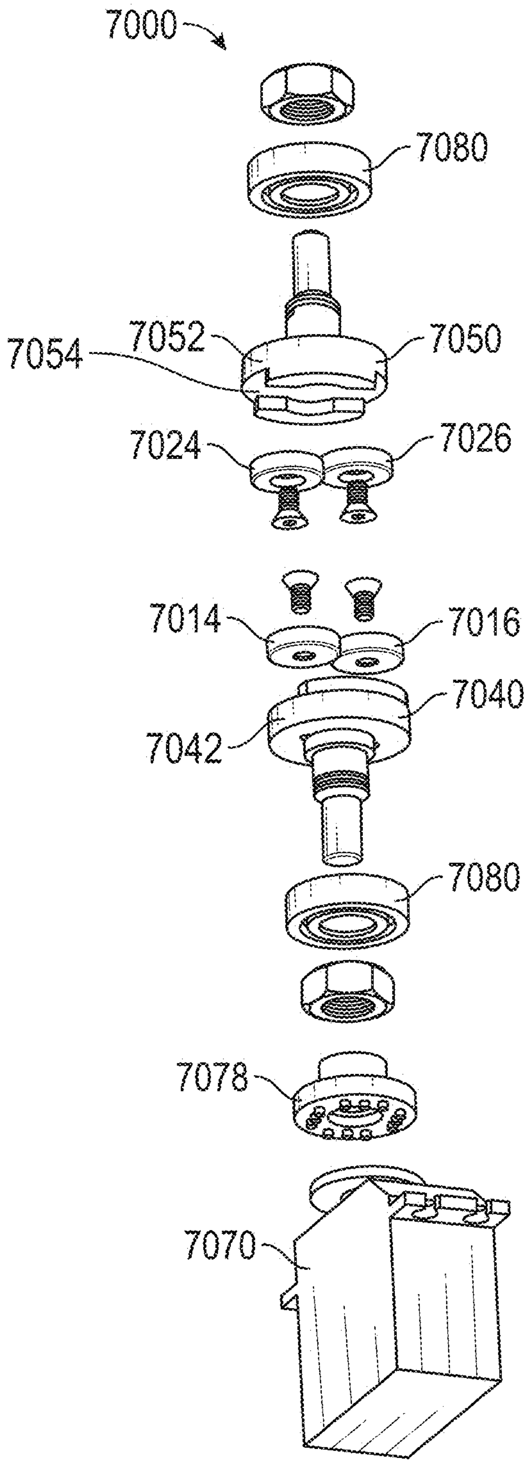
FIG. 43C is a first exploded view of the torque transfer system of FIG. 43A.
Figure 43D:
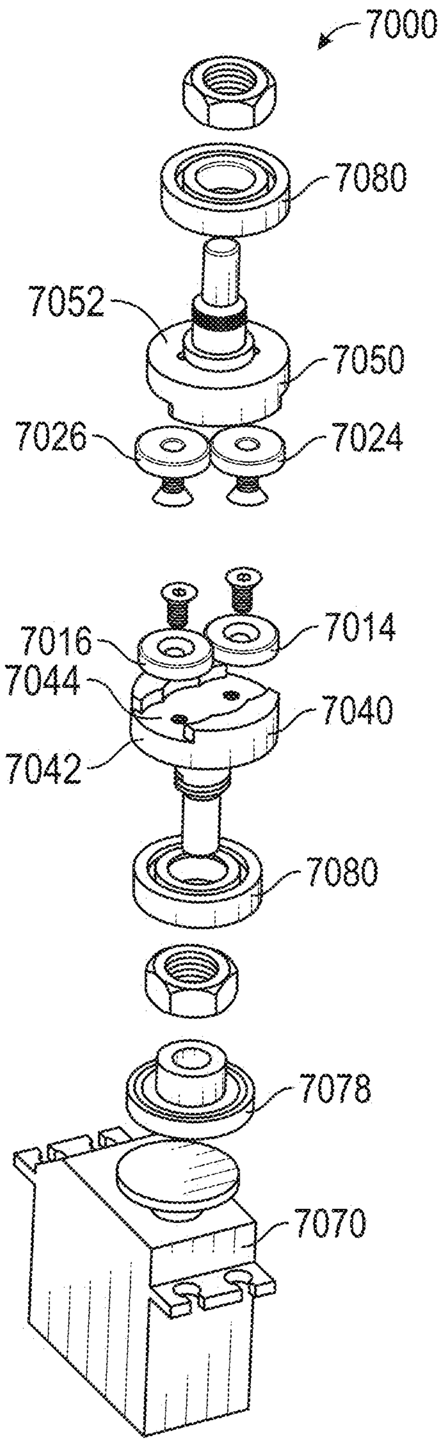
FIG. 43D is a second exploded view of the torque transfer system of FIG. 43A.
Figure 43E:
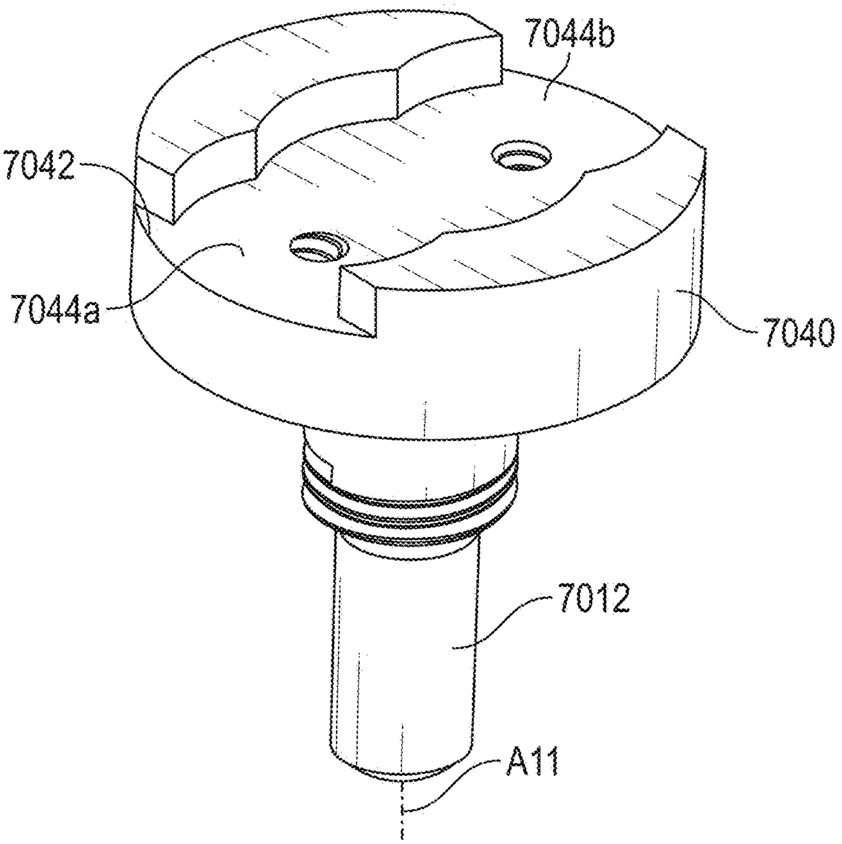
FIG. 43E is a first perspective view of a disc shaped body of an active torque element of the torque transfer system of FIG. 43A.
Figure 43F:
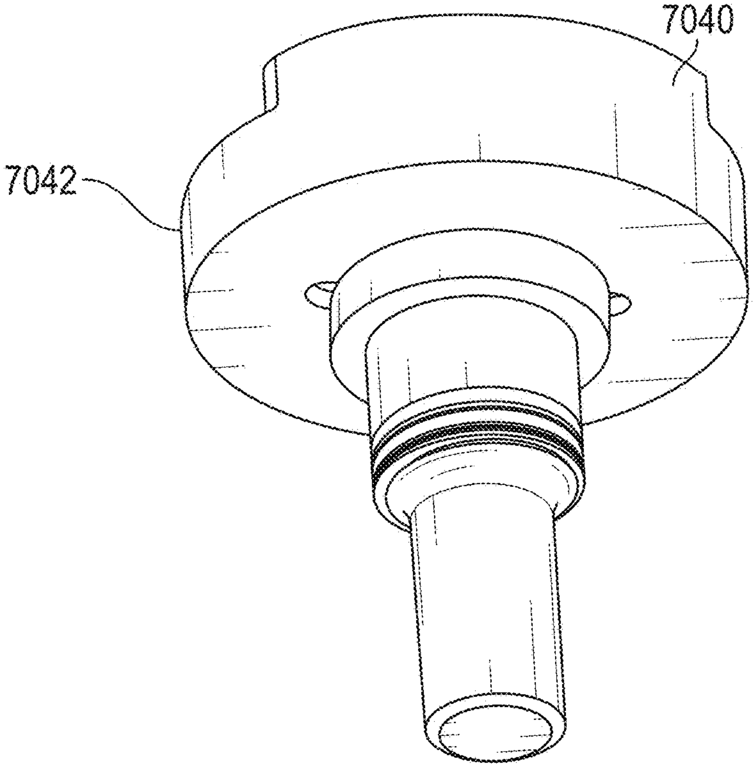
FIG. 43F is a second perspective view of the disc shaped body of FIG. 43E.
Figure 43G:
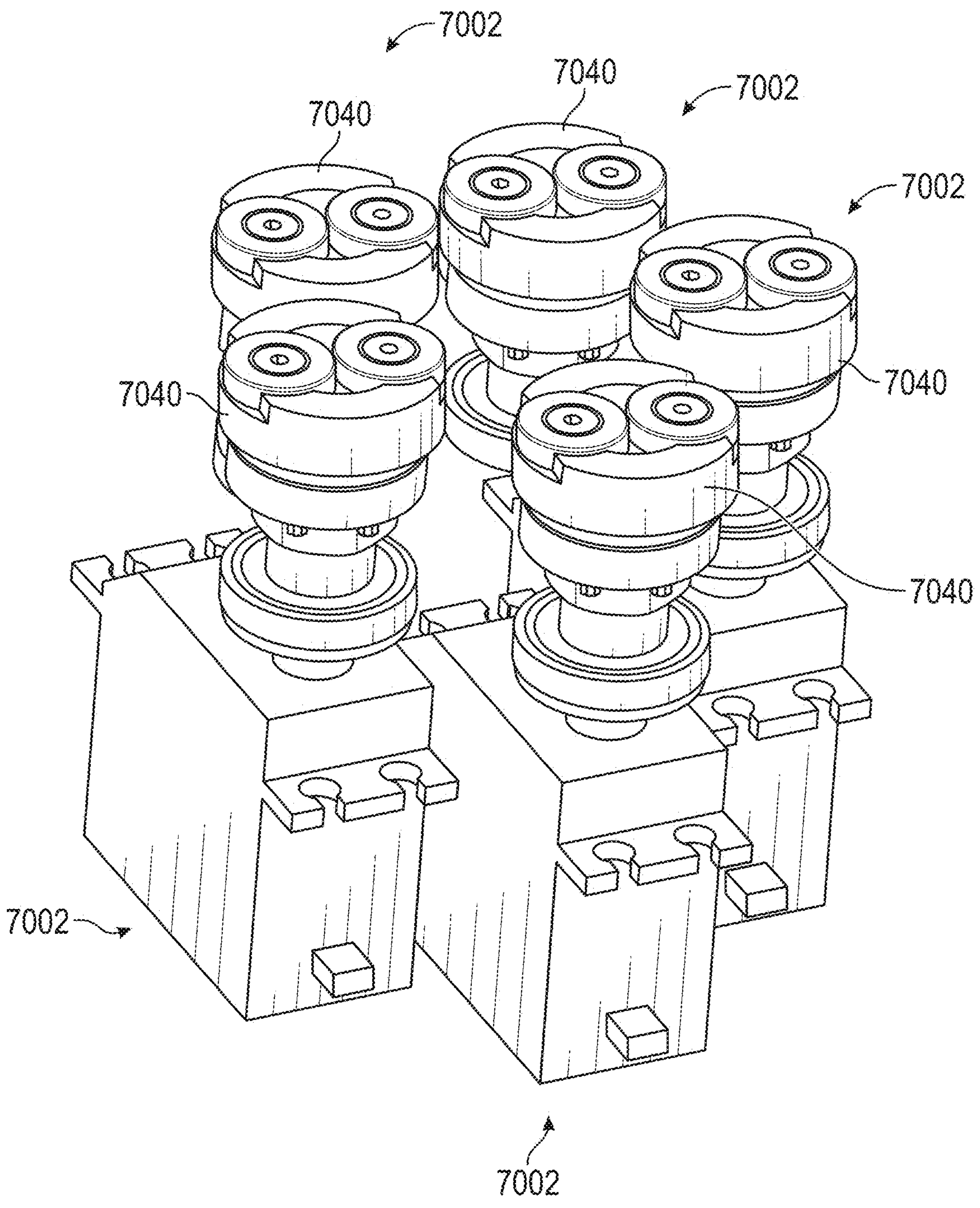
FIG. 43G is a perspective view of a plurality of torque transfer systems of FIG. 43A.
Figure 43H:
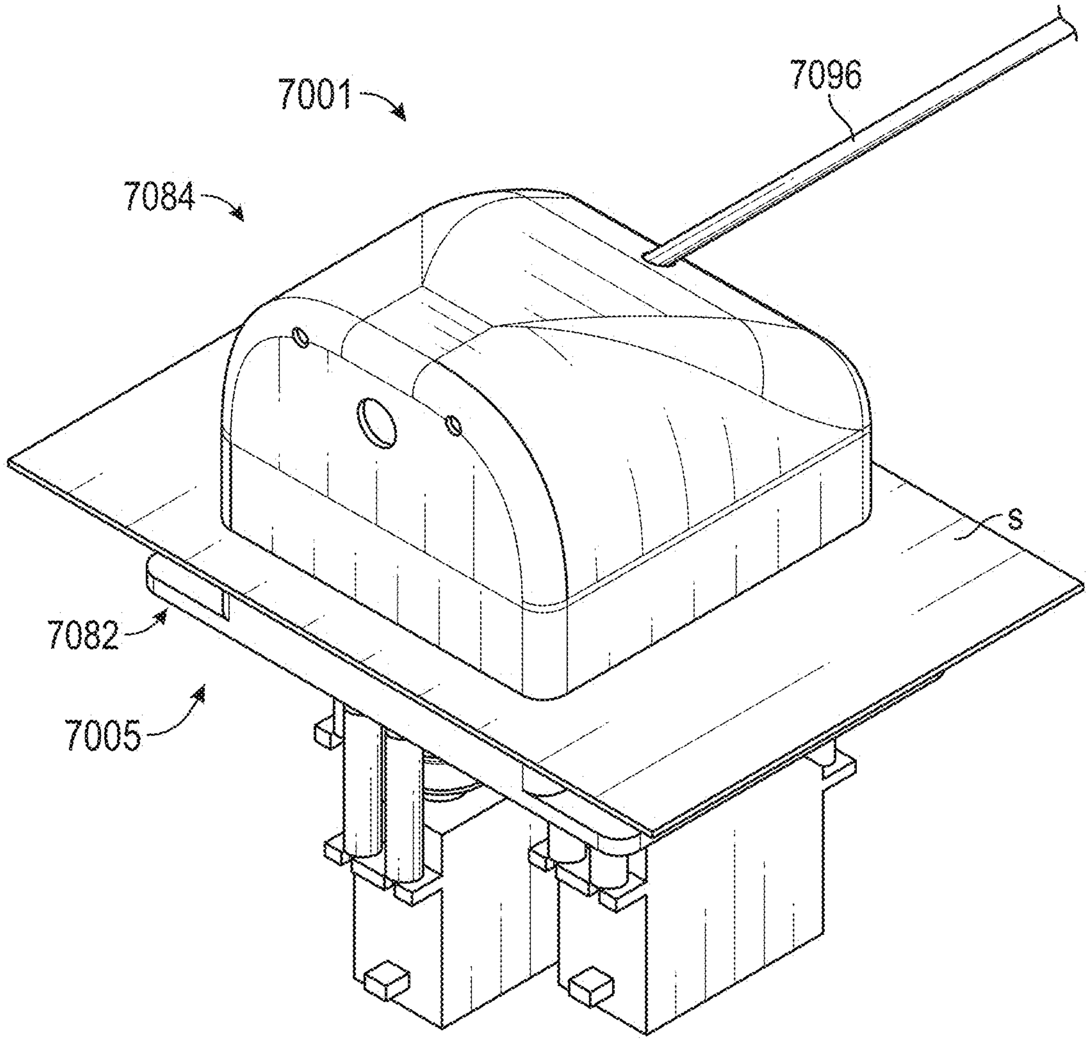
FIG. 43H is a perspective view of a portion of a robotic drive system including a hub, a hub adapter, and the torque transfer system of FIG. 43A.
Figure 43I:
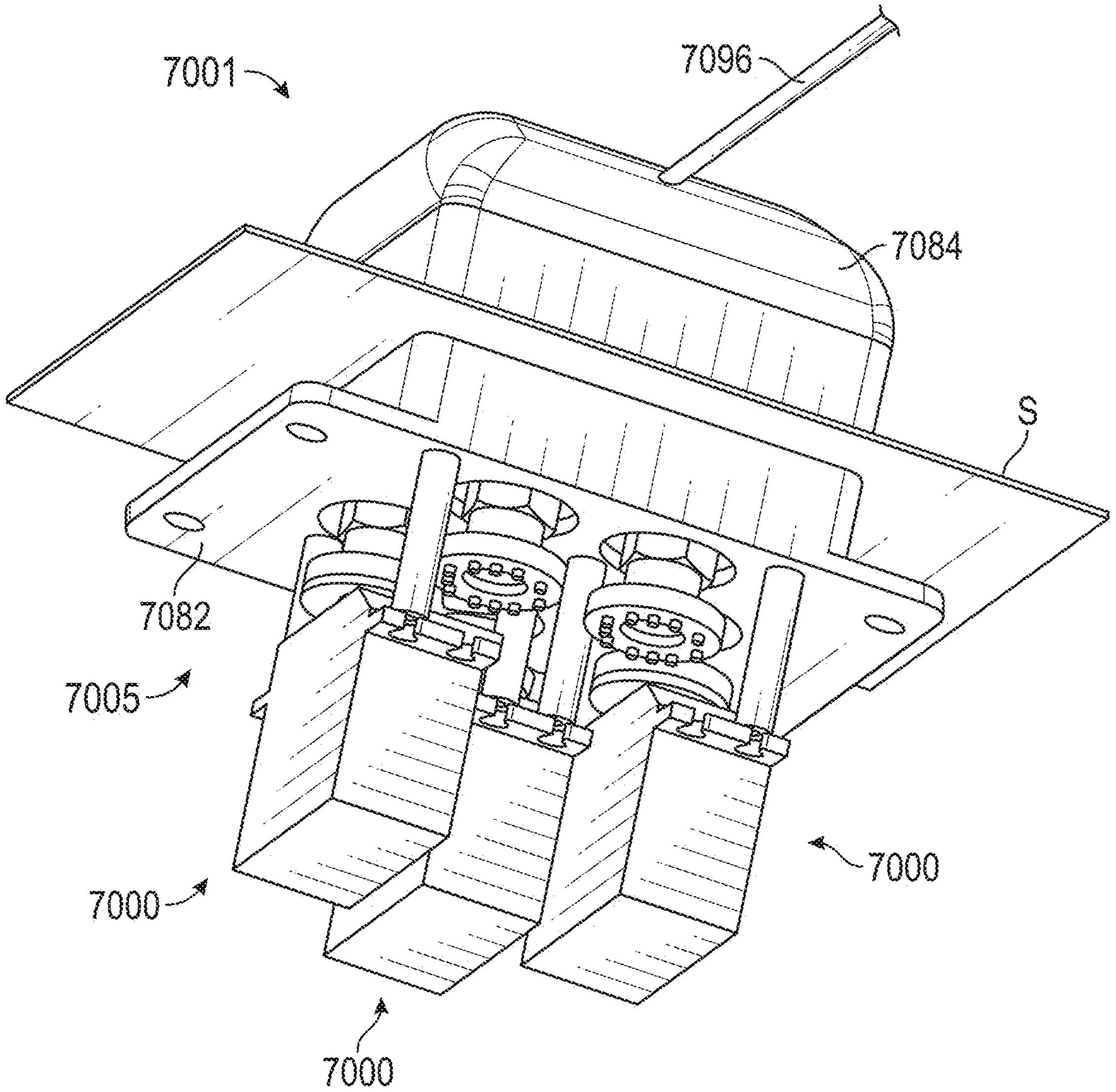
FIG. 43I is a second perspective view of the portion of the robotic drive system of FIG. 43H.
Figure 43J:
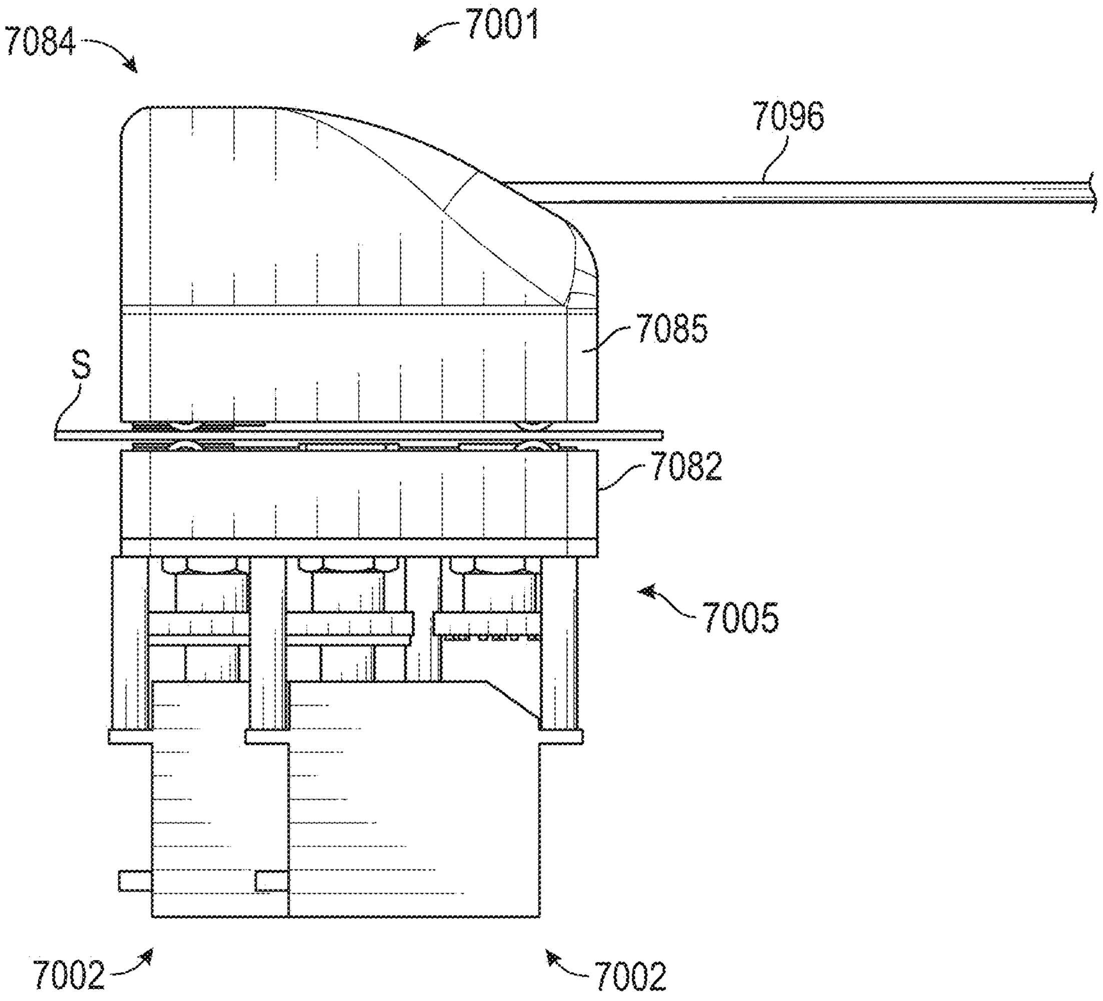
FIG. 43J is a side view of the portion of the robotic drive system of FIG. 43H.
Figure 43K:
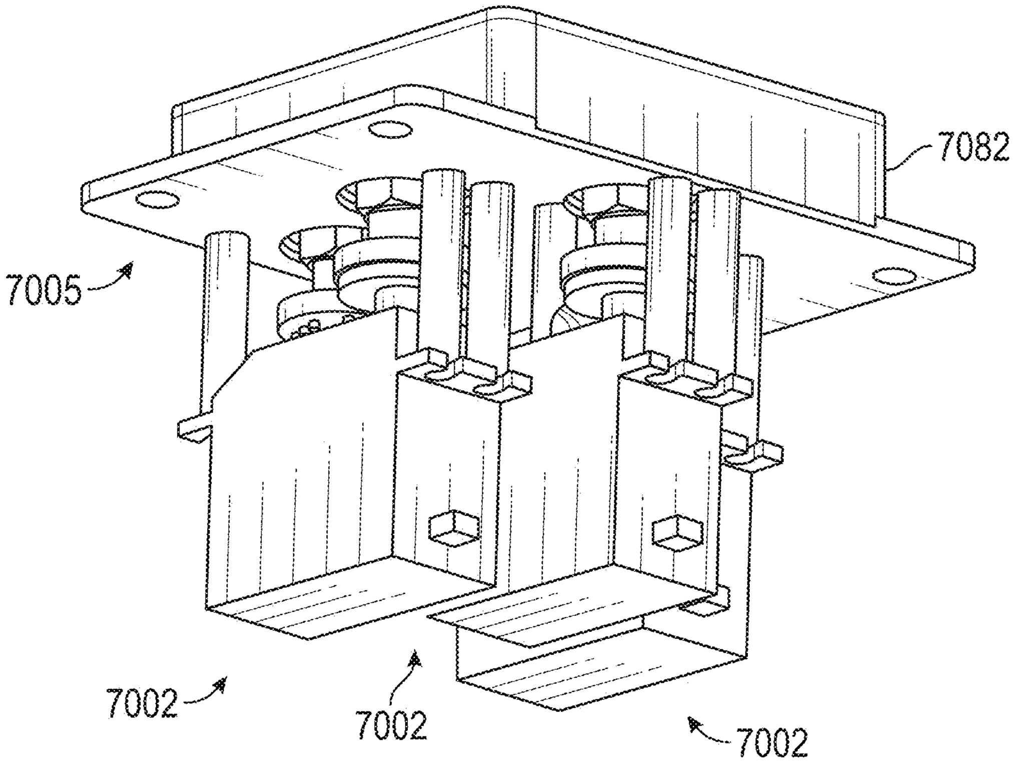
FIG. 43K is a perspective view of the hub adapter of FIG. 43H.
Figure 43L:
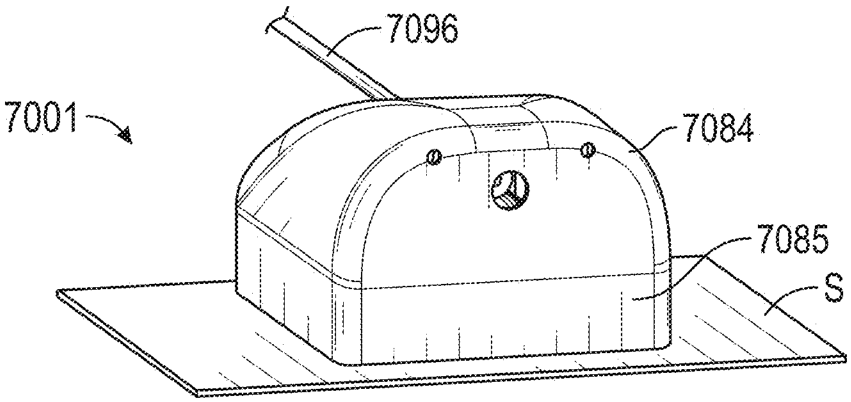
FIG. 43L is a perspective view of the hub of FIG. 43H.
Figure 43M:
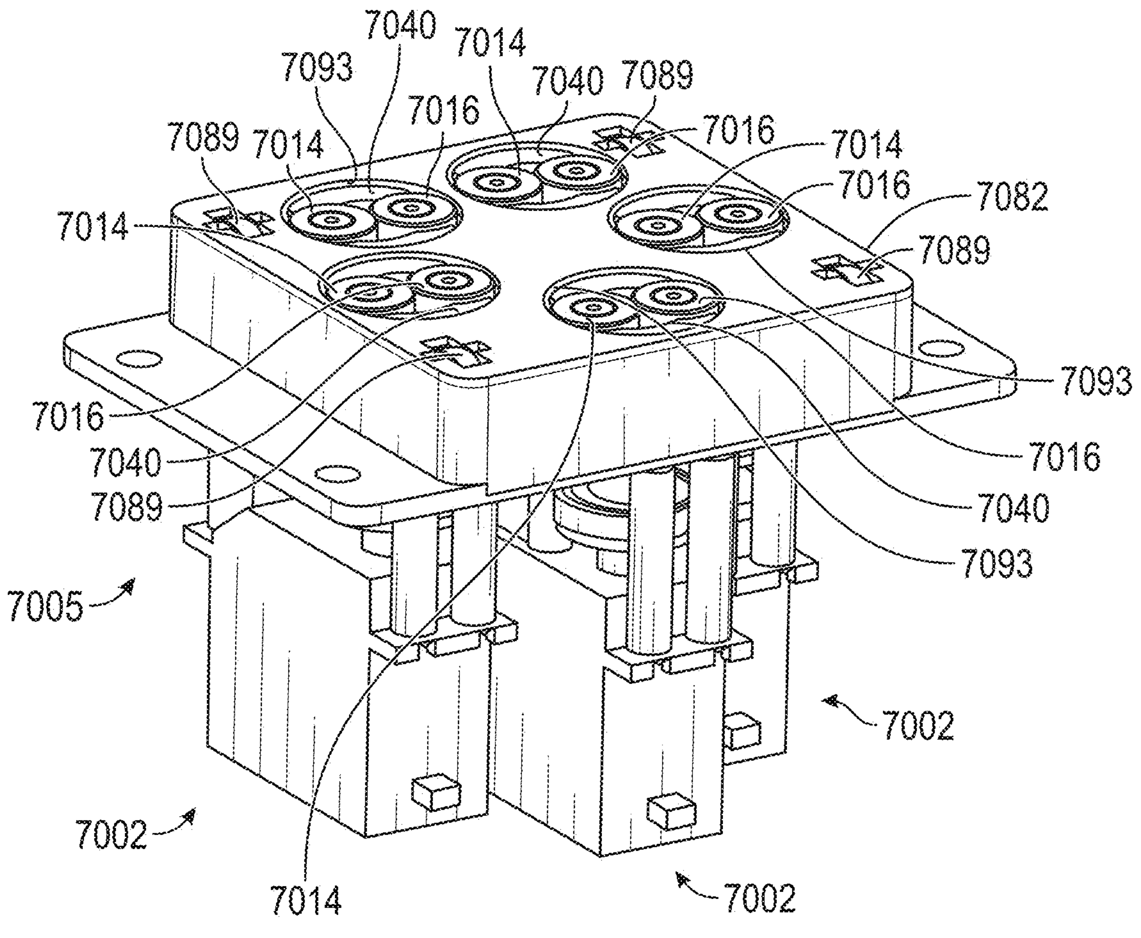
FIG. 43M is a perspective view of the hub adapter of FIG. 43H.
Figure 43N:
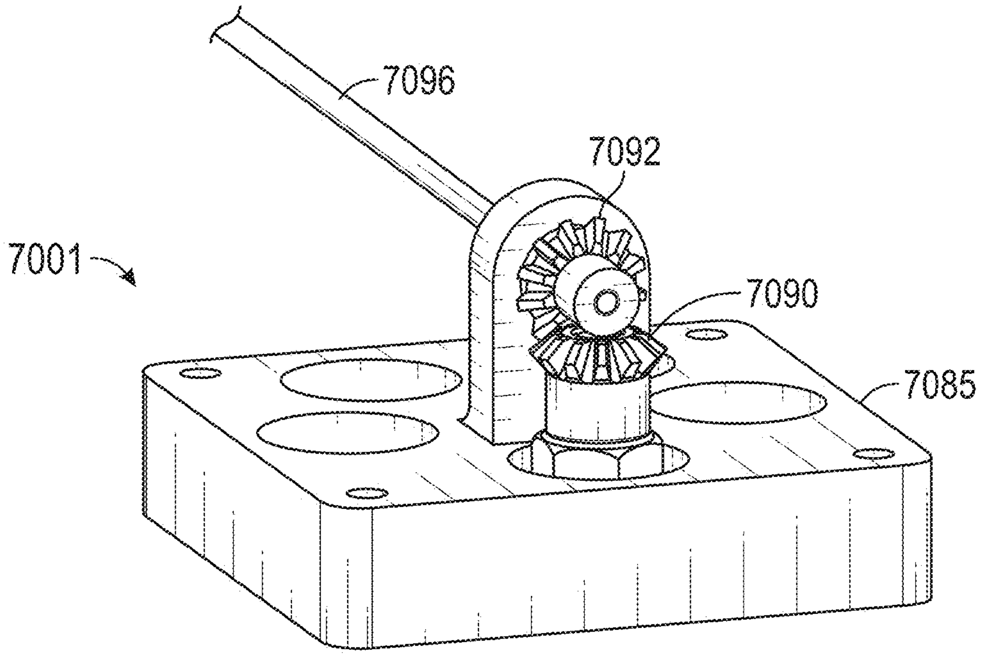
FIG. 43N is a perspective view of a portion of the hub of FIG. 43H.
Figure 43O:
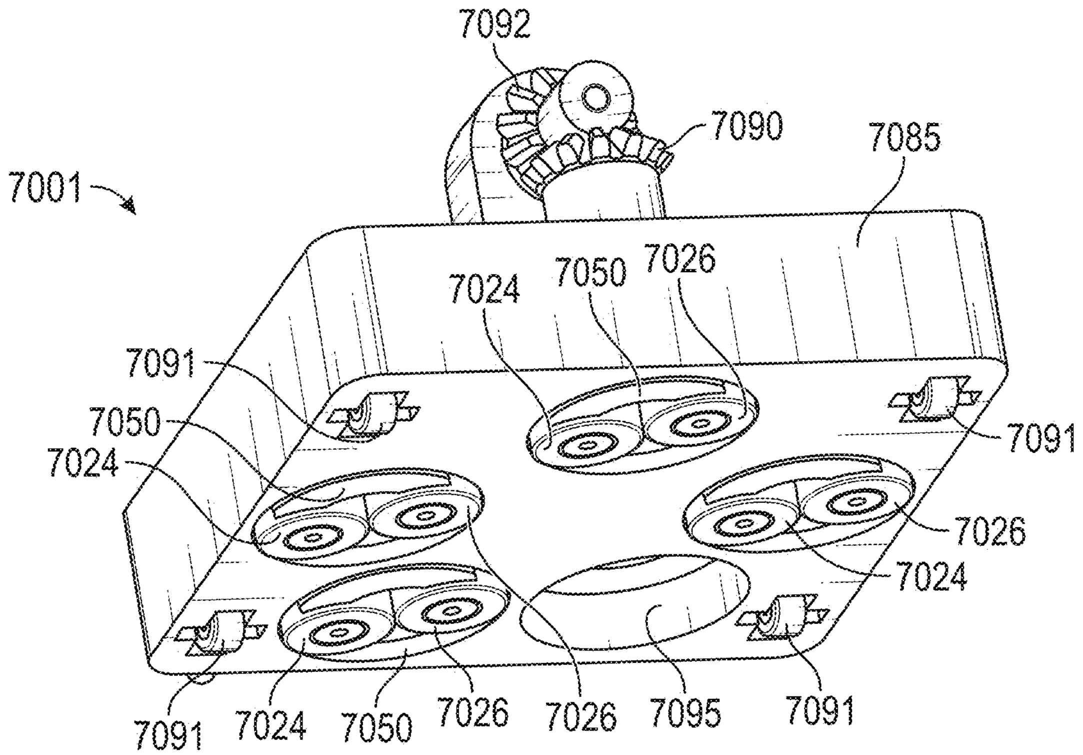
FIG. 43O is a second perspective view of the portion of the hub of FIG. 43N.
Figure 43P:
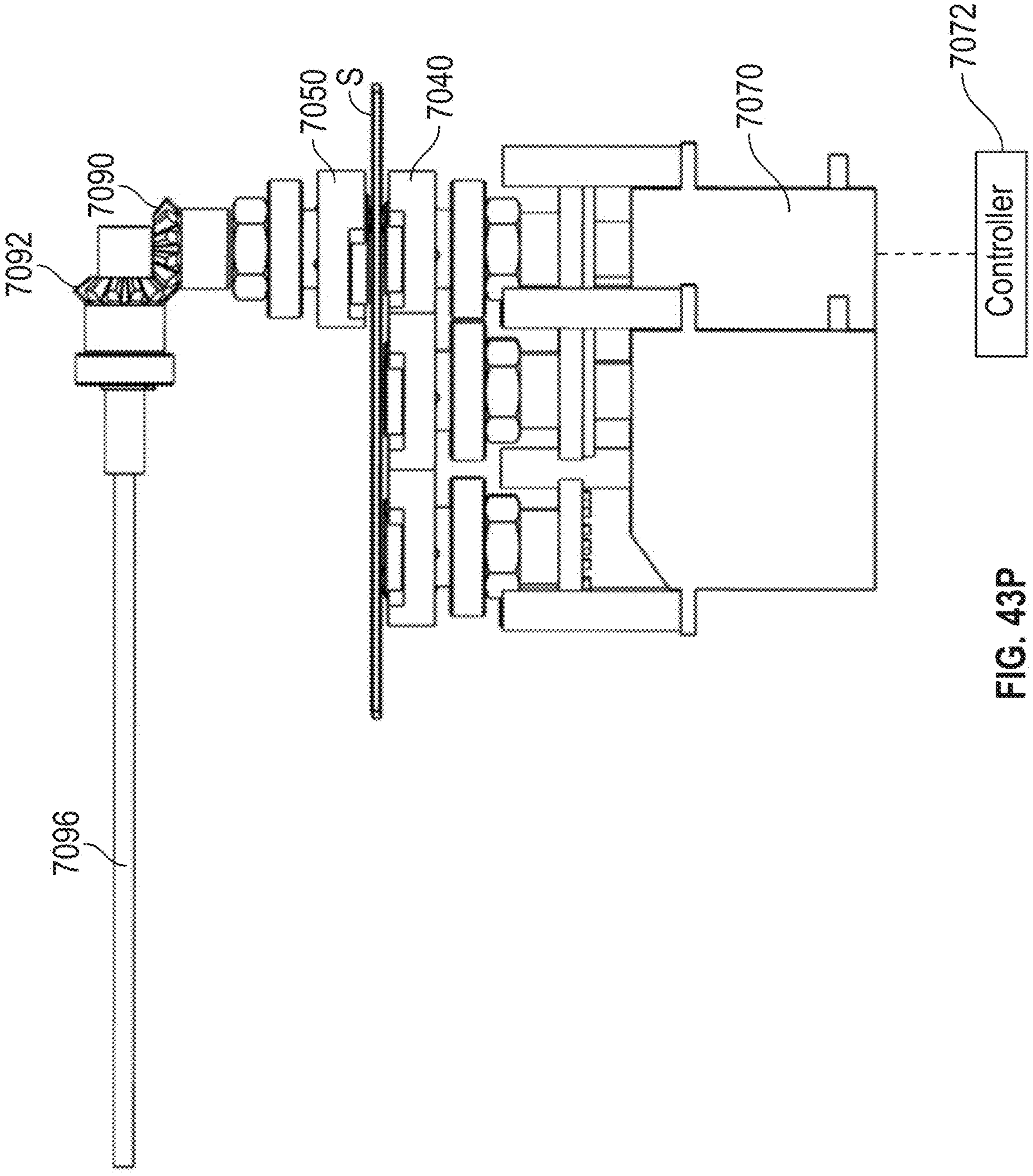
FIG. 43P is a side view of a portion the robotic drive system of FIG. 43H.

With reference to FIGS. 43A-43P, also disclosed herein are embodiments of a torque transfer system 7000 that can be configured to transfer a torque force through a sterile barrier (designated by S in some figures). In some embodiments, the torque transfer system 7000 can include an active torque element 7002 configured to be positioned on a nonsterile side (e.g., a capital equipment side) of a sterile barrier and a passive torque element 7004 configured to be positioned on a sterile side (e.g., a disposable equipment side) of a sterile barrier S.

In some embodiments, the active torque element 7002 can include a shaft 7012 configured to rotate about a longitudinal centerline axis (represented by A11 in FIG. 43E) of the shaft 7012 and at least a first magnet 7014 directly or indirectly coupled with the shaft 7012 of the active torque element 7002. In some embodiments, the passive torque element 7004 can include a shaft 7022 configured to rotate about a longitudinal centerline axis of the shaft 7022 and the passive torque element 7004 can include at least a first magnet 7024 directly or indirectly coupled with the shaft 7022 of the passive torque element 7004.

The torque transfer system 7000 can be configured such that the first magnet 7024 of the passive torque element 7004 can be magnetically coupleable with the first magnet 7014 of the active torque element 7002. The torque transfer system 7000 can be configured such that, when the first magnet 7024 of the passive torque element 7004 is magnetically coupled with the first magnet 7014 of the active torque element 7002, a rotation of the shaft 7012 of the active torque element 7002 about the axis of the shaft 7012 of the active torque element 7002 will cause a torque to be exerted on the shaft 7022 of the passive torque element 7004 that will bias the passive torque element 7004 to rotate about the axis (represented by A12 in FIG. 43A) of the shaft 7022 of the passive torque element 7004. For example, a rotation of the shaft 7012 may cause movement of the first magnet 7014 of the active torque element 7002 (e.g., about the axis of the shaft 7012 or about a central axis of a plurality of magnets of the active torque element 7002). Movement of the first magnet 7014 may cause movement of the first magnet 7024 of the passive torque element 7004 (e.g., about the axis of the shaft 7022 or a central axis of a plurality of magnets of the passive torque element 7004). Movement of the first magnet 7024 may cause rotation of the shaft 7022 about the axis of the shaft 7022.

The first magnet 7024 of the passive torque element 7004 can have an opposite polarity as compared to the first magnet 7014 of the active torque element 7002 so that the first magnet 7024 of the passive torque element 7004 is attracted to the first magnet 7014 of the active torque element 7002. In some embodiments, the active torque element 7002 can further include a second magnet 7016 spaced apart from the first magnet 7014 of the active torque element 7002 and spaced apart from the centerline axis of the shaft 7012 of the active torque element 7002, and the passive torque element 7004 can further include a second magnet 7026 spaced apart from the first magnet 7024 of the passive torque element 7004 and spaced apart from the centerline axis of the shaft 7022 of the passive torque element 7004. The torque transfer system 7000 can be configured such that the second magnet 7026 of the passive torque element 7004 is magnetically coupleable with the second magnet 7016 of the active torque element 7002. The second magnet 7016 of the active torque element 7002 can have an opposite polarity as compared to the first magnet 7014 of the active torque element 7002 and the second magnet 7026 of the passive torque element 7004 can have an opposite polarity as compared to the first magnet 7024 of the passive torque element 7004 so that the second magnet 7016 of the active torque element 7002 is attracted to the second magnet 7026 of the passive torque element 7004.

In any embodiments disclosed herein, the active torque element 7002 can include a plurality of magnets (for example and without limitation, three or more magnets) each spaced radially apart from one another and radially spaced apart from the centerline axis of the shaft 7012 of the active torque element 7002. The magnets of the active torque element 7002 may be cylindrical or disc shaped, having a first polarity on a top side of the disc and an opposite polarity on a bottom side of the disc. Similarly, the passive torque element 7004 can include a plurality of magnets each spaced radially apart from one another and radially spaced apart from the centerline axis of the shaft 7022 of the passive torque element 7004. The magnets of the passive torque element 7004 may be cylindrical or disc shaped, having a first polarity on a top side of the disc and an opposite polarity on a bottom side of the disc. Each of the plurality of magnets of the active torque element 7002 are configured to be alignable with and magnetically coupleable with each of the plurality of magnets of the passive torque element 7004.

In some embodiments, the active torque element 7002 can further include a second magnet 7016 and a third magnet all spaced apart from one another and spaced apart from the first magnet 7014 of the active torque element 7002 and spaced apart from the centerline axis of the shaft 7012 of the active torque element 7002. Similarly, the passive torque element 7004 can further include a second magnet 7026 and a third magnet all spaced apart from one another and spaced apart from the first magnet 7024 of the passive torque element 7004 and spaced apart from the centerline axis of the shaft 7022 of the passive torque element 7004, and wherein the torque transfer system 7000 can be configured such that the second magnet 7026 of the passive torque element 7004 can be alignable and/or magnetically coupleable with the second magnet 7016 of the active torque element 7002 and the third magnet of the passive torque element 7004 can be alignable and/or magnetically coupleable with the third magnet of the active torque element 7002.

In some embodiments, the active torque element 7002 can further include a fourth magnet spaced apart from the first magnet 7014, the second magnet 7016, and the third magnet of the active torque element 7002 and spaced apart from the centerline axis of the shaft 7012 of the active torque element 7002, and the passive torque element 7004 can further include a fourth magnet spaced apart from the first magnet 7024, the second magnet 7026, and the third magnet of the passive torque element 7004 and spaced apart from the centerline axis of the shaft 7022 of the passive torque element 7004. The torque transfer system 7000 can be configured such that the fourth magnet of the passive torque element 7004 is magnetically coupleable with the fourth magnet of the active torque element 7002. An embodiment of a torque transfer system having an active torque element with four magnets and a passive torque element with four magnets is shown in FIGS. 42A-42B.

In any embodiments disclosed herein, the active torque element 7002 can include a magnet support element 7040 positioned at (e.g., coupled with or integrally formed with) a distal end of the shaft 7012 of the active torque element 7002. The magnet support element 7040 of the active torque element 7002 can be configured to support a plurality of magnets in a planar arrangement radially about a central axis of the plurality of magnets (which may be coaxial with the centerline axis of the shaft 7012 of the active torque element 7002). Similarly, the passive torque element 7004 can include a magnet support element 7050 positioned at (e.g., coupled or integrally formed with) a distal end of the shaft 7022 of the passive torque element 7004. The magnet support element 7050 of the passive torque element 7004 can be configured to support a plurality of magnets in a planar arrangement radially about a central axis of the plurality of magnets (which may be coaxial with the centerline axis of the shaft 7022 of the passive torque element 7004). In some embodiments, each of the plurality of magnets of the active torque element 7002 are configured to be alignable with and magnetically coupleable with each of the plurality of magnets of the passive torque element 7004.

In some embodiments, the magnet support element 7040 of the active torque element 7002 can include a disc shaped body 7042 and plurality of recesses 7044 formed in the disc shaped body 7042, wherein each of the plurality of recesses 7044 formed in the disc shaped body 7042 of the active torque element 7002 can be configured to receive therein each of the magnets of the active torque element 7002. The disc shaped body 7042 of the magnet support element 7040 of the active torque element 7002 can have a longitudinal centerline axis that is coincident with the centerline axis of the shaft 7012 of the active torque element 7002.

As shown in FIG. 43E, in certain embodiments, the magnet support element 7040 of the active torque element 7002 can include a disc shaped body 7042 that can include a first recess 7044*a* formed in the disc shaped body configured to receive the first magnet 7014 of the active torque element 7002 and a second recess 7044*b* formed in the disc shaped body 7042 configured to receive the second magnet 7016 of the active torque element 7002. The disc shaped body 7042 of the magnet support element 7040 of the active torque element 7002 can have a longitudinal centerline axis that is coincident with the centerline axis of the shaft 7012 of the active torque element 7002 such that the disc shaped body 7042 of the magnet support element 7040 of the active torque element 7002 is coaxially aligned with the shaft 7012 of the active torque element 7002.

Similarly, the magnet support element 7050 of the passive torque element 7004 can have a disc shaped body 7052 and plurality of recesses 7054 formed in the disc shaped body 7052, wherein each of the plurality of recesses 7054 formed in the disc shaped body 7052 of the passive torque element 7004 can be configured to receive therein each of the magnets of the passive torque element 7004. The disc shaped body 7052 of the magnet support element 7050 of the passive torque element 7004 can have a longitudinal centerline axis that is coincident with the centerline axis of the shaft 7022 of the passive torque element 7004. In any embodiments disclosed herein, the magnet support element 7050 of the passive torque element 7004 can include a disc shaped body 7052 that can include a first recess 7054 formed in the disc shaped body 7052 configured to receive the first magnet 7024 of the passive torque element 7004 and a second recess 7054 formed in the disc shaped body 7052 configured to receive the second magnet 7026 of the passive torque element 7004. The disc shaped body 7052 of the magnet support element 7050 of the passive torque element 7004 can have a longitudinal centerline axis that is coincident with the centerline axis of the shaft 7022 of the passive torque element 7004 such that the disc shaped body 7052 of the magnet support element 7050 of the passive torque element 7004 is coaxially aligned with the shaft 7022 of the passive torque element 7004.

In certain embodiments, the first magnet 7014 (and any other magnets) of the active torque element 7002 can be spaced apart from the axis of the shaft 7012 of the active torque element 7002 such that a center of the first magnet 7014 (and any other magnets) of the active torque element 7002 is eccentric to the axis of the shaft 7012 of the active torque element 7002 and such that the first magnet 7014 (and any other magnets) of the active torque element 7002 is configured to rotate in an orbit around the axis of the shaft 7012 of the active torque element 7002. Similarly, the first magnet 7024 (and any other magnets) of the passive torque element 7004 can be spaced apart from the axis of the shaft 7022 of the passive torque element 7004 such that a center of the first magnet 7024 (and any other magnets) of the passive torque element 7004 is eccentric to the axis of the shaft 7022 of the passive torque element 7004 and such that the first magnet 7024 (and any other magnets) of the passive torque element 7004 is configured to rotate in an orbit around the axis of the shaft 7022 of the passive torque element 7004. In any embodiments disclosed herein, the active torque element 7002 and the passive torque element 7004 each can include only two magnets coupled with the shaft 7012 of the active torque element 7002 and the passive torque element 7004, respectively, or only three magnets coupled with the shaft 7012 of the active torque element 7002 and the passive torque element 7004, respectively, or only four magnets coupled with the shaft 7012 of the active torque element 7002 and the passive torque element 7004, respectively.

In some embodiments, the active torque element 7002 can be configured to be positioned on a nonsterile side (e.g., a capital equipment side) of a sterile barrier and the passive torque element 7004 can be configured to be positioned on a sterile side (e.g., a disposable equipment side) of the sterile barrier. Further, in any embodiments disclosed herein, the torque transfer system 7000 can be configured to use in a surgical robotic drive system as described herein. For example, the active torque element 7002 may be coupled to a hub adapter and the passive torque element 7004 can be coupled to a hub of a robotic drive system.

In certain embodiments, the active torque element 7002 can include a motor 7070 coupled with the shaft 7012 of the active torque element 7002 and configured to selectively exert a torque force on the shaft 7012 of the active torque element 7002 to cause the shaft 7012 of the active torque element 7002 to rotate. In some embodiments, the motor 7070 can be a servo motor. The torque transfer system 7000 can include a controller 7072, as shown in FIG. 43P (also referred to herein as a control module or control circuit) in electrical communication with the motor 7070 of the active torque element 7002 configured to control an operation of the motor 7070 in response to an input to the controller 7072. The controller 7072 may be a microcontroller.

In certain embodiments, the active torque element 7002 can further include a clutch plate 7078 between the shaft 7012 and the motor 7070. The clutch plate 7078 can be configured to limit a magnitude of a torque transferred from the motor 7070 to the shaft 7012. Some embodiments of the active torque element 7002 can further include a ball bearing 7080 around a portion of the shaft 7012 of the active torque element 7002 and the passive torque element 7004 can further include a ball bearing 7080 around a portion of the shaft 7022 of the passive torque element 7004.

As shown in FIGS. 43H and 43I, the active torque element 7002 can be coupled with or supported by a hub adapter 7005. In some embodiments, the active torque element 7002 can be coupled with or supported by a housing 7082 (e.g., of a hub adapter) that can be configured to at least translate axially. The housing 7082 may be in the form of a support plate.

Similarly, the passive torque element 7004 can be coupled with or supported by a hub 7001. In some embodiments, the passive torque element 7004 can be coupled with or supported by a housing 7084 and/or a support plate or housing 7085 (e.g., of a hub) or enclosed or partially enclosed within the housing 7084 and/or housing 7085 that can be configured to at least translate axially.

In some embodiments, the hub adapter 7005 can be configured to couple with a plurality of active torque elements 7002 (e.g., via the housing 7082), including two, three, four, five, or more than five active torque elements 7002. In some embodiments, the hub 7001 can be configured to couple with a plurality of passive torque elements 7004 (e.g., via the housing 7084 and/or the housing 7085), including two, three, four, five, or more than five passive torque elements 7004.

In some embodiments, as shown in FIG. 43M, the support plate or housing 7082 can include a plurality of recesses 7093 each configured to receive the magnet support elements 7040 of the active torque elements 7002 therein. The plurality of recesses 7093 can each be sized slightly larger than the magnet support elements 7040 so that the magnet support elements 7040 can rotate freely within the recesses 7093.

Similarly, as shown in FIG. 43O, in some embodiments, the support plate or housing 7085 of the passive torque element 7004 can include a plurality of recesses 7095 each configured to receive the magnet support elements 7050 of the passive torque elements 7004 therein. The plurality of recesses 7095 can each be sized a little larger than the magnet support elements 7050 so that the magnet support elements 7050 can rotate freely within the recesses 7095. Note that, in some figures, not all of the passive torque elements 7004 are shown, for clarity purposes.

In some embodiments, as shown in FIG. 43M, the hub adapter 7005 can have a plurality of rollers 7089 (e.g., coupled with the housing 7082) configured to roll along the sterile barrier. In some embodiments, as shown in FIG. 43O, the housing 7085 can have a plurality of rollers 7091 (e.g., coupled with the housing 7085) configured to roll along the sterile barrier.

In some embodiments, as shown in FIGS. 43N-43P, the passive torque element 7004 can further include a first gear 7090 coupled with the shaft 7022 of the passive torque element 7004, the first gear 7090 being configured to couple with and rotate a second gear 7092 when the shaft 7022 of the passive torque element 7004 is rotated. In some embodiments, the first gear 7090 and the second gear 7092 can be miter gears (also referred to as bevel gears). In some embodiments, the second gear 7092 can be rotationally and axially coupled with a surgical instrument. As shown in FIGS. 43N-43P, the second gear 7092 can be coupled with an interventional device 7096 (e.g., a guidewire or catheter as described herein). The interventional device 7096 can be configured to rotate when the second gear 7092 rotates. In certain embodiments, the interventional device 7096 can be a guidewire, an insert or access catheter, a guide catheter, or a procedure catheter. In some embodiments, the procedure catheter can be an aspiration catheter, an embolic deployment catheter, a stent deployment catheter, a flow diverter deployment catheter, a diagnostic angiographic catheter, a stent retriever catheter, a clot retriever, a balloon catheter, a catheter to facilitate percutaneous valve repair or replacement, an ablation catheter, or any other suitable or desired instrument.

While a passive torque element 7004 for rotating an interventional device is shown in FIGS. 43N and 43O, it is contemplated that passive torque elements 7004 may be used for controlling a variety of surgical instruments including, for example, additional components and/or functions of a hub 7001. For example, one or more passive torque elements 7004 may be coupled with a valve. The passive torque element 7004 can be configured to rotate the valve between various states (e.g., an open and a closed positioned). The valve can be a rotating hemostatic valve (RHV) or a stopcock valve. In some embodiments, the passive torque element 7004 can be configured to actuate an RHV between various states to allow for and/or restrict movement of the interventional device therethrough and to allow for and/or prevent fluid flow therethrough. For example, the RHV can be actuatable between a first fully open state, a second partially opened (low sealing force state) for sealing around an interventional device but permitting sliding movement of the interventional device, a third state for sealing around an interventional device for high pressure management, and a fourth completely closed state in the absence of any interventional devices extending therethrough.

In some embodiments, a passive torque element 7004 can be configured to be coupled with a guidewire and the passive torque element 7004 or another passive torque element 7004 can be configured to selectively deflect at least a distal portion of the guidewire upon a rotation of the passive torque element 7004. In some embodiments, the passive torque element 7004 can be configured to be coupled with a catheter and the passive torque element 7004 or another passive torque element 7004 can be configured to selectively deflect at least a distal portion of the catheter upon a rotation of the passive torque element 7004. In some embodiments, the passive torque element 7004 can be configured to selectively actuate a function of an interventional device, such as aspiration, fluid delivery, etc.

As described herein, the hub 7001 and hub adapter 7005 can be part of a robotic drive system, which may include a plurality of hub 7001 and hub adapter 7005 combinations for coupling with different interventional devices, as described herein. For example, one or more of the hubs of the interventional device assembly 2900 may be a hub 7001 configured to couple to a hub adapter 7005 to allow for magnetic torque transmission.

The hub 7001 can be configured to be positioned on a sterile side of a sterile barrier and configured to adjust an axial position of an interventional device. The hub adapter 7005 can be configured to be positioned on a non-sterile side of a sterile barrier and configured to move in at least one direction based on an input provided by a user of the robotic drive system.

Any embodiments of the drive system disclosed herein, can have a plurality of torque transfer systems 7000 configured as in any one of the embodiments disclosed herein. In some embodiments, the active torque element 7002 of each of the plurality of torque transfer systems 7000 can be coupled with the hub adapter and the passive torque element 7004 of each of the plurality of torque transfer systems 7000 can be coupled with the one or more hubs of the embodiments of the robotic drive system disclosed herein.

As described herein, for example, with respect to FIGS. 4, the hub adapter 7005 can further include a drive magnet configured to couple with a driven magnet of the hub 7001 such that the driven magnet and the hub 7001 move axially in response to movement of the drive magnet when the driven magnet is magnetically coupled with the drive magnet.

In any embodiments disclosed herein, the robotic drive system can include at least three or at least four hub adapters (e.g., hub adapters 7005), each configured to be positioned on a non-sterile side of a sterile barrier and configured to move in at least one direction based on an input provided by a user of the robotic drive system, and at least four hubs (e.g., hubs 7001), each configured to be positioned on a sterile side of a sterile barrier and configured to adjust an axial position of an interventional device, and a plurality of torque transfer systems 7000 configured as in any one of the embodiments disclosed herein. Each of the at least three or at least four hub adapters can have at least one active torque element 7002 coupled with the hub adapter, and each of the at least three or at least four hubs can have at least one passive torque element 7004 coupled with the hub. In some embodiments, each of the at least three or at least four hub adapters can have a plurality of active torque elements 7002 coupled with the hub adapter and each of the at least three or at least four hubs can have a plurality of passive torque elements 7004 coupled with the hub.

In certain embodiments, the first magnet 7014 of the active torque element 7002 and the first magnet 7024 of the passive torque element 7004 each can have a diameter of 0.25 inches or approximately 0.25 inches, or 0.375 inches or approximately 0.375 inches, or 0.5 inches or approximately 0.5 inches. In certain embodiments, the first magnet 7014 of the active torque element 7002 can be spaced apart from the centerline axis of the shaft 7012 or from a center (e.g., a radial center) of the magnet support element 7040 of the active torque element 7002 by 0.4 inches or approximately 0.4 inches. In certain embodiments, the first magnet 7024 of the passive torque element 7004 can be spaced apart from the centerline axis of the shaft 7022 or from a center (e.g., a radial center) of the magnet support element 7050 of the passive torque element 7004 by 0.4 inches or approximately 0.4 inches. In certain embodiments, the first magnet 7014 of the active torque element 7002 can be spaced apart from the centerline axis of the shaft 7012 or from a center (e.g., a radial center) of the magnet support element 7040 of the active torque element 7002 from 0.25 inches or approximately 0.25 inches to 1 inch or approximately 1 inch. In certain embodiments, the first magnet 7024 of the passive torque element 7004 can be spaced apart from the centerline axis of the shaft 7022 or from a center (e.g., a radial center) of the magnet support element 7050 of the passive torque element 7004 from 0.25 inches or approximately 0.25 inches to 1 inch or approximately 1 inch.

Also disclosed herein are embodiments of a method of rotating a surgical device on a sterile side of a sterile barrier. Some embodiments of the method can include magnetically coupling an active torque element 7002 positioned on a non-sterile side of the sterile barrier with a passive torque element 7004 positioned on a sterile side of the sterile barrier, coupling an instrument, such as an interventional device, with the passive torque element 7004, and rotating the active torque element 7002, thereby causing the passive torque element 7004 magnetically coupled with the active torque element 7002 to rotate and the instrument coupled with the passive torque element 7004 to rotate. In some embodiments, the interventional device can be a catheter or a guidewire.

Some embodiments of the method can include rotating the passive torque element 7004 to move a seal around a catheter between various states as described herein.

Also disclosed herein are embodiments of a method of performing a neurovascular procedure. Some embodiments of the method can include providing an interventional device assembly that can include a guidewire, an access catheter, a guide catheter, and/or a procedure catheter. The method can include one or more of: coupling the guidewire to a first passive torque element 7004 positioned on a sterile side of a sterile barrier, coupling the access catheter to a second passive torque element 7004 positioned on the sterile side of the sterile barrier, coupling the procedure catheter to a third passive torque element 7004 positioned on the sterile side of the sterile barrier, and coupling a guide catheter to a fourth passive torque element 7004. The method can include one or more of magnetically coupling a first active torque element 7002 with the first passive torque element 7004, magnetically coupling a second active torque element 7002 with the second passive torque element 7004, magnetically coupling a third active torque element 7002 with the third passive torque element 7004, and magnetically coupling a fourth active torque element 7002 with the fourth passive torque element. The method can include one or more of rotating the guidewire by rotating the first active torque element 7002, rotating the access catheter by rotating the second active torque element 7002, rotating the procedure catheter by rotating the third active torque element 7002, and rotating the guide catheter by rotating the fourth active torque element 7002. In some embodiments, the first active torque element 7002, the second active torque element 7002, the third active torque element 7002, and the fourth active torque element 7002 are each independently movably carried by separate hub adapters. In some embodiments, the procedure catheter can be an aspiration catheter, an embolic deployment catheter, a stent deployment catheter, a flow diverter deployment catheter, a diagnostic angiographic catheter, a stent retriever catheter, a clot retriever, a balloon catheter, a catheter to facilitate percutaneous valve repair or replacement, or an ablation catheter.

Figure 44A:
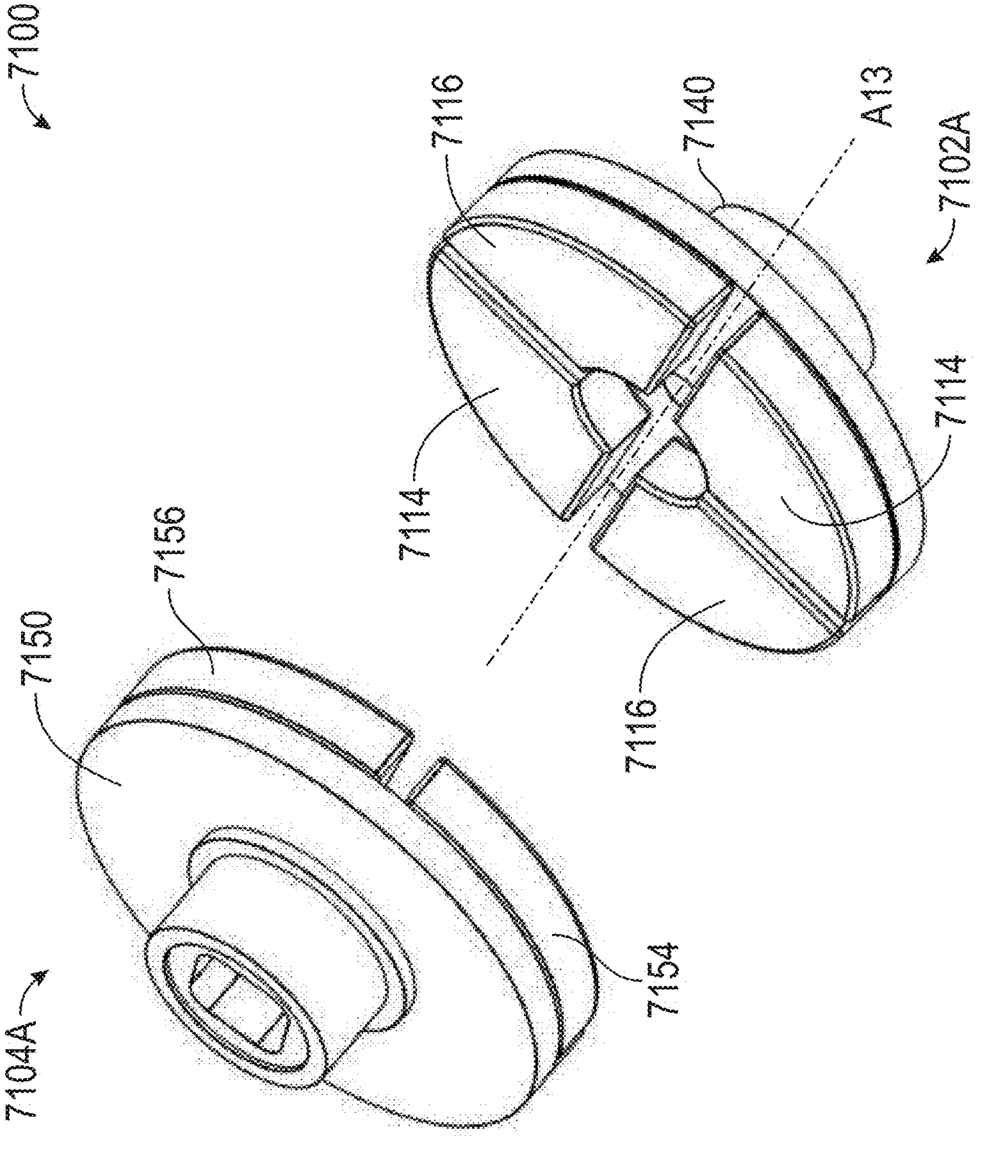
FIG. 44A is a perspective view of a portion of an embodiment of a torque transfer system showing an active torque element and a passive torque element.
Figure 44C:
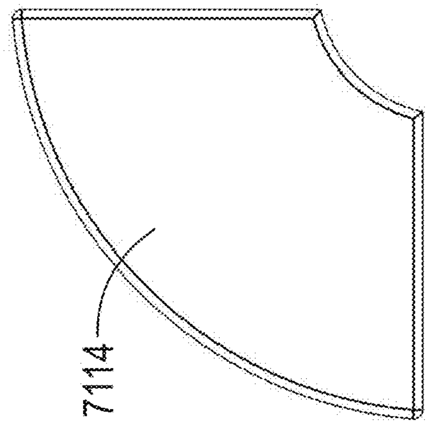
FIG. 44C is a top view of a magnet of the active torque transfer element of FIG. 44A.
Figure 44D:
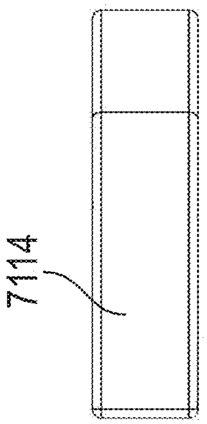
FIG. 44D is a side view of a magnet of the active torque transfer element of FIG. 44A.
Figure 44B:
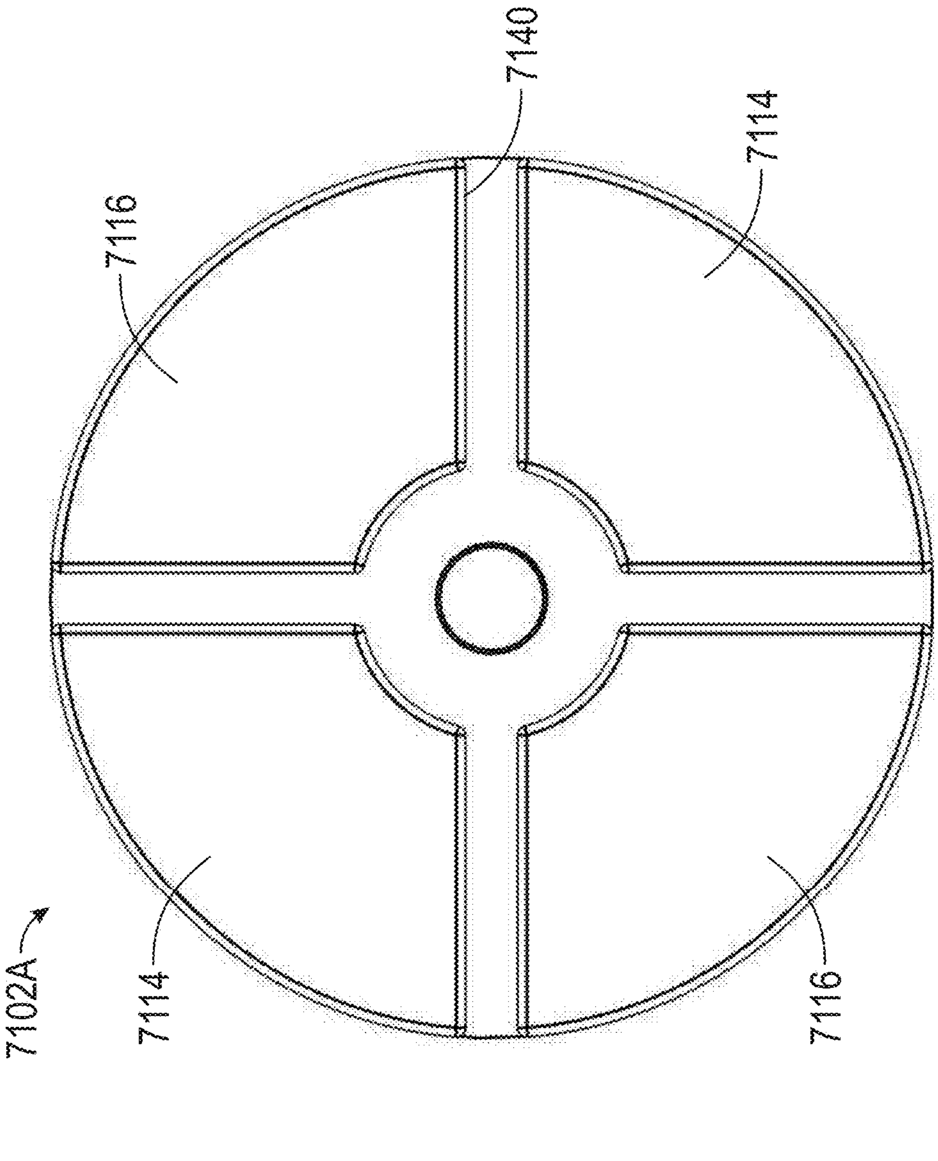
FIG. 44B is a top view of an embodiment of the active torque transfer element of FIG. 44A.

FIG. 44A shows a portion of an embodiment of a torque transfer system 7100 that can be configured to transfer a torque force through a sterile barrier. The torque transfer system 7100 can have any of the same or similar features and/or functions as any of the other torque transfer systems described herein and vice versa. In some embodiments, the torque transfer system 7100 can include an active torque element (e.g., a first active torque element 7102A) configured to be positioned on a nonsterile side (e.g., a capital equipment side) of a sterile barrier and a passive torque element (e.g., a first passive torque element 7104A) configured to be positioned on a sterile side (e.g., a disposable equipment side) of the sterile barrier. The active torque element can have any of the same or similar features and/or functions as any of the other active torque elements described herein and vice versa. The passive torque element can have any of the same or similar features and/or functions as any of the other passive torque elements described herein and vice versa. FIGS. 44A-44B depict a representative magnetic coupling between the first active torque element 7102A and the first passive torque element 7104A. The magnetic coupling may be representative of any magnetic coupling between an active torque element and a passive torque element.

In some embodiments, the active torque element 7102A can include a plurality of magnets arranged around a central axis (represented by axis A13 in FIG. 44A). The plurality of magnets can include one or more first magnets 7114 and one or more second magnets 7116. The one or more first magnets 7114 can include a north or positive pole facing axially towards the passive torque element. The one or more second magnets 7116 can include a south or negative pole facing axially towards the passive torque element. The magnets 7114 and 7116 can be wedge shaped magnets. In some embodiments, wedge shaped magnets may provide a greater magnetic surface area on a magnet support element in comparison to disc shaped magnets positioned on the same magnet support element.

In some embodiments, the plurality of magnets of the active torque element 7102A can be arranged in a planar arrangement on a plane parallel with or generally parallel with the sterile barrier.

The passive torque element can include a plurality of magnets arranged around a central axis, such as axis A13. The plurality of magnets can include one or more first magnets 7154 and one or more second magnets 7156. The one or more first magnets 7154 can include a south or negative pole facing axially towards the active torque element. The one or more second magnets 7156 can include a north or positive pole facing axially towards the active torque element. The magnets 7154 and 7156 can be wedge shaped magnets. In some embodiments, the plurality of magnets of the passive torque element can be arranged in a planar arrangement on a plane parallel with or generally parallel with the sterile barrier.

The first magnets 7114 of the active torque 7102A element can be magnetically coupled with the first magnets 7154 of the passive torque element 7104A, and the second magnets 7116 of the active torque element 7102A can be coupled with the second magnets 7156 of the passive torque element 7104A. Rotation of the plurality of magnets of the active torque element about the central axis of the plurality of magnets of the active torque element 7102A can cause a corresponding rotation of the plurality of magnets of the passive torque element 7104A about the central axis of the plurality of magnets of the passive torque element.

In some embodiments, the central axis of the plurality of magnets of the active torque element 7102A can be coaxial with or parallel with the central axis of the plurality of magnets of the passive torque element 7104. In some embodiments, the central axis of the plurality of magnets of the active torque element 7102A and/or the central axis of the plurality of magnets of the passive torque element 7104A can be transverse to (e.g., perpendicular to) a direction of axial movement of a hub adapter, hub, and/or interventional device to which components of torque transfer system 7100 are coupled.

As shown in FIG. 44A, in some embodiments, the active torque element 7102A can include a magnet support element 7140. The magnet support element 7140 can be configured to support the plurality of magnets of the active torque element. For example, the magnet support element 7140 can be configured to support the plurality of magnets of the active torque element in a planar arrangement radially about a central axis of the plurality of magnets (e.g., axis A13). In some embodiments, the magnet support element 7140 can be formed of a ferrous material (e.g., steel), which may direct magnetic field lines away from the magnet support element 7140 (e.g., towards the passive torque element).

In some embodiments, the passive torque element 7104A can include a magnet support element 7150. The magnet support element 7150 can be configured to support the plurality of magnets of the passive torque element 7104A. For example, the magnet support element 7150 can be configured to support the plurality of magnets of the passive torque element 7104A in a planar arrangement radially about a central axis of the plurality of magnets (e.g., axis A13). In some embodiments, the magnet support element 7150 can be formed of a ferrous material (e.g., steel), which may direct magnetic field lines away from the magnet support element 7150 (e.g., towards the active torque element 7102A).

In some embodiments, the magnet support element 7140 and/or the plurality of magnets of the active torque element 7102A may rotated (e.g., by a motor) to cause rotation of the plurality of magnets and/or the magnet support element 7150 of the passive torque element 7104A. As described herein, the plurality of magnets and/or the magnet support element 7150 of the passive torque element 7104A can be coupled to a surgical instrument (e.g., an interventional device, a valve, etc.) so that rotation of the plurality of magnets of the passive torque element 7104A causes a corresponding movement of the surgical instrument (e.g., rotation of an interventional device, opening and/or closing of a valve (e.g., a stopcock or hemostasis valve), etc.).

As described herein the plurality of magnets of the active torque element 7102A can be configured to cause rotation of the plurality of magnets of the passive torque element 7104A across a sterile barrier.

FIG. 44B depicts the plurality of magnets and the magnet support element 7140 of the active torque element 7102A. FIGS. 44C-44D depict an example of a magnet 7114.

Figure 45A:
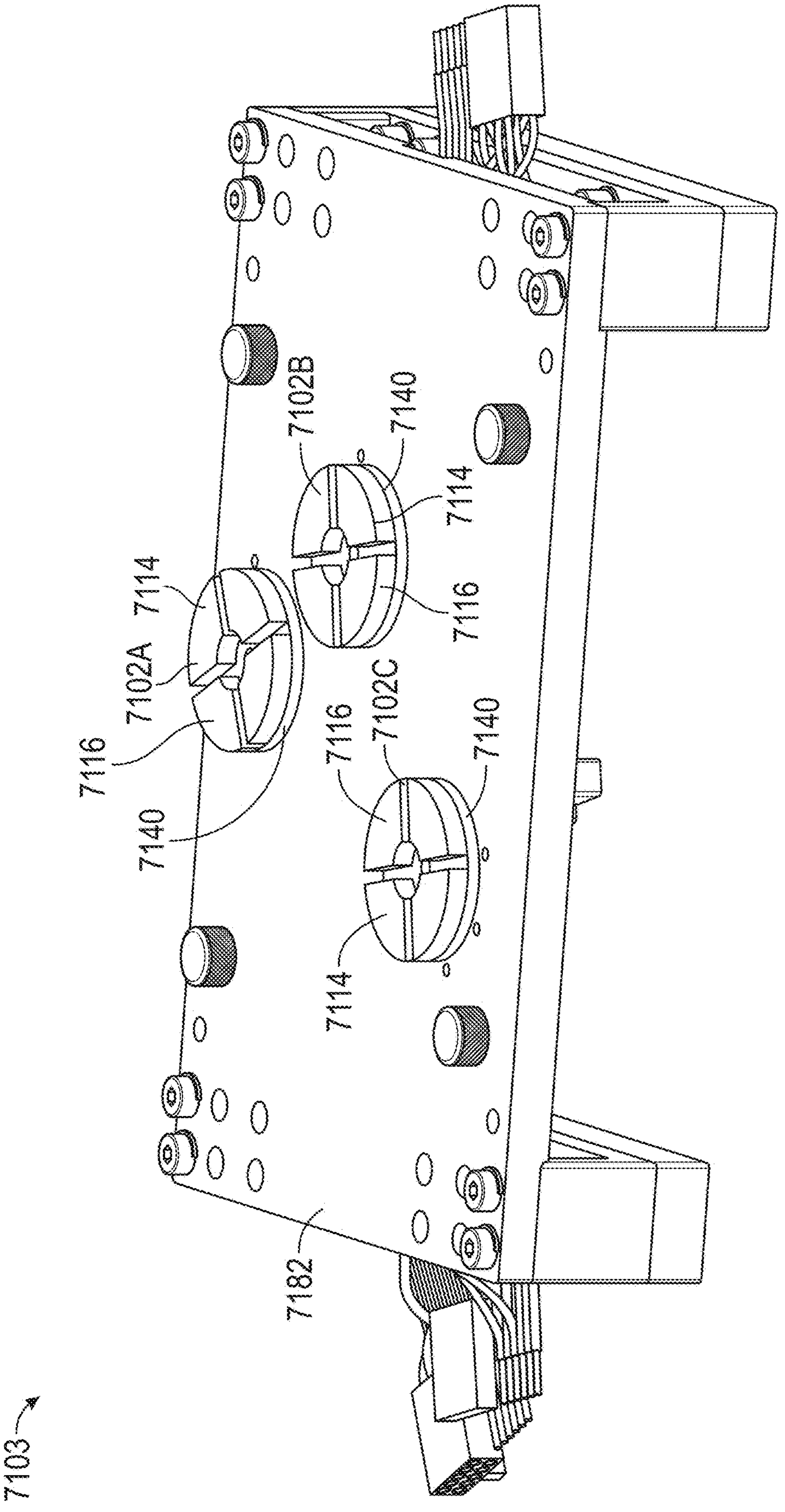
FIG. 45A is a top perspective view of an active torque subsystem of a torque transfer system.
Figure 45B:
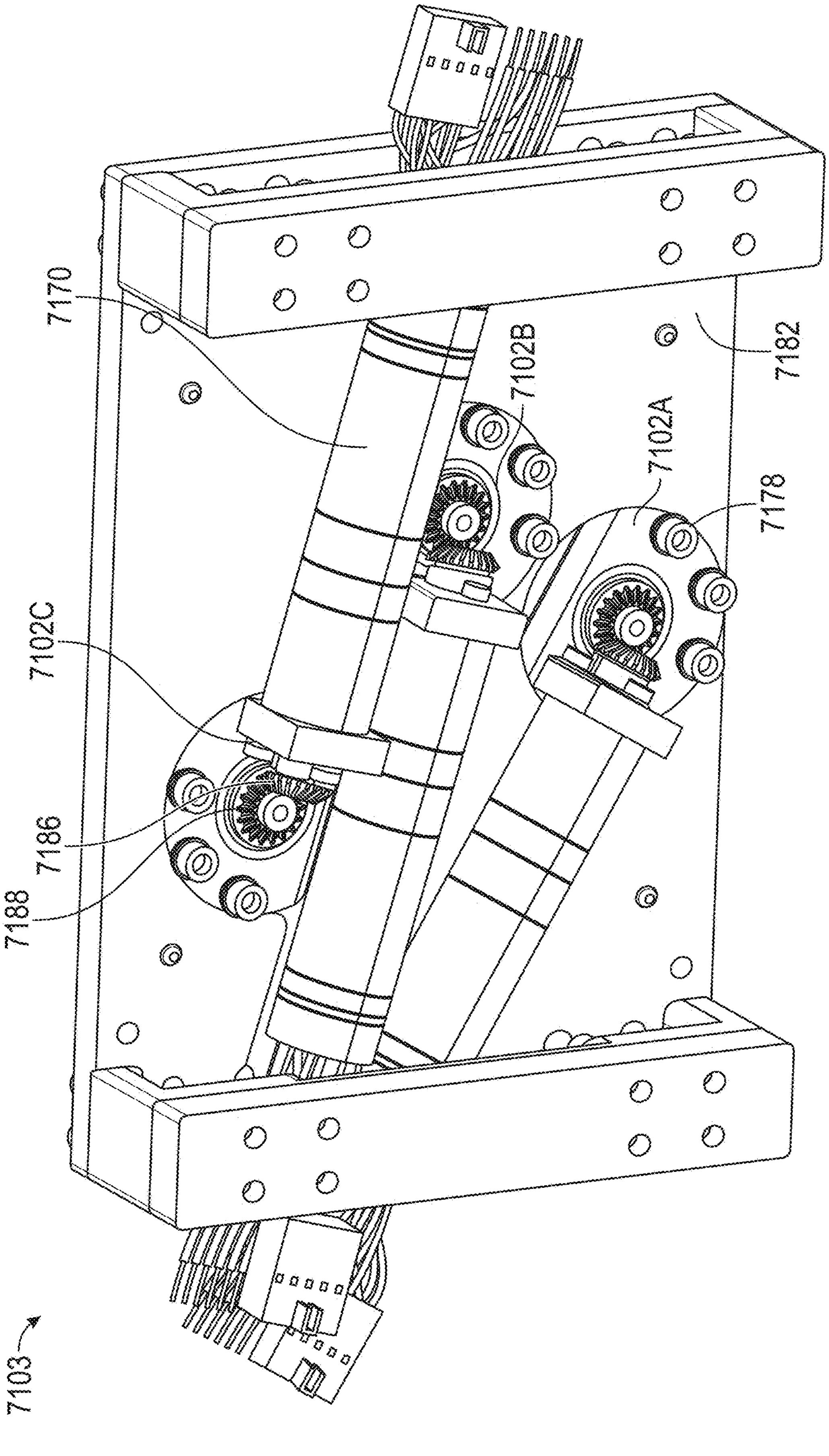
FIG. 45B is a bottom perspective view of the active torque subsystem of FIG. 45A.
Figure 45C:
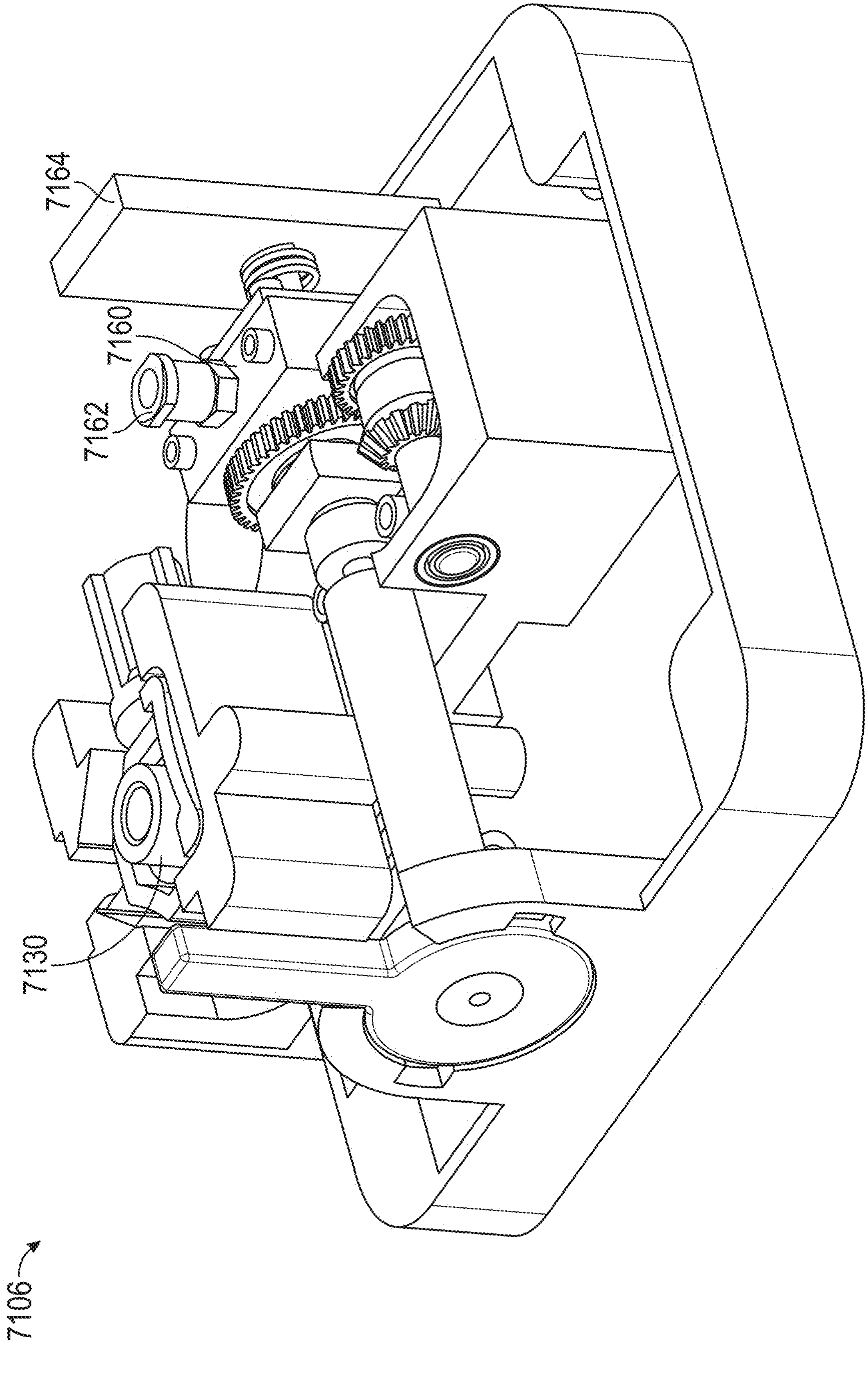
FIG. 45C is a top perspective view of a passive torque subsystem of a torque transfer system.

FIGS. 45A-45B depict an embodiment of an active torque subsystem 7103 of the torque transfer system 7100 that can be used to transfer a torque force through a sterile barrier. FIGS. 45C-45G depict an embodiment of a passive torque subsystem 7106 of the torque transfer system 7100. The active torque subsystem 7103 can be configured to be positioned on a nonsterile side (e.g., a capital equipment side) of a sterile barrier. The passive torque subsystem 7106 can be configured to be positioned on a sterile side (e.g., a disposable equipment side) of a sterile barrier.

The active torque subsystem 7103 can include one or more active torque elements. For example, the active torque subsystem 7103 can include a first active torque element 7102A, a second active torque element 7102B, and a third active torque element 7102C. Each active torque element can include a magnet support element 7140 and a plurality of magnets 7114 and 7116 as described with respect to FIGS. 44A-44D.

In certain embodiments, each of the one or more active torque elements can include a first gear 7186 coupled to a second gear 7188. In some embodiments, the first gear 7186 and the second gear 7188 can be miter gears (also referred to as bevel gears). The first gear 7186 can be coupled with a motor 7170. The motor 7170 can be configured to selectively exert a torque on the first gear 7186 to cause the first gear 7186 to rotate. The first gear 7186 can be configured to rotate the second gear 7188. The second gear 7188 can be coupled with the plurality of magnets 7114 and 7116 of the active torque element. The plurality of magnets of the active torque elements can be configured to rotate when the second gear 7188 rotates. In some embodiments, the second gear 7188 can be coupled to and configured to rotate the magnet support element 7140.

In some embodiments, the motor 7170 can be a servo motor. In some embodiments, as described herein, the torque transfer system 7100 can include a controller in electrical communication with the motor 7170 of the active torque element configured to control an operation of the motor 7170 in response to an input to the controller. The controller may be a microcontroller.

As described herein, in certain embodiments, the active torque subsystem 7103 can be configured to be positioned on a nonsterile side (e.g., a capital equipment side) of a sterile barrier and the passive torque subsystem 7106 can be configured to be positioned on a sterile side (e.g., a disposable equipment side) of the sterile barrier. Further, in any embodiments disclosed herein, the torque transfer system 7100 can be configured for use in a surgical robotic drive system as described herein. For example, the active torque subsystem 7103 may be coupled to a hub adapter and the passive torque subsystem 7106 can be coupled to a hub of a robotic drive system.

In certain embodiments, the active torque subsystem 7103 can include a support plate or housing 7182. The housing 7182 can include a plurality of recesses 7178 each configured to receive the magnet support elements 7140 of the active torque elements therein. The plurality of recesses 7178 can each be sized slightly larger than the magnet support elements 7140 so that the magnet support elements 7140 can rotate freely within the plurality of recesses 7178.

In certain embodiments, the passive torque subsystem 7106 can include one or more passive torque elements. As shown in FIGS. 45C-45G, the passive torque subsystem can include one or more passive torque elements. For example, the passive torque subsystem can include a first passive torque element 7104A, a second passive torque element 7104B, and a third passive torque element 7104C. Each of the one or more passive torque elements can be configured to cause a responsive movement of a surgical instrument or other feature of a robotic surgery system in response to a transfer of a magnetic force (e.g., a torque force) from an active torque element to the passive torque element. For example, the first passive torque element 7104A can be configured to cause a responsive movement of a surgical instrument or other feature of a robotic surgery system in response to a transfer of a magnetic force from the first active torque element 7102A, the second passive torque element 7104B can be configured to cause a responsive movement of a surgical instrument or other feature of a robotic surgery system in response to a transfer of a magnetic force from the second active torque element 7102B, the third passive torque element 7104C can be configured to cause a responsive movement of a surgical instrument or other feature of a robotic surgery system in response to a transfer of a magnetic force from the third active torque element 7102C.

In certain embodiments, the one or more passive torque elements can be configured to control functions of a hub or hub assembly (e.g., hub assembly 7200). In some embodiments, the one or more passive torque elements can be configured to control medical devices or components of a robotic medical system. For example, in some embodiments, the one or more passive torque elements can be configured to control movement of an interventional device, and/or control fluidics components coupled to an interventional device (e.g., controllably select a fluidics configuration for a fluidics management system). For example, the one or more passive torque elements can be configured to rotate an interventional device, such as a catheter or guidewire, translate an interventional device, manipulate an interventional device (in the case of a deflectable tip catheter), and/or rotate a valve to controllably select an active fluidics configuration. In certain embodiments, the one or more passive torque elements may be configured to manipulate a sensor, for example, to position a sensor, such as a bubble sensor, in a desired position for operation. In certain embodiments, the one or more passive torque elements may be configured to increase tension in the system. For example, the one or more passive torque elements may cause the application of tension to a stent retriever to allow the stent retriever to pull other interventional devices.

Figure 45D:
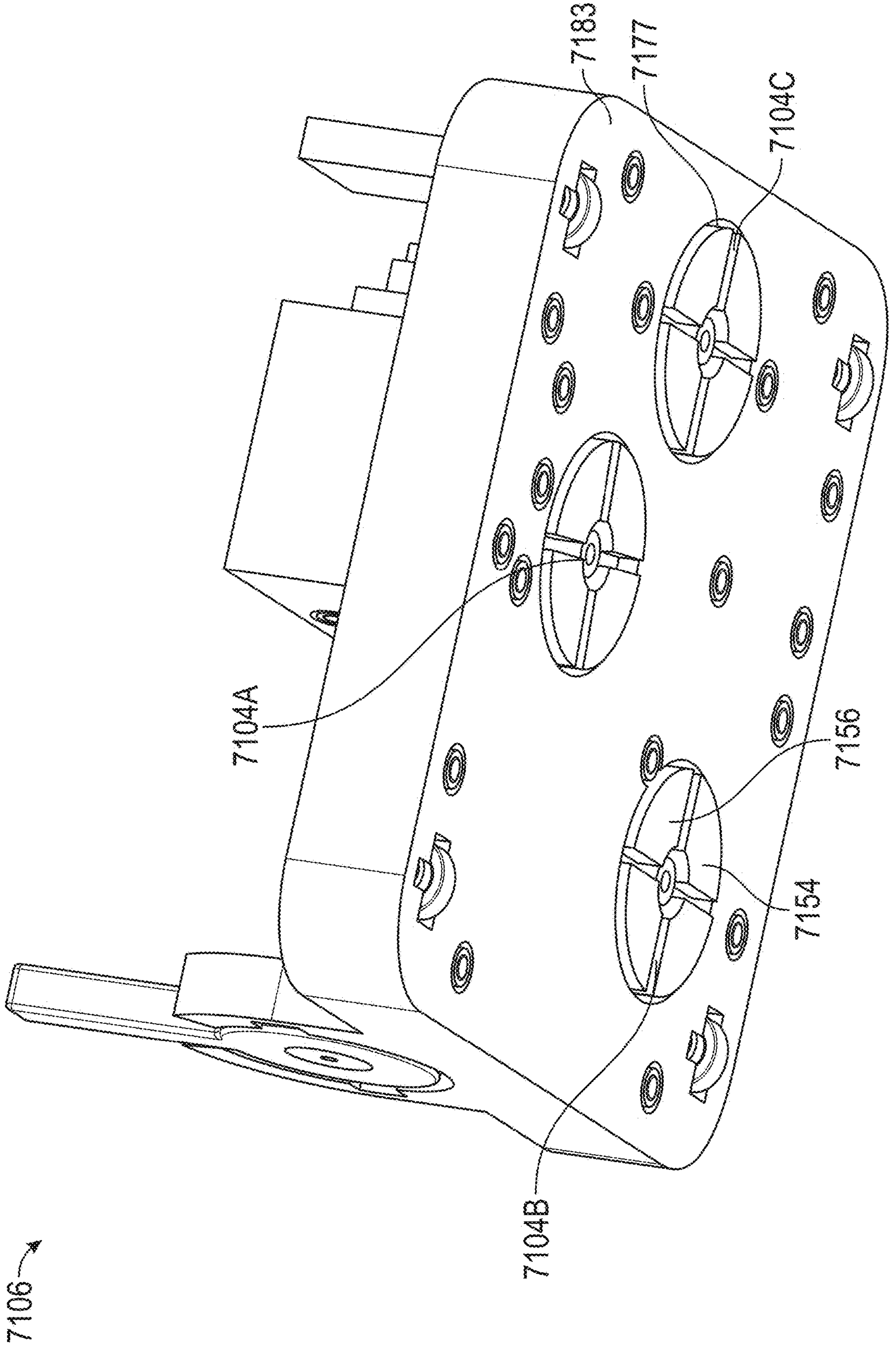
FIG. 45D is a bottom perspective view of the passive torque subsystem of FIG. 45C.
Figure 45E:
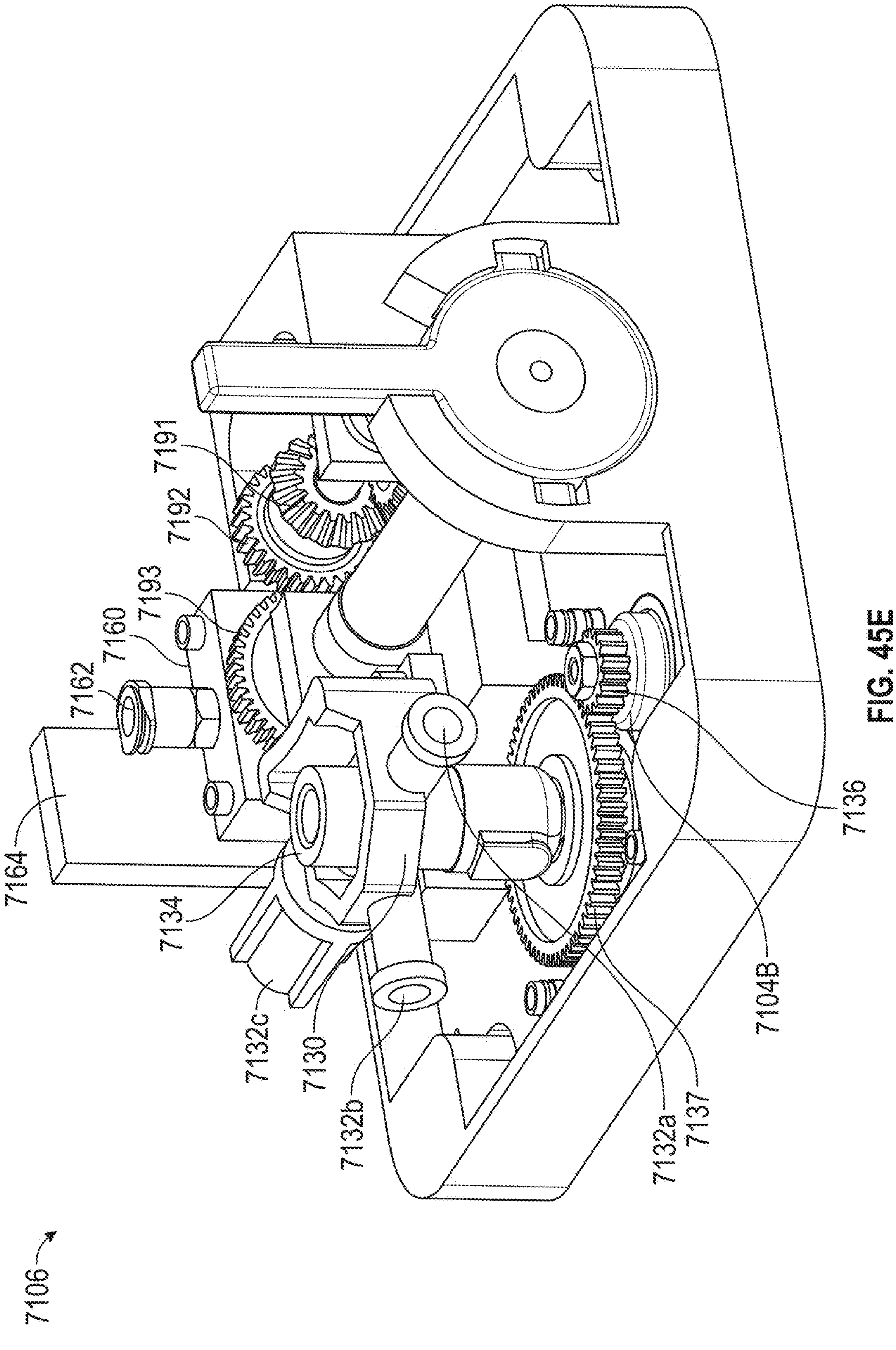
FIG. 45E is a top perspective view of a portion of the passive torque subsystem of a FIG. 45C.
Figure 45F:
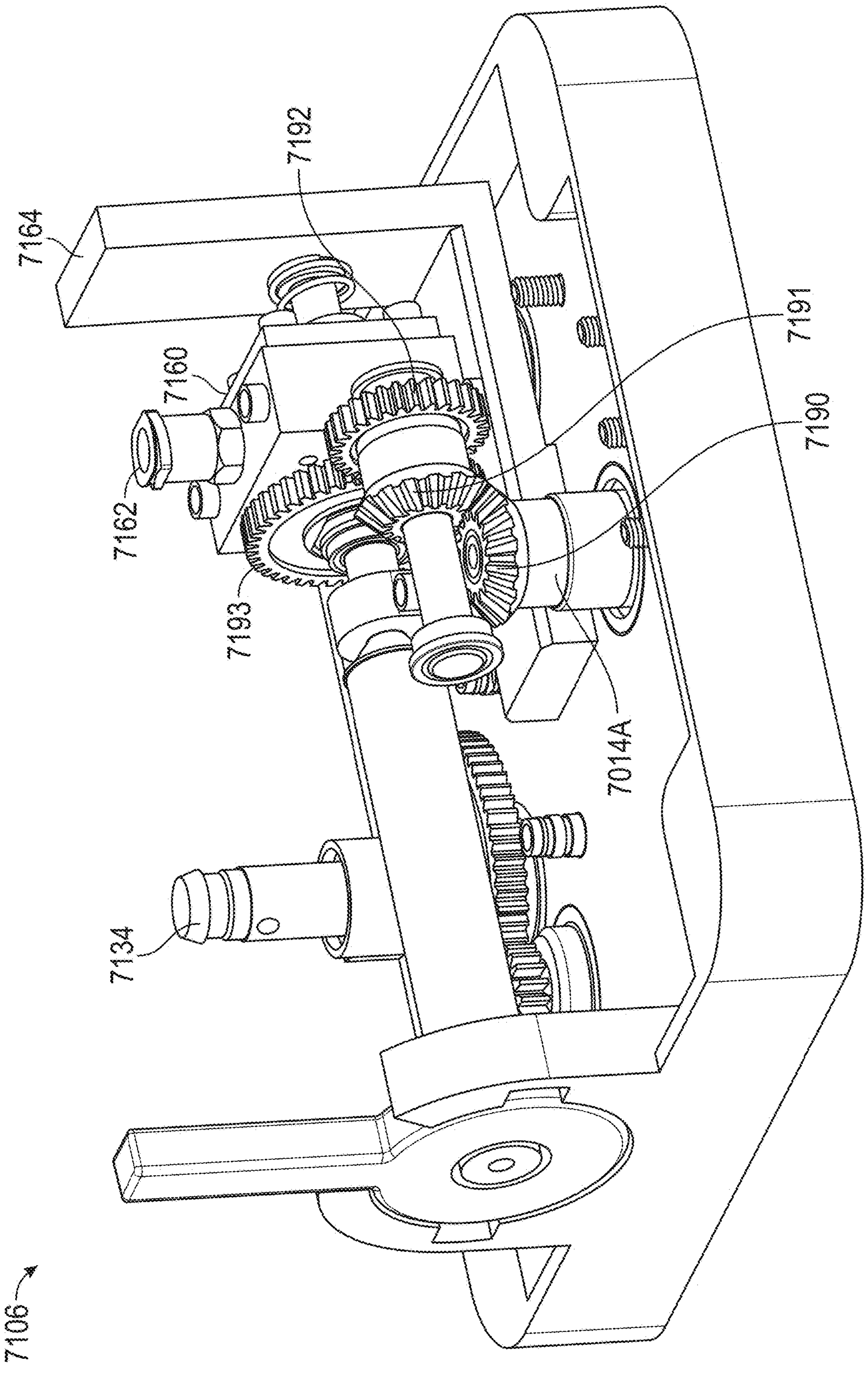
FIG. 45F is a top perspective view of a portion of the passive torque subsystem of a FIG. 45C.
Figure 45G:
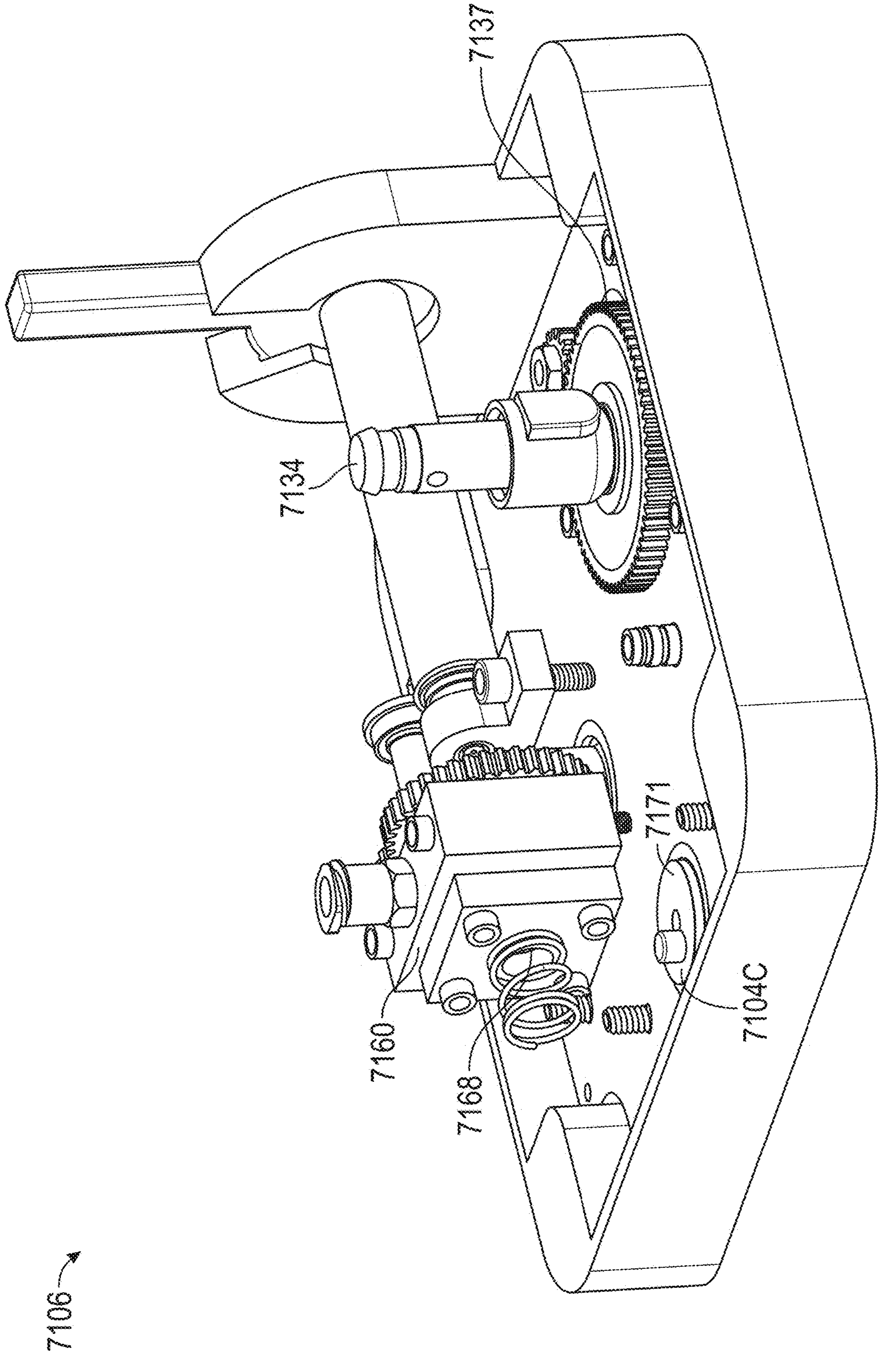
FIG. 45G is a top perspective view of a portion of the passive torque subsystem of a FIG. 45C.

In certain embodiments, the first passive torque element 7104A can be configured to rotate an interventional device, such as a catheter or guidewire. As shown in FIG. 45F, the first passive torque element 7104A can further include a first gear 7090 coupled with the one or more magnets of the first passive torque element 7104A or the magnet support element 7150. The first gear 7190 can be configured to couple with and rotate a second gear 7191 when the one or more magnets of the first passive torque element 7104A is rotated. In some embodiments, the first gear 7190 and the second gear 7191 can be miter gears (also referred to as bevel gears). In some embodiments, the second gear 7191 can be rotationally coupled with a third gear 7192. The third gear 7192 can be coupled with a fourth gear 7193. The third gear 7192 and the fourth gear 7193 may be pinion gears. In some embodiments, the fourth gear 7193 can be rotationally coupled with an interventional device, such as a catheter or guidewire. The interventional device can be configured to rotate when the fourth gear 7193 rotates. Rotation of the plurality of magnets of the first passive torque element 7104A can cause rotation of the interventional device via rotation of a gear assembly, which may be in the form of first gear 7190, second gear 7191, third gear 7192, and fourth gear 7193.

In certain embodiments, the second passive torque element 7104B can be configured to control a stopcock 7130. The stopcock 7130 can be a three-way stopcock having a first port 7132*a*, a second port 7132*b*, and a third port 7132*c*. In some embodiments, the first port 7132*a* can be coupled to a source of contrast media and/or a source of saline. The second port 7132*b* can be coupled to a vacuum source. In certain embodiments, the third port 7132*c* can be coupled to the interventional device to provide contrast and/or saline or apply vacuum thereto. In some embodiments, the third port 7132*c* can be coupled to a fluid port 7162 of a hemostatic valve 7160 coupled to an interventional device to provide contrast and/or saline or apply vacuum thereto.

The stopcock 7130 can include a stopcock valve portion or stopcock control 7134 that can be rotated to selectively provide or prevent fluid communication of the ports 7132*a*-7132*c* with one another (e.g., via fluid passages extending through the stopcock control 7134). In certain embodiments, the stopcock control 7134 can be rotated to a first position in which none of the ports 7132*a*, 7132*b*, and 7132*c* are in fluid communication. In certain embodiments, the stopcock control 7134 can be rotated to a second position in which the ports 7132*a*, 7132*b*, and 7132*c* are each in fluid communication with one another. In certain embodiments, the stopcock control 7134 can be rotated to a third portion in which the ports 7132*a* and 7132*b* are in fluid communication with one another, but fluid communication with the port 7132*c* is blocked. In certain embodiments, the stopcock control 7134 can be rotated to a fourth position in which the ports 7132*a* and 7132*c* are in fluid communication with one another, but fluid communication with the port 7132*b* is blocked. In certain embodiments, the stopcock control 7134 can be rotated to a fifth position in which the ports 7132*b* and 7132*c* are in fluid communication with one another, but fluid communication with the port 7132*a* is blocked.

In certain embodiments, the second passive torque element 7104B can include a first gear 7136. The first gear 7136 can be coupled with the one or more magnets of the second passive torque element 7104B or the magnet support element 7150. The first gear 7136 can be configured to couple with and rotate a second gear 7137 when the one or more magnets of the second passive torque element 7104B are rotated. The first gear 7136 and the second gear 7137 can be pinion gears. The second gear 7137 can be coupled (e.g., rotationally) with the stopcock 7130 (e.g., coupled with the stopcock control 7134) to adjust the configuration of the stopcock 7130 to provide or prevent fluid communication between the ports of the stopcock 7130 as described herein. The stopcock control 7134 can be rotated in response to rotation of the second gear 7137 to provide or prevent fluid communication between the ports of the stopcock 7130. Rotation of the plurality of magnets of the second passive torque element 7104B can cause rotation of the stopcock control 7134 via a gear assembly (e.g., the first gear 7136 and the second gear 7137.

In certain embodiments, the third passive torque element 7104C can be configured to control a hemostasis valve 7160 (e.g., a rotating hemostasis valve). The hemostasis valve 7160 can include a fluid port 7162 that can be placed in fluid communication with a fluidics system for the delivery of fluids (e.g., saline and/or contrast media) to the interventional device and/or for aspiration of fluids from the interventional device. For example, in some embodiments, the fluid port 7162 can be in fluid communication with the stopcock 7130.

The hemostasis valve 7160 can be configured to receive a more proximal interventional device therethrough. For example, the hemostasis valve 7160 can include a channel 7168 for receiving a more proximal interventional device therethrough.

The hemostasis valve 7160 can be actuatable between various states to allow for and/or restrict movement of the interventional device therethrough and to allow for and/or prevent fluid flow therethrough. For example, the hemostasis valve 7160 can be actuatable between a first fully open state, a second partially opened (low sealing force state) for sealing around an interventional device but permitting sliding movement of the interventional device, a third state for sealing around an interventional device for high pressure management, and a fourth completely closed state in the absence of any interventional devices extending therethrough. In certain embodiments, the third passive torque element 7104C can be configured to actuate the hemostasis valve 7160 through one or more of the foregoing states.

In some embodiments, the third passive torque element 7104C can be coupled to a plunger 7164 of the hemostasis valve. The third passive torque element 7104C can be configured to control the plunger 7164 to actuate the hemostasis valve 7160 between various states (e.g., by moving the plunger 7164). In some embodiments, the third passive torque element 7104C can include a scotch yoke 7171. The hemostasis valve 7160 can be actuated between various states in response to movement of the scotch yoke 7171. For example, the plunger 7164 can be actuated by movement of the scotch yoke 7171 to transition the hemostasis valve between various states.

In certain embodiments, the passive torque subsystem 7106 can include a support plate or housing 7183. The housing 7183 can include a plurality of recesses 7177 each configured to receive the magnet support elements 7150 of the passive torque elements therein. The plurality of recesses 7177 can each be sized slightly larger than the magnet support elements 7150 so that the magnet support elements 7150 can rotate freely within the plurality of recesses 7177.

In certain embodiments, one or more of the active torque elements can transmit up to 1.5 in-lb (0.17 N-m) of torque across a 0.2 inch air gap. The air gap can be the distance between a magnet of an active torque element and a magnet of a passive torque element (e.g., between the face of the magnet of the active torque element facing the passive torque element and the face of the magnet of the passive torque element facing the active torque element). In certain embodiments in which there are three active torque element and passive torque element pairs, the passive torque elements can collectively resist shear loads of up to 5.85 lb (26 N) across a 0.2 inch air gap. Shear refers to sliding of the magnets relative to each other in a horizontal plane. In some embodiments, the plurality of magnets of a single passive torque element may resist shear loads of 1.95 lb (8.7 N) across a 0.2 inch air gap. In some embodiments, each active torque element passive torque element pair may rotated at 1 revolution/sec with an acceleration of 1 revolution/$sec^2$. In some embodiments, the hub adapter may be configured to continuously resist 34 lbf pull force from the magnets across a 0.2 inch air gap.

In some embodiments, the magnetic coupling between one or more of the active torque element and passive torque element pairs described herein can be used to provide axial movement to an interventional device hub (for example, in addition to or alternatively to the drive magnet 67 and the driven magnet 69 discussed with respect to FIG. 4). For example, a plurality of magnets of an active torque element of a hub adapter can act as a drive magnet arrangement configured to couple with a driven magnet arrangement formed by a plurality of magnets of a passive torque element carried by a hub. This provides a magnetic coupling through the sterile barrier (and in some embodiments, a section (e.g., wall) of a drive table) such that the hub is moved axially across the top of the sterile barrier in response to movement of the hub adapter axially outside of the sterile field.

For example, in certain embodiments, active torque elements of a hub adapter may be magnetically coupled with one or more of passive torque elements of a hub. The hub adapter can be driven axially to cause a corresponding axial movement of the hub via the magnetic coupling between the active torque elements and the passive torque elements.

The magnetic force between magnets of a hub on the sterile side of a sterile barrier and magnets of a hub adapter on the non-sterile side of the barrier may counteract efforts to remove the hub from the drive table. In certain embodiments, one or more active torque element and passive torque element pairs may be actuated to create a repulsion force between the magnets of the active torque element and the passive torque element so as to reduce an overall magnetic attraction between the hub and the hub adapter, and consequently, the force needed to remove a hub from the drive table. In certain embodiments, a repulsion force may be generated by introducing a rotational misalignment between the magnets of the active torque element and magnets of the passive torque element.

Figure 46C:
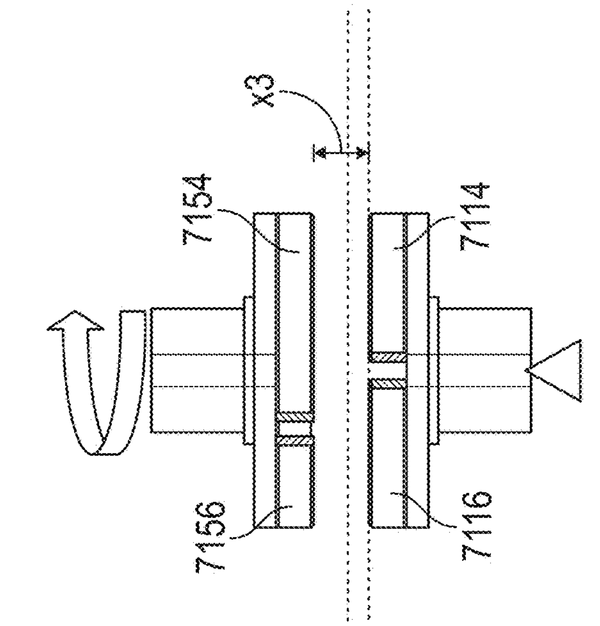
FIGS. 46A-46C depict an example of a method of generating a repulsion force within a torque transfer system.
Figure 46B:
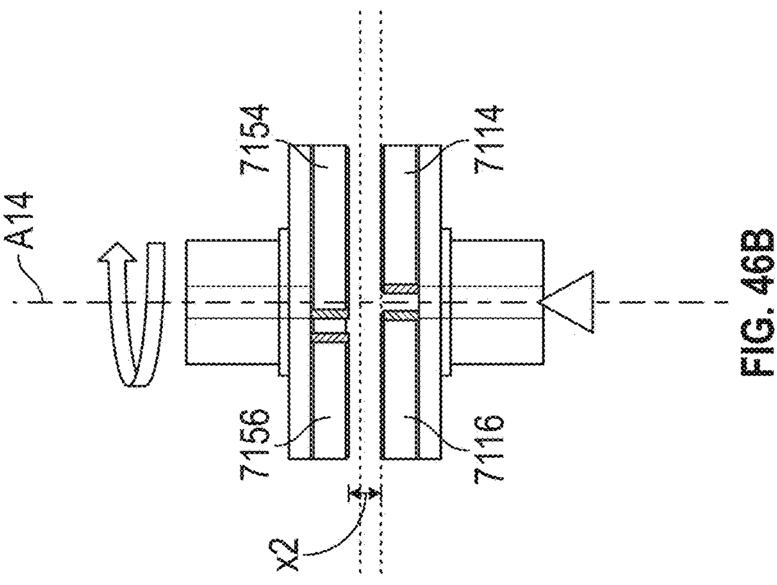
Figure 46A:
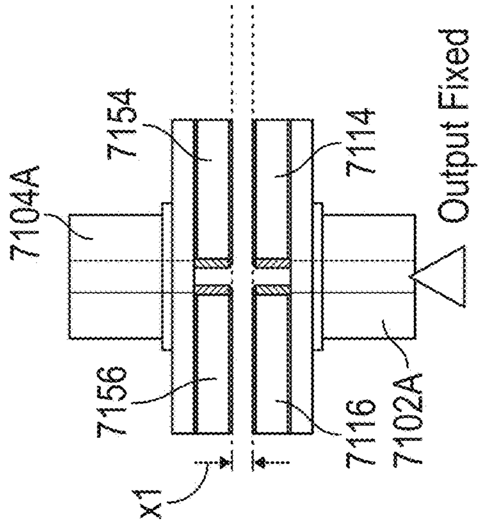

FIGS. 46A-46C depict an example of a method of creating a repulsion force between magnets of an active torque element and magnets of a passive torque element. FIGS. 46A-46C depict a representative magnetic coupling between the first active torque element 7102A and the first passive torque element 7104A. The magnetic coupling may be representative of any magnetic coupling between an active torque element and a passive torque element. As shown, the first active torque element 7102A can include one or more first magnets 7114 and one or more second magnets 7116. The one or more first magnets 7114 can include a north or positive pole facing axially towards a plurality of magnets of the first passive torque element 7104A. The one or more second magnets 7116 can include a south or negative pole facing axially towards the first passive torque element 7104A.

The first passive torque element 7104A can include one or more first magnets 7154 and one or more second magnets 7156. The one or more first magnets 7154 can include a south or negative pole facing axially towards the first active torque element 7102A. The one or more second magnets 7156 can include a north or positive pole facing axially towards the first active torque element 7102A.

FIG. 46A depicts a magnet 7114 of the first active torque element 7102A aligned with a magnet 7154 of the first passive torque element 7104A and a magnet 7116 aligned with a magnet 7156. When opposite pole pairs are aligned, as shown in FIG. 46A, and the first active torque element 7102A and the first passive torque element 7104A are stationary, no torque is provided between the first active torque element 7102A and the first passive torque element 7104A. In this state, the magnets of the first active torque element 7102A and the magnets of the first passive torque element 7104A are separated by a distance x1.

As described herein, rotation of the first active torque element 1702A can cause a rotation torque to be exerted on the first passive torque element 7104A, resulting in a corresponding rotation of the first passive torque element 7104A.

In certain embodiments, first active torque element 7102A can be rotated at a sufficient speed and/or acceleration to cause a rotational misalignment between the magnets of the first active torque element 7102A and the magnets of the first passive torque element 7104A. For example, as shown in FIG. 46B, the first active torque element 7102A has been rotated about an axis A14 to cause rotation of the first passive torque element 7104A, and a portion of the magnet 7116 is aligned with a portion of the magnet 7154. Although not shown, a portion of the magnet 7114 is also aligned with a portion of the magnet 7156. Due to the misalignment of magnets (e.g., similar pole pairs at least partially aligning with one another), the magnets having similar pole pairs repel one another, a repulsion load results, which generates a rotational torque and an axial thrust load along the axis A14. As shown in FIGS. 46A-46C, the magnets of the active torque element and the magnets of the passive torque element are axially unconstrained relative to each other. In such an unconstrained arrangement, the axial thrust load causes a separation between the magnets of the active torque element and the magnets of the passive torque element as they repel each other. As shown in FIGS. 46B, the magnets of the first active torque element 7102A are separated from the magnets of the first passive torque element 7104A by a distance x2, which is greater than the distance x1.

FIG. 46C depicts the magnets of the first active torque element 7102A further misaligned with the magnets of the first passive torque element 7104A in comparison to FIG. 46B such that magnets having similar pole pairs further overlap with one another. As shown in FIG. 46C, as misalignment increases, and the similar pole pairs are more directly over one another, the repulsion force between the magnets of the first active torque element 7102A and the first passive torque element 7104A increases. This repulsion force causes further separation of the magnets, resulting in a separation distance x3, which is greater than x2. The separation distance in turn weakens the torque generated between the first active torque element 7102A and the first passive torque element 7104A.

When the first active torque element 7102A and the first passive torque element 7104A of FIGS. 46A-46C are positioned within a hub adapter and hub, respectively, the repulsion force (and/or separation between the magnets) may reduce an overall magnetic attraction force between the hub adapter and hub to reduce a force required to separate the hub from the hub adapter.

As described above, certain embodiments include hub and hub adapter pairs having a plurality of active torque element and passive torque element pairs. In some embodiments, misalignment may be created in one of the active torque element 7102A-C and passive torque element 7104A-C pairs to reduce an overall magnetic attraction force between the hub adapter and the hub. For example, between the first active torque element 7102A and the first passive torque element 7104A. In certain embodiments, a robotic drive system may include a plurality of hub and hub adapter pairs. In some procedures, a user may desire to remove multiple hubs simultaneously. In some embodiments, a repulsion force may be created in one hub and hub adapter pair to reduce a total force required to separate a plurality of hubs from their respective hub adapters.

Figure 47A:
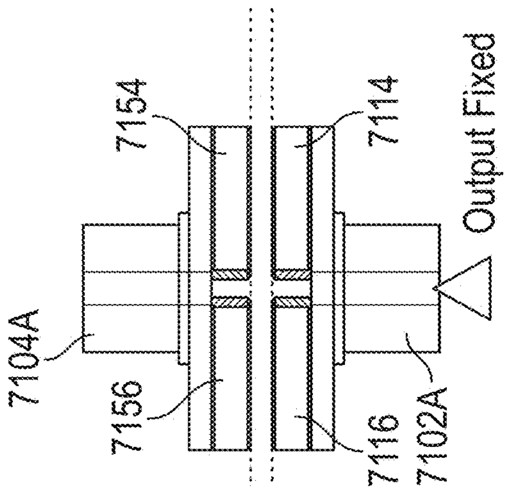
FIGS. 47A-47C depict an example of a method of generating a repulsion force within a torque transfer system.
Figure 47B:
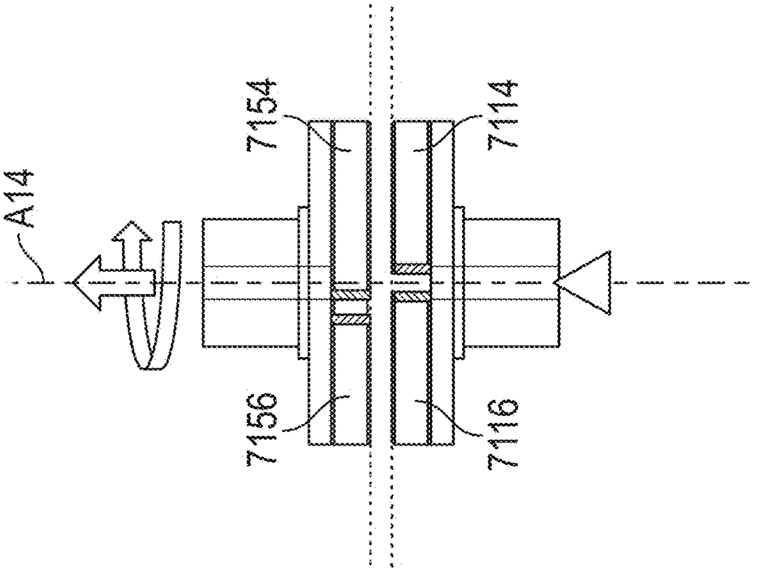
Figure 47C:
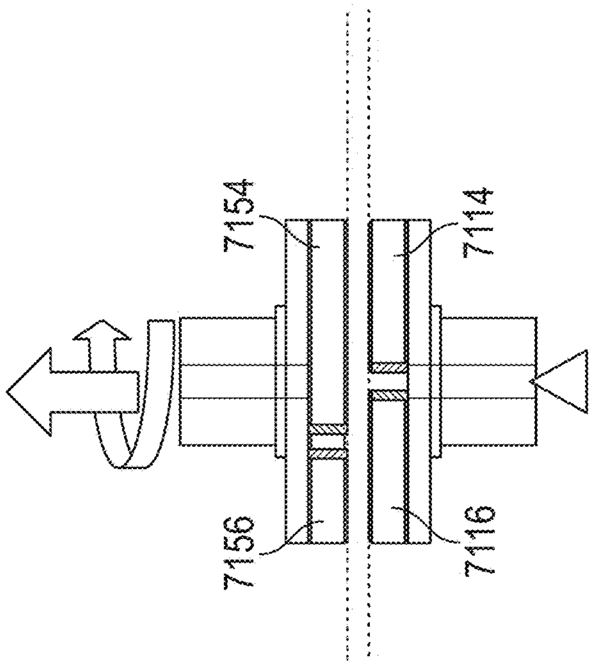

FIGS. 47A-47C depict an example of a method of creating a repulsion force between magnets of an active torque element and magnets of a passive torque element. FIGS. 47A-47C depict a representative magnetic coupling between the first active torque element 7102A and the first passive torque element 7104A. The magnetic coupling may be representative of any magnetic coupling between an active torque element and a passive torque element. In contrast to the example of FIGS. 46A-46C, the first active torque element 7102A and the first passive torque element 7104A are axially constrained relative to one another so that the separation distance does not change as the magnets are misaligned.

FIG. 47A depicts a magnet 7114 of the first active torque element 7102A aligned with a magnet 7154 of the first passive torque element 7104A and a magnet 7116 aligned with a magnet 7156. When opposite pole pairs are aligned, as shown in FIG. 47A, and the first active torque element 7102A and the first passive torque element 7104A are stationary, no torque is provided between the first active torque element 7102A and the first passive torque element 7104A.

As described herein, rotation of the first active torque element 7102A can cause a rotation torque to be exerted on the first passive torque element 7104A, resulting in a corresponding rotation of the first passive torque element 7104A.

As shown in FIG. 47B, the first active torque element 7102A has been rotated about an axis A14 causing rotation of the first passive torque element 7104A and a portion of the magnet 7116 is aligned with a portion of the magnet 7154. Although not shown, a portion of the magnet 7114 is also aligned with a portion of the magnet 7156. Due to the misalignment of magnets (e.g., similar pole pairs at least partially aligning with one another), the magnets having similar pole pairs repel one another, a repulsion load results, which generates a rotational torque and an axial thrust load along the axis A14. Because the magnets of the first active torque element 7102A and the first passive torque element 7104A are axially constrained relative to one another, the axial thrust load is unresolved.

FIG. 47C depicts the magnets of the first active torque element 7102A further misaligned with the magnets of the first passive torque element 7104A in comparison to FIG. 47B such that magnets having similar pole pairs further overlap with one another. As shown in FIG. 47C, as misalignment increases, and the similar pole pairs are more directly over one another, the repulsion force between the magnets of the first active torque element 7102A and the first passive torque element 7104A increases, causing both torque and unresolved axial thrust loads to peak. When the torque is significantly higher that a torque required to drive the passive torque element (e.g., when the resulting torque exceeds a threshold value, the magnets of the passive torque element may "skip" by quickly rotating over the magnets of similar pole pair to align with a next available magnet of an opposite pole pair.

As described with respect to FIGS. 46A-46C, the repulsion force may reduce an overall magnetic attraction force between the hub adapter and hub to reduce a force required to separate the hub from the hub adapter.

In certain embodiments, the first active torque element 7102A may be controlled to cause torques to occur that are close to the torque resulting in skipping of the passive torque element without causing skipping of the passive torque element. It may be desirable to produce a torque at or near a maximum torque between the magnets without causing skipping of the passive torque element. In certain embodiments, such a maximum torque may provide a maximum repulsion force.

Certain embodiments of hub assemblies described herein, such as hub assembly ("hub") 36 shown in FIG. 4, include a housing (e.g., housing 38) for coupling an interventional device thereto, components (e.g., rollers 53 and 55) for directly coupling to and moving along a drive table, and magnet(s) (e.g., magnet 69) for magnetically coupling to a hub adapter across a sterile barrier. A hub (or hub assembly) can refer to a single assembly with a housing, or a hub (or hub assembly) can generally refer to an apparatus having two (or more) subassemblies (e.g., a first subassembly and a second subassembly). In some embodiments of a hub assembly having two subassemblies, a hub can refer to a first subassembly that can be configured to couple to and house an interventional device, and that may be removably attachable to a second subassembly (or mount) configured to magnetically couple to a hub adapter across a sterile barrier and move along a drive table. Such a hub and mount may together form a hub assembly. Such hub assemblies may allow for a hub (first subassembly) to be removed from a mount (second subassembly) which can be advantageous, for example, so that a different hub can be coupled to the same mount or so that the hub may be used separately from the mount (e.g., for a manual procedure). Certain components of advantageous example configurations of a mount are shown and described in reference to FIGS. 48A-48J.

An arrangement of a hub assembly having a hub that is releasably couplable to mount can allow for replacement of a hub with a different hub having a different interventional device coupled thereto without breaking a magnetic connection with a hub adapter. For example, such an arrangement may allow for a hub coupled to an access catheter to be removed from a mount and replaced with a hub coupled to a procedure catheter without breaking a magnetic connection between active and passive magnetic sides of the coupling of the hub adapter and hub assembly (e.g., between the hub adapter and the mount). In some embodiments, the mount may be a magnetically driven member, an axially driven member, a puck, a slider, a shuttle, or a stage. The torque transfer systems described herein can relate to various embodiments of systems that include a hub, or a hub and a mount, regardless of whether they are described in reference to a hub, or a hub and mount, unless explicitly indicated or indicated by context. In some embodiments, a mount may be magnetically coupled to hub adapter across a sterile barrier prior to the coupling a hub to the mount, for example, when preparing the drive table for a medical procedure.

Figure 48A:
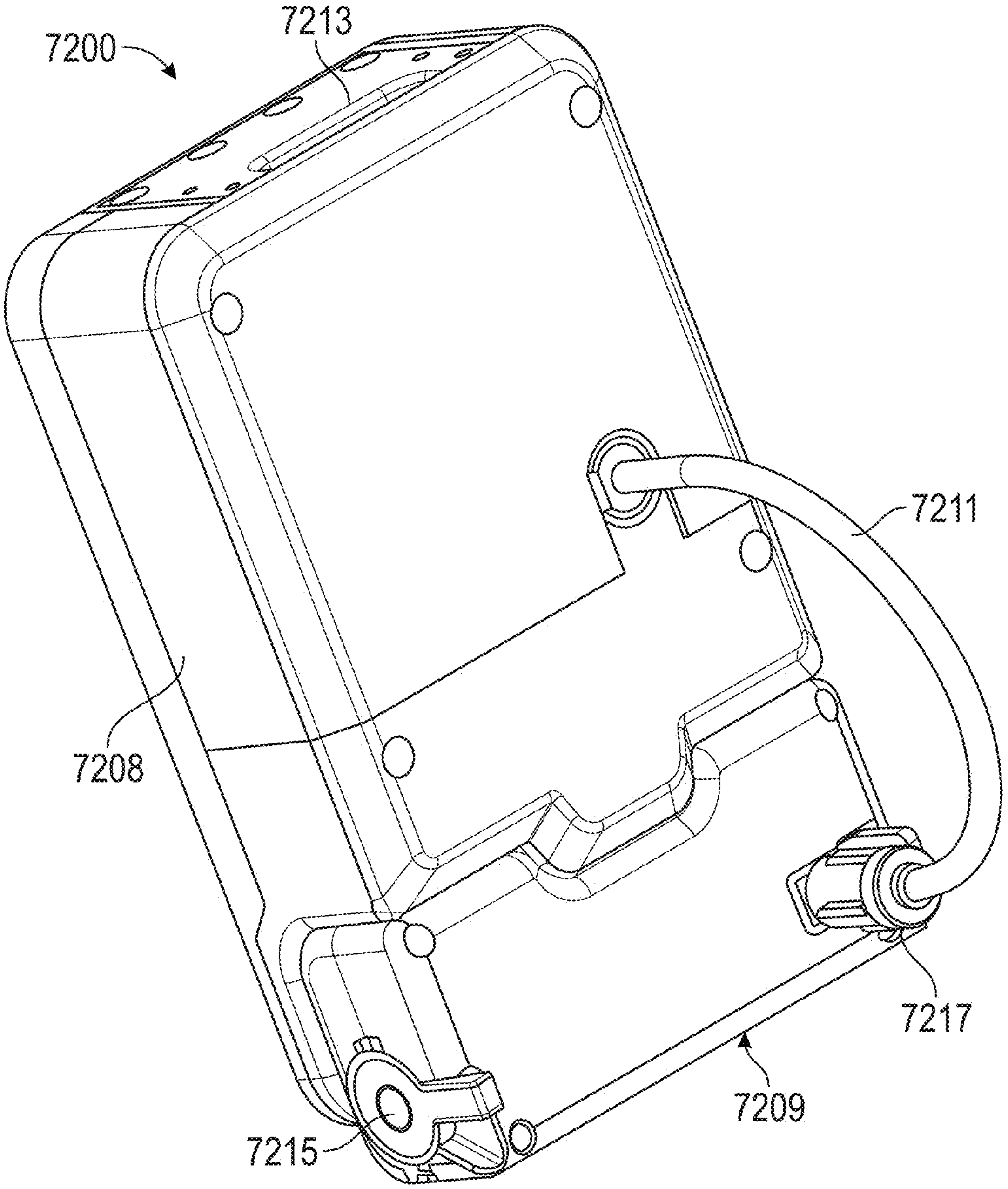
FIG. 48A is a perspective view of a hub assembly.

FIG. 48A illustrates a hub assembly 7200. The hub assembly 7200 may include any of the same or similar features and/or functions as the other embodiments of hubs and hub assemblies described herein and vice versa.

In some embodiments, the hub assembly 7200 can include a first subassembly, puck, or mount 7208 and a second subassembly or hub 7209. The mount 7208 can also be referred to as a catheter puck, a hub mount, and/or a first hub member. The mount 7208 can be configured to couple to and move along a drive table. The hub assembly 7200 can be configured to be positioned on a sterile side (e.g., a disposable equipment side) of a sterile barrier.

In some embodiments, the hub 7209 can be referred to as a second hub member. The hub 7209 may include or couple to an interventional device, such as a catheter or guidewire.

As described herein, in certain embodiments an interventional device may be coupled to a fluidics management system (e.g., to receive fluids such as contrast or saline, or for aspiration). In some embodiments, the mount 7208 can be coupled to the fluidics management system. In some embodiments, a fluidics connector 7211 can extend between and fluidly couple the mount 7208 and the hub 7209.

The mount 7208 can further include a first housing. The first housing can define one or more openings 7213 and a plurality of internal components described in greater detail below. The first housing can form an outer shell to protect the internal components of the mount 7208. The first housing can include at least one side shaped and/or dimensioned (e.g., having a contour) for receiving the hub 7209.

The one or more openings 7213 can provide access for fluidics and/or electrical connections into the mount 7208. In some embodiments, a contrast tube, a saline tube, and/or an aspiration tube may extend through the one or more openings 7213 into the mount 7208. Additionally, in some embodiments, a power line may extend through the one or more openings 7213 to provide electrical power into the mount 7208. The mount 7208 can be configured to receive an input from one or more active torque elements 7102A-C of the active torque subsystem 7103. In some embodiments, the inputs from the one of more active torque elements 7102A-C may be a magnetic rotary force as described herein. The mount 7208 can be configured to transmit one or more outputs to the hub 7209. In some embodiments, the mount 7208 may transform one or more rotary inputs of the one or more active torque elements 7102A-C into corresponding linear and/or rotary outputs. In some embodiments, the mount 7208 may be configured to translate linearly along a drive table (e.g., in response to linear movement of hub adapter within the drive table due to a magnetic coupling between mount 7208 and the hub adapter).

The hub 7209 can further include a second housing. The hub 7209 can include a lumen 7215 for receiving an interventional device therein. The hub 7209 can include a luer 7217. The hub 7209 can further include a plurality of internal components described in greater detail below. The second housing can form an outer shell to protect the internal components of the hub 7209. In some embodiments, the second housing may include at least one side shaped and/or dimensioned (e.g., having a contour) to correspond to shape of the first housing. For example, the contour of the second housing can correspond to the contour of the first housing of the mount 7208. The hub 7209 can be configured to receive one or more inputs from the mount 7208. The hub 7209 can be configured to transmit one or more outputs. In some embodiments, the hub 7209 may transform the outputs of the mount 7208 into corresponding linear and/or rotary motion of components within or coupled to the hub 7209 (e.g., the interventional device coupled to the hub 7209 and/or one or more fluidics components).

The fluidics connector 7211 can be a tubular body defining an interior lumen extending from one end of the fluidics connector 7211 to a second end of the fluidics connector 7211. In some embodiments, the fluidics connector may be configured to transport fluids between the mount 7208 and the hub 7209. For example, the fluidics connector 7211 may facilitate the flow of contrast, saline, bodily fluids, and/or air between the mount 7208 and the hub 7209. The fluidics connector 7211 can transport fluids from the mount 7208 to the hub 7209, or vice versa. The fluidics connector 7211 may form an airtight seal.

The hub 7209 may be removably coupled to the mount 7208. In some embodiments, the hub 7209 can be mounted to a mounting element defined by the mount 7208. The fluidics connector 7211 may be coupled to both the mount 7208 and the hub 7209. In some embodiments, the hub 7209 may be in fluid communication with the mount 7208 via the fluidics connector 7211. Accordingly, fluids may be transferred between the mount 7208 and the hub 7209 via the fluidics connector 7211.

In certain embodiments, a mount 7208 can include at least a portion of a passive torque subsystem 7206. In certain embodiments, a portion of a passive torque subsystem 7206 may be included in a mount 7208, and another portion of a passive torque subsystem 7206 may be included in a hub 7209 coupled to the mount 7208.

FIGS. 48B-48K illustrate an embodiment of a hub assembly 7200 including a passive torque subsystem 7206. In some embodiments, the passive torque subsystem 7206 can be configured to magnetically couple to an active torque subsystem, such as active torque subsystem 7103 for magnetically controlling one or more degrees of freedom of a mount and/or hub as described herein. In some embodiments, the passive torque subsystem 7206 can be similar to the passive torque subsystem 7106, described above. In some embodiments, the one or more degrees of freedom can include a rotation of an interventional device 7218, actuation of a hemostasis valve 7020, and/or rotation of a fluidics valve 7214. In some embodiments, the shear force from the magnetic coupling within the torque subsystem can be sufficient to drag and/or pull the hub assembly 7200.

Figure 48B:
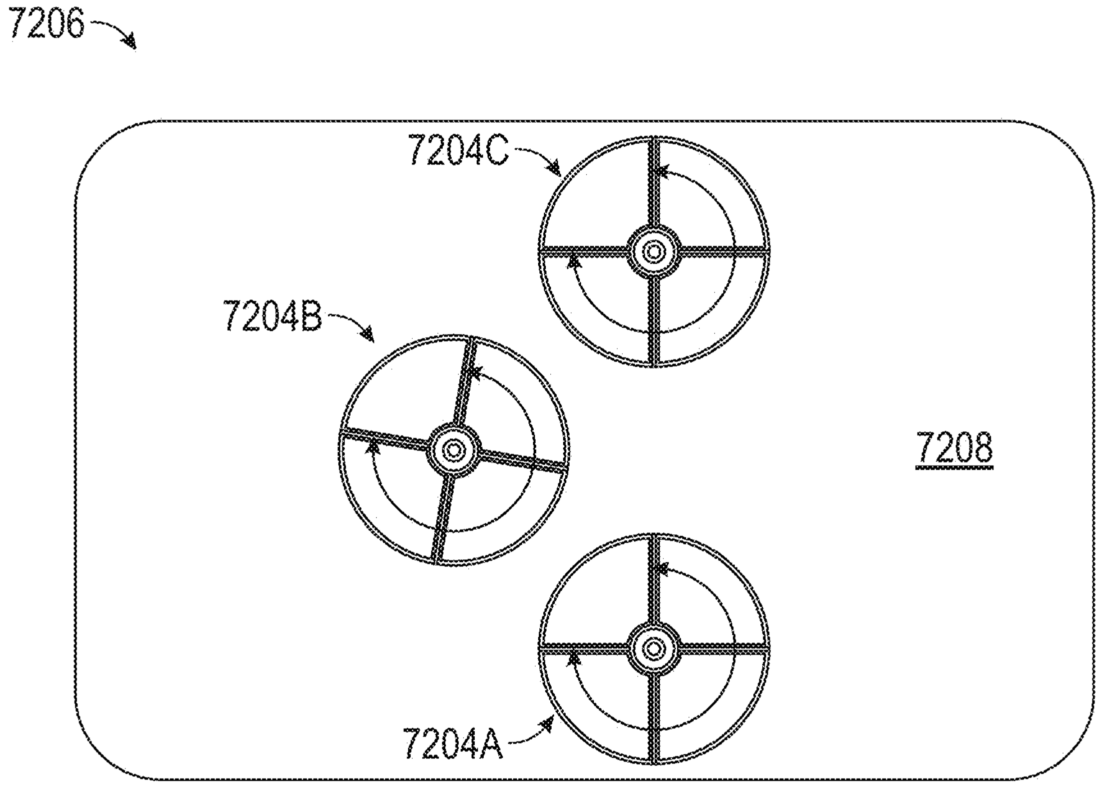
FIG. 48B is a bottom view of the hub assembly of FIG. 48A.

FIG. 48B depicts an embodiment of the passive torque subsystem 7206 of the torque transfer system. The passive torque subsystem 7206 can include a number of passive torque elements corresponding to a number of degrees of freedom for a hub. As shown in FIG. 48B, the passive torque subsystem 7206 can include a first passive torque element 7204A, a second passive torque element 7204B, and a third passive torque element 7204C. The passive torque elements can be magnetically coupled with the active torque elements described above. In some embodiments, the first passive torque element 7204A can be magnetically coupled to a first active torque element (e.g., active torque element 7102A) and configured to operatively actuate a first degree of freedom of the hub, the second passive torque element 7204B can be magnetically coupled to a second active torque element (e.g., active torque element 7102B) and configured to operatively actuate a second degree of freedom of the hub, the third passive torque element 7204C can be magnetically coupled to a third active torque element (e.g., active torque element 7102C) and configured to operatively actuate a third degree of freedom of the hub.

In some embodiments, the passive torque subsystem 7206 can be positioned at least partially on or within a mount 7208. For example, in certain embodiments, one or more of the passive torque elements 7204A-C can be positioned on or within the mount 7208. The mount 7208 can be configured to translate along the sterile side of a drive table. In some embodiments, the passive torque subsystem 7206 can be positioned at least partially on a first side of the mount 7208. For example, the passive torque subsystem 7206 may be positioned at least partially on the bottom side of the mount 7208.

Figure 48C:
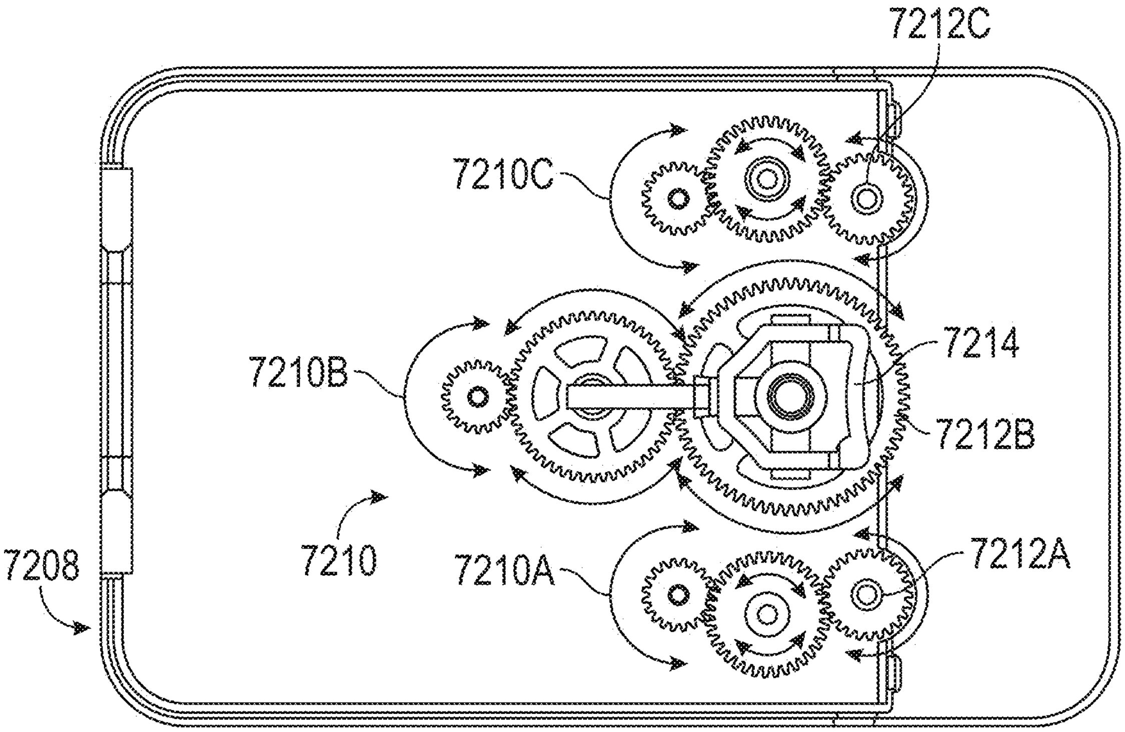
FIG. 48C is a top view of the internal mechanism of the hub assembly of FIG. 48A.

FIG. 48C illustrates a top view of the mount 7208. The mount 7208 can include an actuation system 7210. The actuation system 7210 can be positioned at least partially on a second side of the mount 7208. For example, the actuation system 7210 can be positioned at least partially on the top side of a base of the mount 7208.

The actuation system 7210 can be configured to actuate one or more degrees of freedom of the hub 7209. In some embodiments, the actuation system 7210 can include one or more gear trains. The one or more gear trains can include a first gear train 7210A, a second gear train 7210B, and a third gear train 7210C. In certain embodiments, the actuation system 7210 can be part of the passive torque subsystem 7206. In other embodiments, the actuation system 7210 can be coupled to the passive torque subsystem 7206.

The first gear train 7210A can include a first output gear 7212A. In some embodiments, the first output gear 7212A can be configured to provide an output of the mount 7208. The first gear train 7210A can be operatively driven by the first active torque element 7102A via the first passive torque element 7204A. For example, the first passive torque element 7204A may be coupled to an input gear of the first gear train 7210A through the base of the mount 7208. In some embodiments, the first output gear 7212A can provide an input to the hub 7209. The first output gear 7212A can be configured to drive a degree of freedom within the hub 7209 when the hub 7209 is coupled to the mount 7208. For example, the first output gear 7212A can be actuated to provide a rotational motion of an interventional device 7218, as described in greater detail below.

The second gear train 7210B can include a second output gear 7212B. In some embodiments, the second output gear 7212B can be configured to control a valve within the mount 7208. The second gear train 7210B can be operatively driven by the second active torque element 7102B via the second passive torque element 7204B. For example, the second passive torque element 7204B may be coupled to an input gear of the second gear train 7210B through the base of the mount 7208. The second output gear 7212B can be configured to drive a degree of freedom within the mount 7208. In some embodiments, the second output gear 7212B can be actuated to provide a rotational motion of a valve 7214 coupled to a fluidics management system through the mount 7208. For example, the valve 7214 can be a stopcock (i.e., a three-way valve) configured to selectively allow fluids to pass through the mount 7208, as described in greater detail below.

The third gear train 7210C can include a third output gear 7212C. In some embodiments, the third output gear 7212C can be configured to provide an output of the mount 7208. The third gear train 7210C can be operatively driven by the third active torque element 7102C via the third passive torque element 7204C. For example, the third passive torque element 7204C may be coupled to an input gear of the third gear train 7210C through the base of the mount 7208. In some embodiments, the third output gear 7212C can provide an input to the hub 7209. The third output gear 7212C can be configured to drive a degree of freedom within the hub 7209 when the hub 7209 is coupled to the mount 7208. For example, the third output gear 7212C can be used to actuate a hemostasis valve positioned within the hub 7209, as described in greater detail below.

Figure 48D:
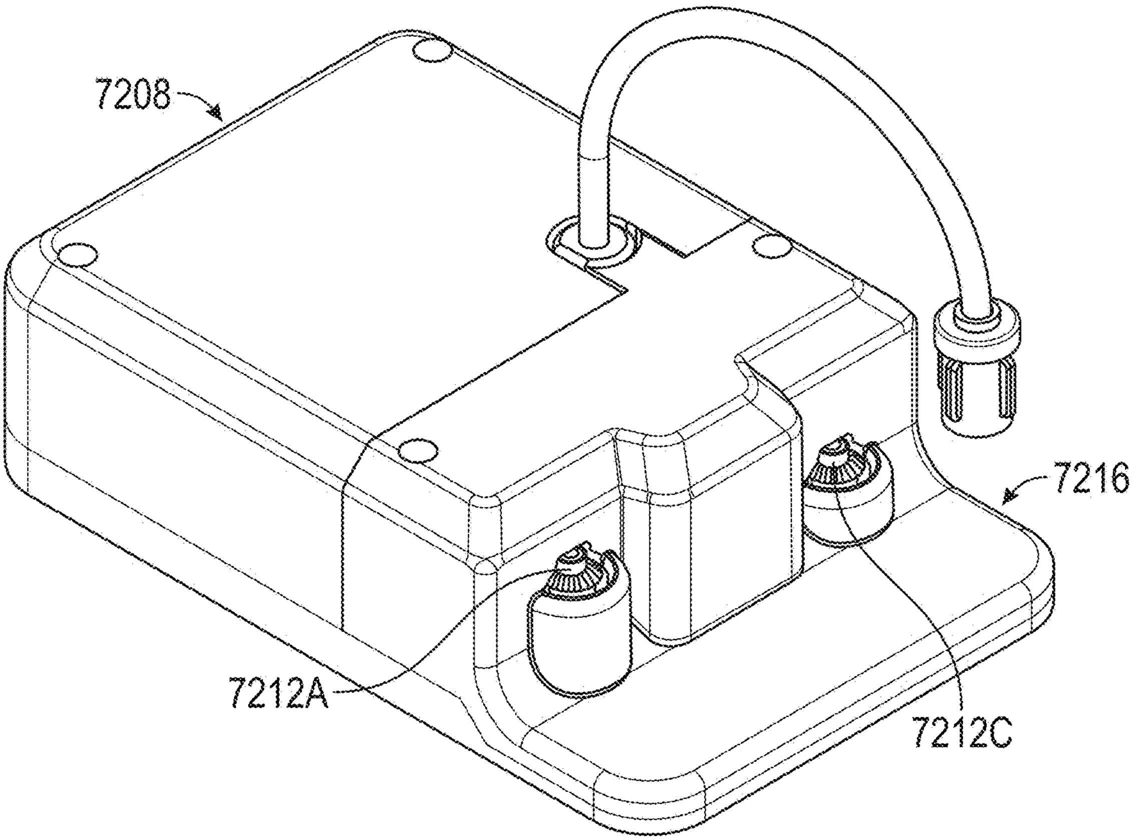
FIG. 48D is a perspective view of a mount of the hub assembly of FIG. 48A.

FIG. 48D depicts a hub interface 7216 of the mount 7208. The hub 7209 can be configured to couple to the mount 7208 via the hub interface 7216. As shown in FIG. 48D, the first output gear 7212A and the third output gear 7212C can extend through mount 7208 and intersect the hub interface 7216. Accordingly, the first output gear 7212A and the third output gear 7212C can provide an input to the hub 7209, respectively.

Figure 48E:
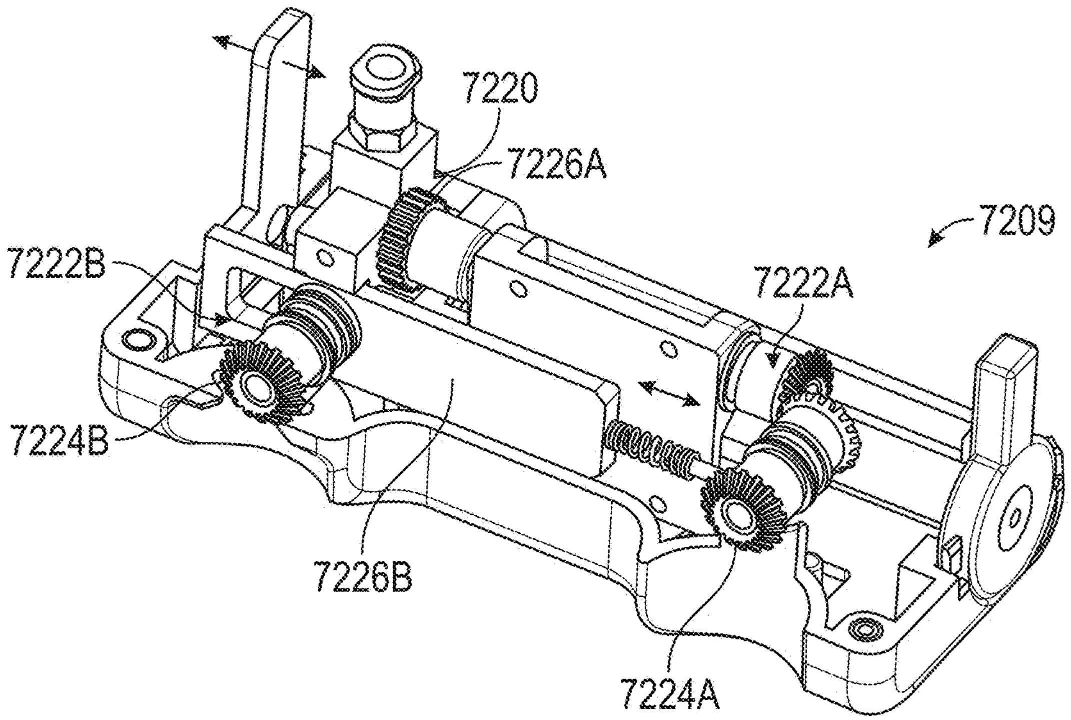
FIG. 48E is a perspective view of the internal components of a hub of the hub assembly of FIG. 48A.
Figure 48F:
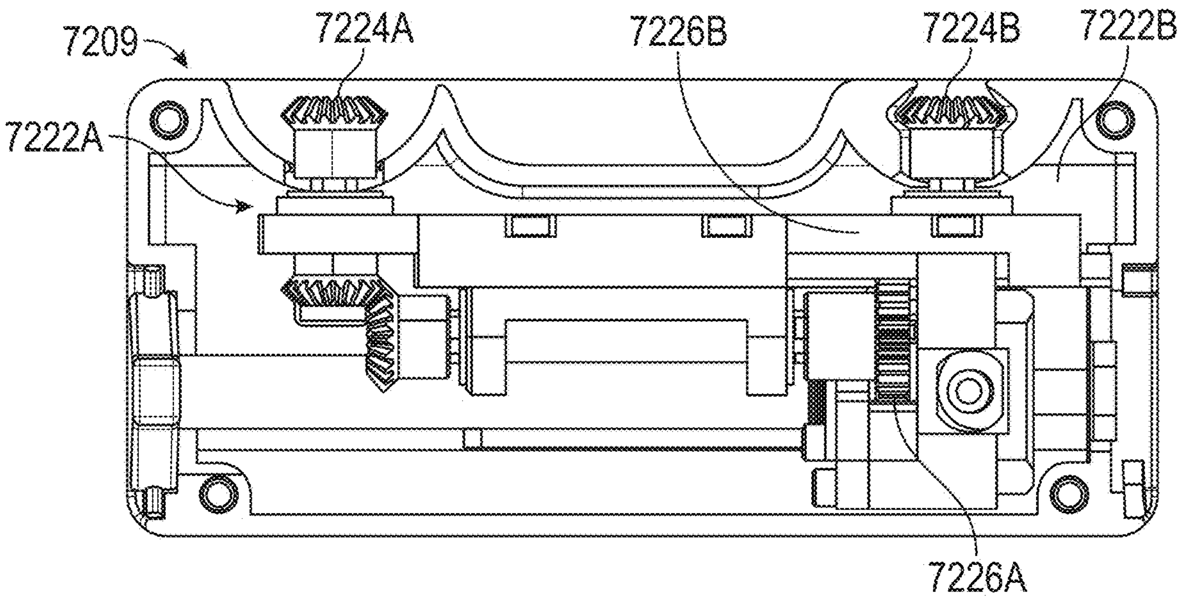
FIG. 48F is a top view of the internal components of the hub of FIG. 48E.
Figure 48G:
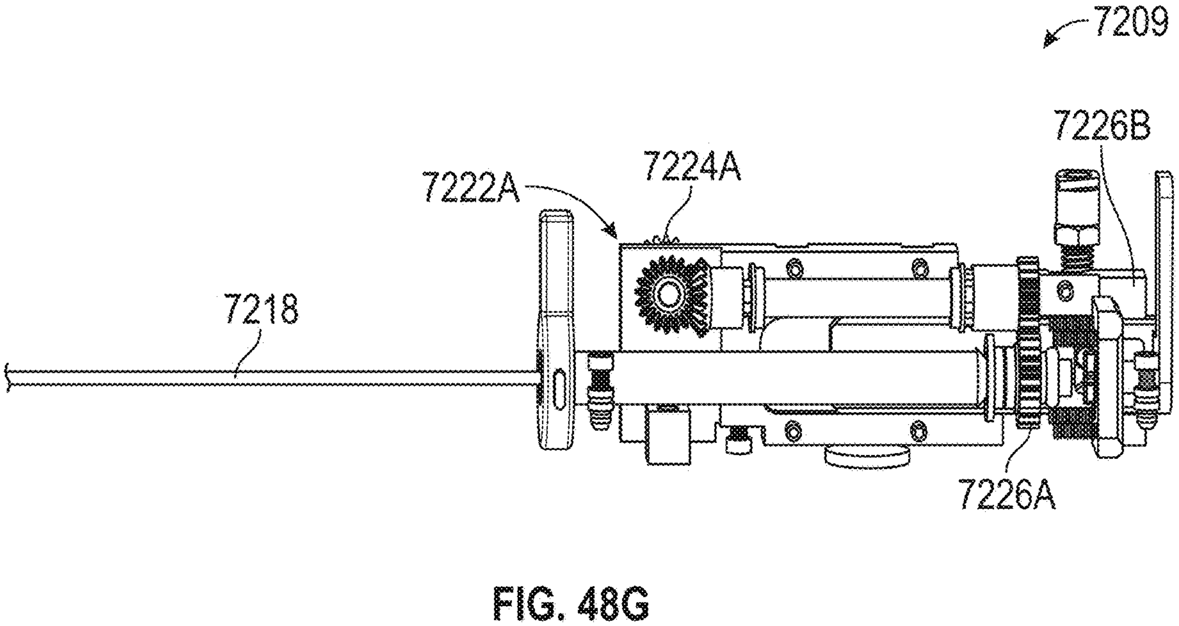
FIG. 48G is a side view of the internal components of the hub of FIG. 48E.
Figure 48H:
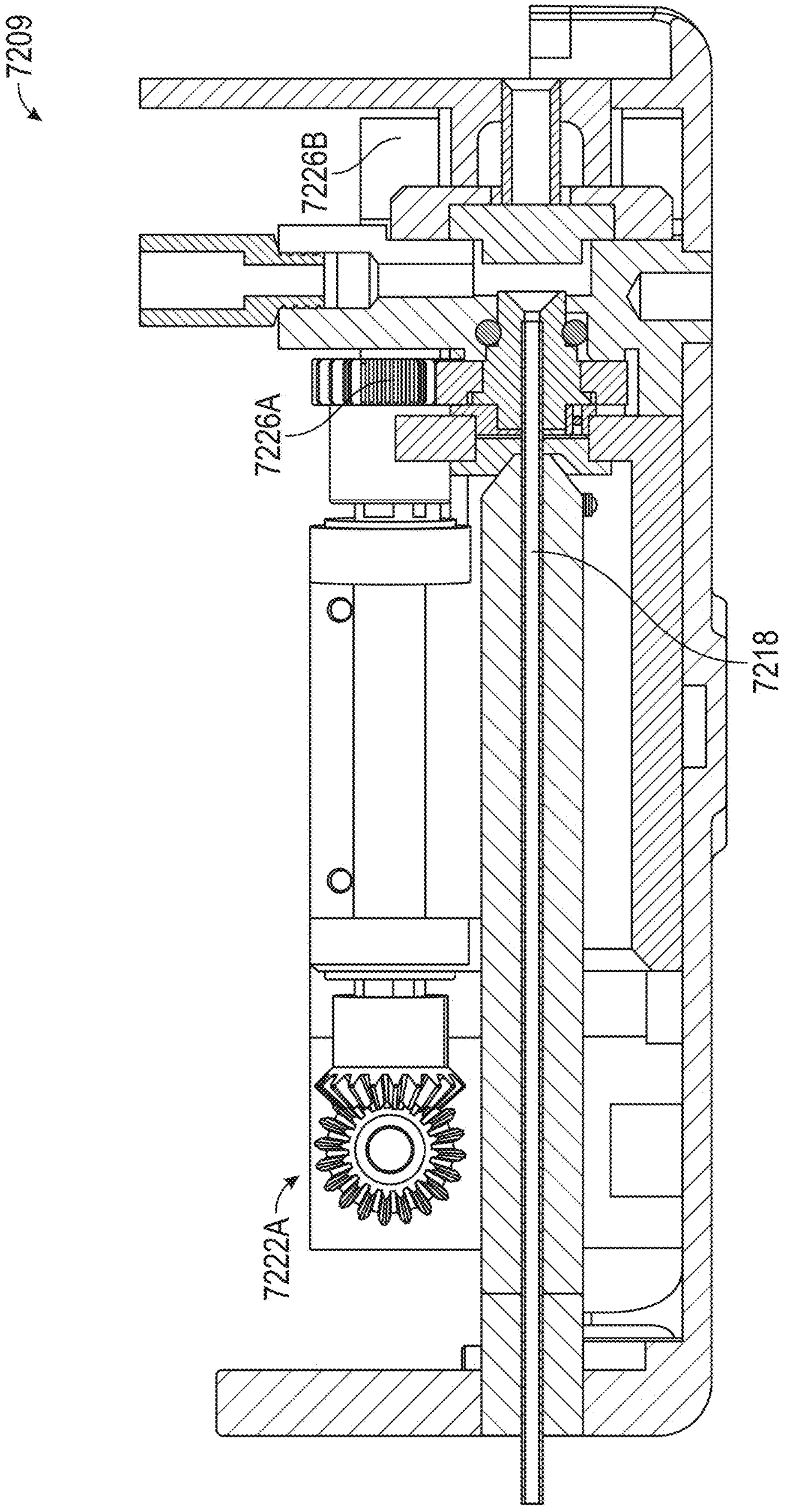
FIG. 48H is a cross-sectional view of the internal components of the hub of FIG. 48E.
Figure 48I:
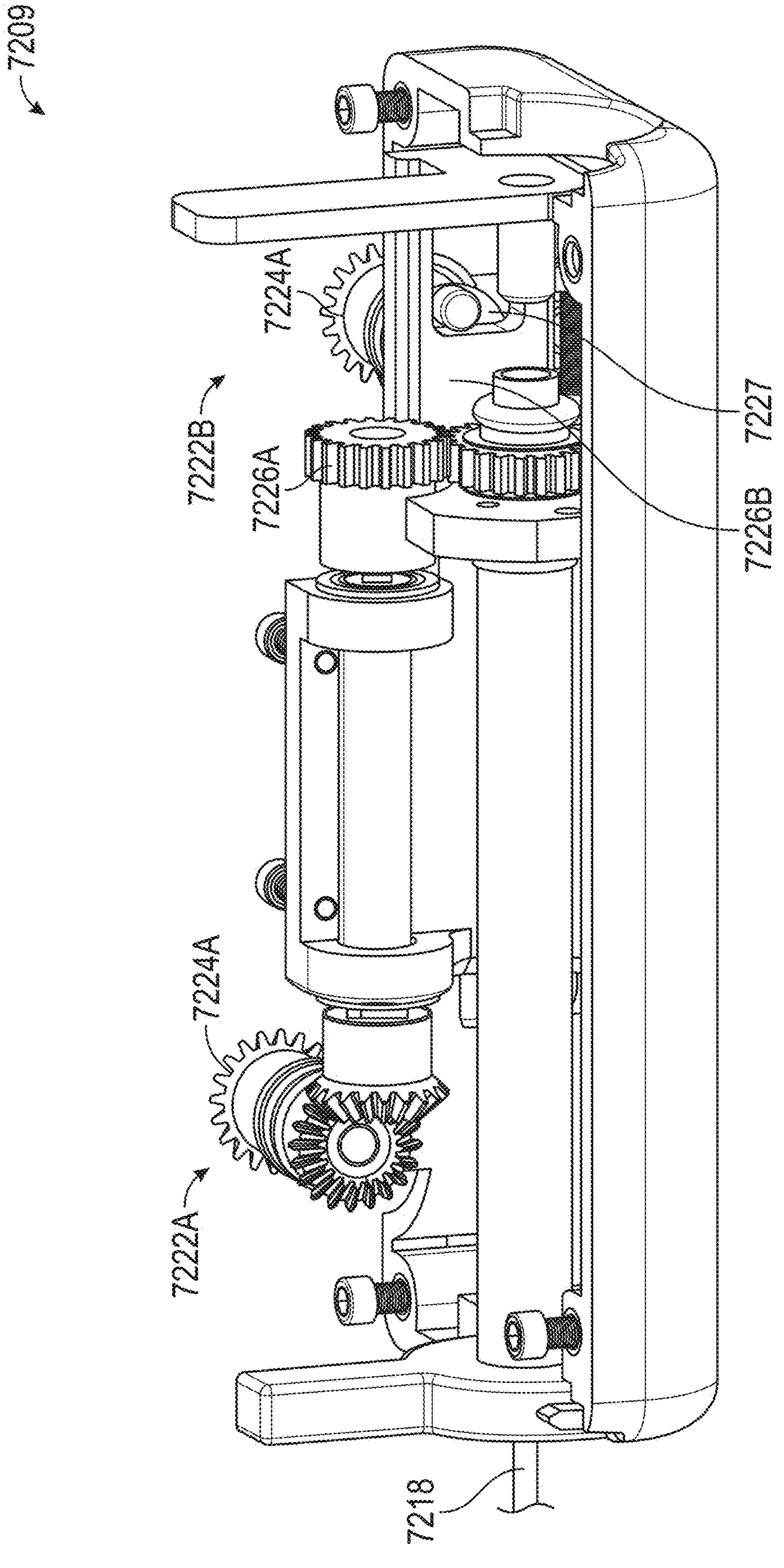
FIG. 48I is a perspective view of the internal components of the hub of FIG. 48E.

FIGS. 48E-48I illustrate various views of the hub 7209. In some embodiments, the hub 7209 may function similarly to the hub described above in relation to FIGS. 45C-45G. FIG. 48E depicts an example of the internal components of the hub 7209. FIG. 48F depicts a top view of the internal components of the hub 7209. FIG. 48G depicts an elevation view of the internal components of the hub 7209 and an interventional device 7218 such as a catheter. FIG. 48H depicts a cross-sectional side view of the hub 7209 with the interventional device 7218 such as a catheter. FIG. 48I depicts a perspective view of the internal components of the hub 7209 with the interventional device 7218 such as the catheter.

As shown in FIGS. 48E-48I, the hub 7209 can include a first hub gear train 7222A. The hub 7209 can further include a second hub gear train 7222B. In some embodiments, the hub 7209 can include a hemostasis valve 7220. In some embodiments, the hub 7209 can include an interventional device 7218 such as a catheter.

The first hub gear train 7222A can control a first degree of freedom within the hub 7209. The first hub gear train 7222A can include a first hub input gear 7224A and a first hub output 7226A. The first hub input gear 7224A can be operatively coupled to the first hub output 7226A. As shown in FIGS. 48E-48I, the first hub gear train 7222A can include a series of links interconnected via gears. As further shown in FIGS. 48F-48I, the first hub gear train 7222A can culminate in the first hub output 7226A. In some embodiments, the first hub output 7226A can be a gear. Accordingly, a rotation of the first hub input gear 7224A can cause a corresponding rotation of the first hub output 7226A. A rotation of the first hub output 7226A can cause an actuation of a first degree of freedom of the hub 7209. In some embodiments, the first hub output 7226A can be operatively coupled to the interventional device 7218 such as a catheter. Accordingly, a rotation of the first hub input gear 7224A can actuate a rotation of the interventional device 7218 such as a catheter.

In an operable state, the first hub gear train 7222A can be operatively coupled to the first gear train 7210A. For example, the first hub input gear 7224A can mesh with the first output gear 7212A. Accordingly, the first hub gear train 7222A can be operatively driven by the first active torque element 7102A.

The second hub gear train 7222B can control a second degree of freedom within the hub 7209. The second hub gear train 7222B can include a second hub input gear 7224B and a second hub output 7226B. The second hub input gear 7224B can be operatively coupled to the second hub output 7226B. As shown in FIGS. 48F-48I, the second hub gear train 7222B can include a shaft having a protrusion 7227. As further shown in FIGS. 48F-48I, the second hub output 7226B can be yoke or slider. The protrusion 7227 can be radially positioned off center from the shaft. Accordingly, the protrusion 7227 can follow an annular path as the shaft rotates. The annular path of the protrusion 7227 can linearly actuate the second hub output 7226B between a first position and a second position. A translation of the second hub output 7226B can cause an actuation of a second degree of freedom of the hub 7209. In some embodiments, the second hub output 7226B can be operatively coupled to the hemostasis valve 7220. For example, the second hub output 7226B can transition the hemostasis valve 7220 between an open position and a closed position as described in greater detail below.

In an operable state, the second hub gear train 7222B can be operatively coupled to the third gear train 7210C. For example, the third output gear 7212C can engage with the second hub input gear 7224B. Accordingly, the second hub gear train 7222B can be operatively driven by the third active torque element 7102C.

The hemostasis valve 7220 can be configured to receive an interventional device therethrough. For example, the hemostasis valve 7220 can include a channel for receiving a proximally positioned interventional device coupled to another hub assembly therethrough. In some embodiments the channel may be coaxial with an interventional device lumen of the hub 7209. The hemostasis valve 7220 can be actuatable between various states to allow for and/or restrict movement of the interventional device therethrough and to allow for and/or prevent fluid flow therethrough. For example, in some embodiments, the hemostasis valve 7220 may actuate between an open state and a closed state. In some embodiments, the hemostasis valve 7220 can be actuatable between a first fully open state, a second partially opened (low sealing force state) for sealing around an interventional device but permitting sliding movement of the interventional device, a third state for sealing around an interventional device for high pressure management, and a fourth completely closed state in the absence of any interventional devices extending therethrough. In certain embodiments, the third active torque element 7102C can be configured to actuate the hemostasis valve 7220 through one or more of the foregoing states. In some embodiments, the third output gear 7212C can engage the second hub input gear 7224B to actuate the hemostasis valve 7220 through one or more of the foregoing states. In some embodiments, the hemostasis valve 7220 can be actuated between various states in response to movement of the second hub gear train 7222B. For example, a plunger can be actuated by movement of the second hub output 7226B to transition a seal of the hemostasis valve 7220 between various states. In some embodiments, the second hub output 7226B can part of the plunger. In other embodiments, the second hub output 7226B can be a separate component coupled to the plunger.

Figure 48J:
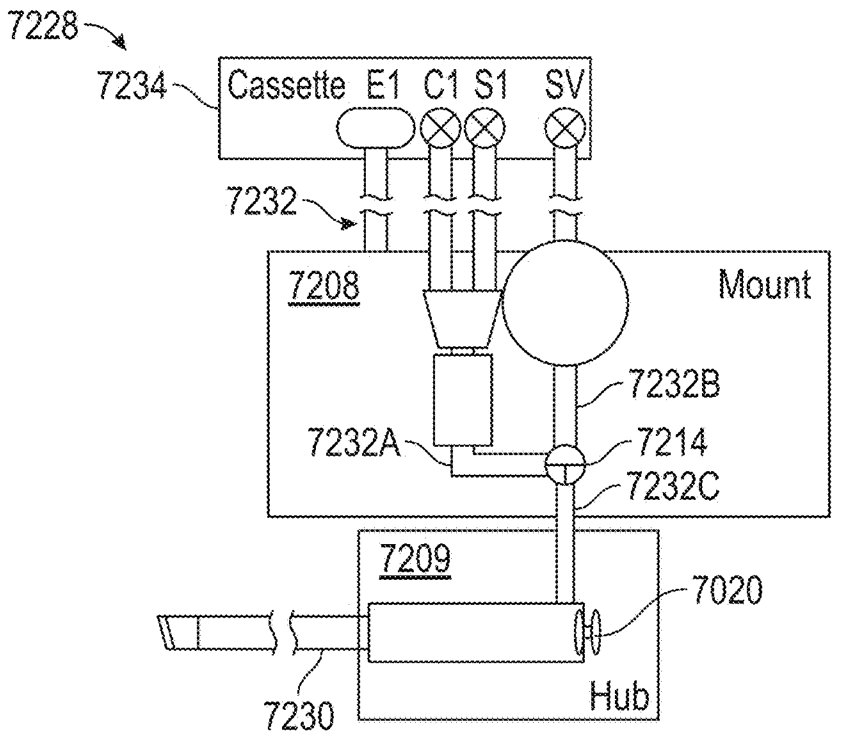
FIG. 48J is a schematic of a fluid management system.
Figure 48K:
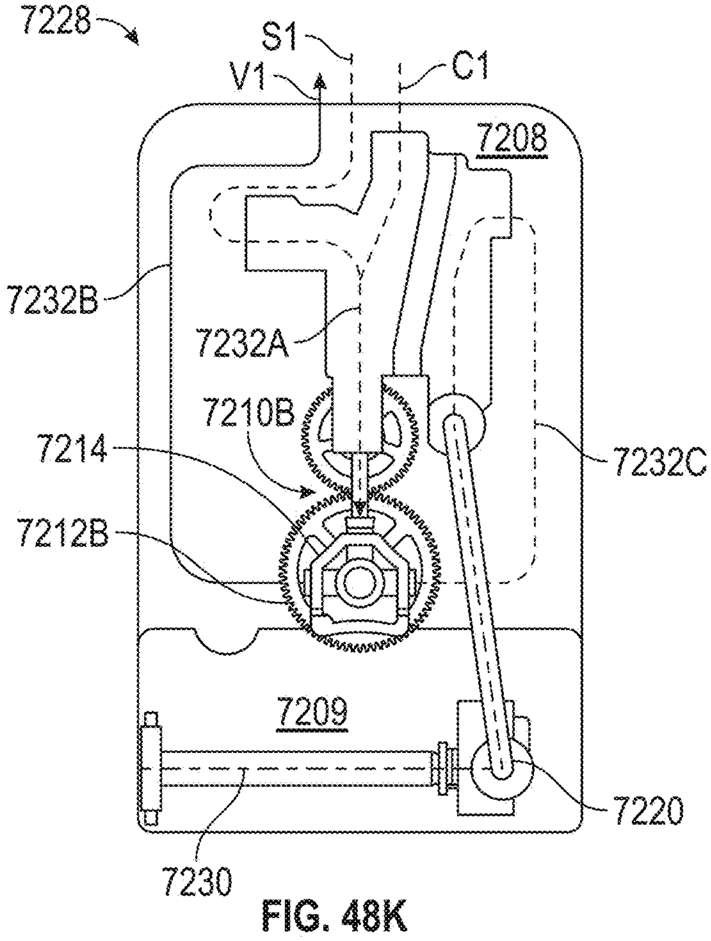
FIG. 48K is a top view of a fluid management system in the mount of FIG. 48D.

FIGS. 48J-48K depict an example of a fluidics management system 7228. The fluidics management system 7228 can include any or all of the features identified in U.S. patent application Ser. No. 18/666,217, filed May 16, 2024, tilted FLUIDICS CONTROL SYSTEM FOR MULTI CATHETER STACK, the entire content of which is incorporated by reference herein for all purposes and forms a part of this specification.

FIG. 48J illustrates an example of an interventional device 7230 (e.g., a catheter) coupled to an embodiment of a tubing set 7232. The tubing set 7232 can extend between the interventional device 7230 and a cassette 7234. The cassette 7234 can include all or part of a saline subsystem, all or part of a contrast subsystem, and/or all or part of a vacuum subsystem of the fluidics management system 7228. A saline tube containing saline S1 can extend from the cassette 7234 to the mount 7208. A contrast tube containing contrast C1 can extend from the cassette 7234 to the mount 7208. An aspiration tube 7232B containing negative pressure (i.e., vacuum V1) can extend from the cassette 7234 to the mount 7208.

The mount 7208 can include a manifold to receive the saline tube and the contrast tube. In some embodiments, the manifold may further receive the aspiration tube. In some embodiments, the manifold may further receive a tube and/or lumen extending to the hub 7209 to fluidly connect the interventional device 7230 to the mount 7208. The manifold may further include a branch point in the form of a two-to-one connector that couples the contrast line C1 and the saline line S1 to a single saline/contrast tube 7232A. As described above, the mount 7208 can further include the valve 7214 (i.e., stopcock) that can be actuated to selectively place the catheter 7230 in communication with the single saline/contrast tube 7232A or the aspiration tube 7232B. As shown in FIGS. 48F-48G, the valve 7214 can be in fluid communication with the single saline/contrast tube 7232A, the aspiration tube 7232B, and the interventional device tube 7232C. As described above, the valve 7214 can be mechanically coupled to the second gear train 7210B. Accordingly, the valve 7214 can be rotatably actuated by the second active torque element 7102B via the second passive torque element 7204B. A rotation of the valve 7214 can selectively control the flow of the fluidics from the cassette 7234 to the interventional device 7230.

FIGS. 49A-49G illustrate a carriage or hub adapter 8000. The hub adapter 8000 may include any of the same or similar features and/or functions as any of the other hub adapters described herein and vice versa. As described herein, the hub adapter 8000 can include one or more magnets configured to couple to corresponding magnets of a hub assembly so that rotation of the one or more magnets of the hub adapter 8000 can cause a corresponding rotation of the one or more magnets of the hub assembly. In certain embodiments, the hub adapter can have an active torque subsystem 8203. The active torque subsystem 8203 may include any of the same or similar features and/or functions as any of the other active torque subsystem described herein and vice versa.

In some embodiments, the active torque subsystem can include a plurality of active torque elements 8202. The plurality of active torque elements 8202 can each be configured to control a degree of freedom of a hub assembly (e.g., a mount and/or hub), respectively. In some embodiments, the active torque subsystem 8203 can provide an additional degree of freedom in comparison to the active torque subsystem 7103 described above.

Figure 49A:
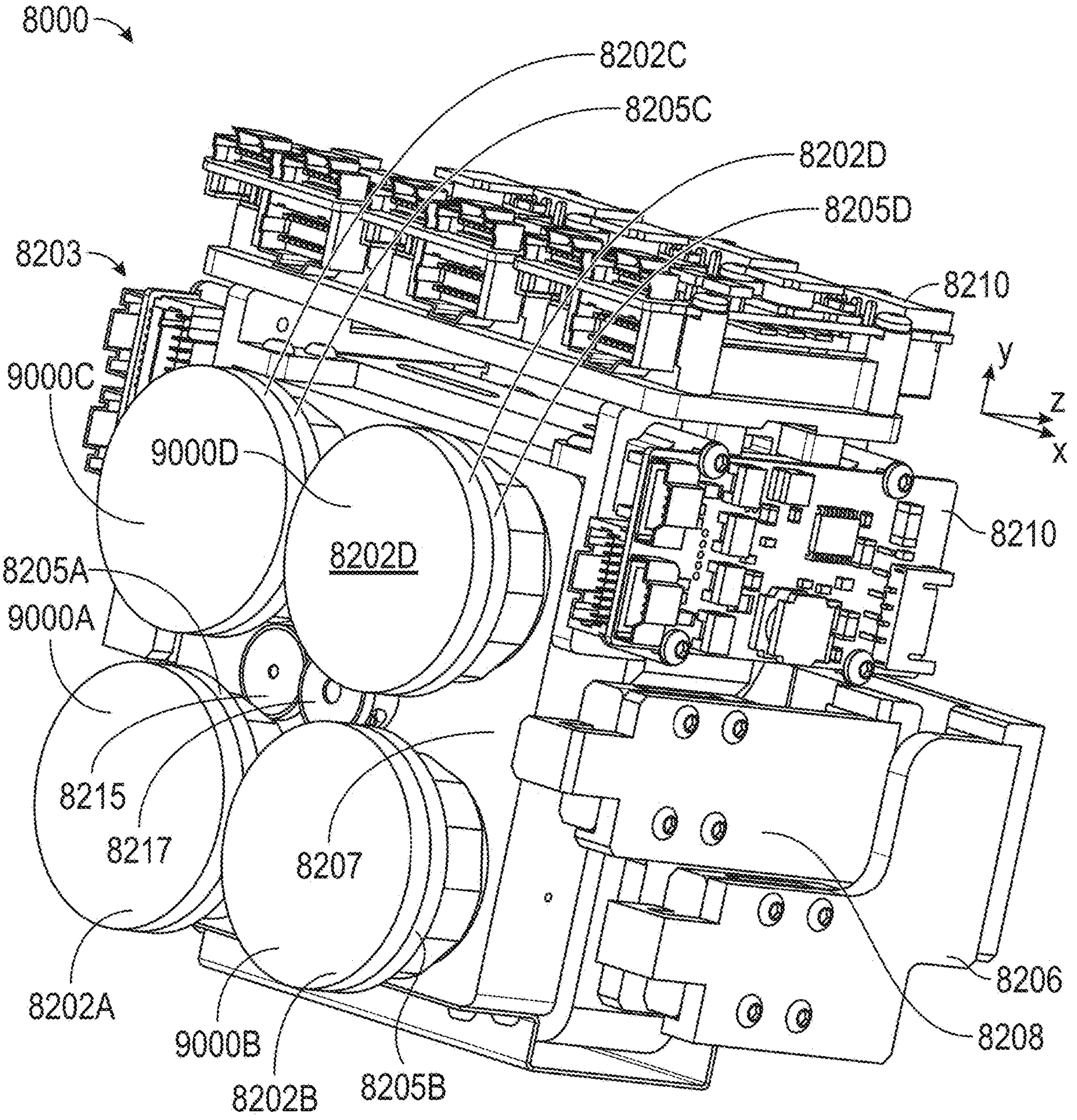
FIG. 49A is a perspective view of a hub adapter.
Figure 49B:
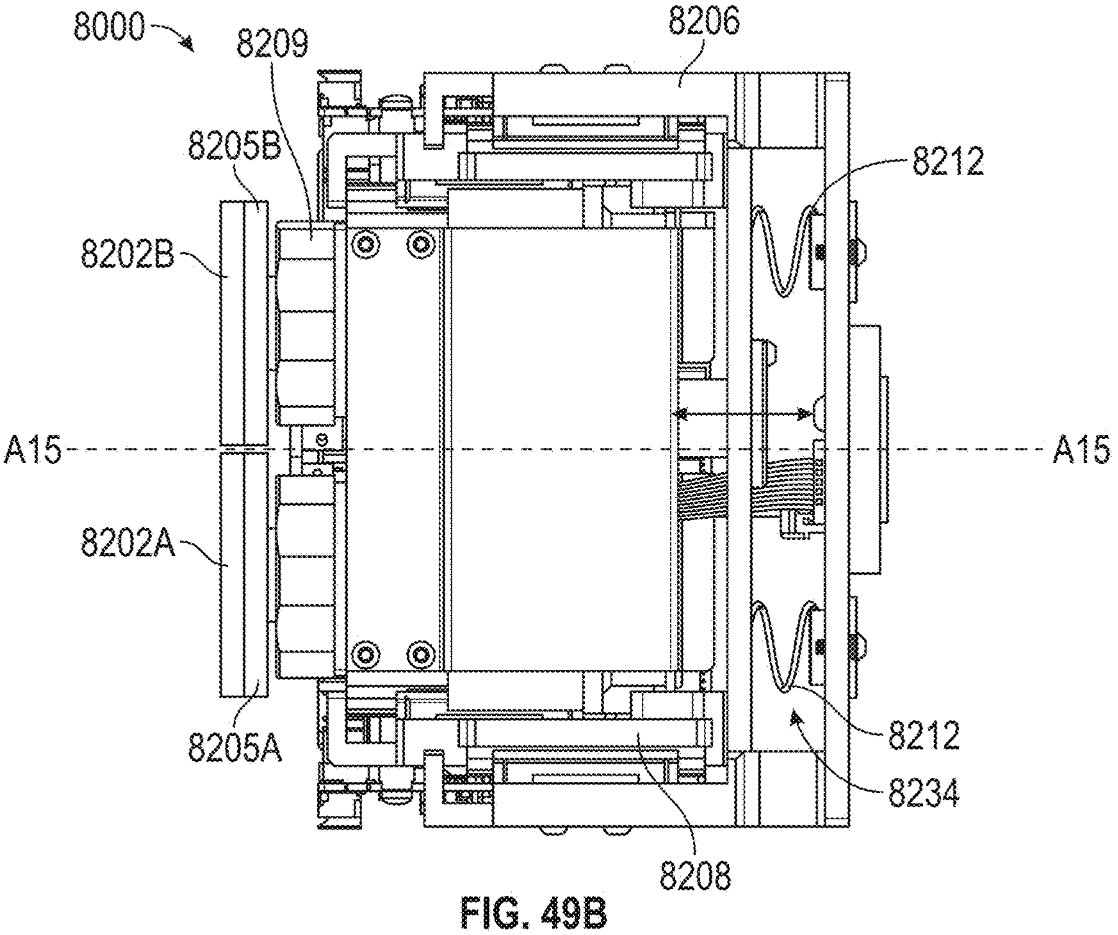
FIG. 49B is a bottom view of the hub adapter of FIG. 49A.
Figure 49C:
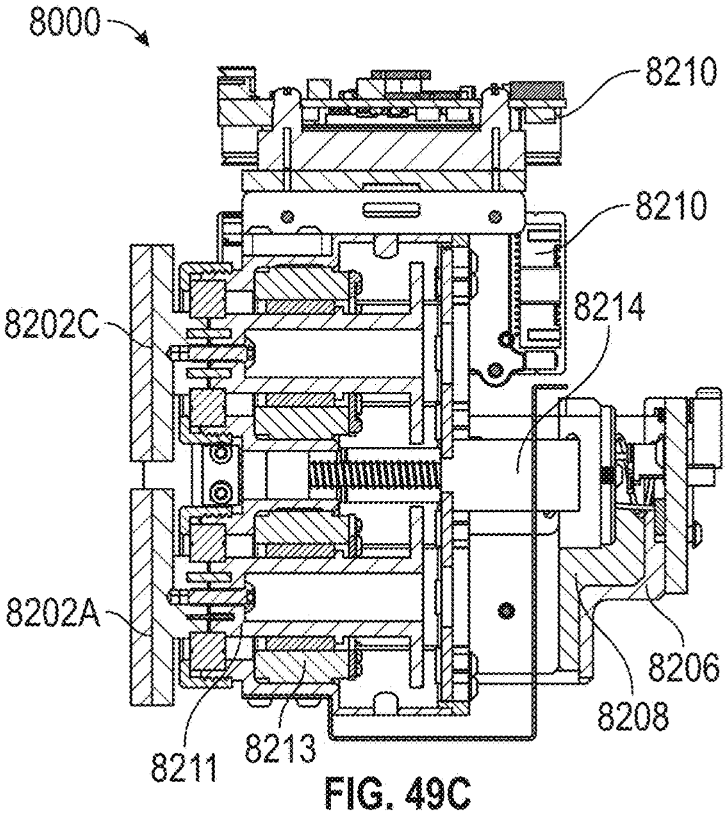
FIG. 49C is a side view of the hub adapter of FIG. 49A.
Figure 49D:
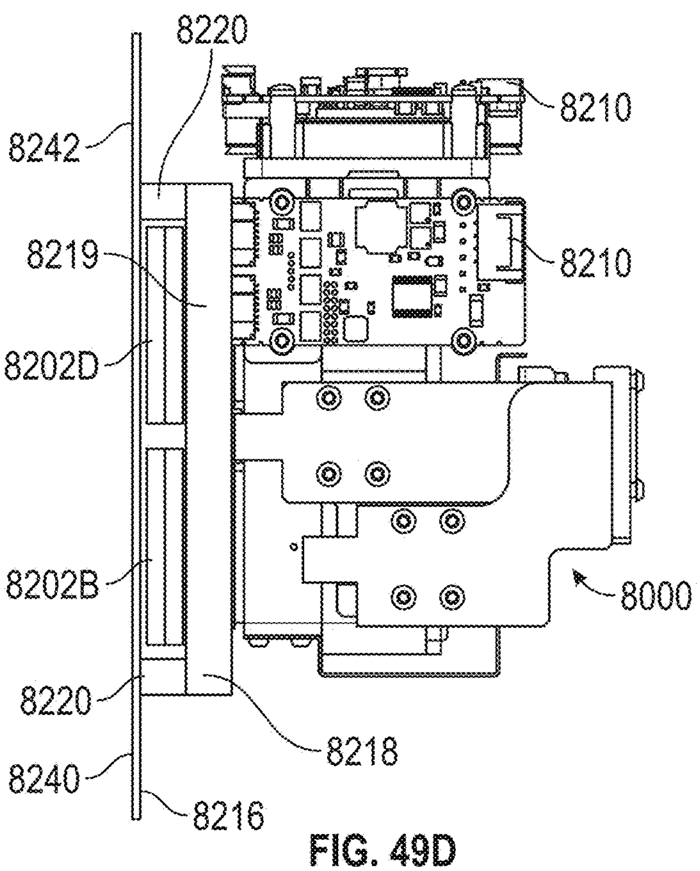
FIG. 49D is a side view of the hub adapter of FIG. 49A in an expanded state.
Figure 49E:
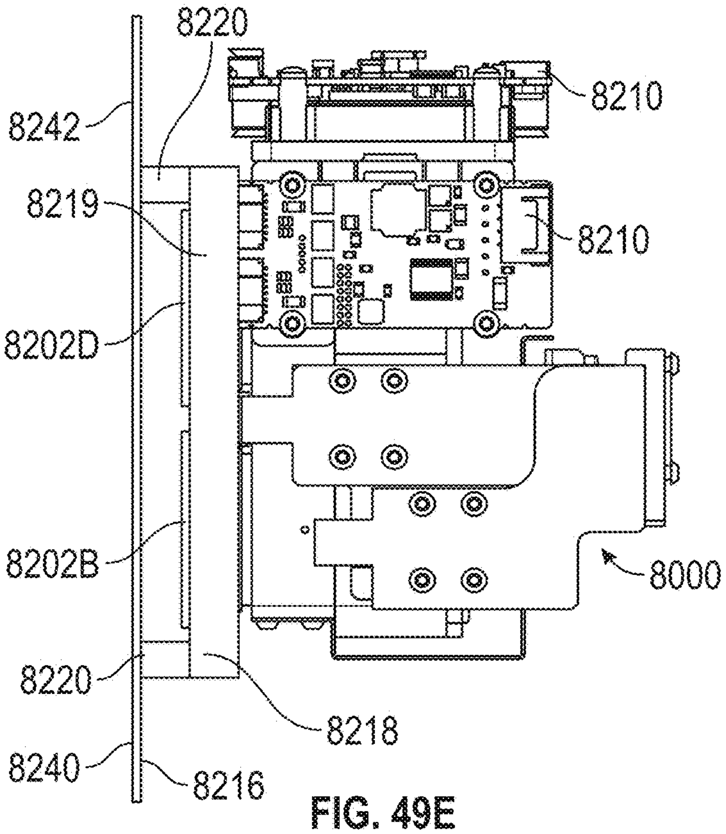
FIG. 49E is a side view of the hub adapter of FIG. 49A in a retracted state.
Figure 49G:
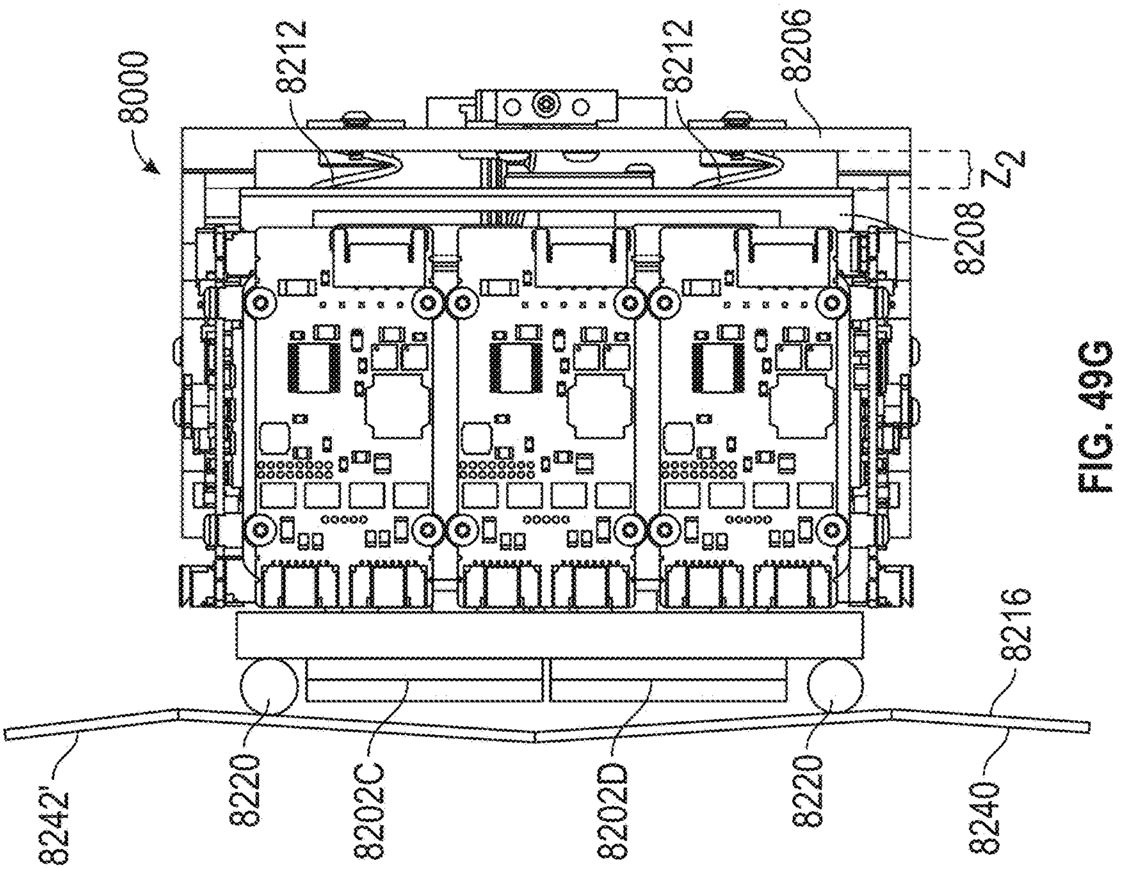
FIG. 49G is a top view of the hub adapter of FIG. 49A with a nonplanar drive surface.
Figure 49F:
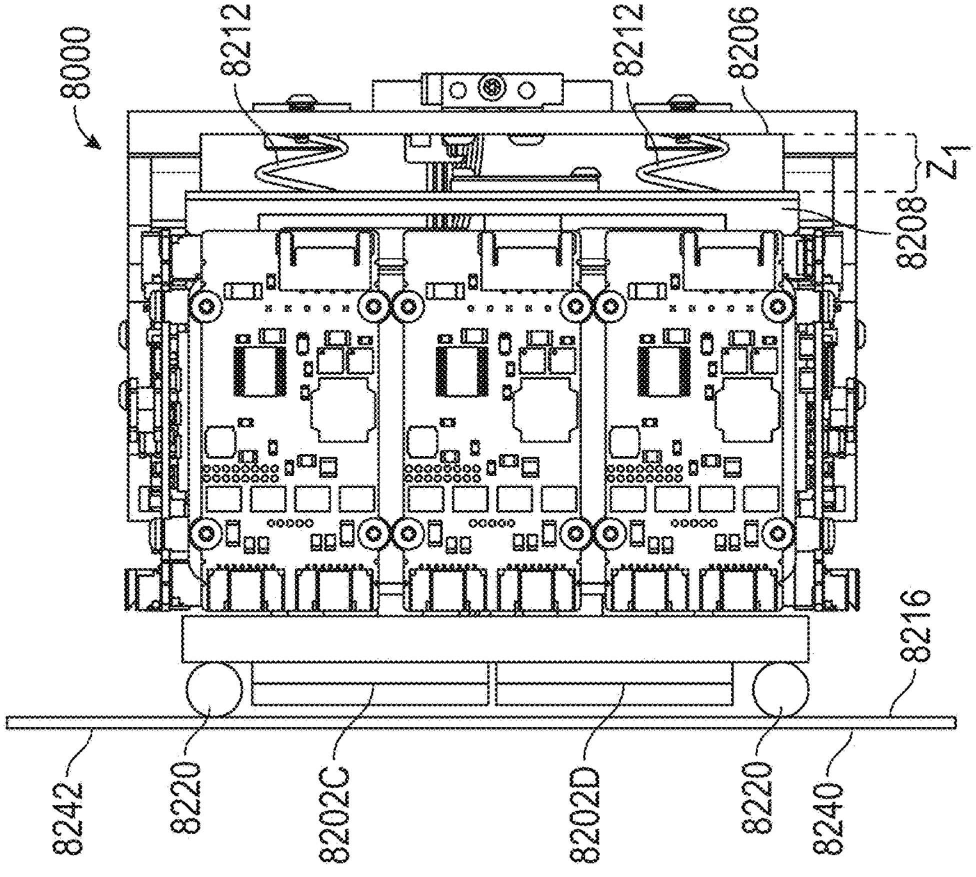
FIG. 49F is a top view of the hub adapter of FIG. 49A.

FIG. 49A illustrates a perspective view of the hub adapter 8000. FIG. 49B illustrates a bottom view of the hub adapter 8000. FIG. 49C illustrates a side cross-sectional view of the hub adapter 8000. FIG. 49D is a side view of the hub adapter 8000 with the plurality of active torque elements in an extended position. FIG. 49E is a side view of the hub adapter 8000 with the plurality of active torque elements 8202 in a retracted position. FIG. 49F illustrates a top view of the hub adapter 8000 in contact with a barrier 8242. As shown in FIG. 49F, the barrier 8242 can be planar. FIG. 49G illustrates a top view of the hub adapter 8000 in contact with a barrier 8242'. As shown in FIG. 49G, the barrier 8242' can be non-planar.

The hub adapter 8000 can be configured to drive axially along the longitudinal length of a drive table and displace the plurality of active torque elements 8202A-D relative to a planar surface of the drive table.

The plurality of active torque elements 8202A-D can include a first active torque element 8202A, a second active torque element 8202B, a third active torque element 8202C, and a fourth active torque element 8202D. In some embodiments, the active torque elements 8202A-D can be a magnet as described in greater detail below.

Each of the plurality of active torque elements 8202A-D can be configured to control a degree of freedom of a corresponding mount. In some embodiments, each of the plurality of active torque elements 8202A-D can magnetically couple with a corresponding passive torque element of a corresponding mount. In an operable configuration, the rotation of each of the plurality of active torque elements 8202A-D can result in an actuation of a corresponding degree of freedom of the coupled mount. For example, rotation of the first active torque element 8202A can actuate a first degree of freedom, rotation of the second active torque element 8202B can actuate a second degree of freedom, rotation of the third active torque element 8202C can actuate a third degree of freedom, and rotation of the fourth active torque element 8202D can actuate a fourth degree of freedom. The degrees of freedom of the corresponding mount and/or hub can include rotating an interventional device, actuating a hemostasis valve, and/or actuating one or more valves. Additionally, in an operable configuration, the magnetic coupling between the hub adapters 8000 and a corresponding hub assembly (e.g., mount of the hub assembly) can be used to provide a shear force for driving the corresponding hub assembly (e.g., mount) along a drive surface 8240 (e.g., a planar drive surface) of the barrier 8242 as the hub adapter 8000 is axially translated within the drive table. In some embodiments, the barrier 8242 may be a sterile barrier. In other embodiments, a sterile barrier may be placed over the barrier 8242. In such embodiments, the drive surface 8240 may be a surface of the sterile barrier positioned over the barrier 8242. For example, in some embodiments, the barrier 8242 may be a section (e.g., a wall) of a drive table, and a separate sterile barrier having a drive surface 8240 may be positioned over the section of the drive table. In some embodiments, the drive surface 8240 may be referred to as an external drive surface. The hub adapter 8000 may be configured to translate axially along a drive surface 8216 (e.g., a planar drive surface), which may be referred to as an interior drive surface.

Figure 52A:
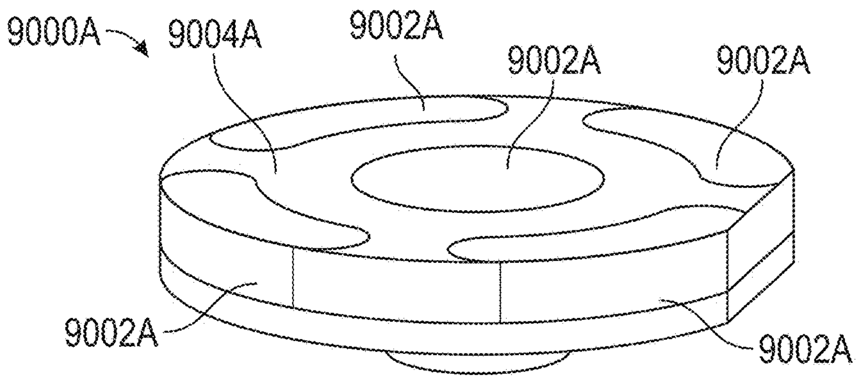
FIG. 52A is a perspective view of a magnet.

Each of the active torque element 8202A-D can include a magnet or array of magnets. For example, as shown in FIG. 49A, active torque elements 8202A, 8202B, 8202C, and 8202D can include magnets 9000A, 9000B, 9000C, and 9000D, respectively. While each of the active torque elements 8202A-D is shown having a single magnet 9000A-D in FIGS. 49A, in other embodiments, each active torque element can include a plurality of magnets, for example, as shown in FIG. 45A. In some embodiments, each active torque element 8202A-8202D may include a plurality of regions of magnetization, for example, as shown in FIG. 52A. The regions of magnetization may be considered part of a single magnet 9000A-D or may be separate magnets. In some embodiments, the active torque elements 8202A-D (e.g., magnets 9000A-D) may be a monolithic object having regions of polarity. For example, in some embodiments, each of the active torque elements 8202A-D (e.g., magnet 9000A-D) can have a plurality of regions with a common first polarity and a second region with a common second polarity. In some embodiments, the regions of polarity of adjacent passive torque elements 8202A-D may differ. The configuration of the passive torque elements 8202A-D can reduce backlash.

In certain embodiments, each active torque element 8202A, 8202B, 8202C, and 8202D can include a magnet support or magnet support element 8205A, 8205B, 8205C, and 8205D, respectively. Each magnet support elements 8205A-D can be configured to support the magnet 9000A-D of its corresponding active torque element. In some embodiments, the magnet support elements 8205A-D can be formed of a ferrous material (e.g., steel), which may direct magnetic field lines away from the magnet support element 8205A-D (e.g., towards the passive torque element).

In certain embodiments, the hub adapter 8000 can include a plurality of bearings 8209. The hub adapter 8000 can include one bearing 8209 for each active torque element 8202A-D.

In certain embodiments, the hub adapter 8000 can include a platform or frame 8207. The frame 8207 can couple to the active torque elements 8202A-D and/or the bearings 8209. In certain embodiments, the frame 8207 can house components for rotating the active torque elements 8202A-D (e.g., magnets 9000A-D), such as rotors 8211 and stators 8213, and/or components for moving the active torque elements 8202A-D (e.g., magnets 9000A-D) between a retracted and extended position as described herein.

In an operable configuration, rotation of one of the magnets 9000A-D can cause a corresponding rotation in a magnet or array of magnets of a passive torque element to actuate a degree of freedom of a hub assembly. For example, rotation of the first magnet 9000A can actuate a first degree of freedom, rotation of the second magnet 9000B can actuate a second degree of freedom, rotation of the third magnet 9000C can actuate a third degree of freedom, and rotation of the fourth magnet 9000D can actuate a fourth degree of freedom. The degrees of freedom of the corresponding hub assembly can include rotating an interventional device, actuating a hemostasis valve, and/or actuating one or more valves. Additionally, in an operable configuration, the magnetic coupling between the magnets 9000A-D and the magnets of a corresponding hub assembly (e.g., a mount of the hub assembly) can be used to provide a shear force for driving the corresponding mount along a drive surface of the drive table as the hub adapter 8000 is axially translated within the drive table.

In certain embodiments, the active torque elements 8202A-D (e.g., magnets 9000A-D) can be coupled to one or more motors for driving rotation of the active torque elements 8202A-D (e.g., magnets 9000A-D), as described herein. In certain embodiments, each of the active torque element 8202A-D (e.g., magnets 9000A-D) can be coupled to a rotor 8211. In certain embodiments, the hub adapter 8000 can include a stator 8213 for each rotor 8211. In certain embodiments, the active torque elements 8202A-D (e.g., magnets 9000A-D) can be movable towards and away from the drive surface 8216 and/or the sterile barrier between hub adapter 8000 and the hub assemblies. For example, the active torque elements 8202A-D (e.g., magnets 9000A-D) may be movable along an axis A15. The axis A15 may be parallel to an axis of rotation of the active torque elements 8202A-D (e.g., magnets 9000A-D). In certain embodiments, the active torque elements 8202A-D (e.g., magnets 9000A-D) can be movable towards and away from corresponding passive torque elements (e.g., corresponding magnets) of a hub assembly. For example, in certain embodiments, the active torque elements 8202A-D (e.g., magnets 9000A-D) can be moved from a retracted position to an extended position. In certain embodiments, in the extended position, the active torque elements 8202A-D (e.g., magnets 9000A-D) can be positioned at sufficient distance from the passive torque elements (e.g., magnets) of a corresponding hub assembly to magnetically couple with the passive torque elements (e.g., magnets) of the corresponding hub assembly so that rotational movement of one of the active torque elements 8202A-D (e.g., magnets 9000A-D) can cause a corresponding rotational movement of one of the passive torque elements (e.g., magnets) of the corresponding hub assembly.

In certain embodiments, the magnetic force between the active torque elements 8202A-D (e.g., magnets 9000A-D) and the passive torque elements (e.g., magnets) of the hub assembly may oppose removal of the hub assembly from the drive table. In certain embodiments, when the active torque elements 8202A-D (e.g., magnets 9000A-D) are in the extended position, the magnetic force between the active torque elements 8202A-D (e.g., magnets 9000A-D) and the passive torque elements (e.g., magnets) of the hub assembly may make removal of the hub assembly from the drive table difficult. In certain embodiments, in the retracted position, the magnetic force between the active torque elements 8202A-D (e.g., magnets 9000A-D) and aligned passive torque elements (e.g., magnets) of a corresponding hub assembly may be zero or sufficiently small such that movement of the hub assembly relative to the active torque elements 8202A-D (e.g., magnets 9000A-D) is unaffected or minimally affected by the magnetic force.

In some embodiments, the active torque elements 8202A-D (e.g., magnets 9000A-D) can be positioned in the retracted position to allow for alignment of one or more hub adapters 8000 with corresponding hub assemblies (e.g., during an initial setup step prior to performing a surgical procedure). The active torque elements 8202A-D (e.g., magnets 9000A-D) can then be advanced to the extended position once aligned (e.g., to magnetically couple the hub adapters 8000 to the hub assemblies and/or magnetically couple the active torque elements 8202A-D (e.g., magnets 9000A-D) of the hub adapters to the passive torque elements (e.g., magnets) of the hub assemblies).

In some embodiments, the active torque elements 8202A-D (e.g., magnets 9000A-D) can be positioned in the retracted position to allow alignment of opposing pole pairs of magnets 9000A-D and corresponding magnets of a hub assembly as described in further detail herein.

In some embodiments, when active torque elements 8202A-D (e.g., magnets 9000A-D) of a hub adapter 8000 are coupled to passive torque elements (e.g., magnets) of a hub assembly, the active torque elements 8202A-D (e.g., magnets 9000A-D) can be retracted towards the retracted position to reduce the magnetic force on the passive torque elements (e.g., magnets) of the hub assembly to allow removal of the hub assembly from the drive table.

In certain embodiments, the active torque elements 8202A-D (e.g., magnets 9000A-D) can be moved between the retracted position and the extended position by movement of the frame 8207, for example, along the axis A15.

In certain embodiments, the hub adapter 8000 can include a linear actuator 8214 for linearly driving the active torque elements 8202A-D (e.g., magnets 9000A-D) and/or frame 8207 between the retracted position and the extended position, for example, along the axis A15. In certain embodiments, the linear actuator 8214 can be a ball screw. In some such embodiments, the ball screw may be coupled to the frame 8207 so rotation of the ball screw causes axial movement of the frame 8207 and consequently the active torque elements 8202A-D along the axis A15. In certain embodiments, the hub adapter 8000 can include a motor gear 8215 that can be coupled with a motor and rotated to rotate a linear actuator gear 8217 to cause movement of the frame 8207 and consequently the active torque elements 8202A-D.

FIGS. 49D and 49E illustrate the linear actuation of the plurality of active torque elements 8202A-D (e.g., magnets 9000A-D) of the hub adapter 8000. As shown in FIG. 49D, the plurality of active torque elements 8202A are in the extended position (e.g., a fully extended state). As shown in FIG. 49E, the plurality of active torque elements 8202A-D are in the retracted position (e.g., a fully retracted state). As shown in FIGS. 49D and 49E, the plurality of active torque elements 8202A-D can be translated relative to the drive surface 8216 of the barrier 8242 from the retracted position, at which the active torque elements are positioned farther from the drive surface 8216 to the extended position, at which the active torque elements 8202A-D are positioned closer to the drive surface 8216, and vice versa.

In some embodiments, the hub adapter 8000 can include a support assembly 8218. In some embodiments, the support assembly 8218 can include a plurality of rollers 8220 (e.g., in the form of bearings, wheels (e.g., pinch wheels), rotatable balls, or drums), as shown in FIGS. 49D and 49E. In some embodiments, the plurality of rollers 8220 may be configured to roll along the drive surface 8216 of the barrier 8242. For example, the axis of rotation of the plurality of rollers 8220 may be orthogonal to the longitudinal axis of the drive surface 8216 of the barrier 8242. In some embodiments, the support assembly 8218 may be configured to maintain the spacing (e.g., a minimum spacing) between the drive surface 8216 and the plurality of magnets 9000A-D in the extended position. For example, the support assembly 8218 may maintain an air gap spacing of about 0.5 mm or at least about 0.5 mm when the plurality of magnets 9000A-D are in the extended position.

In certain embodiments, the active torque elements 8202A-D can be moved between the retracted position and the extended position (e.g., by the linear actuator 8214) independently of the rollers 8220 so that the rollers 8220 remain in contact with the drive surface regardless of the axial position of the actuators 8202A-D between the retracted position and the extended position. In certain embodiments, the support assembly 8218 can include a stage 8219. The rollers 8220 can be coupled to the stage 8219. In certain embodiments, as described above, the active torque elements 8202A-D can be moved relative to the stage 8219 when moving between the extended position and the retracted position, for example, so that the rollers remain in contact with the drive surface 8216 as the active torque elements are moved between the retracted position and the extended position. In some embodiments, a corresponding hub assembly may include a support assembly that is generally the same or similar to the support assembly 8218.

In the retracted position (e.g., the fully retracted state), as shown in FIG. 49E, the plurality of active torque elements 8202 may emit a minimum magnetic force or flux through the barrier 8242. In some embodiments, the minimum magnetic force may be sufficiently strong to magnetically hold a corresponding hub assembly (e.g., mount) against the drive surface 8240 but not strong enough to magnetically couple the plurality of active torque elements 8202 to a plurality of passive torque elements of the mount or to drive the hub assembly along the drive surface 8240. For example, the plurality of active torque elements 8202 may be configured to emit a magnetic force of about 1 lbf. In some embodiments, there is an air gap of about 6.5 mm or at least about 6.5 mm between the plurality of magnets 9000A-D and the drive surface 8216 in the retracted position.

In the extended position (e.g., the fully extended state), as shown in FIG. 49D, the plurality of active torque elements 8202 may emit a maximum magnetic force or flux through the barrier 8242. In some embodiments, the maximum magnetic force or flux may be sufficiently strong to magnetically couple to the plurality of passive torque elements of a corresponding mount and to drive the corresponding mount along the drive surface 8240. For example, the plurality of active torque elements 8202 may be configured to emit a magnetic force of about 21 pounds of force ("lbf"). In some embodiments, there is an air gap of about 0.5 mm or at least about 0.5 mm between the plurality of magnets 9000A-D and the drive surface 8216 in the extended position. In some embodiments, there is an air gap of about 12 mm, about 6 mm, about 4 mm, less than 12 mm, less than 6 mm, or less than 4 mm between the plurality of magnets 9000A-D and a plurality of magnets of a hub assembly when the plurality of magnets 9000A-D are in the extended position. Smaller air gaps may be preferable for providing a stronger magnetic coupling.

In some embodiments, the hub adapter can include a platform or frame 8208. As shown in FIGS. 49A-49E, in some embodiments, the frame 8208 can extend along a plurality of edges of the hub adapter 8000. In some embodiments, the frame 8208 can extend along three edges of the hub adapter 8000. For example, the frame 8208 can extend along the sides and rear surface of the hub adapter 8000.

In certain embodiments, the linear actuator 8214 can move the frame 8207 relative to the frame 8208.

In some embodiments, as shown in FIGS. 49F and 49G, the frame 8208 may be configured to be displaced, for example, along the axis A15 (e.g., away from or towards the drive surface 8216). In certain embodiments, the frame 8208 may be coupled to the one or more active torque elements 8202A-D, for example, via the frame 8207 and/or the stage 8219. In certain embodiments, the stage 8219 can be coupled to the frame 8208. In certain embodiments, the frame 8208, active torque elements 8202A-D (e.g., via the frame 8207), and/or stage 8219 can be displaceable together along, for example, along the axis A15 (e.g., away from or towards the drive surface 8216) in response to changes in height or flatness of the barrier 8242. For example, in certain embodiments, the stage 8219 may be displaced in a direction away from the drive surface 8216 (e.g., along the axis A15) and may contact the frame 8207 and/or the frame 8208 to advance the active torque elements 8202A-D away from the drive surface. This may prevent contact between the active torque elements 8202A-D (e.g., magnets 9000A-D) and the drive surface 8216 and/or prevent issues with the axial advancement mechanism moving the hub adapter 8000 axially within the drive table caused high friction.

In certain embodiments, a spring mechanism or spring assembly 8234 may be provided. The spring mechanism may to absorb shock and/or accommodate for the variations along the barrier 8242 as the hub adapter 8000 translates within the drive table. In certain embodiments, the spring mechanism may exert a force on the active torque elements 8202A-D, frame 8208 and/or stage 8219 towards the drive surface 8216 (e.g., along the axis A15), for example, to return the active torque elements 8202A-D, frame 8208, and/or stage 8219 to their previous positions after the hub assembly advances over a non-planar section of the drive surface 8216 and/or to maintain a desired air gap between the active torque elements 8202A-D (e.g., magnets 9000A-D) and the drive surface 8216).

For example, in certain embodiments, the hub adapter 8000 can include a platform or frame 8206. The frame 8206 can be a spring frame.

As shown in FIGS. 49A-49E, the frame 8206 can extend along a plurality of edges of the hub adapter 8000. In some embodiments, the frame 8206 can extend along three edges of the hub adapter 8000. For example, the frame 8206 can extend at least partially along the sides and rear surface of the hub adapter 8000.

In some embodiments, the hub adapter 8000 can include one or more springs 8212. The springs 8212 can be configured to dampen forces and/or displacement as the hub adapter 8000 translates within the drive table. In some embodiments, the springs 8212 can be helical compression springs configured to absorb axial forces and/or to bias the hub adapter 8000 toward the drive surface 8216. The springs 8212 may extend between the frame 8206 and the frame 8208. In some embodiments, the springs 8212 may be provided between a fully extended state and a fully compressed state. Accordingly, the springs 8212 can bias the plurality of active torque elements 8202A-D to maintain a desired air gap, while being configured to be further compressed to accommodate for axial displacement. For example, the springs 8212 may exert a force on the frame 8208 in a direction towards the drive surface to apply a force on the frame 8208, the active torque elements 8202A-D (e.g., via the frame 8207), and/or the stage 8219 in the direction towards the drive surface 8216 to move towards the drive surface 8216.

An example of the hub adapter 8000 in contact with a planar section of the drive surface 8216 of the barrier 8242 is depicted in FIG. 49F. An example of the hub adapter 8000 in contact with a non-planar section of the drive surface 8216 of the barrier 8242 is depicted in FIG. 49G. As shown, in FIG. 49G, the frame 8208 is positioned closer to the frame 8206 than in FIG. 49F, and the springs 8212 are compressed. In FIG. 49F, the frame 8208 is positioned at a distance $Z_1$ from the frame 8206. In FIG. 49G, the frame 8208 is positioned at a distance $Z_2$ from the frame 8206, wherein $Z_2$ is smaller than $Z_1$.

The above-described spring mechanism (e.g., the frame 8206, the frame 8208, and the springs 8212, can allow the support assembly 8218 and the active torque elements 8202A-D to move together to allow variations along the barrier 8242 while maintaining a desired air gap. In certain embodiments, at the same time, the active torque elements 8202A-D can be moved independently from the support assembly 8218 as described herein (e.g., via the linear actuator 8214).

As shown in FIG. 49A, in some embodiments, the hub adapter 8000 can include one or more control circuits 8210. The one or more control circuits 8210 can be configured to control one or more of the active torque elements 8202A-D. In some embodiments, each active torque element may be controlled by a unique control circuit 8210. In some embodiments, one or more of the control circuits 8210 can control a motor configured to drive the hub adapter 8000 within the drive table. In some embodiments, one or more of the control circuits 8210 can drive movement of the active torque elements (e.g., magnets 9000A-D) towards and away from the drive surface 8216 and/or the sterile barrier, for example by driving movement of the linear actuator 8214, as described herein.

Figure 50A:
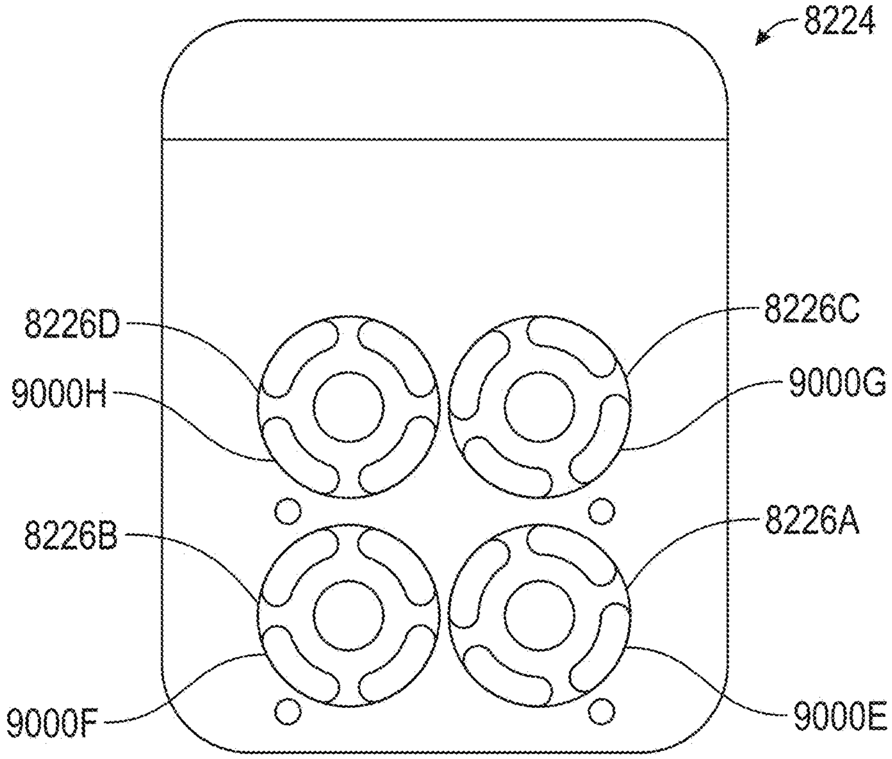
FIG. 50A is a rear view of a hub assembly.
Figure 50B:
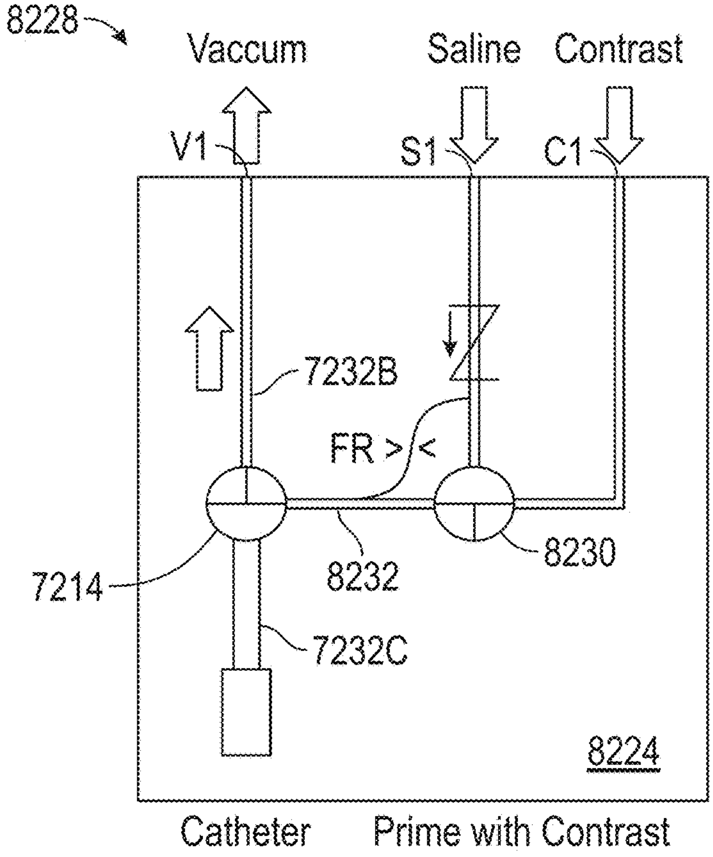
FIG. 50B is a schematic of a fluidics management system within the hub assembly of FIG. 50A.

FIGS. 50A-50B illustrate an embodiment of a first hub assembly 8224A. As described herein, the first hub assembly 8224A may include a mount and a hub. The first hub assembly 8224A may be representative of a of any of the hub assemblies described herein.

As shown in FIG. 50A, the first hub assembly 8224A (e.g., mount) can include a plurality of passive torque elements 8226A-D. In certain embodiments, the number of passive torque elements 8226A-D may correspond to a number of active torque elements 8202 of a corresponding hub assembly. In some embodiments, the plurality of passive torque elements 8226A-D can include a first passive torque element 8226A, a second passive torque element 8226B, a third passive torque element 8226C, and a fourth passive torque element 8226D. In an operable configuration, the rotation of each of the passive torque elements 8226A-D can result in an actuation of a corresponding degree of freedom of the hub assembly 8224 (e.g., of a mount and/or hub). For example, rotation of the first passive torque element 8226A can actuate a first degree of freedom, rotation of the second passive torque element 8226B can actuate a second degree of freedom, rotation of the third passive torque element 8226C can actuate a third degree of freedom, and rotation of the fourth passive torque element 8226D can actuate a fourth degree of freedom. In some embodiments, the degrees of freedom of the hub assembly 8224 (e.g., mount and/or hub) can include rotating an intravascular device, actuating a hemostasis valve, and/or actuating a valve. Each of the passive torque elements 8226A-D may be operatively coupled to a corresponding gear train for transferring a rotational motion of the passive torque element 8226A-D to a feature of the hub assembly (e.g., an intravascular device, a valve, etc.).

As further shown in FIG. 50A, in some embodiments, each of the passive torque element 8226A-D can include a magnet or array of magnets. For example, as shown in FIG. 50A, passive torque elements 8226A, 8226B, 8226C, and 8226D can include magnets 9000E, 9000F, 9000G, and 9000H, respectively. While each of the passive torque elements 8226A-D is shown having a single magnet 9000E-H in FIGS. 50A, in other embodiments, each active torque element can include a plurality of magnets, for example, as shown in FIG. 45D.

In certain embodiments, each passive torque element 8226A, 8226B, 8226C, and 8226D can include a magnet support or magnet support element, respectively. Each magnet support element can be configured to support the magnet 9000E-H of fits corresponding passive torque element 8226A-D. In some embodiments, the magnet support elements can be formed of a ferrous material (e.g., steel), which may direct magnetic field lines away from the magnet support element (e.g., towards the active torque element).

In some embodiments, each passive torque element 8226A-D can include a plurality of regions of magnetization, as described in further detail with respect to FIG. 52A. The regions of magnetization may be considered part of a single magnet 9000E-H or may be separate magnets. In some embodiments, the passive torque elements 8226A-D (e.g., magnets 9000E-H) may be a monolithic object having regions of polarity. For example, as shown in FIG. 50A, each of the passive torque elements 8226A-D (e.g., magnet 9000E-H) can have a plurality of regions with a common first polarity and a second region with a common second polarity. In some embodiments, the regions of polarity of adjacent passive torque elements 8226A-D may differ. The configuration of the passive torque elements 8226A-D can reduce backlash. The active torque elements 8202A-D may similarly be monolithic structures with regions of polarity. The active torque elements 8202A-D can have regions of polarity opposite the corresponding regions of polarity of the passive torque elements 8226A-D.

The first passive torque element 8226A can be the same or similar to the first passive torque element 7204A described above. The first passive torque element 8226A can magnetically couple with the first active torque element 8202A for controlling the rotation of the interventional device (e.g., catheter, guidewire, etc.). The second passive torque element 8226B can be the same or similar to the third passive torque element 7204C described above. The second passive torque element 8204B can magnetically couple with the second active torque element 8202B for controlling the actuation of a hemostatic valve. In some embodiments, the third passive torque element 8226C may be the same or similar to the second passive torque element 7204B described above. The third passive torque element 8226C can couple with the third active torque element 8202C, for controlling the actuation of a valve 7214 as shown in FIG. 50B. In some embodiments, the fourth passive torque element 8226D can couple with the fourth active torque element 8202D, respectively, for controlling the actuation of a second valve 8230, as shown in FIG. 50B.

The fluidics management system 8228 can be similar to the fluidics management system 7228 described above. As shown in FIG. 50B, the fluidics management system 8228 can control the flow from a saline tube containing saline S1, a contrast tube containing contrast C1, and an aspiration tube 7232B containing negative pressure (i.e., vacuum V1) to a catheter. As further shown in FIG. 50B, the fluidics management system 8228 can further include a second valve 8230 (e.g., a stopcock). The saline tube and the contrast tube can couple together at the second valve 8230 to form a single valve input tube 8232. Accordingly, the fluidics management system 8228 can provide additional controls on the flow of fluidics through the hub assembly 8224 (e.g., mount and/or hub). The fluidics management system 8228 can include any or all of the features identified in U.S. patent application Ser. No. 18/666,217, filed May 16, 2024, tilted FLUIDICS CONTROL SYSTEM FOR MULTI CATHETER STACK, the entire content of which is incorporated by reference herein for all purposes and forms a part of this specification.

FIGS. 51A-51D describe methods and systems for aligning and coupling one or more hub assemblies 8224A-D (e.g., mounts) with one or more hub adapters 8000A-D across a sterile a barrier.

In some embodiments, each of the hub assemblies 8224A-D (e.g., mounts) may be configured to couple to a respective one of the plurality of hub adapters 8000A-D. The hub adapters 8000A-D and the hub assemblies 8224A-D (e.g., mounts) can be configured to identify and align with one other. In some examples, the hub adapters 8000A-D can include identification components for use in identifying and aligning the hub adapters 8000A-D with the hub assemblies 8224A-D. For example, the hub adapters 8000A-D and the hub assemblies 8224A-D (e.g., mounts) can include identifiers and/or sensors. The identifiers may be configured to be detected by the sensors. For example, the hub adapters 8000A-D may include the sensors and the hub assemblies 8224A-D (e.g., mounts) may include the identifiers as described herein with reference to FIGS. 51C-51G and 51Q-51T. In other embodiments, the hub assemblies 8224A-D (e.g., mounts) may be configured to identify and align with the hub adapters 8000A-D. For example, the hub assemblies 8224A-D (e.g., mounts) may include the sensors and the hub adapters 8000A-D may include the identifiers as described herein with reference to FIGS. 51H-51P.

The identifiers can be any device, system, or means for conveying identifying and/or positional information. In some embodiments, the one or more identifiers can be detectable objects 8223 (e.g., identifier magnets). Although the examples provided herein are described with reference to magnets, other means are also possible. For example, in some embodiments, the detectable objects can include colors or lights. In some embodiments, optical sensors may be used to identify and align hub adapters 8000A-D and hub assemblies 8224A-D (e.g., mounts). In some embodiments, optical sensors may be configured to scan a code (e.g., optical product codes (OPC), a quick response (QR) code, etc.) or may be used with machine learning to identify and determine an alignment between hub adapters 8000A-D and hub assemblies 8224A-D. In some embodiments, capacitive sensing or inductive sensing may be used to detect one or more detectable objects.

The detectable objects 8223 may be arranged in an identifying configuration. In some examples, the detectable objects 8223 may be arranged in a unique pattern. For example, each of the hub adapters 8000A-D or each of the hub assemblies 8224A-D (e.g., mounts) can include two or more detectable objects 8223 arranged in a unique pattern. The unique pattern can be based in part on the quantity of the detectable objects 8223, the shape and/or positions of the detectable objects 8223, and/or a state of each of the detectable objects 8223.

In some embodiments, each of the plurality of hub adapters 8000A-D or hub assemblies 8224A-D, whichever do not include the detectable objects, can include a corresponding arrangement of sensors 8227 configured to measure the detectable objects 8223. For example, the hub adapters 8000A-D or hub assemblies 8224A-D may include the same number of sensors 8227 as the number of detectable objects 8223. Additionally, the sensors 8227 may be arranged in the same spatial configuration on the hub adapters 8000A-D as the spatial arrangement of the detectable objects 8223. In some embodiments, the number of sensors 8227 may differ from the number of detectable objects 8223 and/or may be in a different spatial arrangement. For example, in analog sensing methods (e.g., sensing a magnitude of a magnetic field created by one or more magnets), one sensor 8227 may detect multiple detectable objects. In some embodiments, multiple sensors 8227 may be positioned on the hub adapters 8000A-D or hub assemblies 8224A-D to detect a smaller number of detectable objects at different locations. For example, a hub adapter 8000A-D may include four sensors 8227 to detect hub assemblies each having two or three detectable objects at different locations.

In some embodiments, each of the detectable objects 8223 may be a binary or trinary device. A binary device can refer to a device using a system based on only two states (e.g., true/false, on/off, north/south, etc.). A trinary device can refer to a device using a system based on only three states. The three states can include the states from a binary device with the addition of an intermediate state. Accordingly, each of the detectable objects 8223 may exist in only one state at a time. In other embodiments, each of the detectable objects 8223 may be an analog device, or may be detectable by an analog sensor. For example, the detectable objects 8223 may be magnets having different magnetic field strengths that can be detected by one or more analog sensors or magnets arranged in different locations so that different magnetic field strengths are detected by one or more analog sensors.

As described herein, the detectable objects 8223 may be magnets. Accordingly, each of the detectable objects 8223 may have a first magnetic pole and a second magnetic pole. The first magnetic pole may correspond to a magnetic north pole and the second magnetic pole may correspond to a magnetic south pole, or vice versa. The first magnetic pole and the second the second magnetic pole can correspond to a first state and a second state, respectively. In other words, the first state may correspond to when a sensor detects the first magnetic pole and the second state may correspond to when a sensor detects the second magnetic pole. Additionally, in some embodiments, the detectable objects 8223 may be capable of being selectively activated, or may be missing (e.g., magnetic field not present). Accordingly, the detectable objects 8223 may include a third state corresponding to no magnetic field.

In some embodiments, each of the detectable objects 8223 may exist within a spectrum of possible states (e.g., brightness instead of on/off, magnetic strength instead of north/south, etc.). In some examples, each of the detectable objects 8223 may have a magnetic strength. The magnetic strength of the detectable objects 8223 may be within a range of possible values. The possible values may be separated into predetermined ranges, wherein a state of the detectable objects 8223 may be assigned based on the range within which the detectable object 8223 exists. In a non-limiting example, the detectable objects 8223 may have a magnetic strength between 0 mTesla and 2 mTesla. In such examples, a magnetic strength between 0 mTesla and ½ mTesla can correspond to a first state, a magnetic strength between ½ mTesla and 1 mTesla can correspond to a second state, a magnetic strength between 1 mTesla and 1½ mTesla can correspond to a third state, and a magnetic strength between 1½ mTesla and 2 mTesla can correspond to a fourth state. To accommodate additional states, the predetermined ranges for each state may be made adjusted (e.g., 2 mTesla range, 1½ mTesla range, 1 mTesla range, ½ mTesla range, ¼ mTesla range, ⅛ mTesla range, 1/16 m Tesla range, etc.), or the total range may be made wider (0 mTesla to 4 mTesla, 0 mTesla to 8 mTesla, 0 mTesla to 16 mTesla, etc.). Other examples of non-binary state detection can include brightness, capacitance, or inductance sensing. Capacitance sensing measures the capacitance between the two charged plates. Inductance sensing measures the inductance. In some embodiments, an electrical coupling may occur between the hub adapters 8000A-D and the corresponding hub assemblies 8224A-D. In some embodiments, a combination of magnetic strength, brightness, capacitance, or inductance sensing may be used.

The number of possible configurations may be limited by the quantity of detectable objects 8223 per device and the quantity of possible states for each of the detectable objects 8223. For example, the number of possible combinations of states of detectable objects may follow the relationship: n', wherein n is the number of possible states per detectable object 8223 and r is the number of detectable objects 8223. Table 1 provided below illustrates how the possible combinations of states of detectable objects that may be used for detecting different hub assemblies 8224A-D or hub adapters 8000A-D changes based on the quantity of detectable objects 8223 per device and the quantity of possible states for each of the detectable objects 8223. For example, as shown, two detectable objects each having two different states may allow for four possible combinations of states: (1) North-North, (2) North-South, (3) South-North, (4) South-South. Each of these combinations can be used on a different hub adapters 8000A-D or hub assembly 8224A-D to allow for detection and identification of four separate hub adapters 8000A-D or hub assemblies 8224A-D. This can be beneficial to distinguish hub adapters 8000A-D or hub assemblies 8224A-D, for example, when the detectable objects are positioned in the same locations on each hub adapter 8000A-D or hub assembly 8224A-D

TABLE 1

Number of Possible Combinations Based on Quantity of Possible States per Detectable Object

| Possible States (n) | Detectable Objects (r) | Number of Possible Combinations |
|---|---|---|
| 1 | 1 | 1 |
| 1 | 2 | 1 |
| 1 | 3 | 1 |
| 2 | 1 | 2 |
| 2 | 2 | 4 |
| 2 | 3 | 8 |
| 3 | 1 | 3 |
| 3 | 2 | 9 |
| 3 | 3 | 27 |
| 4 | 1 | 4 |
| 4 | 2 | 16 |
| 4 | 3 | 64 |

As shown and described herein, the system may include four hub assemblies 8221A-D for driving a stack of four interventional devices (e.g., guidewire, access catheter, procedure catheter, guide catheter). Accordingly, the quantity of detectable objects 8223 and the quantity of possible states for each of the detectable objects 8223 may provide for at least four configurations. In some embodiments, additional devices or sets of devices may be provided. For example, a first set of devices may include the interventional devices described herein and a second set of devices may include a different set of interventional devices than those described herein. In some embodiments, the differences between the first set and the second set may include the sizes of the interventional devices. Each set of devices may have a different intended use. Accordingly, the quantity of detectable objects 8223 and the quantity of possible states for each of the detectable objects 8223 may provide for more than four configurations. For example, the number of configurations may be a multiple of four such as 8, 16, 20, 24, etc. In some examples, a first and a second detectable device 8223 may be used to identify a device in a particular set of devices (e.g., first device, second device, third device, fourth device, etc.) and a third detectable object 8223 may be used to identify which set of devices is present (e.g., first set, second set, third set, fourth set, etc).

In some embodiments, each of the hub assemblies 8224A-D (e.g., mounts) can include one or more identifiers that may be detected, for example, by a sensor. The identifiers may be used to determine the identity of a hub assembly 8224A-D for coupling the hub assembly 8224A-D with a desired hub adapter 8000A-D. In some embodiments, the identifiers may be detected by one or more sensors 8227 of the hub adapters 8000A-D or otherwise associated with the one or more hub adapters 8000A-D.

Figure 51A:
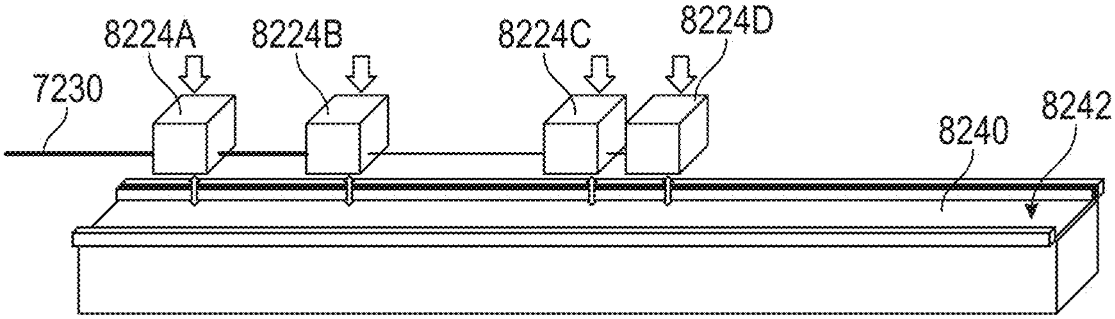
FIGS. 51A-51B are perspective views of a plurality of hub assemblies being mounted to a drive table.
Figure 51B:
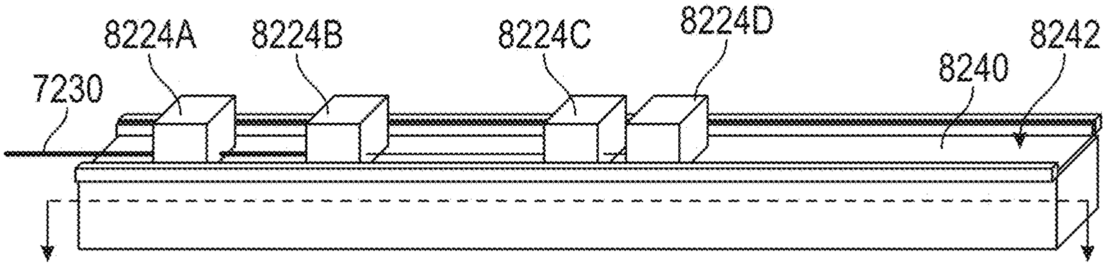

FIGS. 51A-51B show a plurality of hub assemblies 8224A-D (e.g., mounts) being placed on a drive surface 8240 (e.g., a planar drive surface or substantially planar drive surface) to be magnetically coupled to corresponding hub adapters 8000A-D. In some embodiments, the drive surface 8240 may be part of a barrier 8242 that includes the drive surface 8216 on its opposing side. The barrier 8242 may be a sterile barrier. In other embodiments, the drive surface 8216 may be part of a separate barrier, and the barrier 8242 can be placed over the separate barrier and act as a sterile barrier.

In the operable configuration, the hub assemblies 8224A-D (e.g., mounts) can be driven along the drive surface 8240 by the shear force applied by the active torque elements one the active torque elements via the coupling between the active torque elements and the passive torque elements.

In some embodiments, the hub assemblies 8224A-D can include a first hub assembly 8224A, a second hub assembly 8224B, a third hub assembly 8224C, and a fourth hub assembly 8224D. Each of the hub assemblies 8224A-D can include an intervascular device. For example, FIGS. 51A and 51B depict an intravascular device such as the catheter 7230 of the hub assembly 8224A. The intervascular devices coupled to the hub assemblies 8224 can be devices configured to access the vascular system of a patient. For example, the intervascular devices can be catheters and/or guidewires. In some embodiments, the intervascular devices of the plurality of hub assemblies 8224 can be coaxially nested, as shown in FIGS. 51A-51B.

In some embodiments, an intravascular device having the smallest diameter may be coupled to the fourth hub assembly 8224D, an intravascular device having a lumen with an inner diameter greater than the intravascular device of the fourth hub assembly 8224D may be coupled to the third hub assembly 8224C, an intravascular device having a lumen with an inner diameter greater than the outer diameter of the intravascular device of the third hub assembly 8224C may be coupled to the second hub assembly 8224B, and an intravascular device having a lumen with an inner diameter greater than the outer diameter of the intravascular device of the second hub assembly 8224B may be coupled to the first hub assembly 8224A. For example, a guidewire may be coupled to the fourth hub assembly 8224D, a catheter may be coupled to the third hub assembly 8224C, another catheter may be coupled to the second hub assembly 8224B, and another catheter may be coupled to the first hub assembly 8224A.

In some embodiments, for example, during a setup of a robotic surgical system, the hub assemblies 8224A-D can be placed (e.g., manually) on the drive surface 8240. In some embodiments, the hub assemblies 8224A-D may be placed at a designated location along the drive surface 8240. For example, one or more indicators (e.g., colors, lines, images, etc.) may indicate a location along the drive surface 8240 at which to place the hub assemblies. In some embodiments, the designated locations for the hub assemblies 8224A-D may correspond to designated locations for the hub adapters 8202A-D in a setup configuration (e.g., at which the hub adapters 8202A-D are positioned or to which the hub adapters 8202A-D may be automatically driven to). In such embodiments, placing the hub assemblies 8224A-D in their designated locations may align the hub assemblies 8224A-D with their corresponding hub adapters 8202A-D.

In some embodiments, one or more of the hub assemblies 8224A-D may not be accurately placed over the corresponding hub adapters 8000A-D during the initial setup or if a hub assembly 822A-D is replaced during a procedure. In some examples, the entire stack of hub assemblies 8224A-D may be added or removed together. Accordingly, if one of the hub assemblies 8224A-D needs to be replaced, the entire stack of hub assemblies 8224A-D may be replaced simultaneously. In such embodiments, the hub adapters 8224A-D can be configured to perform an automated alignment process to align with the hub assemblies 8224A-D. In other embodiments, the plurality of hub assemblies 8224A-D can be placed anywhere along the drive surface 8240 regardless of the position of the plurality of hub adapters 8000 and/or a designated position for the hub assemblies 8224A-D, and the hub adapters 8000A-D can be configured to perform an automated alignment process to align with the hub assemblies 8224A-D. In such embodiments, the plurality of hub adapters 8000 can detect whether the corresponding hub assemblies 8224A-D are aligned with the hub adapters 8000A-D. If the hub assemblies 8224A-D are not aligned with the hub adapters 8000, the hub adapters can perform an automated alignment process.

FIGS. 51C-51F depict embodiments of a method for spatial alignment between the hub adapters 8000A-D and the hub assemblies 8224A-D. FIG. 51G depicts an embodiment of a method for rotational alignment between torque elements of the hub adapters 8000A-D and the hub assemblies 8224A-D, as described in greater detail below.

The methods for spatial alignment and rotational alignment described herein may be performed together, for example, as part of a setup procedure, or may be performed separately. For example, in certain embodiments, a hub assembly may be placed along a drive table in a known or designated position for coupling the hub assembly to the hub adapter, and the method of rotational alignment described with respect to FIG. 51G may be performed without performing a method of spatial alignment as described with respect to FIGS. 51C-51F.

Figure 51C:
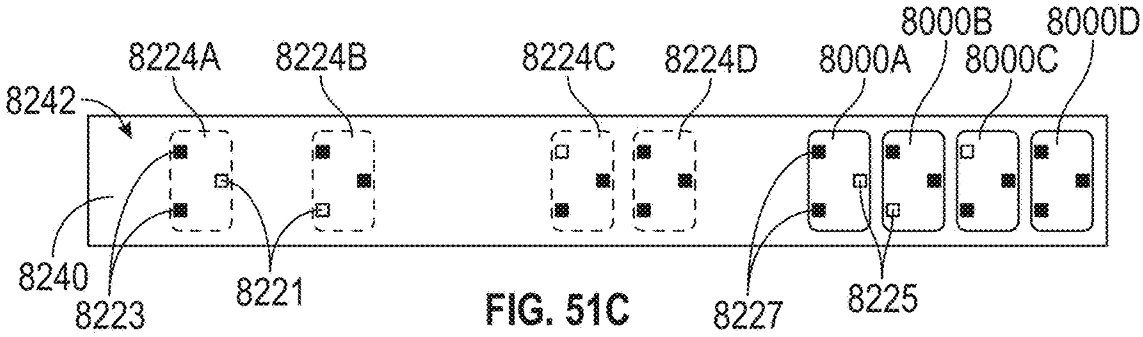
FIGS. 51C-51D are top views of a plurality of hub adapters having sensors aligning with a corresponding hub assembly having detectable objects.
Figure 51D:
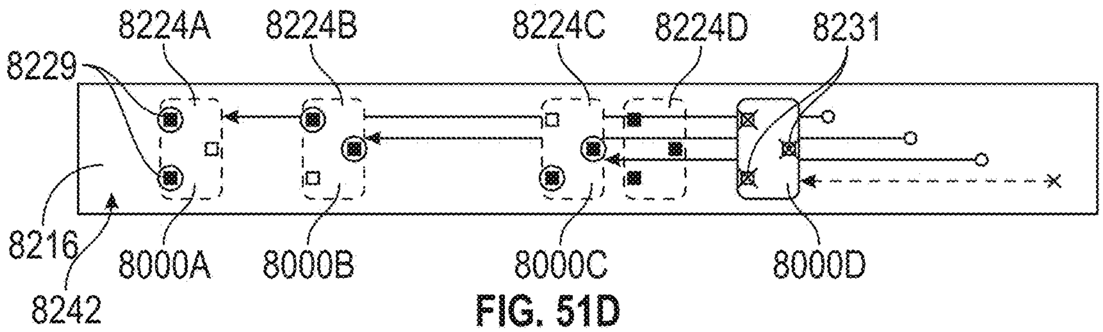

FIGS. 51C-51D illustrate an embodiment of driving the plurality of hub adapters 8000A-D beneath the barrier 8242 to align with and magnetically couple with a corresponding one of the plurality of hub assemblies 8224A-D. In some embodiments, the first hub adapter 8000A may be paired with and/or programmed to identify the first hub assembly 8224A (e.g., mount), the second hub adapter 8000B may be paired with and/or programmed to identify the second hub assembly 8224B (e.g., mount), the third hub adapter 8000C may be paired with and/or programmed to identify the third hub assembly 8224C (e.g., mount), and the fourth hub adapter 8000D may be paired with and/or programmed to identify the fourth hub assembly 8224D (e.g., mount).

The hub assemblies 8224A-D (e.g., mounts) are shown in dashed lines and are located on a first side (e.g., above) of the barrier 8242 (e.g., on the drive surface 8240). The one or more hub adapters 8000 are shown in solid lines and are located on a second side (e.g., below) of the barrier 8242 (e.g., on the interior drive surface 8216).

In certain embodiments, each of hub assemblies 8224A-D can include one or more detectable objects 8223 (e.g., identifier magnets, specific colors, light diodes, or other detectable objects) that may be detected by one or more sensors 8227 of one of the hub adapters 8000A-D to confirm alignment between the hub assemblies 8224A-D and hub adapters 8000A-D. The detectable objects 8223 of each hub assembly 8224A-D may be arranged in unique positions (e.g., patterns) relative to the other hub assemblies 8224A-D to allow for identification of the individual hub assemblies 8224A-D. Additionally or alternatively, at least some of the hub assemblies 8224A-D may include a different number of detectable objects 8223 relative to one another (e.g., two objects vs. three objects) to allow for identification of the individual hub assemblies.

The one or more hub adapters 8000A-D may include sensors 8227 configured to align with the positions of the detectable objects 8223 to detect the detectable objects 8223 of the hub assemblies 8224A-D for identifying and aligning with the hub assemblies 8224A-D.

The detectable objects 8223 may be placed at multiple points along a hub assembly 8224A-D to allow for detection of proper alignment of the hub assemblies 8224A-D. For example, each hub assembly 8224A-D may include detectable objects 8223 at multiple locations. If a hub adapter 8000A-D, only detects a detectable object 8223 at a single location, it may indicate that the corresponding hub assembly 8224A-D is misaligned. For example, it may be indicate that the hub assembly 8224A-D is misaligned rotationally relative to the hub adapter 8000A-D (e.g., due to an undesired yaw rotation). In some examples, increasing the distance between detectable objects 8223 may increase the accuracy of alignment detection. For example, increasing a distance between two adjacent detectable objects 8223 can make rotational misalignment easier to detect. The distance can be at least a lateral distance. In some examples, separating the detectable objects 8223 along a diagonal may increase a detection of rotational misalignment.

In FIGS. 51C and 51D, the plurality of hub assemblies 8224A-D are shown with a plurality of squares 8221 identifying examples of potential positions of detectable objects 8223 (e.g., identifiers) on the hub assemblies 8224A-D. As shown, in this example, each of the hub assemblies has the same arrangement of potential positions, although in other embodiments, different arrangements are possible. In some embodiments, the filled squares may represent a first state and the empty squares may represent a second state. For example, filled squares may represent a first magnetic pole and the empty squares may represent a second magnetic pole, or vice versa. In some embodiments, the filled squares may represent detectable objects 8223 having a detectable output and the empty squares may represent detectable objects 8223 without a detectable output. In some embodiments, the filled squares of the hub assemblies 8224A-D can represent identifier magnets, specific colors, light diodes, or other detectable objects and the empty squares of the hub assemblies 8224A-D can represent a missing or an inactive detectable object 8223. The sensors 8227 can determine which state (first or second state) the detectable objects 8223 are in. In some embodiments, the empty squares can represent a third state.

The detectable objects 8223 can be arranged in a pattern. In some embodiments, each of the hub assemblies 8224A-D can share a common general pattern of possible positions for the detectable objects 8223. For example, each of the plurality of hub assemblies 8224A-D can include detectable objects 8223 positioned in one or more common positions along a chevron pattern. The common general pattern can be based on the collective possible positions of the detectable objects 8223. In some embodiments, each of the hub assemblies 8224A-D can have a unique pattern or placement of detectable objects 8223 within the common general pattern.

As shown in FIG. 51C, the first hub assembly 8224A has a different unique specific pattern than the unique specific patterns of the hub assembly 8224B, the third hub assembly 8224C, and the fourth hub assembly 8224D. In one example, each of the first hub assembly 8224A, the second hub assembly 8224B, the third hub assembly 8224C, and the fourth hub assembly 8224D can have the same number of detectable objects 8223 sharing a common general pattern, but each hub assembly having a unique specific pattern of states for their respective detectable objects 8223. In another example, each of the first hub assembly 8224A, the second hub assembly 8224B, and the third hub assembly 8224C can have two detectable objects 8223 positioned at different locations relative to one another (e.g., different locations within the common general pattern) and a missing or inactive detectable object 8223 positioned at different locations relative to one another (e.g., different locations within the common general pattern), and the fourth hub assembly 8224D can have a different number of detectable objects 8223 (3) than the hub assemblies 822A-C. Accordingly, the unique specific patterns of detectable objects 8223 may allow for identification of a specific one of the plurality of hub assemblies 8224A-D. This may be advantageous to identify a hub assembly 8224A-D coupled to a particular intravascular device or positioned within a particular order along the drive table.

The hub adapters 8000A-D are also shown with a plurality of squares 8225 identifying examples of potential positions of sensors 8227 on the hub adapters for detecting detectable objects 8223 of the hub assemblies 8224A-D. As shown, in this example, each of the hub adapters 8224A-D has the same arrangement of potential positions, although in other embodiments, different arrangements are possible. As shown, empty squares can represent locations in which a sensor 8227 is not present, and filled in squares can represent a sensor position on the hub adapters 8224A-D. The sensors 8227 may be hall effect sensors, imaging sensors, or any other suitable sensors. The sensors 8227 of the plurality of hub adapters 8000A-D can be arranged in a pattern. In some embodiments, each of the hub adapters 8000A-D can share a common general pattern of possible positions for the sensors 8227. The common general pattern of the hub adapters 8000A-D may correspond to the common general pattern of the plurality of hub adapters 8224A-D. For example, each of the hub adapters 8000 can include sensors 8227 arranged along a chevron pattern.

In some embodiments, each hub adapter 8000A-D may have a sensor 8227 in each location of the common general pattern, such that each hub adapter 8000A-D can detect and identify each hub assembly 8224A-D. In other embodiments, each hub adapter 8000A-D can have a unique pattern or placement of sensors 8227 corresponding to the unique patterns or placements of detectable objects 8223 of the hub assemblies 8224A-D, for example, such that each hub adapter 8000A-D detects only a single corresponding hub assembly 8224A-D.

In some embodiments, the general pattern of the detectable objects 8223 of the hub assemblies 8224A-D and/or specific patterns of detectable objects 8223 of each hub assembly 8224A-D can be selected so that the detectable objects 8223 are sufficiently spaced apart that misalignment of the hub assemblies 8224A-D can be detected if all of the detectable objects 8223 of the particular hub assembly 8224A-D are not detected by a corresponding hub adapter 8000A-D. For example, if a hub assembly 8224A-D has two detectable objects 8223, but only a single detectable object 8223 is detected by a corresponding hub adapter 8000A-D, it may indicate that the hub assembly 8224A-D is misaligned along the drive table.

As shown in FIG. 51C, the plurality of hub adapters 8000A-D may be located at respective default positions. In some embodiments, the default positions may be at a longitudinal end of the drive table. As further shown in FIG. 51C, the plurality of hub assemblies 8224A-D may be placed on the drive surface 8240 at positions that do not correspond to the respective default positions of the corresponding hub adapters 8000A-D.

As shown in FIG. 51D, each of the hub adapters 8000A-D may be driven beneath the barrier 8242 until the hub adapter 8000A-D arrives at a position of a corresponding hub assembly 8224A-D. For example, each of the hub adapters 8000A-D may drive along the length of the drive table until the hub adapter 8000A-D identifies its corresponding hub assembly 8224A-D and/or detects that it is aligned with its corresponding hub assembly 8224A-D, respectively.

Each of the plurality of hub adapters 8000A-D may be independently driven. Accordingly, it is possible to drive a single hub adapter 8000A-D to align with its corresponding hub assembly 8224A-D. As shown in FIG. 51D, the first hub adapter 8000A can be driven past the fourth hub assembly 8224D, the third hub assembly 8224C, and the second hub assembly 8224B until the first hub adapter 8000A is aligned with the first hub assembly 8224A (e.g., alignment between the first hub adapter 8000A and the first hub assembly 8224A is detected via the sensors 8227 of the first hub adapter 8000A). In some embodiments, the sensors 8227 of the first hub adapter 8000A may scan for detectable objects 8223 as it is advanced within the drive table until alignment is detected. Similarly, the second hub adapter 8000B can be driven past the fourth hub assembly 8224D and the third hub assembly 8224C until the second hub adapter 8000B arrives at the second hub assembly 8224B. The third hub adapter 8000C can also be driven past the fourth hub assembly 8224D until the third hub adapter 8000C arrives at the third hub assembly 8224C. The plurality of hub adapters 8000 may be driven simultaneously or one at a time. Under either approach, the plurality of hub adapters 8000 may be driven independently.

As further shown in FIG. 51D, circles 8229 are provided to illustrate detectable objects 8223 of the hub assemblies 8224A-D that are aligned with corresponding sensors 8227 of the hub adapters 8000A-D indicating an alignment between those hub assemblies and hub adapters. For example, circles 8229 are shown over the detectable objects 8223 of the first hub assembly 8224A, the second hub assembly 8224B, and the third hub assembly 8224C because they are successfully aligned with their corresponding hub adapters 8000A-C. In FIG. 51D, "x" symbols 8231 are provided over the sensors 8227 of the fourth hub adapter 8000D to indicate that none of the sensors 8227 of the fourth hub adapter 8000D have successfully detected a detectable object 8223 of a hub assembly 8224A-D.

Figures 51E, 51F, 51G:
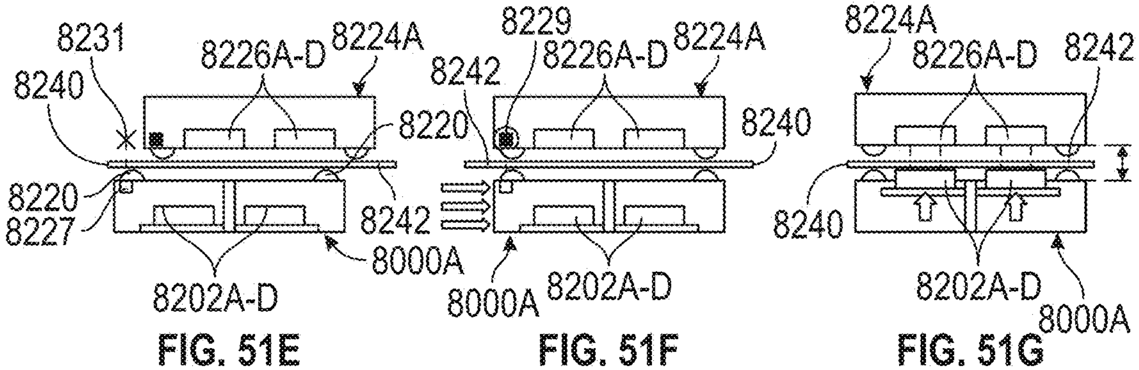
FIGS. 51E-51G are side views of a hub adapter having sensors aligning with a hub assembly having detectable objects.

FIGS. 51E-51F illustrate a method of aligning a hub adapter 8000A with a corresponding hub assembly 8224A. While a hub adapter 8000A and hub assembly 8224B are discussed, other hub adapters and hub assemblies may be aligned using the same methods.

As shown in FIGS. 51E-51F, the hub adapter 8000A may align with a corresponding hub assembly 8224A by sensing an identifier, such as a detectable object 8223 as described with respect to FIGS. 51C and 51D. In some embodiments, the hub adapter 8000A may recognize the respective corresponding hub assembly 8224A by sensing one or more identifier magnets, for example, using one or more sensors 8227. Each sensor 8227 of the hub adapter 8000A can be configured to detect the presence of a detectable object 8223 of the corresponding hub assembly 8224A.

In some embodiments, each of the hub adapters 8000A-D can be configured to identify each of the hub assemblies 8224A-D. In some embodiments, the plurality of hub adapters 8000A-D may be configured to identify only a particular one of the plurality of hub assemblies 8224A-D.

As shown in FIG. 51E, the sensor(s) 8227 of the hub adapter 8000A are not aligned with the detectable object(s) 8223 of the hub assembly 8224A. Accordingly, the hub adapter 8000A may be translated within the drive table (e.g., sweep) until the sensor(s) 8227 of the hub adapter 8000A detect the detectable object(s) of the hub assembly 8224A, as shown in FIG. 51F.

In some embodiments, during the alignment of the hub adapters 8000A-D with the hub assemblies 8224A-D, the active torque elements 8202A-D may be positioned in the retracted position away from the drive surface 8216. In the retracted position, a magnetic field may extend through the barrier 8242 from the active torque elements 8202A-D. In some embodiments, the magnetic field may be weak and insufficient to rotate the passive torque elements 8226A-D of the corresponding hub assemblies 8224A-D. For example, in some embodiments, the magnetic coupling may have a magnetic force of about 1 lbf. In some embodiments, the magnetic field may be sufficient to provide a magnet hold to constrain the hub assemblies 8224A-D in at least one direction. For example, the magnetic hold may prevent the hub assemblies 8224A-D from being removed away from the drive surface 8240.

FIG. 51G depicts an embodiment of rotationally aligning and magnetically coupling the active torque elements 8202 with the passive torque elements 8226A-D. For example, an embodiment of annularly aligning the pole pairs of the active torque elements 8202A-D with the passive torque elements 8226A-D.

In some embodiments, the passive torque elements 8226A-D may be rotationally misaligned from the active torque elements 8202A-D, for example, during an initial setup of the robotic surgery system.

In some embodiments, a hub assembly 8224A-D may be manufactured with passive torque elements 8226A-D having magnets arranged in a first arrangement. In some embodiments, the first arrangement may correspond to a predetermined default and/or anticipated position of the magnets of the active torque elements 8202A-D. For example, the angular orientation of the passive torque elements 8226A-D may be set during manufacturing and held in the first arrangement by the lateral magnetic fields of the adjacent magnets. Accordingly, in some embodiments, the passive torque elements 8226A-D may be initially angularly aligned with the active torque elements 8202A-D. In such embodiments, an alignment process may not be required.

However, misalignment may occur either through human error, machine error, or happenstance. For instance, the active torque elements 8202A-D of a hub adapter 8000A-D may be arranged in a second arrangement different from the first arrangement. This may occur after a previous use of the hub adapter 8000A-D if the active torque elements 8202A-D are not returned to a default position corresponding to the first arrangement. Alternatively, the angular orientation of the passive torque elements 8226A-D may change after manufacturing. For example, the angular orientation of the passive torque elements 8226A-D may be altered during shipping. Accordingly, in some embodiments, the rotational orientation of the passive torque elements 8226A-D may differ from the rotational orientation of the corresponding active torque elements 8202A-D. For example, the passive torque elements 8226A-D may be angularly offset from the corresponding active torque elements 8202A-D. The following discussion discloses solutions for aligning the active torque elements 8202A-D with the passive torque elements 8226A-D.

In some embodiments, the active torque elements 8202A-D of the hub adapter 8000A-D may be translated (e.g., from a retracted position as shown in FIG. 51F) to an extended position toward the drive surface 8216 after the hub adapter 8000A is axially aligned with the hub assembly 8224A, as shown in FIG. 51G. In such embodiments, pole pairs between the passive torque elements 8226A-D and active torque elements 8202A-D may be automatically aligned as the magnets of the active torque elements 8202A-D are moved from the retracted position towards the extended position. For example, the active torque elements 8202A-D, passive torque elements 8226A-D, or both the active torque elements 8202A-D and passive torque elements 8226A-D may rotate until corresponding pole pairs are aligned.

Translating the active torque elements 8202A-D to a position adjacent to the drive surface 8216 can increase the magnetic field extending through the barrier 8242 from the active torque elements 8202A-D. The increased magnetic field may sufficiently magnetically couple the active torque elements 8202A-D with the passive torque elements 8226A-D. In some embodiments, the active torque elements 8202A-D may be advanced slowly to the extended position. Advancing the active torque elements 8202A-D slowly can advantageously allow the corresponding passive torque elements 8226A-D to rotationally adjust to align with the active torque elements 8202A-D. By comparison, advancing the active torque elements 8202A-D too quickly can secure the passive torque elements 8226A-D in an improper alignment. Accordingly, in some embodiments, the active torque elements 8202A-D can be advanced at a rate sufficient to allow proper alignment of the active torque elements 8202A-D before reaching the extended position.

Additionally, translating the active torque elements 8202A-D can incrementally increase the magnetic coupling between the active torque elements 8202A-D and the passive torque elements 8226A-D. For example, the magnetic coupling may increase from a force of about 1 lbf to a force exceeding 20 lbf. Accordingly, in the extended position, a rotation of the active torque elements 8202A-D can cause a corresponding rotation of the passive torque elements 8226A-D. Additionally and/or alternatively, the magnetic coupling may be sufficiently strong for the shear force of the magnetic coupling to pull the hub assembly 8224A as the hub adapter 8000A translates within the drive table.

In some embodiments, a motor operatively coupled to an active torque element 8202A-D may attempt to position the corresponding active torque element 8202A-D to match a corresponding passive torque element 8226A-D. In some embodiments, the motor current may fluctuate based on the relative alignment between the active torque element 8202A-D and the passive torque element 8226A-D. For example, misalignment may result in high current while alignment may result in low current. Accordingly, the motor can drive the active torque element 8202A-D to a rotational position aligned with the passive torque element 8226A-D based on the measured motor current. In some embodiments, the motor current can be sensed while moving the active torque elements 8202A-D towards the passive torque elements 8226A-D at one or more points in time or positions prior to the fully extended position, and the motor can rotate the active torque elements 8202A-D prior to reaching the fully extended position so that the active torque elements 8202A-D and the passive torque elements 8226A-D are aligned and engaged upon the active torque elements 8202A-D reaching the extended position. In some embodiments, the active torque elements 8202A-D can rotate to try to achieve a current of zero or almost zero, which may indicate that the active torque elements 8202A-D and passive torque elements 8226A-D are aligned.

Figure 51H:
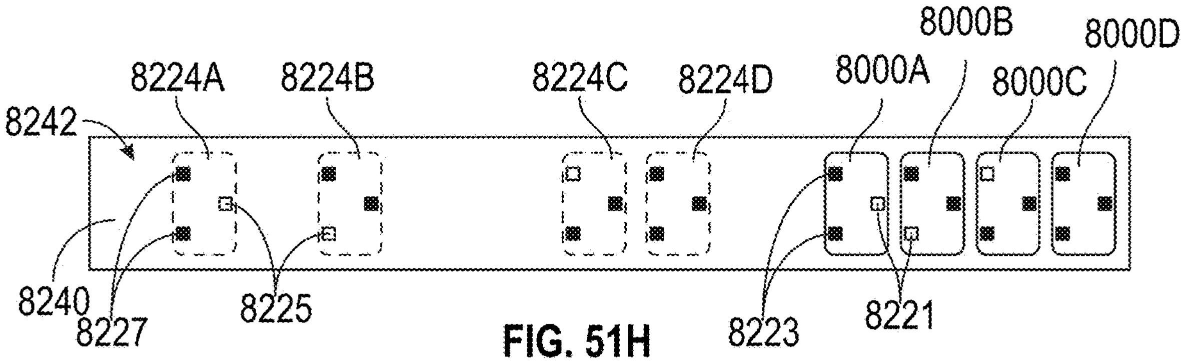
FIGS. 51H-51I are top views of a plurality of hub adapters having detectable objects aligning with a corresponding hub assembly having sensors.
Figure 51I:
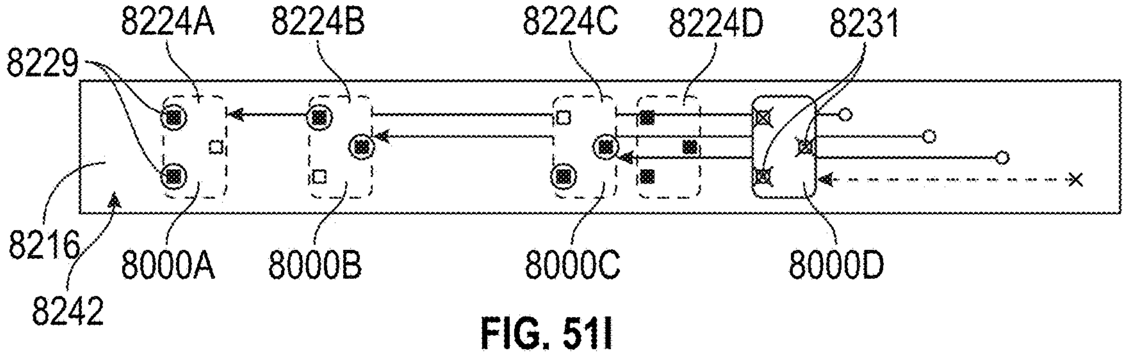

While certain embodiments having hub adapters 8000A-D with sensors for detecting detectable objects of hub assemblies 8224A-D are described herein, in other embodiments, hub assemblies 8224A-D may include sensors for detecting detectable objects of hub adapters 8000A-D as shown in FIGS. 51H-51I.

In some embodiments, a robotic surgery system and/or drive table thereof may include a fixed number of hub adapters (e.g., four hub adapters), but may allow for coupling of multiple different hub assemblies or portions thereof (e.g., mounts) to a single hub adapter. In some embodiments, a robotic surgery system and/or drive table thereof may allow for coupling of more than four distinct types of hub assemblies (e.g., hub assemblies having different types of interventional devices coupled thereto) to the hub adapters. In such embodiments, arranging detectable objects on hub assemblies to provide a unique combination of outputs or states for detection by sensors to distinctly identify each type of hub assembly, as described in further detail here, may require a greater number of unique combinations of outputs or states than would be required to distinctly identify each hub adapter. In such embodiments, the hub assemblies may require a greater number of detectable objects or different arrangements of detectable objects between hub assemblies (which may require a greater number of corresponding sensors) for identifying the hub assemblies by sensors positioned within the hub adapters than would be needed for identifying the hub adapters by sensors positioned within the hub assemblies. For example, in certain embodiments, a robotic surgery system and/or drive table thereof may include four hub adapters. In such embodiments, the hub adapters may be distinguishable using magnetic detectable objects arranged in pairs in two locations on the hub adapters (e.g., a first hub adapter having north magnetic poles in a first position and a second position, a second hub adapter having a north magnetic pole in a first position and south magnetic pole in a second position, a third hub adapter having a south magnetic pole in a first position and a north magnetic pole in a second position, and a fourth hub adapter having a south magnetic poles in a first position and a second position). In such an embodiment, any number of different types of hub assemblies may be couplable to the system and able to identify the four hub adapters. In contrast, such magnetic pairs would not be able to be similarly positioned on the hub assemblies to distinguish between more than four types of hub assemblies. Instead, if detectable objects were arranged on more than four types of hub assemblies for distinguishing between the types of hub assemblies, they may need to be of a different type (other than magnetic poles), of a greater number (e.g., three or more magnets per hub assembly), or positioned in different positions on a hub assembly (which may result in the need for a greater number of corresponding sensors on the hub adapters). Accordingly, it may be beneficial for detectable objects to be positioned on the hub adapters as opposed to the hub assemblies, because placement on the hub adapters would allow for a smaller number of detectable objects and/or sensors to distinguish between different hub adapters than would be required if the detectable objects were positioned on the hub assemblies and the sensors were positioned on the hub adapters.

As shown in FIGS. 51H-51K, in certain embodiments, each of hub assemblies 8224A-D can include one or more sensors 8227 that can detect one or more detectable objects 8223 (e.g., identifier magnets, specific colors, light diodes, or other detectable objects) positioned on the hub adapters 8000A-D. In certain embodiments, the sensors 8227 of the hub assemblies 8224A-D can detect the detectable objects 8223 of the hub adapters 8000A-D to confirm alignment between the hub assemblies 8224A-D and hub adapters 8000A-D. In certain embodiments, the sensors 8227 of the hub assemblies 8224A-D can detect the detectable objects 8223 of the hub adapters 8000A-D to determine identification of the hub adapters 8000A-D. The embodiment shown in FIGS. 51H-51K can be generally the same as those of FIGS. 51C-51F with the differences noted below.

As shown in FIG. 51I, each of the hub adapters 8000A-D may be driven beneath the barrier 8242 until the hub adapter 8000A-D arrives at a position of a corresponding hub assembly 8224A-D. For example, each of the hub adapters 8000A-D may drive along the length of the drive table until the corresponding hub assembly 8224A-D identifies the hub adapter 8224A-D and/or detects an alignment between the corresponding hub assembly 8224A-D and the hub adapter 8224A-D. In other embodiments, as described herein, the hub assemblies 8224A-D may be placed on the drive table to predetermined locations for alignment with the hub adapters 8224A-D.

As described herein with reference to FIGS. 51C-51F, each of the plurality of hub adapters 8000A-D may be independently driven. Accordingly, it is possible to drive a single hub adapter 8000A-D to align with its corresponding hub assembly 8224A-D. As shown in FIG. 511, the first hub adapter 8000A can be driven past the fourth hub assembly 8224D, the third hub assembly 8224C, and the second hub assembly 8224B until the first hub assembly 8224A detects its alignment with the first hub adapter 8000A (e.g., alignment between the first hub adapter 8000A and the first hub assembly 8224A is detected via the sensors 8227 of the first hub assembly 8224A). In some embodiments, the sensors 8227 of the first hub assembly 8224A may scan for detectable objects 8223 as the first hub adapter 8000A is advanced within the drive table until alignment is detected. Similarly, the second hub adapter 8000B can be driven past the fourth hub assembly 8224D and the third hub assembly 8224C until the second hub assembly 8224B detects its alignment with the second hub adapter 8000B. The third hub adapter 8000C can also be driven past the fourth hub assembly 8224D until the third hub assembly 8224C detects its alignment with the third hub adapter 8000C. The plurality of hub adapters 8000 may be driven simultaneously or one at a time. Under either approach, the plurality of hub adapters 8000 may be driven independently. In some embodiments, the hub assemblies 8224A-D may be loaded on the drive table at predetermined locations corresponding to an initial position or loading position of the hub adapters 8000A-D so that each hub assembly 8224A-D is aligned with a hub adapter 8000A-D upon loading. The sensors 8227 and detectable objects 8223 can be used to confirm proper positioning and/or identify the hub adapters 8000A-D.

As further shown in FIG. 51I, circles 8229 are provided to illustrate detectable objects 8223 of the hub adapters 8000A-D that are aligned with corresponding sensors 8227 of the hub assemblies 8224A-D indicating an alignment between those hub assemblies and hub adapters. For example, circles 8229 are shown over the detectable objects 8223 of the first hub adapter 8000A, the second hub adapter 8000B, and the third hub adapter 8000C because they are successfully aligned with their corresponding hub assemblies 8224A-C. In FIG. 51I, "x" symbols 8231 are provided over the sensors 8227 of the fourth hub assembly 8224D to indicate that none of the sensors 8227 of the fourth hub assembly 8224D have successfully detected a detectable object 8223 of a hub adapter 8000A-D.

Figure 51J:
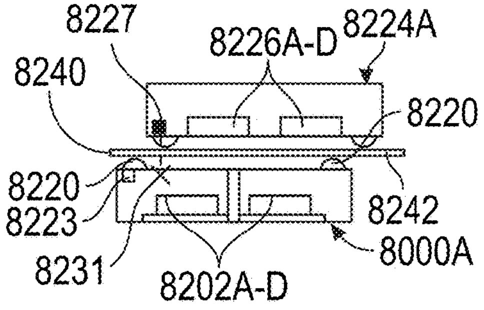
FIGS. 51J-51K are side views of a hub adapter having detectable objects aligning with a hub assembly having sensors.
Figure 51K:
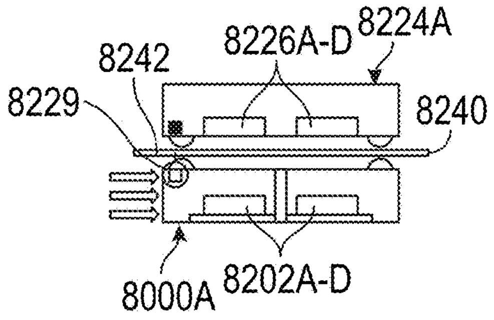
Figure 51L:
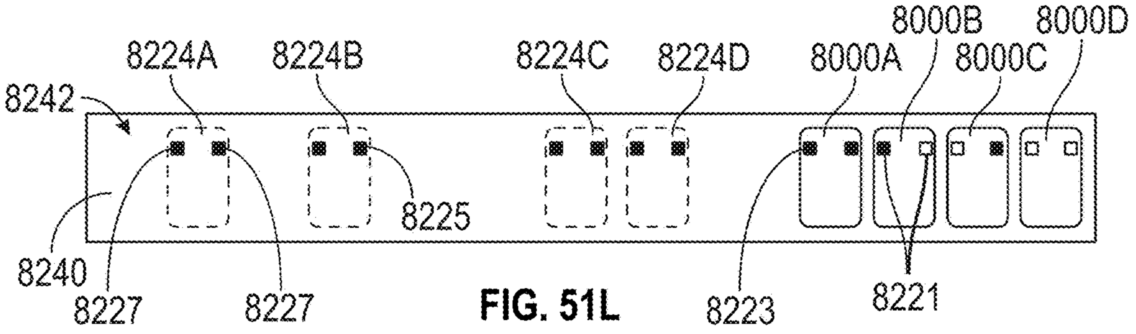
FIGS. 51L-51M are top views of a plurality of hub adapters having detectable objects aligning with a corresponding hub assembly having sensors.

FIGS. 51J-51L illustrate a method of aligning a hub adapter 8000A with a corresponding hub assembly 8224A. While a hub adapter 8000A and hub assembly 8224B are discussed, other hub adapters and hub assemblies may be aligned using the same methods.

As shown in FIG. 51J, the sensor(s) 8227 of the hub assembly 8224A are not aligned with the detectable object(s) 8223 of the hub adapter 8000A. Accordingly, the hub adapter 8000A may be translated within the drive table (e.g., sweep) until the sensor(s) 8227 of the hub assembly 8224A detect the detectable object(s) of the hub adapter 8000A, as shown in FIG. 51K.

FIGS. 51L-51P illustrate another embodiment of the hub adapters 8000A-D and hub assemblies 8224A-D. As described herein with reference to FIGS. 51A-51K, the sensors 8227 and the detectable objects 8223 may be included in the hub assemblies 8224A-D or the hub adapters 8000A-D, respectively. The embodiment shown in FIGS. 51L-51P may be generally the same as those described herein with reference to FIGS. 51A-51K with the differences described below.

Figure 51M:
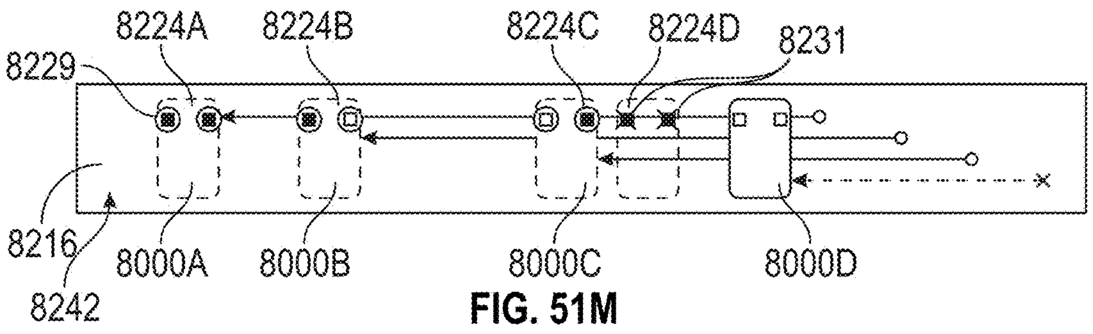

In some embodiments, each of the one or more hub adapters 8000A-D can include the same number of detectable objects 8223. In some embodiments, the detectable objects 8223 can be positioned at the same location for each of the one or more hub adapters 8000A-D (sharing a common general pattern). This may facilitate detection by sensors 8227 placed at the same location of each of the one or more hub assemblies 8224A-D. In some embodiments, each of the one or more hub adapters 8000A-D can include two detectable objects 8223, as shown in FIGS. 51L-51M. As shown in FIGS. 51L-51M, the two detectable objects 8223 of each hub adapter 8000A-D can be positioned at opposite sides of the hub adapter 8000A-D. For example, one detectable object can be placed at or near a distal end of the hub adapter 8000A-D and the other hub adapter can be placed at or near a proximal end of the hub adapter 8000A-D. The one or more hub assemblies 8224A-D can be configured to read, identify, or detect the detectable objects 8223 of each of the one or more hub adapters 8000A-D via the sensors 8227.

As described herein, the detectable objects 8223 may be binary or trinary detectable objects. For example, each of the detectable objects 8223 can be configured to provide one of multiple possible outputs or states. For example, the detectable objects 8223 can either be on or off, a north magnetic pole or a south magnetic pole, a first color or a second color, etc. Each of the one or more hub adapters 8000A-D can include a unique combination of outputs or states of the detectable objects 8223. The number of available unique combinations of outputs or states of the detectable objects 8223 can be based on the number of detectable objects 8223 provided on each of the one or more hub adapters 8000A-D. Additionally and/or alternatively, the number of available unique combinations of outputs or states of the detectable objects 8223 can be based on the number of outputs or states available to each of the detectable objects 8223. For example, embodiments providing two binary detectable objects on each of the one or more hub adapters 8000A-D can provide four unique combinations, embodiments providing three binary detectable objects can provide eight unique combinations, embodiments providing four binary detectable objects can provide sixteen unique combinations, etc. The outputs or states of the detectable objects 8223 can be represented by a filled or empty square 8221. In some cases, a filled square can represent a first output or state and an empty square can represent a second output or state, or vice versa. For example, as shown in FIGS. 51L-51M, the first hub adapter 8000A can have a first unique combination of outputs or states of the two binary detectable objects (e.g., on-on and/or north-north), the second hub adapter 8000B can have a second unique combination of outputs or states of the two binary detectable objects (e.g., on-off and/or north-south), the third hub adapter 8000C can have a third unique combination of outputs or states of the two binary detectable objects (e.g., off-on and/or south-north), and the fourth hub adapter 8000D can have a fourth unique combination of outputs or states of the two binary detectable objects (e.g., off-off and/or south-south). Accordingly, the unique combinations of outputs or states of the corresponding detectable objects can correspond to a particular one of the one or more hub adapters 8000A-D.

Each of the one or more hub assemblies 8224A-D can include the same number of sensors 8227 as the one or more hub adapters 8000A-D have detectable objects 8223. Additionally, the sensors 8227 can be positioned in the same or a corresponding location of the one or more hub assemblies 8224A-D as the positions of the detectable objects 8223 on the one or more hub adapters 8000A-D. The sensors 8227 can be configured to read, identify, or detect the presence and state of the detectable objects 8223. Accordingly, each of the one or more hub assemblies 8224A-D can be configured to identify each of the one or more hub adapters 8000A-D.

Due to the unique combination of outputs or states of each hub adapter 8000A-D, the sensors 8227 of the hub assemblies 8224A-D can detect the identity of a hub adapter 8000A-D aligned with the sensors 8227. Having unique combinations of outputs or states of detectable objects on the hub adapters 8000A-D may be more efficient than having unique combinations of outputs or states on the hub assemblies 8224A-D as described in other embodiments. For example, in certain embodiments, a greater number of types of hub assemblies 8224A-D than the number of hub adapters 8000A-D may be couplable with the hub adapters 8000A-D (e.g., six types of hub assemblies 8224A-D could be couplable with four hub adapters 8000A-D), which may require a greater number of unique combinations of outputs or states to distinguish between hub assemblies 8224A-D if the detectable outputs were positioned on the hub assemblies 8224A-D instead of the hub adapters 8000A-D.

In some embodiments, if a hub assembly 8224A-D only detects a single detectable object 8223, it may indicate that the corresponding hub assembly 8224A-D is misaligned with a hub adapter 8000A-D. For example, it may indicate that the hub assembly 8224A-D is axially misaligned with the corresponding hub adapter 8000A-D (e.g., a proximal detectable object 8223 of the hub adapter is aligned with a distal sensor of the hub assembly 8224A-D or a distal detectable object 8223 of the hub adapter 8000A-D is aligned with a proximal distal sensor of the hub assembly 8224A-D). In some embodiments, it may be indicate that the hub assembly 8224A-D is misaligned rotationally relative to the hub adapter 8000A-D (e.g., due to an undesired yaw rotation).

As shown in FIG. 51L, the plurality of hub adapters 8000A-D may be located at respective default positions. In some embodiments, the default positions may be at a longitudinal end of the drive table. As further shown in FIG. 51L, the plurality of hub assemblies 8224A-D may be placed on the drive surface 8240 at positions that do not correspond to the respective default positions of the corresponding hub adapters 8000A-D. In other embodiments, the hub assemblies 8224A-D may be placed at positioned intended to correspond to the default positions of the corresponding hub adapters. However, an alignment procedure may still be performed to ensure precise alignment.

As shown in FIG. 51M, each of the one or more hub adapters 8000A-D may be driven beneath the barrier 8242 until one of the one or more hub assemblies 8224A-D identifies the corresponding hub adapter 8000A-D as hub adapter 8000A-D arrives at a position of a corresponding hub assembly 8224A-D. For example, each of the hub adapters 8000A-D may drive along the length of the drive table until the hub assembly 8224A-D identifies its corresponding hub adapter 8000A-D and/or detects that it is aligned with its corresponding hub adapter 8000A-D, respectively.

Each of the plurality of hub adapters 8000A-D may be independently driven. Accordingly, it is possible to drive a single hub adapter 8000A-D to align with its corresponding hub assembly 8224A-D. As shown in FIG. 51M, the first hub adapter 8000A can be driven past the fourth hub assembly 8224D, the third hub assembly 8224C, and the second hub assembly 8224B until the first hub adapter 8000A is aligned with the first hub assembly 8224A (e.g., alignment between the first hub adapter 8000A and the first hub assembly 8224A is detected via the sensors 8227 of the first hub assembly 8224A). In some embodiments, the sensors 8227 of the first hub assembly 8224A may scan for detectable objects 8223 as the first hub adapters 8000A is advanced within the drive table until alignment is detected. Similarly, the second hub adapter 8000B can be driven past the fourth hub assembly 8224D and the third hub assembly 8224C until the second hub adapter 8000B arrives at the second hub assembly 8224B. The third hub adapter 8000C can also be driven past the fourth hub assembly 8224D until the third hub adapter 8000C arrives at the third hub assembly 8224C. The one or more hub adapters 8000A-D may be driven simultaneously or one at a time. Under either approach, the one or more hub adapters 8000 may be driven independently.

As further shown in FIG. 51M, circles 8229 are provided to illustrate detectable objects 8223 of the hub adapters 8000A-D that are aligned with corresponding sensors 8227 of the hub assemblies 8224A-D indicating an alignment between those hub assemblies and hub adapters. For example, circles 8229 are shown over the detectable objects 8223 of the first hub adapter 8000A, the second hub adapter 8000B, and the third hub adapter 8000C because they are successfully aligned with their corresponding hub assemblies 8224A-C. In FIG. 51M, "x" symbols 8231 are provided over the sensors 8227 of the fourth hub assembly 8224D to indicate that none of the sensors 8227 of the fourth hub assembly 8224 have successfully detected a detectable object 8223 of a hub adapter 8000A-D.

Figure 51N:
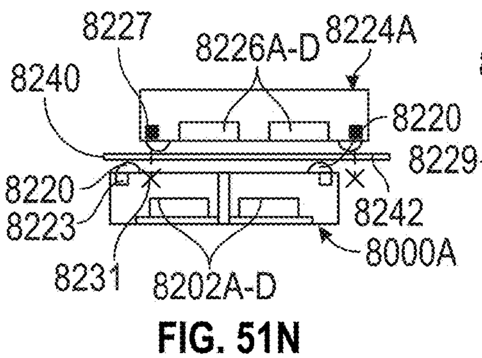
FIGS. 51N-51P are side views of a hub adapter having detectable objects aligning with a hub assembly having sensors.
Figure 51O:
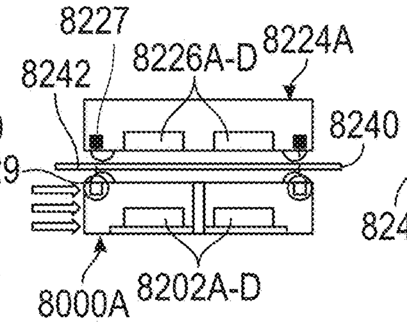
Figure 51P:
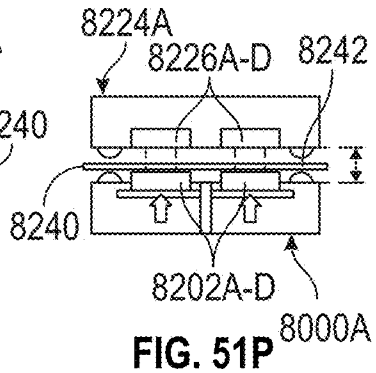

FIGS. 51N-51P illustrate a method of aligning a hub adapter 8000A with a corresponding hub assembly 8224A. While a hub adapter 8000A and hub assembly 8224B are discussed, other hub adapters and hub assemblies may be aligned using the same methods.

As shown in FIGS. 51N-51P, the hub adapter 8000A may align with a corresponding hub assembly 8224A by having an identifier, such as a detectable object 8223 as described with respect to FIGS. 51L and 51M, sensed by the hub assembly 8224A. In some embodiments, the hub assembly 8224A may recognize the respective corresponding hub adapter 8000A by sensing one or more identifier magnets, for example, using one or more sensors 8227. Each sensor 8227 of the hub assembly 8224A can be configured to detect the presence of a detectable object 8223 of the corresponding hub adapter 8000A.

In some embodiments, each of the hub assemblies 8224A-D can be configured to identify each of the hub adapters 8000A-D. In some embodiments, the plurality of hub assemblies 8224A-D may be configured to identify only a particular one of the plurality of hub adapters 8000A-D.

As shown in FIG. 51N, the sensors 8227 of the hub assembly 8224A are not aligned with the detectable objects 8223 of the hub adapter 8000A. Accordingly, the hub adapter 8000A may be translated within the drive table (e.g., sweep) until the sensor(s) 8227 of the hub assembly 8224A detect the detectable object(s) of the hub adapter 8000A, as shown in FIG. 51O.

In some embodiments, during the alignment of the hub adapters 8000A-D with the hub assemblies 8224A-D, the active torque elements 8202A-D may be positioned in the retracted position away from the drive surface 8216. In the retracted position, a magnetic field may extend through the barrier 8242 from the active torque elements 8202A-D. In some embodiments, the magnetic field may be weak and insufficient to rotate the passive torque elements 8226A-D of the corresponding hub assemblies 8224A-D. For example, in some embodiments, the magnetic coupling may have a magnetic force of about 1 lbf. In some embodiments, the magnetic field may be sufficient to provide a magnet hold to constrain the hub assemblies 8224A-D in at least one direction. For example, the magnetic hold may prevent the hub assemblies 8224A-D from being removed away from the drive surface 8240.

FIG. 51P depicts an embodiment of rotationally aligning and magnetically coupling the active torque elements 8202A-D with the passive torque elements 8226A-D. For example, an embodiment of annularly aligning the pole pairs of the active torque elements 8202A-D with the passive torque elements 8226A-D.

In some embodiments, the passive torque elements 8226A-D may be rotationally misaligned from the active torque elements 8202A-D, for example, during an initial setup of the robotic surgery system.

In some embodiments, a hub assembly 8224A-D may be manufactured with passive torque elements 8226A-D having magnets arranged in a first arrangement. In some embodiments, the first arrangement may correspond to a predetermined default and/or anticipated position of the magnets of the active torque elements 8202A-D. For example, the angular orientation of the passive torque elements 8226A-D may be set during manufacturing and held in the first arrangement by the lateral magnetic fields of the adjacent magnets. Accordingly, in some embodiments, the passive torque elements 8226A-D may be initially angularly aligned with the active torque elements 8202A-D. In such embodiments, an alignment process may not be required.

However, misalignment may occur either through human error, machine error, or happenstance. For instance, the active torque elements 8202A-D of a hub adapter 8000A-D may be arranged in a second arrangement different from the first arrangement. This may occur after a previous use of the hub adapter 8000A-D if the active torque elements 8202A-D are not returned to a default position corresponding to the first arrangement. Alternatively, the angular orientation of the passive torque elements 8226A-D may change after manufacturing. For example, the angular orientation of the passive torque elements 8226A-D may be altered during shipping. Accordingly, in some embodiments, the rotational orientation of the passive torque elements 8226A-D may differ from the rotational orientation of the corresponding active torque elements 8202A-D. For example, the passive torque elements 8226A-D may be angularly offset from the corresponding active torque elements 8202A-D. The following discussion discloses solutions for aligning the active torque elements 8202A-D with the passive torque elements 8226A-D.

In some embodiments, the active torque elements 8202A-D of the hub adapter 8000A-D may be translated (e.g., from a retracted position as shown in FIG. 51O) to an extended position toward the drive surface 8216 after the hub adapter 8000A is axially aligned with the hub assembly 8224A, as shown in FIG. 51P. In such embodiments, pole pairs between the passive torque elements 8226A-D and active torque elements 8202A-D may be automatically aligned as the magnets of the active torque elements 8202A-D are moved from the retracted position towards the extended position. For example, the active torque elements 8202A-D, passive torque elements 8226A-D, or both the active torque elements 8202A-D and passive torque elements 8226A-D may rotate until corresponding pole pairs are aligned.

Translating the active torque elements 8202A-D to a position adjacent to the drive surface 8216 can increase the magnetic field extending through the barrier 8242 from the active torque elements 8202A-D. The increased magnetic field may sufficiently magnetically couple the active torque elements 8202A-D with the passive torque elements 8226A-D. In some embodiments, the active torque elements 8202A-D may be advanced slowly to the extended position. Advancing the active torque elements 8202A-D slowly can advantageously allow the corresponding passive torque elements 8226A-D to rotationally adjust to align with the active torque elements 8202A-D. By comparison, advancing the active torque elements 8202A-D too quickly can secure the passive torque elements 8226A-D in an improper alignment. Accordingly, in some embodiments, the active torque elements 8202A-D can be advanced at a rate sufficient to allow proper alignment of the active torque elements 8202A-D before reaching the extended position.

Additionally, translating the active torque elements 8202A-D can incrementally increase the magnetic coupling between the active torque elements 8202A-D and the passive torque elements 8226A-D. For example, the magnetic coupling may increase from a force of about 1 lbf to a force exceeding 20 lbf. Accordingly, in the extended position, a rotation of the active torque elements 8202A-D can cause a corresponding rotation of the passive torque elements 8226A-D. Additionally and/or alternatively, the magnetic coupling may be sufficiently strong for the shear force of the magnetic coupling to pull the hub assembly 8224A as the hub adapter 8000A translates within the drive table.

In some embodiments, a motor operatively coupled to an active torque element 8202A-D may attempt to position the corresponding active torque element 8202A-D to match a corresponding passive torque element 8226A-D. In some embodiments, the motor current may fluctuate based on the relative alignment between the active torque element 8202A-D and the passive torque element 8226A-D. For example, misalignment may result in high current while alignment may result in low current. Accordingly, the motor can drive the active torque element 8202A-D to a rotational position aligned with the passive torque element 8226A-D based on the measured motor current. In some embodiments, the motor current can be sensed while moving the active torque elements 8202A-D towards the passive torque elements 8226A-D at one or more points in time or positions prior to the fully extended position, and the motor can rotate the active torque elements 8202A-D prior to reaching the fully extended position so that the active torque elements 8202A-D and the passive torque elements 8226A-D are aligned and engaged upon the active torque elements 8202A-D reaching the extended position. In some embodiments, the active torque elements 8202A-D can rotate to try to achieve a current of zero or almost zero, which may indicate that the active torque elements 8202A-D and passive torque elements 8226A-D are aligned.

The embodiment shown in FIGS. 51Q-51T can be generally the same as that shown in FIGS. 51L-510 with the following differences. As shown in FIGS. 51Q-51T, the detectable objects 8223 are included on the hub assemblies 8224A-D and the sensors 8227 are included on the hub adapters 8000A-D. For example, each of the one or more hub adapters 8000A-D can include the same number of sensors 8227 as the one or more hub assemblies 8000A-D have detectable objects 8223.

Due to the unique combination of outputs or states of each hub assembly 8224A-D, the sensors 8227 of the hub adapters 8000A-D can detect the identity of a hub assembly 8224A-D aligned with the sensors 8227. Having unique combinations of outputs or states of detectable objects on the hub assemblies 8224A-D may accommodate a greater number of unique combinations of outputs or states on the hub assemblies 8224A-D. For example, in certain embodiments, a greater number of types of hub assemblies 8224A-D than the number of hub adapters 8000A-D may be couplable with the hub adapters 8000A-D (e.g., six types of hub assemblies 8224A-D could be couplable with four hub adapters 8000A-D), which may require a greater number of unique combinations of outputs or states to distinguish between hub assemblies 8224A-D.

Figure 51Q:
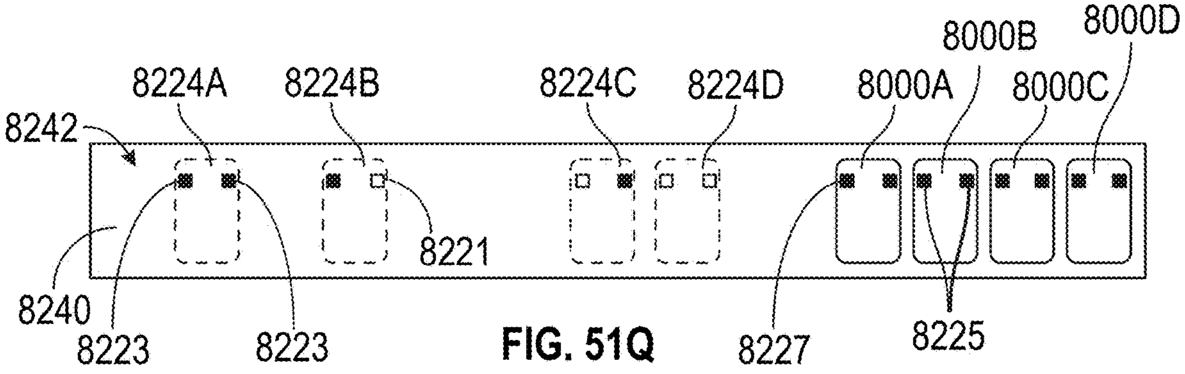
FIGS. 51Q-51R are top views of a plurality of hub adapters having sensors aligning with a corresponding hub assembly having detectable objects.
Figure 51R:
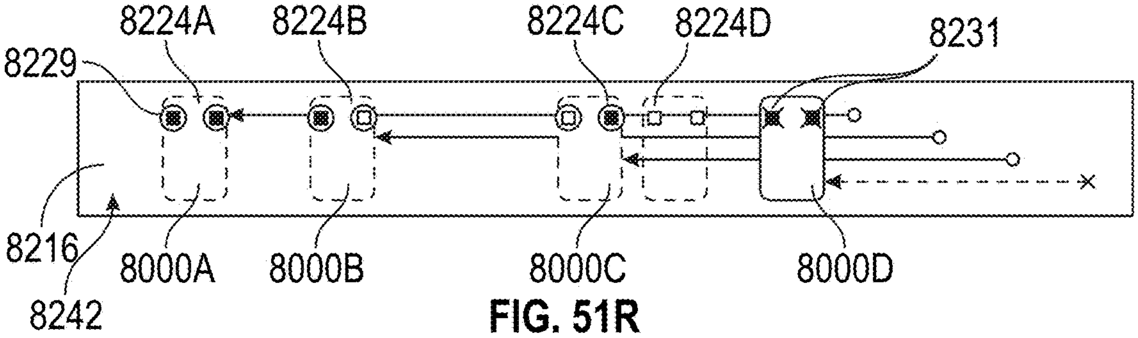

As shown in FIG. 51R, each of the one or more hub adapters 8000A-D may be driven beneath the barrier 8242 until the hub adapters 8000A-D identify the corresponding hub assembly 8224A-D. Each of the plurality of hub adapters 8000A-D may be independently driven. Accordingly, it is possible to drive a single hub adapter 8000A-D to align with its corresponding hub assembly 8224A-D. As shown in FIG. 51R, the first hub adapter 8000A can be driven past the fourth hub assembly 8224D, the third hub assembly 8224C, and the second hub assembly 8224B until the first hub adapter 8000A is aligned with the first hub assembly 8224A (e.g., alignment between the first hub adapter 8000A and the first hub assembly 8224A is detected via the sensors 8227 of the first hub adapter 8000A). Similarly, the second hub adapter 8000B can be driven past the fourth hub assembly 8224D and the third hub assembly 8224C until the second hub adapter 8000B arrives at the second hub assembly 8224B. The third hub adapter 8000C can also be driven past the fourth hub assembly 8224D until the third hub adapter 8000C arrives at the third hub assembly 8224C. The one or more hub adapters 8000A-D may be driven simultaneously or one at a time. Under either approach, the one or more hub adapters 8000 may be driven independently. In some embodiments, the hub assemblies 8224A-D may be loaded on the drive table at predetermined locations corresponding to an initial position or loading position of the hub adapters 8000A-D so that each hub assembly 8224A-D is aligned with a hub adapter 8000A-D upon loading. The sensors 8227 and detectable objects 8223 can be used to confirm proper positioning and/or identify the hub assemblies 8224A-D.

As further shown in FIG. 51R, circles 8229 are provided to illustrate detectable objects 8223 of the hub assemblies 8224A-D that are aligned with corresponding sensors 8227 of the hub adapters 8000A-D indicating an alignment between those hub assemblies and hub adapters. For example, circles 8229 are shown over the detectable objects 8223 of the first hub assembly 8224A, the second hub assembly 8224B, and the third hub assembly 8224C because they are successfully aligned with their corresponding hub adapters 8000A-C. In FIG. 51R, “x” symbols 8231 are provided over the sensors 8227 of the fourth hub adapter 8000D to indicate that none of the sensors 8227 of the fourth hub adapter 8000D have successfully detected a detectable object 8223 of a hub assembly 8224A-D.

Figure 51S:
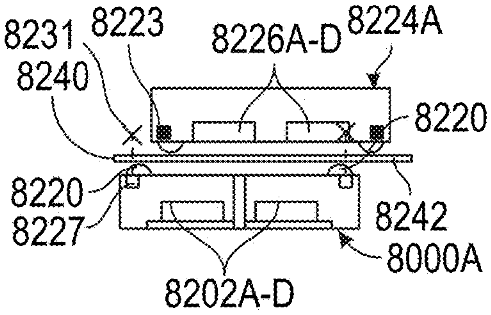
FIGS. 51S-51T are side views of a hub adapter having sensors aligning with a corresponding hub assembly having detectable objects.
Figure 51T:
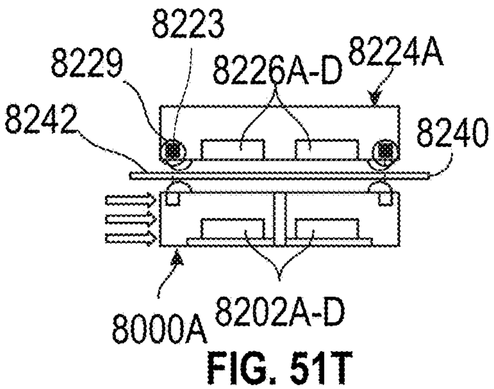

FIGS. 51S-51T illustrate a method of aligning a hub adapter 8000A with a corresponding hub assembly 8224A. While a hub adapter 8000A and hub assembly 8224B are discussed, other hub adapters and hub assemblies may be aligned using the same methods.

As shown in FIGS. 51S-51T, the hub adapter 8000A may align with a corresponding hub assembly 8224A by detecting a detectable object 8223 as described with respect to FIGS. 51Q and 51R. In some embodiments, the hub adapter 8000A may recognize the respective corresponding hub assembly 8224A by sensing one or more identifier magnets, for example, using one or more sensors 8227. Each sensor 8227 of the hub adapter 8000A can be configured to detect the presence of a detectable object 8223 of the corresponding hub assembly 8224A.

In some embodiments, each of the hub adapters 8000A-D can be configured to identify each of the hub assemblies 8224A-D. In some embodiments, the plurality of hub adapters 8000A-D may be configured to identify only a particular one of the plurality of hub assemblies 8224A-D.

As shown in FIG. 51S, the sensors 8227 of the hub adapter 8000A are not aligned with the detectable objects 8223 of the hub assembly 8224A. Accordingly, the hub adapter 8000A may be translated within the drive table (e.g., sweep) until the sensor(s) 8227 of the hub adapter 8000A detect the detectable object(s) of the hub assembly 8224A, as shown in FIG. 51T.

Figure 51V:
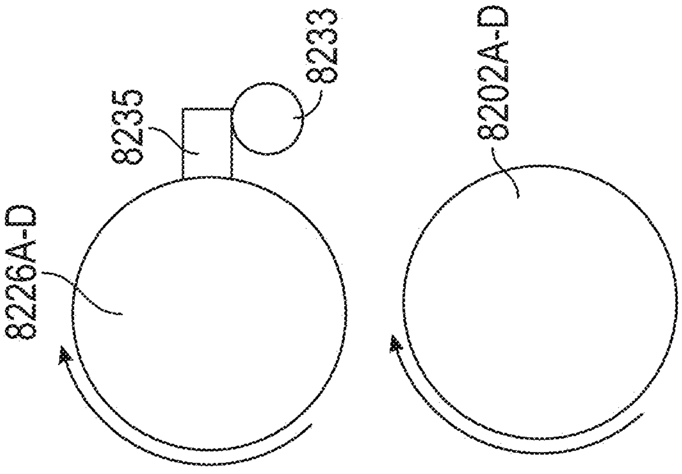
FIGS. 51U-51V are schematic views of a hub adapter aligning with a hub assembly having a hard stop mechanism.
Figure 51U:
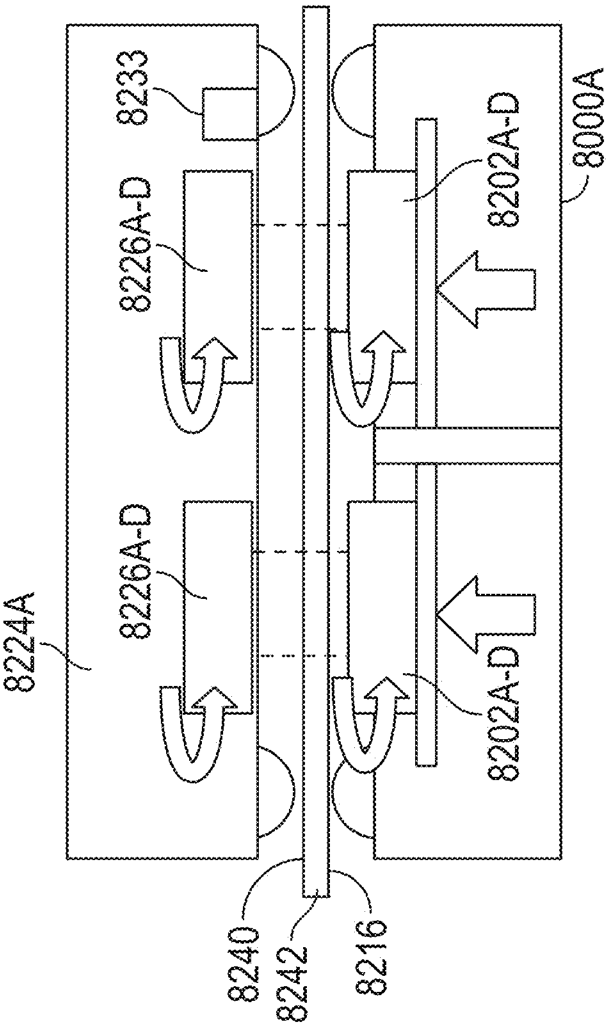

In some embodiments, the hub assembly can include a hard stop mechanism for the passive torque elements 8226A-D to drive the passive torque elements 8226A-D to a known initialization position or home position. For example, as shown in FIGS. 51U and 51V, the passive torque elements 8226A-D may include a protruding element 8235 configured to engage with a stop 8233. The stop 8233 may be a fixed and immovable object. Accordingly, the passive torque elements 8226A-D can be rotated until the protruding element 8235 contacts the stop 8233 thereby preventing the passive torque elements 8226A-D to continue rotating. In some embodiments, the passive torque elements 8226A-D may be driven for a given duration and/or distance. For example, the passive torque elements 8226A-D may be driven for one revolution. Accordingly, the passive torque element 8226A-D will have contacted the stop 8233 via the protruding element 8235. In other embodiments, the hard stop mechanism for each passive torque element 8226A-D may be positioned elsewhere within a gear train coupled to the passive torque element 8226A-D or in connection with a component coupled to the gear train (e.g., in connection with a valve (such as a hemostatic valve) or stopcock).

Additionally and/or alternatively, the hub adapter can include a hard stop mechanism, as described above so that the active torque elements 8202A-D can be driven to a known initialization or home position. Driving the active torque elements 8202A-D and/or passive torque elements 8226A-D to a known initialization position or home position may allow the robotic control system to know the rotational positions of the active torque elements 8202A-D and/or passive torque elements 8226A-D.

Figure 51X:
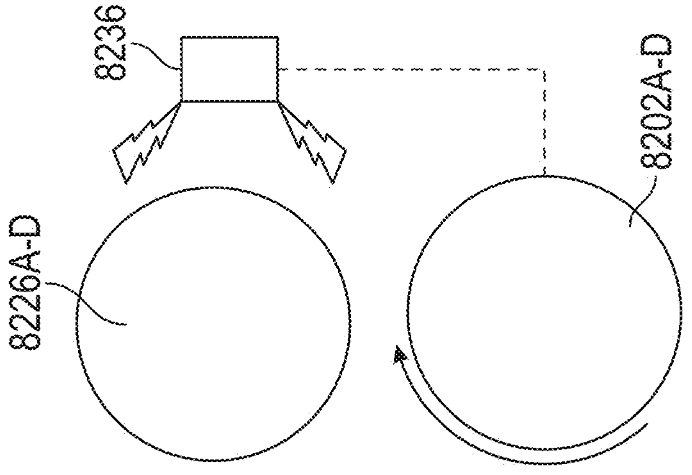
FIGS. 51W-51X are schematic views of a hub adapter aligning with a hub assembly having a disposable position sensor.
Figure 51W:
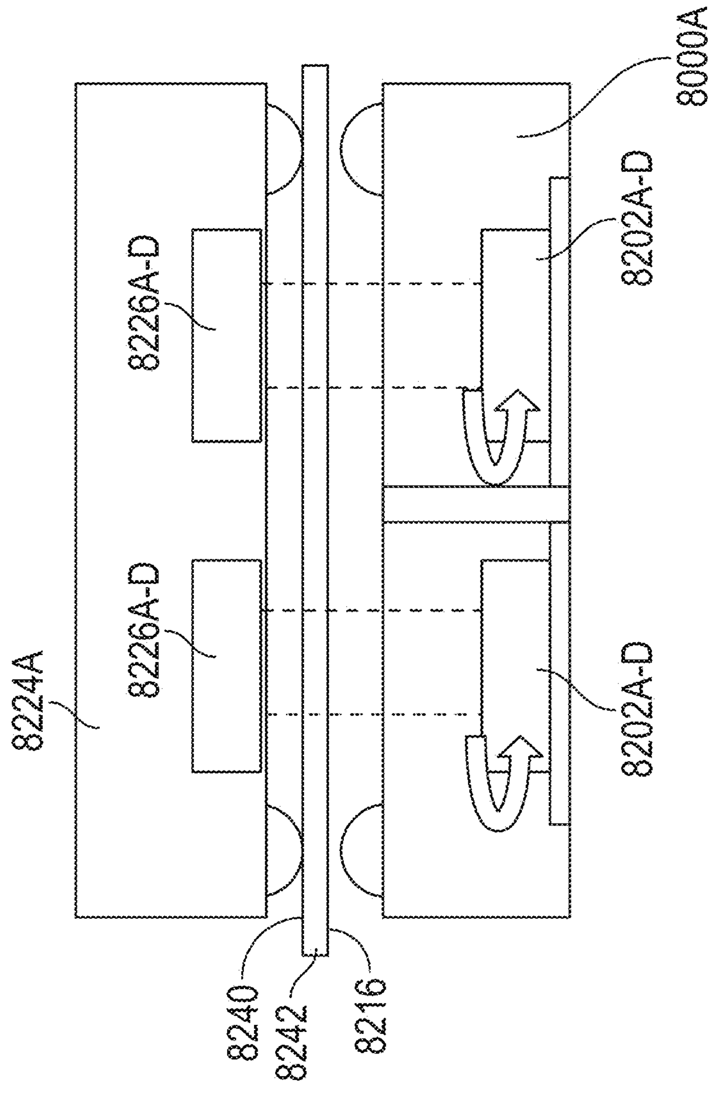

In some embodiments, the hub assembly can include a disposable position sensor. For example, as shown in FIGS. 51W and 51X, a disposable position sensor 8236 can be configured to detect the rotational orientation of the passive torque elements 8226A-D. A signal from the disposable position sensor 8236 can be used (e.g., by a control system) to drive the active torque elements 8202A-D to a rotational orientation corresponding to the rotational orientation of the passive torque elements 8226A-D. In some embodiments, a disposable position sensor 8236 may be provided for each passive torque element 8226A-D. After rotational alignment is achieved, the active torque elements 8202A-D may be elevated to the extended position.

In some embodiments, the active torque elements 8202A-D can include programmable magnets. The programmable magnets may be configured to be programmed to correspond to an axially aligned passive torque element 8226A-D. For example, the polarity of the active torque elements 8202A-D can be selectively programmed based on the polarity of a spatially aligned passive torque element 8226A-D.

In some embodiments, the rotational position of the passive torque elements 8226A-D can be determined by sweeping the first hub adapter 8000A past the first hub assembly 8224A at a constant speed. One or more sensors can measure a corresponding voltage as the first hub adapter 8000A translates past the first hub assembly 8224A. The corresponding voltage may be measured as Voltage-Time chart. Peaks and valleys on the chart may represent the position of maximum magnetic flux. In some embodiments, the peaks may represent a first polarity and the valleys may represent a second polarity opposite the first polarity. The rotational position of the magnetic elements of the passive torque elements 8226A-D can be determined based on the time corresponding to the measured voltages and the known constant speed of translating the first hub adapter 8000A past the first hub assembly 8224A.

In some embodiments, the first hub assembly 8224A may be removed by retracting the active torque elements 8202A-D from the drive surface 8216. For example, the active torque elements 8202A-D may be translated to the first position away from the drive surface 8216 to reduce the magnetic field interacting with the passive torque elements 8226A-D. When the magnetic field is sufficiently weak, the hub assembly 8224A can be removed.

Other possibilities of coupling and uncoupling a hub adapter 8000A with a hub assembly 8224A are possible. For example, in some embodiments, the active torque elements 8202A-D and/or the passive torque elements 8226A-D may be electromagnets. In such embodiments, an electrical current supplied to the active torque elements 8202A-D and/or the passive torque elements 8226A-D may provide a magnetic coupling force therebetween. In some embodiments, the electoral current may be turned off to eliminate the magnetic coupling. The hub assembly 8224A can be removed when the electromagnets are turned off.

In some embodiments, a portion of the drive surface may be configured to create a larger physical separation between active torque elements 8202A-D and passive torque elements 8226A-D to reduce the magnetic coupling force. For example, the drive surface 8216 can include a ramped or sloped section or a ramp or sloped surface may be coupled to and positioned along the drive surface 8216. Accordingly, the hub adapter 8000A can be driven along the ramped surface to physically separate the active torque elements 8202A-D from the passive torque elements 8226A-D. The hub assembly 8224A can be removed when the magnetic coupling is sufficiently reduced by the distance between the active torque elements 8202A-D and the passive torque elements 8226A-D. Similarly, in some embodiments, a portion of the drive surface 8240 and/or barrier 8242 can create a larger physical separation between the active torque elements 8202A-D and passive torque elements 8226A-D. For example, the drive surface 8240 and/or barrier 8242 can include a ramped or sloped section or a ramp or sloped surface may be coupled to and positioned along the drive surface 8216.

In some embodiments, the barrier 8242 can be physically moved away from the hub adapters 8000A-D to decouple the hub assemblies 8224A-D from the hub adapters 8000A-D.

In some embodiments, one or more intermediate components that may affect magnetic coupling force can be placed between one or more active torque elements and one or more passive torque elements, for example, to reduce the magnetic coupling force and allow removal of the hub assemblies from the hub adapters. In some embodiments, a shunt having magnetic material (e.g., steel), can be placed between one or more active torque element/passive torque element pairs to reduce the magnetic coupling force therebetween. In some embodiments, a non-ferrous conductive material (e.g., copper) can be placed between one or more active torque element/passive torque element pairs and an eddy current can be applied to dampen magnetic coupling force. In some embodiments, one or more repulsive magnets or an arrangement of repulsive magnets can be placed between one or more active torque element/passive torque element pairs to create a repulsive force on the magnets of the active torque element and/or the magnets of the passive torque element to counteract the magnetic coupling force. In some embodiments, an intermediate member (e.g., a disk or insert) may have one or more repulsive magnets configured to counteract the magnetic coupling force of the active torque element(s) and one or more repulsive magnets configured to counteract the magnetic coupling force of the passive torque element(s). In some embodiments, one or more magnets or an arrangement of magnets having a fixed and known rotational position can be aligned with the magnets of one or more active torque elements and/or one or more passive torque elements to cause the magnets of the one or more active torque elements and/or passive torque elements to rotate to a predetermined position (e.g., a home position). In some embodiments, an intermediate component that covers a portion of the magnets of one or more active torque elements and/or one or more passive torque elements can be placed between one or more active torque element/passive torque element pairs to reduce the magnetic coupling force.

Figure 55A:
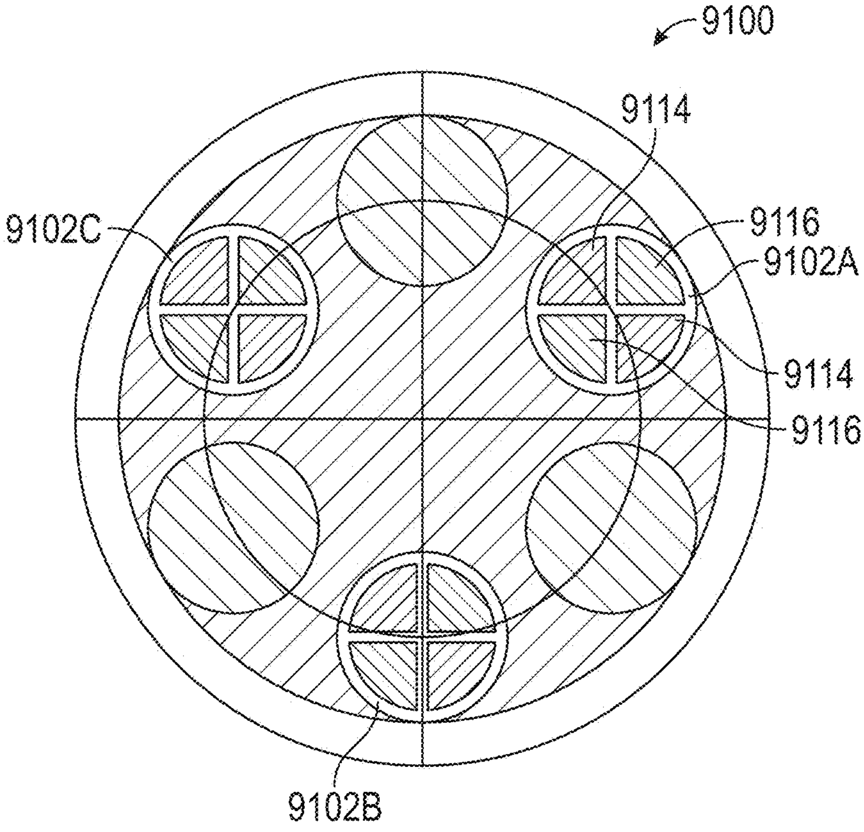
FIG. 55A is a schematic view of a portion of a hub adapter.
Figure 55B:
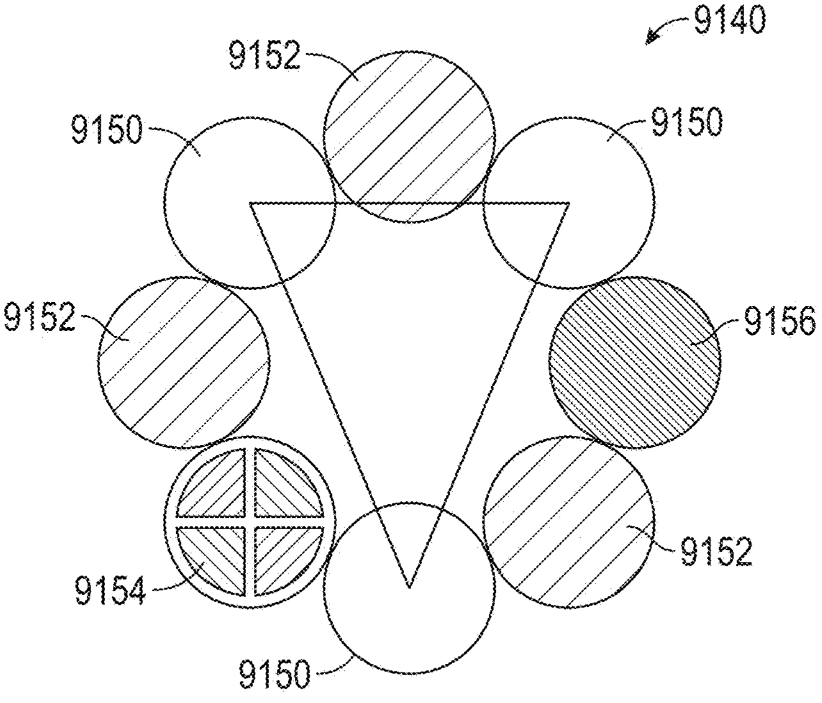
FIG. 55B is a schematic view of a movable member that may be used with the hub adapter of FIG. 55A.

Another embodiment of a mechanism for facilitating magnetic coupling and decoupling is shown in FIGS. 55A-55B. FIG. 55A illustrates a section of an embodiment of a hub adapter 9100. The hub adapter 9100 can include a plurality of active torque elements 9102A-C having first magnets 9114 having a first polarity and second magnets 9116 having a second polarity. The second polarity may be the inverse of the first. As described herein, the active torque elements 9102A-C can be configured to couple with passive torque elements of a hub assembly. The hub assembly may have a corresponding arrangement of passive torque elements with magnets having opposite polarities for coupling with the magnets of the active torque elements 9102A-C.

FIG. 55B depicts a movable member 9140. The movable member 9140 may be a rotatable member. The movable member 9140 may be in the form of a disk. The movable member 9140 can be positioned between the active torque elements 9102A-C of the hub adapter 9100 and the passive torque elements of the hub assembly. For example, the movable member 9140 may be positioned on or coupled to the hub adapter or the hub assembly. In some embodiments, a movable member 9140 can be placed on or coupled to the hub adapter 9100 and a second movable member 9140 may be placed on or coupled to the hub assembly.

The movable member 9140 can include a plurality of features configured to align with the active torque elements 9102A-C and/or passive torque elements in certain rotational positions of the movable member 9140 (e.g., to manage magnetic flux). For example, in some embodiments, the movable member 9140 can include one or more openings 9150. The openings 9150 can be aligned by rotation of the movable member 9140 with the active torque elements 9102A-C and/or passive torque elements. The openings 9150 may have a size that corresponds to the active torque elements 9102A-C and/or passive torque elements so that the magnetic forces between the active torque elements 9102A-C and passive torque elements are not blocked by the movable member 9140 when aligned with the openings 9150.

In some embodiments, the movable member 9140 can include one or more inserts 9152. The inserts 9152 may be aligned with the active torque elements 9102A-C and/or passive torque elements to reduce or prevent magnetic coupling forces between the active torque elements 9102A-C and the corresponding passive torque elements. For example, the inserts 9152 can include shunts using magnetic material (e.g., steel). The inserts 9152 can include non-ferrous conductive material (e.g., copper) that can be used with eddy current to dampen magnetic coupling force. The inserts 9152 can include repulsive magnets (e.g., magnets having all south or all north polarities). In some embodiments, the inserts 9152 can include partial openings (e.g., with smaller openings than the size of the arrangement of magnets 9114, 9116 of the active torque elements) to reduce the magnetic coupling force between the active torque elements 9102A-C and corresponding passive torque elements.

In some embodiments, magnetic coupling force may be modulated by continuous rotation of the movable member 9140. For example, ferromagnetic inserts 9152 can be rotated to attenuate the magnetic field between the active torque elements 9102A-C and the passive torque elements.

In some embodiments, the movable member 9140 can include a reset magnet element 9154. The reset magnet element 9154 may have fixed magnetic positions. The reset magnet element 9154 may be aligned with one of the active torque elements 9102A-C and/or passive torque elements to cause a realignment of the corresponding magnets of the active torque element and/or passive torque element to a desired position (e.g., a home position). In some embodiments, the movable member 9140 can be rotated so that the reset magnet element 9154 passes over all of the active torque elements 9102A-C and/or passive torque elements to reset the positions of all of the magnets of the active torque elements 9102A-C and/or passive torque elements.

In some embodiments, the movable member 9140 can include an open space 9156 that may receive different inserts.

While a particular arrangement of a movable member 9140 is shown in FIG. 55B, one of skill in the art would understand that different arrangements may be used. A movable member 9140 may include only a subset of the openings 9150, inserts 9152, reset magnet element 9154, and space 9156 shown in FIG. 55B or different arrangements or numbers of the openings 9150, inserts 9152, reset magnets 9154, and spaces 9156.

In some embodiments, a torque transfer system may include multiple movable members 9140. For example, in some embodiments, different movable members 9140 may be positioned to have features that align with different active torque elements 9102A-C and/or passive torque elements when rotated. In some embodiments, a different movable member may be provided for each active torque element/passive torque element pair. For example, with respect to the hub adapter 9100 of FIG. 55A, in some embodiments, a torque transfer system may include three movable members, each configured to rotate to align features (e.g., openings 9150, inserts 9152, reset magnet elements 9154, and/or spaces 9156) with a different one of the active torque elements 9102A-C and/or their corresponding passive torque elements. In some embodiments, a first movable member 9140 can be configured to rotate to align features (openings 9150, inserts 9152, reset magnet elements 9154, and/or spaces 9156) with first and second active torque elements 9102A-C and/or their corresponding passive torque elements and a second movable member can be configured to rotate to align features (e.g., openings 9150, inserts 9152, reset magnet elements 9154, and/or spaces 9156) with the third active torque element 9102A-C and/or its corresponding passive torque element. Similarly, while three active torque elements 9102A-C are shown in FIG. 55A, one or more movable members 9140 may be used with torque subsystems having a different number of active torque elements (e.g., four active torque elements).

While movable members 9140 that are generally in the form of rotating disks are described, in some embodiments, other movable members 9140, such as translatable members, may be used to align different features (e.g., openings 9150, inserts 9152, reset magnet elements 9154, and/or spaces 9156) with one or more active torque elements and/or passive torque elements.

In some embodiments, the hub assemblies 8224A-D and/or the hub adapters 8000A-D may include monolithic magnets. In some embodiments, the monolithic magnet can be programmable. For example, the active torque elements and/or the passive torque elements may be configured to have programmable polarity. In such embodiments, the polarity of the active torque elements and/or the passive torque elements may be changed. For example, attracting polarities may be changed to repelling polarities. Accordingly, the hub adapter 8000A can be removed.

Figure 52B:
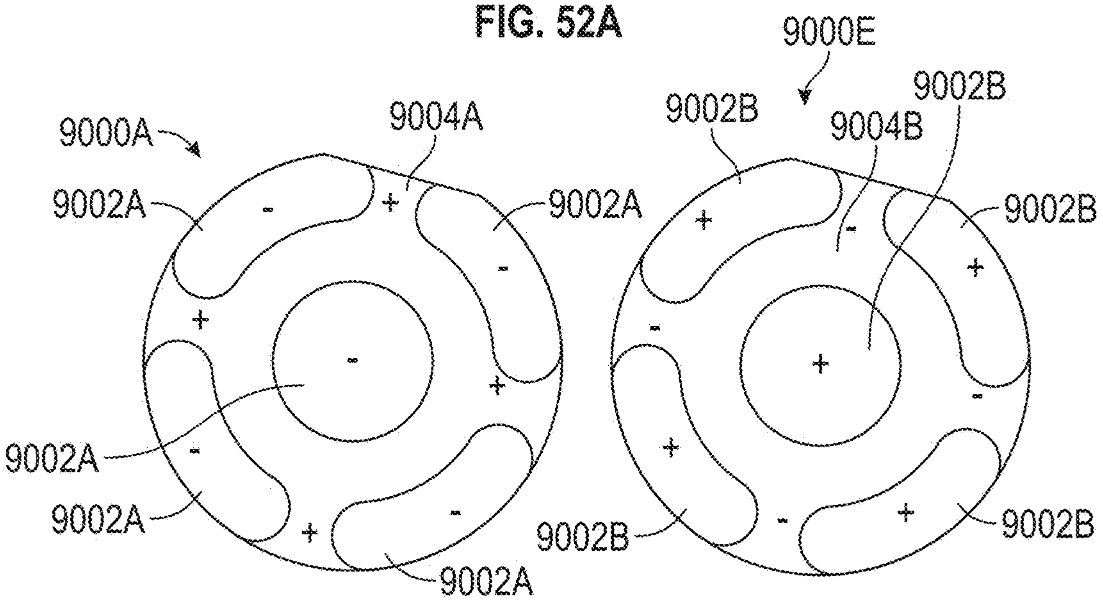
FIG. 52B is a top view of two magnets.

FIGS. 52A-52B depict an embodiment of a magnet 9000A (e.g., of an active torque element). FIG. 52B further depicts an embodiment of a magnet 9000E (e.g., of a passive torque element). In certain embodiments, other magnets (e.g., magnets 9000B-D) of a hub adapter (e.g., magnets 9000B-D) may have the same or a generally similar structure as the magnet 9000A. In some embodiments, other magnets (e.g., magnets 9000E-H) of a corresponding hub assembly (e.g., magnets 9000F-H) may have the same or similar structure as the magnet 9000E. In some embodiments, the magnetization of the magnets 9000E-H of the passive torque elements may be the inverse of the magnets 9000A-D of the active torque elements. In some embodiments, the magnetization of each of the magnets 9000E-H of the passive torque subsystem may be the inverse of a corresponding magnet of the active torque subsystem. Accordingly, while an embodiment of the magnet 9000A is discussed, the other magnets of the active torque elements and passive torque elements may include any of the same and/or similar features and/or functions. Similarly, while the magnet 9000A is described as a single magnet, in other embodiments, the magnet 9000A may be a magnetic array having multiple magnets.

As shown in FIG. 52A, the magnet 9000A can be a monolithic magnet. For example, the magnet 9000A can be a polymagnet. The polymagnet can have one or more magnetic regions within a body (e.g., a monolithic body). The magnet 9000A can include one or more first magnetic regions 9002A and one or more second magnetic regions 9004A. In some embodiments, the one or more first magnetic region 9002A can have an opposite polarity than the one or more second magnetic regions 9004A. As shown in FIG. 52A, the one or more first magnetic regions 9002A can include the center of the magnet 9000A and intermediate annular portions of the magnet 9000A. The one or more second magnetic regions 9004A can include any portion of the magnet 9000A that is not part of the one or more first magnetic regions 9002A.

In some embodiments, the one or more first magnetic regions 9002A can have an opposite polarity than the one or more second magnetic regions 9004A.

FIG. 52B depicts the magnet 9000A (e.g., of an active torque element 8202A-D) and another magnet 9000E (e.g., of a passive torque element 8224A-D). The magnet 9000E can have first magnetic regions 9002B and second magnetic regions 9004B. As shown in FIG. 52B, the magnet 9000A can have a first polarity and the magnet 9000E can have a second polarity. The second polarity can be the inverse of the first polarity. In some embodiments, the magnet 9000A and the magnet 9000E can be configured to be axially aligned and magnetically coupled.

Figure 52C:
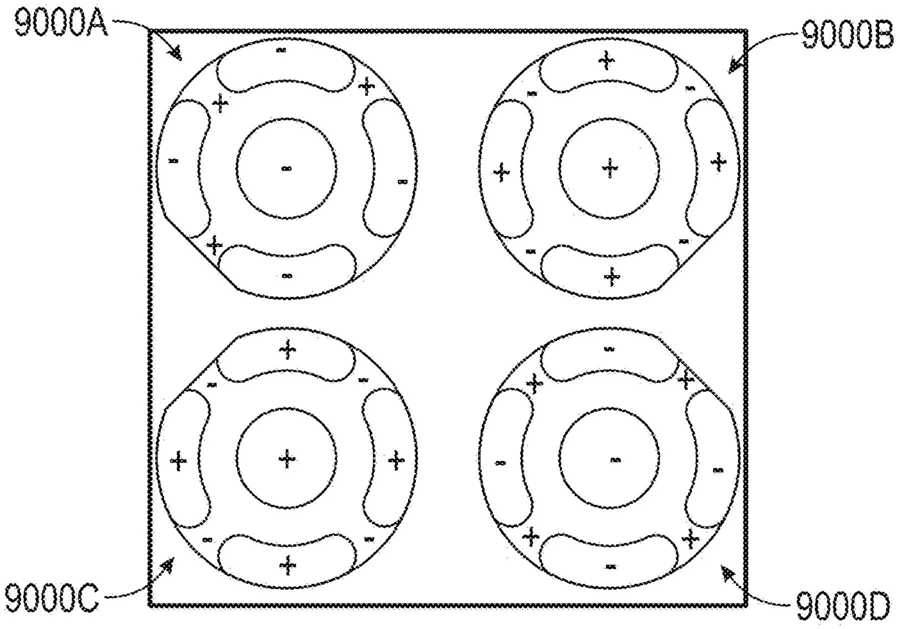
FIG. 52C is a top view of a torque element subassembly.

FIG. 52C depicts an arrangement of magnets 9000A-D of an active torque element (e.g., of an active torque element 8202A-D) As shown, in some embodiments, the magnets 9000A and 9000D may generally have the same structure and/or polarity, and the magnets 9000B and 9000C may generally have the same structure and/or polarity. The magnets 9000E-H of the passive torque elements 8224A-D may have a generally similar, but inverted, arrangement.

Figure 53A:
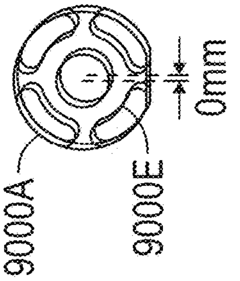
FIGS. 53A-53D are top views of magnetic couplings between the magnets of FIG. 52B.
Figure 53B:
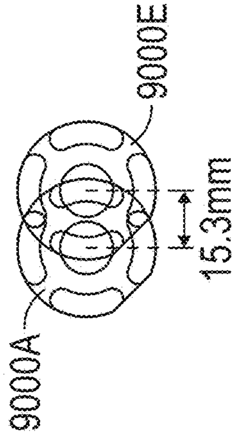
Figure 53C:
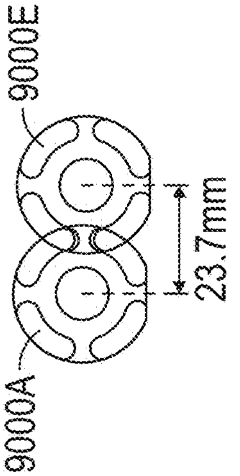
Figure 53D:
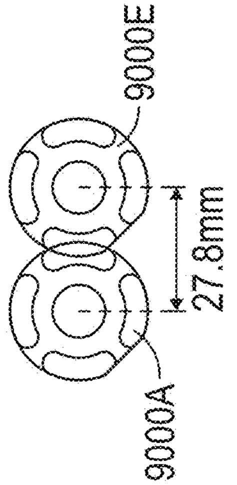

FIGS. 53A-53D depict magnetic arrangements between an active torque element and a passive torque element. FIG. 53A illustrates an embodiment when a magnet 9000E of the passive torque subsystem of a hub assembly is axially aligned with a corresponding magnet 9000A of the active torque subsystem of a hub adapter. FIGS. 53B-53D illustrate embodiments when a magnet 9000E is laterally displaced from an axial alignment with a corresponding magnet 9000A of the active torque subsystem of a hub adapter.

As described above, the magnets of the passive torque subsystem may have an opposite polarity than the magnets of the active torque subsystem. Accordingly, the one or more first regions 9002A, 9002B may be magnetically attracted to one another. As further described above, the one or more first magnetic regions 9002A, 9002B can include the center of the magnets 9000A, 9000B and intermediate annular portions of the magnets 9000A, 9000E. Accordingly, the centers of the magnets 9000A, 9000E and the intermediate annular portions of the magnets 9000A, 9000E may be magnetically attracted to one another. Thus, the magnets have the potential to axially couple together in one of many possible first region alignments. In some embodiments, the magnets 9000A, 9000E may be automatically driven to a stable and/or bistable position. For example, the magnets 9000A, 9000E may be magnetically driven to a closest stable position corresponding to an axial alignment.

As shown in FIG. 53A, the center of magnet 9000A can be axially aligned with the center of magnet 9000E and the intermediate annular portions of the magnet 9000A can be axially aligned with corresponding intermediate annular portions of the magnet 9000E. This can represent a proper axial alignment with minimal lateral displacement between the magnet 9000A and the magnet 9000E. For example, the magnet 9000E may be laterally displaced about 0 mm from the magnet 9000A. In such embodiments, a rotation of the magnet 9000A about its center can cause a corresponding rotation of the magnet 9000E about its center. For example, the magnet 9000E may track the rotation of the magnet 9000A in a clockwise and/or counterclockwise direction.

As shown in FIG. 53B, the center of the magnet 9000A can be axially aligned with one of the intermediate annular portions of the magnet 9000E, and vice versa. This can represent an improper axial alignment with some lateral displacement between the magnet 9000A and the magnet 9000E. For example, the magnet 9000E may be laterally displaced about 15 mm from the magnet 9000A. In such embodiments, a rotation of the magnet 9000A about its center may cause a corresponding rotation of the magnet 9000E about an intermediate annular portion.

As shown in FIG. 53C, two of the intermediate annular portions of the magnet 9000A positioned along a first radial side of the magnet 9000A can be axially aligned with two corresponding intermediate annular portions of the magnet 9000E positioned along a second radial side of the magnet 9000E, and vice versa. This can represent an improper axial alignment with significant lateral displacement between the magnet 9000A and the magnet 9000E. For example, the magnet 9000E may be laterally displaced about 24 mm from the magnet 9000A. In such embodiments, a rotation of the magnet 9000A about its center may cause a counter rotation in the magnet 9000E about its center.

As shown in FIG. 53D, a single intermediate annular portion of the magnet 9000A positioned along a first radial side of the magnet 9000A can be axially aligned with a single corresponding intermediate annular portion of the magnet 9000E positioned along a second radial side of the magnet 9000E. This can represent an improper axial alignment with another significant lateral displacement between the magnet 9000A and the magnet 9000E. For example, the magnet 9000E may be laterally displaced about 28 mm from the magnet 9000A. In such embodiments, a rotation of the magnet 9000A about its center may cause a counter rotation in the magnet 9000E about its center. Additionally, the magnet 9000E may be decoupled from the magnet 9000A as the magnet 9000A rotates.

Accordingly, proper axial alignment between the hub assemblies 8224A-D and the corresponding hub adapters 8000A-D is essential to mitigate possible risks to a patient during an operation. In some embodiments, a spatial alignment method may be implemented, as described above, to ensure proper axial alignment. The spatial alignment method described above, may be sufficiently accurate to prevent misalignment due to the coupling of improper magnet regions. For example, the spatial alignment methods described herein may be configured to position a center point of each of the magnets 9000A-D of a hub adapter within a particular distance from the center point of its corresponding magnet 9000E-H of a hub assembly so that the proper alignment position shown in FIG. 53A is its closest stable position. When the proper alignment position is the closest stable position, the magnetic coupling between the magnets can automatically cause the magnets to be driven to the proper alignment position. Accordingly, in some embodiments, the spatial alignment methods described herein may position the center point of each of the magnets 9000A-D of a hub adapter within distance of less than 15.3 mm, less than 14 mm, less than 12 mm, or less than 10 mm from the center point of its corresponding magnet 9000E-H.

Figure 54A:
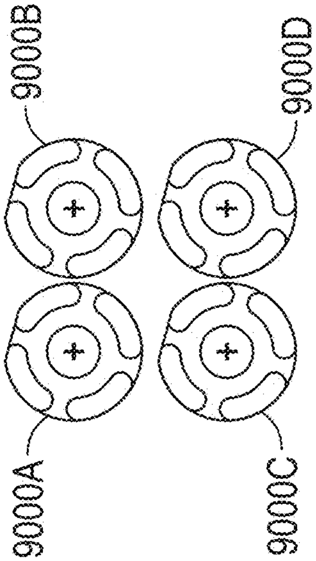
FIGS. 54A-54E are top views of a torque element subassembly.
Figure 54B:
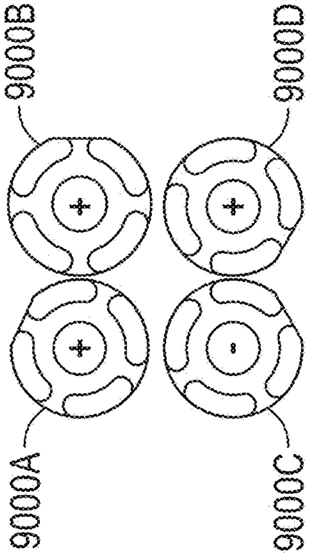
Figure 54C:
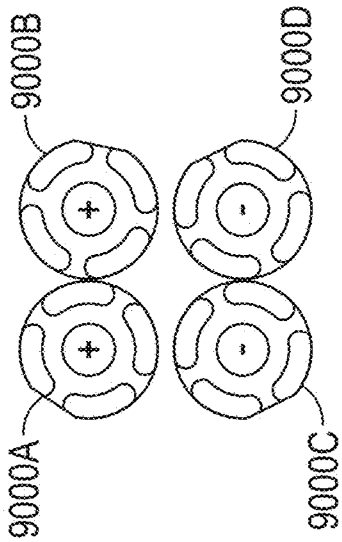
Figure 54D:
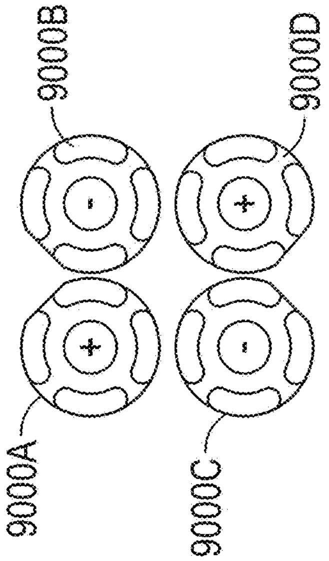
Figure 54E:
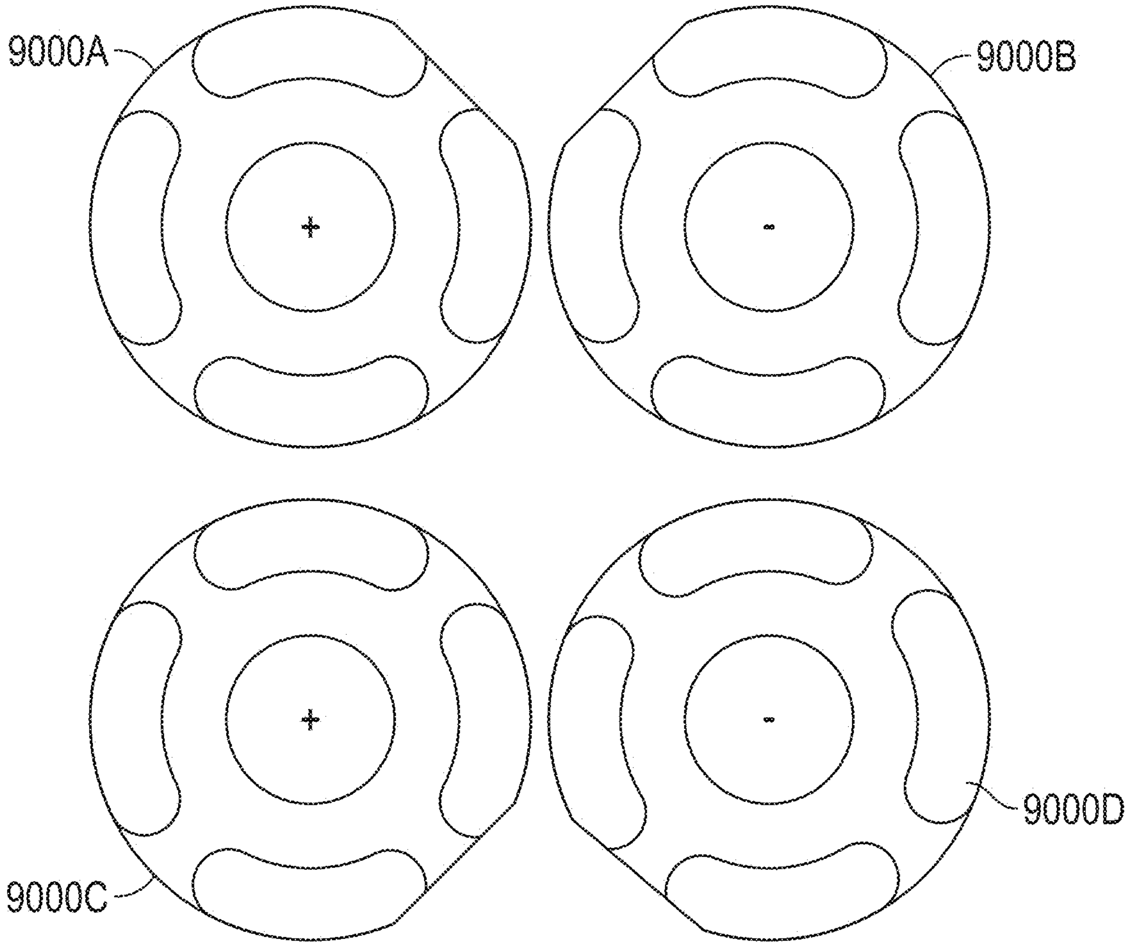

FIGS. 54A-54E depict various implementations of a torque element subsystem. The torque element subsystem can be an active torque element subsystem or a passive torque element subsystem. As shown in FIGS. 54A-54E, the torque element subsystem can include four magnets 9000A-D. FIG. 54A shows an embodiment of a torque element subsystem having a homogeneous combination of magnets wherein the magnets 9000A-D have the same polarity. FIG. 54B shows an embodiment of a torque element subsystem having three magnets with the same polarity and one magnet with a different polarity. For example, magnets 9000A-B and 9000D have a common first polarity and magnet 9000C has second polarity opposite the first polarity. FIGS. 54C-54E show embodiments of a torque element subsystem having two magnets having a common first polarity and two magnets having a common second polarity opposite the first polarity. As shown in FIG. 54C, magnets along a common row can share a common polarity. For example, the magnets 9000A-B can have the common first polarity and the magnets 9000C-D can have the common second polarity. As shown in FIG. 54D, diagonal magnets may share a common polarity. For example, magnets 9000A and 9000D can have the common first polarity and magnets 9000B-C can have the common second polarity. As shown in FIG. 54E, magnets along a common column can share a common polarity. For example, the magnets 9000A and 9000C can have a common first polarity and the magnets 9000B and 9000D can have a common second polarity.

Certain embodiments of methods and systems are described herein primarily in the context of aligning and/or coupling hub assemblies with hub adapters or aligning and/or coupling magnets of hub assemblies with magnets of hub adapters. As described herein, in certain embodiments, the magnets of the hub assembly are positioned within a mount thereof. Accordingly, the methods and systems described herein can also be described as aligning and/or coupling mounts with hub adapters or aligning and/or coupling magnets of mounts with magnets of hub adapters.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the robotic drive systems and methods described herein may be made without departing from the spirit of the disclosure. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less 10% or less than the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree. The ranges disclosed herein also encompass any and all overlap, sub-ranges, and combinations thereof, and any specific values within those ranges. Language such as "up to," "at least," "greater than," "less than," "between," and the like includes the number recited. Numbers and values used herein preceded by a term such as "about" or "approximately" include the recited numbers. For example, "approximately 7 mm" includes "7 mm" and numbers and ranges preceded by a term such as "about" or "approximately" should be interpreted as disclosing numbers and ranges with or without such a term in front of the number or value such that this application supports claiming the numbers, values and ranges disclosed in the specification and/or claims with or without the term such as "about" or "approximately" before such numbers, values or ranges such, for example, that "approximately two times to approximately five times" also includes the disclosure of the range of "two times to five times." The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A robotic medical system for performing a vascular procedure, comprising:
- a plurality of hub assemblies positioned on a sterile side of a sterile field barrier, wherein the plurality of hub assemblies comprises:
  - a first hub assembly comprising a first plurality of detectable objects having a first combination of detectable outputs or states; and
  - a second hub assembly comprising a second plurality of detectable objects having a second combination of detectable outputs or states, the second combination of detectable outputs or states being different than the first combination of detectable outputs or states;
- a plurality of hub adapters positioned on a non-sterile side of a sterile field barrier, wherein the plurality of hub adapters comprises:
  - a first hub adapter having a first plurality of sensors configured to detect one or more detectable objects of one or more of the plurality of hub assemblies; and
  - a second hub adapter having a second plurality of sensors configured to detect one or more detectable objects of one or more of the plurality of hub assemblies; and
- a control system configured to axially drive the first hub adapter and the second hub adapter to align the first hub adapter with the first hub assembly based on detection of the first plurality of detectable objects by the first plurality of sensors and align the second hub adapter with the second hub assembly based on detection of the second plurality of detectable objects by the second plurality of sensors.

2. The robotic medical system of claim 1, wherein the first plurality of detectable objects comprises a first magnet having a first polarity in a direction of the sterile field barrier and a second magnet having a second polarity in the direction of the sterile field barrier, wherein the second plurality of detectable objects comprises a first magnet having a first polarity in the direction of the sterile field barrier and a second magnet having a second polarity in the direction of the sterile field barrier, wherein the second polarity of the second magnet of the second plurality of detectable objects is different than the second polarity of the second magnet of the first plurality of detectable objects.

3. The robotic medical system of claim 1, wherein each hub assembly of the plurality of hub assemblies comprises at least one magnet configured to magnetically couple to a corresponding one of the plurality of hub adapters so that the hub assembly moves axially in response to axial movement of the corresponding one of the plurality of hub adapters.

4. The robotic medical system of claim 1, wherein each hub assembly of the plurality of hub assemblies comprises a mount and an interventional device hub removably coupled to the mount.

5. The robotic medical system of claim 1, wherein the plurality of hub assemblies further comprises:
- a third hub assembly comprising a third plurality of detectable objects having a third combination of detectable outputs or states; and
- a fourth hub assembly comprising a fourth plurality of detectable objects having a fourth combination of detectable outputs or states;
- wherein the third combination of detectable outputs or states and the fourth combination of detectable outputs or states are different than the first combination of detectable outputs or states and the second combination of detectable outputs or states.

6. The robotic medical system of claim 5, wherein the first hub assembly is coupled to a guide catheter, the second hub assembly is coupled to an access catheter, the third hub assembly is coupled to a procedure catheter, and the fourth hub assembly is coupled to a guidewire.

7. The robotic medical system of claim 5, wherein the plurality of hub adapters further comprises:

a third hub adapter having a third plurality of sensors configured to detect one or more detectable objects of one or more of the plurality of hub assemblies; and a fourth hub adapter having a fourth plurality of sensors configured to detect one or more detectable objects of one or more of the plurality of hub assemblies.

8. The robotic medical system of claim 1, wherein the first plurality of sensors and the second plurality of sensors are hall sensors.

9. The robotic medical system of claim 1, wherein the first plurality of detectable objects comprises a first detectable object positioned on a proximal side of the first hub assembly and a second detectable object positioned on a distal side of the first hub assembly.

10. The robotic medical system of claim 1, wherein each of the plurality of hub assemblies comprises a plurality of rollers configured to contact a drive surface.

11. A robotic medical system for performing a vascular procedure, comprising:

a plurality of hub adapters positioned on a non-sterile side of a sterile field barrier;

a plurality of hub assemblies positioned on a sterile side of the sterile field barrier;

a plurality of sensors disposed on each of either the plurality of hub adapters or the plurality of hub assemblies, wherein the plurality of sensors face the sterile field barrier;

a plurality of detectable objects disposed on each of the other of the plurality of hub adapters or the plurality of hub assemblies different from the plurality of sensors, wherein the plurality of detectable objects face the sterile field barrier; and a control system configured to axially drive the plurality of hub adapters;

wherein:

each of the plurality of hub adapters are configured to couple to a corresponding one of the plurality of hub assemblies so that the corresponding one of the plurality of hub assemblies moves axially in response to axial movement of the corresponding hub adapter;

the plurality of sensors are configured to detect the presence of the detectable objects across the sterile field barrier; and the control system is configured to align each of the plurality of hub adapters with the corresponding one of the plurality of hub assemblies based on the detection of the detectable objects.

12. The robotic medical system of claim 11, wherein the plurality of hub assemblies comprises a first hub assembly, a second hub assembly, a third hub assembly, and a fourth hub assembly.

13. The robotic medical system of claim 12, wherein the first hub assembly is coupled to a guide catheter, the second hub assembly is coupled to an access catheter, the third hub assembly is coupled to a procedure catheter, and the fourth hub assembly is coupled to a guidewire.

14. The robotic medical system of claim 11, wherein each hub assembly of the plurality of hub assemblies comprises a mount and an interventional device hub removably coupled to the mount.

15. The robotic medical system of claim 11, wherein the plurality of hub adapters comprises a first hub adapter, a second hub adapter, a third hub adapter, and a fourth hub adapter.

16. The robotic medical system of claim 11, wherein the plurality of detectable objects comprises a plurality of sets of detectable objects, wherein each set of detectable objects has a unique combination of detectable outputs or states.

17. The robotic medical system of claim 11, wherein each of the plurality of detectable objects comprises a detectable magnet.

18. The robotic medical system of claim 11, wherein the plurality of sensors comprises a plurality of sets of sensors, wherein each set of sensors has a unique combination of sensors.

19. The robotic medical system of claim 11, wherein each of the plurality of sensors comprises a hall sensor.

20. The robotic medical system of claim 11, wherein each of the plurality of hub assemblies comprises a plurality of rollers configured to contact a drive surface.

* * * * *